(12) United States Patent
Yaghi et al.

(10) Patent No.: US 10,287,304 B2
(45) Date of Patent: May 14, 2019

(54) ACID, SOLVENT, AND THERMAL RESISTANT METAL-ORGANIC FRAMEWORKS

(71) Applicant: The Regents of the University of California, Oakland, CA (US)

(72) Inventors: Omar M. Yaghi, Berkeley, CA (US); Seungkyu Lee, Oakland, CA (US); Juncong Jiang, Berkeley, CA (US); Yuebiao Zhang, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/116,186

(22) PCT Filed: Feb. 19, 2015

(86) PCT No.: PCT/US2015/016555
§ 371 (c)(1),
(2) Date: Aug. 2, 2016

(87) PCT Pub. No.: WO2015/127033
PCT Pub. Date: Aug. 27, 2015

(65) Prior Publication Data
US 2017/0008915 A1 Jan. 12, 2017

Related U.S. Application Data

(60) Provisional application No. 61/941,791, filed on Feb. 19, 2014.

(51) Int. Cl.
| | | |
|---|---|---|
| *C07F 7/00* | (2006.01) |
| *B01J 21/00* | (2006.01) |
| *B01D 33/00* | (2006.01) |
| *B01J 31/00* | (2006.01) |
| *B01D 53/047* | (2006.01) |
| *B01D 53/22* | (2006.01) |
| *B01D 63/02* | (2006.01) |
| *B01J 20/22* | (2006.01) |
| *B01J 20/30* | (2006.01) |
| *B01J 31/16* | (2006.01) |
| *B01J 37/04* | (2006.01) |

(52) U.S. Cl.
CPC ............. *C07F 7/003* (2013.01); *B01D 33/00* (2013.01); *B01D 53/047* (2013.01); *B01D 53/228* (2013.01); *B01D 63/02* (2013.01); *B01J 20/226* (2013.01); *B01J 20/3085* (2013.01); *B01J 31/00* (2013.01); *B01J 31/1691* (2013.01); *B01J 37/04* (2013.01); *B01D 2253/204* (2013.01)

(58) Field of Classification Search
CPC ............. C07F 7/00; B01J 21/00; C01G 25/00
USPC ................... 556/55, 51; 502/242; 423/417
See application file for complete search history.

(56) References Cited

U.S. PATENT DOCUMENTS

| | | |
|---|---|---|
| 2,684,967 A | 7/1954 | Berg |
| 4,532,225 A | 7/1985 | Tsao |
| 5,064,804 A | 11/1991 | Soo |
| 5,160,500 A | 11/1992 | Chu |
| 5,208,335 A | 5/1993 | Ramprasad |
| 5,617,467 A | 4/1997 | Bacher et al. |
| 5,648,508 A | 7/1997 | Yaghi |
| 5,733,505 A | 3/1998 | Goldstein |
| 5,779,904 A | 7/1998 | Ruderman |
| 6,479,447 B2 | 11/2002 | Bijl |
| 6,501,000 B1 | 12/2002 | Stibrany |
| 6,617,467 B1 | 9/2003 | Mueller |
| 6,624,318 B1 | 9/2003 | Mueller |
| 6,686,428 B2 | 2/2004 | Zhang |
| 6,893,564 B2 | 5/2005 | Mueller |
| 6,929,679 B2 | 8/2005 | Mueller |
| 6,930,193 B2 | 8/2005 | Yaghi |
| 7,196,210 B2 | 3/2007 | Yaghi |
| 7,202,385 B2 | 4/2007 | Mueller |
| 7,229,943 B2 | 6/2007 | Gibson |
| 7,279,517 B2 | 10/2007 | Mueller |
| 7,309,380 B2 | 12/2007 | Mueller |
| 7,343,747 B2 | 3/2008 | Mueller |
| 7,411,081 B2 | 8/2008 | Mueller |
| 7,524,444 B2 | 4/2009 | Hesse |
| 7,582,798 B2 | 9/2009 | Yaghi |
| 7,637,983 B1 | 12/2009 | Liu |
| 7,652,132 B2 | 1/2010 | Yaghi |
| 7,662,746 B2 | 2/2010 | Yaghi |
| 7,799,120 B2 | 9/2010 | Yaghi |
| 7,815,716 B2 | 10/2010 | Mueller |
| 8,343,260 B2 | 1/2013 | Omary |
| 8,480,955 B2 | 7/2013 | Yaghi |
| 8,501,150 B2 | 8/2013 | Schubert |
| 8,518,264 B2 | 8/2013 | Kiener |
| 8,524,932 B2 | 9/2013 | Leung |
| 8,709,134 B2 | 4/2014 | Yaghi |
| 8,735,161 B2 | 5/2014 | Yaghi |
| 8,742,152 B2 | 6/2014 | Yaghi |
| 8,900,352 B2 * | 12/2014 | Wilmer .................. B01J 20/223 502/401 |
| 9,078,922 B2 | 7/2015 | Yaghi |
| 9,139,601 B2 * | 9/2015 | Buso ....................... C07F 3/003 |
| 9,393,548 B2 * | 7/2016 | Matzger ............... B01J 20/3085 |

(Continued)

FOREIGN PATENT DOCUMENTS

| | | |
|---|---|---|
| CN | 1910191 A | 2/2007 |
| CN | 101270094 A | 9/2008 |

(Continued)

OTHER PUBLICATIONS

Carboni et al., "Highly porous and stable metal-organic frameworks for uranium extraction," Chemical Science, 4:2396-2402, Apr. 4, 2013.

(Continued)

*Primary Examiner* — Charanjit Aulakh
(74) *Attorney, Agent, or Firm* — Gavrilovich, Dodd & Lindsey LLP

(57) ABSTRACT

The disclosure provides for thermal, solvent, and/or acid resistant metal organic frameworks and the use of these frameworks in devices and methods for gas separation, gas storage, and catalysis. The disclosure further provides for MOFs that are strong solid acids, and the use of these strong solid acid MOFs in catalytic devices and catalytic methods.

18 Claims, 56 Drawing Sheets

(56) References Cited

U.S. PATENT DOCUMENTS

| | | |
|---|---|---|
| 2003/0004364 A1 | 1/2003 | Yaghi |
| 2003/0078311 A1 | 4/2003 | Muller |
| 2003/0148165 A1 | 8/2003 | Muller |
| 2003/0222023 A1 | 12/2003 | Mueller |
| 2004/0081611 A1 | 4/2004 | Muller |
| 2004/0225134 A1 | 11/2004 | Yaghi |
| 2004/0249189 A1 | 12/2004 | Mueller |
| 2004/0265670 A1 | 12/2004 | Muller |
| 2005/0004404 A1 | 1/2005 | Muller |
| 2005/0014371 A1 | 1/2005 | Tsapatsis |
| 2005/0124819 A1 | 6/2005 | Yaghi |
| 2005/0154222 A1 | 7/2005 | Muller |
| 2005/0192175 A1 | 9/2005 | Yaghi |
| 2006/0057057 A1 | 3/2006 | Muller |
| 2006/0135824 A1 | 6/2006 | Mueller |
| 2006/0154807 A1 | 7/2006 | Yaghi |
| 2006/0185388 A1 | 8/2006 | Muller |
| 2006/0252641 A1 | 11/2006 | Yaghi |
| 2006/0252972 A1 | 11/2006 | Pilliod |
| 2006/0287190 A1 | 12/2006 | Eddaoudi |
| 2007/0068389 A1 | 3/2007 | Yaghi |
| 2007/0202038 A1 | 8/2007 | Yaghi |
| 2007/0217982 A1 | 9/2007 | Wright |
| 2007/0248575 A1 | 10/2007 | Connor |
| 2008/0017036 A1 | 1/2008 | Schultink |
| 2008/0184883 A1 | 8/2008 | Zhou |
| 2008/0190289 A1 | 8/2008 | Muller |
| 2009/0155588 A1 | 6/2009 | Hesse |
| 2009/0183996 A1 | 7/2009 | Richter |
| 2009/0216059 A1 | 8/2009 | Reyes |
| 2009/0247654 A1 | 10/2009 | Rajendran |
| 2010/0069234 A1 | 3/2010 | Willis |
| 2010/0132549 A1 | 6/2010 | Yaghi |
| 2010/0143693 A1 | 6/2010 | Yaghi |
| 2010/0186588 A1 | 7/2010 | Yaghi |
| 2010/0286022 A1 | 11/2010 | Yaghi |
| 2011/0015388 A1 | 1/2011 | Youngblood |
| 2011/0137025 A1 | 6/2011 | Yaghi |
| 2011/0282067 A1 | 11/2011 | Li |
| 2011/0282071 A1 | 11/2011 | Shi |
| 2012/0028846 A1 | 2/2012 | Yaghi |
| 2012/0031268 A1 | 2/2012 | Yaghi |
| 2012/0130113 A1 | 5/2012 | Yaghi |
| 2012/0133939 A1 | 5/2012 | Yaghi |
| 2013/0047849 A1 | 2/2013 | Zhang |
| 2013/0096210 A1 | 4/2013 | Yaghi |
| 2014/0037944 A1 | 2/2014 | Dichtel |
| 2014/0148596 A1 | 5/2014 | Dichtel |

FOREIGN PATENT DOCUMENTS

| | | |
|---|---|---|
| DE | 102005023856 A1 | 11/2006 |
| DE | 102005054523 A1 | 5/2007 |
| EP | 1070538 A2 | 1/2001 |
| EP | 1674555 A1 | 6/2006 |
| JP | 2007534658 A | 11/2007 |
| KR | 20100055350 A | 5/2010 |
| WO | 9905151 A1 | 2/1999 |
| WO | 03035717 A1 | 5/2003 |
| WO | 2004101575 A2 | 11/2004 |
| WO | 2006047423 A2 | 5/2006 |
| WO | 2006072573 A2 | 7/2006 |
| WO | 2006110740 A2 | 10/2006 |
| WO | 2006116340 A1 | 11/2006 |
| WO | 2006122920 A1 | 11/2006 |
| WO | 2006125761 A2 | 11/2006 |
| WO | 2007007113 A2 | 1/2007 |
| WO | 2007054581 A2 | 5/2007 |
| WO | 2007098263 A2 | 8/2007 |
| WO | 2007101241 A2 | 9/2007 |
| WO | 2007111739 A2 | 10/2007 |
| WO | 2007118843 A1 | 10/2007 |
| WO | 2008091976 A1 | 7/2008 |
| WO | 2008138989 A1 | 11/2008 |
| WO | 2008140788 A1 | 11/2008 |
| WO | 2009020745 A2 | 2/2009 |
| WO | 2009042802 A1 | 4/2009 |
| WO | 2009056184 A1 | 5/2009 |
| WO | 2009073739 A1 | 6/2009 |
| WO | 2009149381 A2 | 12/2009 |
| WO | 2010056092 A2 | 5/2010 |
| WO | 2010078337 A1 | 7/2010 |
| WO | 2010080618 A2 | 7/2010 |
| WO | 2010083418 A1 | 7/2010 |
| WO | 2010088629 A1 | 8/2010 |
| WO | 2010090683 A1 | 8/2010 |
| WO | 2010148276 A2 | 12/2010 |
| WO | 2010148296 A2 | 12/2010 |
| WO | 2010148374 A2 | 12/2010 |
| WO | 2011014503 A1 | 2/2011 |
| WO | 2011038208 A2 | 3/2011 |
| WO | 2011127301 A2 | 10/2011 |
| WO | 2011146155 A2 | 11/2011 |
| WO | 2012012495 A2 | 1/2012 |
| WO | 2012082213 A2 | 6/2012 |
| WO | 2012100224 A2 | 7/2012 |
| WO | 2012106451 A2 | 8/2012 |

OTHER PUBLICATIONS

Corma et al., "From MOFs to zeolites: zirconium sites for epoxide rearrangement," New J. of Chem. 37:3496-3502, Aug. 2, 2013.

Garibay et al., "Isoreticular synthesis and modification of frameworks with the UiO-66 topology," Chemical Communications, 46:7700-7702, Sep. 27, 2010.

Kandiah et al., "Post-synthetic modification of the metal-organic framework compound UiO-66," J. of Materials Chem., 20:9848-9851, Oct. 13, 2010.

Yang et al., "$CH_4$ storage and $CO_2$ capture in highly porous zirconium oxide based metal-organic frameworks," Chem. Commun., 48:9831-9833, Aug. 15, 2012.

Hurenkamp, Jaap, International Search Report and Written Opinion, PCTUS2015/016555, European Patent Office, dated May 6, 2015.

Mineko Mohri, International Preliminary Report on Patentability and Written Opinion, PCT/US2015/016555, The International Bureau of WIPO, dated Sep. 1, 2016.

Kim et al., "Isoreticular MOFs based on a rhombic dodecahedral MOP as a tertiary building unit", CrystEngComm, Mar. 3, 2014, vol. 16, pp. 6391-6397.

Kim, Su Mi, International Search Report and Written Opinion for PCT/US2009/068731, dated Aug. 19, 2010.

Kim, Su Mi, International Search Report and Written Opinion, PCT/US2010/039154, Korean Intellectual Property Office, dated Feb. 23, 2011.

Kim, Su Mi. International Search Report for PCT/US2010/039154, dated Feb. 23, 2011.

Kim, Su Mi, International Search Report and Written Opinion, Application No. PCT/US09/046463, dated Feb. 24, 2010.

Kirai et al., 'Homocoupling of arylboronic acids catalyzed by 1,10-phenanthroline—ligated copper complexes in air,' European Journal of Organic Chemistry 12:1864-1867 (2009).

Klaes, Daphane, International Search Report and Written Opinion for PCT/US2010/021201, European Patent Office, dated Apr. 27, 2010.

Klaes, Daphne. International Search Report and Written Opinion for PCT/US2010/021201, dated Apr. 27, 2010.

Klein et al., 'Combinatorial Material Libraries on the Microgram Scale with an Example of Hydrothermal Synthesis,' Angew. Chemie 37(24):3369-3372 (1998).

Klemperer et al., "New Directions in Polyvanadate Chemistry: From Cages and Clusters to Baskets, Belts, Bowls, and Barrels", Angew. Chem. Int. Ed. Engl. 31 (1992) No. 1, pp. 49-51.

Koh et al., 'A Crystalline Mesoporous Coordination Copolymer with High Microporosity,' Angew Chem Int'l, 2008, pp. 677-680, vol. 47.

Koh et al., "A Crystalline Mesoporous Coordination Copolymer with High Microporosity", Angew. Chem. Int. Ed. 2008, 120, pp, 689-692.

(56) References Cited

OTHER PUBLICATIONS

Koh, Kyoungmoo, et al., "A Crystalline Mesoporous Coordination Copolymer with High Microporosity", Angewandte Chemie International Edition, (Jan. 11, 2008), vol. 47, No. Issue, pp. 689-692, XP008150670.

Kokubo, Atsuki, Office Action, Japanese Patent Application No. 2012-553065, dated Feb. 3, 2015.

Kong et al., 'Mapping of Functional Groups in Metal-Organic Frameworks', Science, vol. 341, No. 6148, Jul. 25, 2013, pp. 882-885.

Koza et al., 'An efficient High Yielding Approach for the Homocoupling of Aryl Boronic Acids,' Synthesis 15:2183-2186 (2002).

Kyoungmoo et al., 'A Crystalline Mesoporous Coordination Copolymer with High Microporosity,' Angew. Chem. Int. Ed. 47(4):677-680 (2008).

Kyoungmoo et al., "A Crystalline Mesoporous Coordination Copolymer with High Microporosity," Angew. Chem. Int. Ed. 47(4):689-92 (2008).

Lange, Tim, International Search Report, Application No. PCT/US2015/021090, dated Sep. 21, 2015.

Lawrence, Frank M. Nonfinal Office Action for U.S. Appl. No. 12/699,616, dated Apr. 10, 2012.

Lawrence, Frank M., Non-Final Office Action for U.S. Appl. No. 12/699,616, United States Patent and Trademark Office, dated Aug. 3, 2012.

Lee et al., 'Synthesis and Gas Sorption Properties of a Metal-Azolium Framework (MAF) Material,' Inorganic Chemistry, Nov. 2, 2009, pp. 9971-9973, vol. 48, No. 21.

Lee, Ji Min, International Search Report and Written Opinion, Application No. PCT/US2010/039284, dated Feb. 23, 2011.

Leus et al., "The remarkable catalytic activity of the saturated metal organic framework V-MIL-47 in the cyclohexene oxidation", Chem. Comm., Jun. 18, 2010, 46, 5085-5087.

Li et al., '[Cd16In64S134]44-: 31-A Tetrahedron with a Large Cavity,' Angew. Chem. Int. Ed., 42:1819-1821 (2003).

Li et al., '20 A [Cd4In16S35]14—Supertetrahedral T4 Clusters as Building Units in Decorated Cristobalite Frameworks,' J. Am. Chem. Soc, 2001, 123, 4867-4868.

Li et al., 'A Catenated Strut in a Catenated Metal-Organic Framework,' Angew. Chem. Int. Ed. 49:6751-6755 (2010).

Li et al., 'A metal-organic framework replete with ordered donor-acceptor catenanes,' Chem. Commun. 46:380-382 (2010).

Li et al., 'An Open-Framework Germanate with Polycubane-Like Topology,' Angew. Chem. Int. Ed., 38:653-655 (1999).

Li et al., 'Coordinatively Unsaturated Metal Centers in the Extended Porous Framework of Zn3(BDC)36CH3OH (BDC=1,4-Benzenedicarboxylate),' J. Am. Chem. Soc, 1998, 120, 2186-2187.

Li et al., 'Design and Synthesis of an Exceptionally Stable and Highly Porous Metal-Organic Framework,' Nature, 1999, 402, 276-279: Featured in (1) Chemical and Engineering News, Nov. 22, 1999, and (2) Science News, Nov. 20, 1999.

Li et al., 'Docking in Metal-Organic Frameworks', Science, 325, 855 (2009).

Li et al., 'Establishing Microporosity in Open Metal-Organic Frameworks: Gas Sorption Isotherms for Zn(BDC) (BDC=1,4-Benzenedicarboxylate),' J. Am. Chem. Soc, 1998, 120, 8571-8572.

Li et al., 'Ge2Zr06F2 (H2DAB)H20: A 4-Connected Microporous Material with 'Bow Tie' Building Units and an Exceptional Proportion of 3-Rings,' J. Am. Chem. Soc, 2000, 122, 12409-12410.

Li et al., 'Non-interpenetrating Indium Sulfide with a Supertetrahedral Cristobalite Framework,' J. Am. Chem. Soc, 1999, 121,6096-6097.

Li, Hailian, et al., 'Porous Germanates: Synthesis, Structure and Inclusion Properties of Ge7O14.5F2[(CH3)2NH2]3(H20) 0.86,' J. Am. Chem. Soc, 1998, 120, 8567-8568.

Li et al., 'Supertetrahedral Sulfide Crystals with Giant Cavities and Channels,' Science, 1999, 283, 1145-1147.

Li et al., 'Synthesis and Structural Characterization of a New 3D Lead Coordination Polymer with a Tetrazole-1-acetate Ligand,' Chinese J. Struct. Chem. 30(7): 1049-1053 (2011).

Li et al., 'Transformation of Germanium Dioxide to 4-Connected Porous Germanate Net,' J. Am. Chem. Soc, 1998, 120, 10569-10570.

Li, Y. et al., 'Hydrogen Storage in Metal-Organic and Covalent-Organic Frameworks by Spillover,' AlChe Journal 54(1):269-279 (2008).

Linder, Nora, International Preliminary Report on Patentability and Written Opinion, Application No. PCT/US2010/022777, dated Aug. 2, 2011.

Lindner, Nora, International Preliminary Report on Patentability and Written Opinion, The International Bureau of WIPO, PCT/US2011/044625, dated Jan. 31, 2013.

Lindner, Nora, International Preliminary Report on Patentability, PCT/US2011/053423, The International Bureau of WIPO, dated Apr. 2, 2013.

Ling et al., 'A zinc(II) metal-organic framework based on triazole and dicarboxylate ligands for selective adsorption of hexane isomers,' Chem. Comm. 47:7197-7199 (2011).

Liu, Lei, First Office Action, Chinese Patent Application No. 201180009370.6,The State Intellectual Property Office of the People's Republic of China, dated Mar. 3, 2014.

Liu., Y., "Dynamic Chirality in Donor-Acceptor Pretzelanes", Journal of Organic Chemistry, 2005, 70, 9334-9344.

Llabres, Francesc X. et al., 'Activity, reusability and shape-sensitivity of a Pd-containing MOF', Journal of Catalysis, Sep. 10, 2007, 250, pp. 294-298.

Loeb, 'Rotaxanes as ligands: from molecules to materials', Chem. Soc. Rev., 2007, 36, 226-235.

Long et al., 'The Pervasive Chemistry of Metal-Organic Frameworks,' Chem. Soc. Rev. 38:1213-1214 (2009).

Lu et al., 'Synthesis and Structure of Chemically Stable Metal-Organic Polyhedra,' J. Am. Chem. Soc. 131:(35)12532-12533 (2009).

Luo et al., 'Two new metal-triazole-benzenedicarboxylate frameworks affording an uncommon 3,4-connected net and unique 4,6-connected rod packing: hydrothermal synthesis, structure, thermostability and luminescence studies,' CrystEngComm 11 (6): 1097-1102 (2009).

Mashiyama, Shinya, Office Action issued in Japanese Patent Application No. 2012-522962, Japanese Patent Office, dated May 27, 2014.

Mason, Jarad A., "Evaluating metal-organic frameworks for natural gas storage", Chemical Science, vol. 5, Accepted Oct. 22, 2013, pp. 32-51.

McKeown et al., 'Phthalocyanine-Based Nanoporous Network Polymers,' Chem. Comm. 23:2780-2781 (Oct. 31, 2002).

McKeown et al., 'Porphyrin-Based Nanoporous Network Polymers,' Chem. Comm. 23:2782-2783 (Oct. 31, 2002).

Mendoza-Cortes et al., 'Adsorption Mechanism and Uptake of Methane in Covalent Organic Frameworks: Theory and Experiment,' J. Phys. Chem. 114:10824-10833 (2010).

Michalitsch, Richard, International Search Report and Written Opinion for PCT/US2009/069700, European Patent Office, dated May 7, 2010.

Millward et al., 'Metal-Organic Frameworks with Exceptionally High Capacity for Storage of Carbon Dioxide at Room Temperature,' J. Am. Chem. Soc. 127:17998-17999 (2005).

Holler, Christoph J.,et. al., "The first dinitrile frameworks of the rare earth elements: [LnCl3(1,4-Ph(CN)2] and [Ln2Cl6(1,4Ph(CN)2], Ln=Sm, Gd, Tb, Y;Access to novel metal-organic frameworks by solvent free synthesis in molten 1,4-benzodinitril", Inorganic Chemistry, (Aug. 10, 2008), vol. 47, No. 21, p. 10141, XP002574067.

Morris et al., 'A Combined Experimental—Computational Investigation of Carbon Dioxide Capture in a Series of Isoreticular Zeolitic Imidazolate Frameworks,' J. Am. Chem. Soc. 132:11006-11008 (2010).

Morris et al., 'Crystals as Molecules: Postsynthesis Covalent Functionalization of Zeolitic Imidazolate Frameworks,' J. Am. Chem. Soc. 130:12626-12627 (2008).

Morris et al., 'Framework mobility in the metal-organic framework crystal IRMOF-3: Evidence for aromatic ring and amine rotation,' Journal of Molecular Structure 1004:94-101 (2011).

(56) References Cited

OTHER PUBLICATIONS

Morris et al., 'NMR and X-ray Study Revealing the Rigidity of Zeolitic Imidazolate Frameworks,' J. Phys. Chem. 116(24):13307-13312 (Jun. 1, 2012).
Morris et al., 'Postsynthetic Modification of a Metal-Organic Framework for Stabilization of a Hemiaminal and Ammonia Uptake,' Inorg. Chem. 50:6853-6855 (2011).
Morris et al., 'Synthesis, Structure, and Metalation of Two New Highly Porous Zirconium Metal-Organic Frameworks,' Inorg. Chem. 51:6443-6445 (Jun. 7, 2012).
Morris, et al., 'Crystals as Molecules: Postsynthesis Covalent Functionalization of Zeolitic Imidazolate Frameworks', J. Am. Chem. Soc., (Aug. 2008), vol. 130, No. 38, pp. 12626-12627.
Moyse, Ellen, International Preliminary Report on Patentability and Written Opinion, dated Nov. 17, 2009, International Application No. PCT/US08/006008.
Moyse, Ellen, International Preliminary Report on Patentability and Written Opinion, PCT/US08/006008, The International Bureau of WIPO, dated Nov. 26, 2009.
Mulfort et al., 'Chemical Reduction of Metal-Organic Framework Materials as a Method to Enhance Gas Uptake and Binding,' J. Am. Chem. Soc. 129:9604-9605 (2007).
Mulhausen, Dorothee, International Preliminary Report on Patentability, PCT/US2009/069700, The International Bureau of WIPO, dated Jul. 7, 2011.
Mulhausen, Dorothee, International Preliminary Report on Patentability, PCT/US2010/021201, The International Bureau of WIPO, dated Jul. 28, 2011.
Mulhausen, Dorothee. International Preliminary Report on Patentability for PCT/US2010/021201, dated Jul. 28, 2011.
Natarajan et al., 'Non-carboxylate based metal-organic frameworks (MOFs) and related aspects,' Current Opinion in Solid State and Materials Science 13(3-4):46-53 (2009).
Nickitas-Etienne, Athina, International Preliminary Report on Patentability and Written Opinion, dated Jan. 19, 2010, International Application No. PCT/US08/70149.
Nickitas-Etienne, Athina, International Preliminary Report on Patentability and Written Opinion, Application No. PCT/US2015/023173, dated Oct. 4, 2016.
Nickitas-Etienne, Athina, International Preliminary Report on Patentability for PCT/US2009/068731, dated Jun. 21, 2011.
Nickitas-Etienne, Athina, International Preliminary Report on Patentability, PCT/US2009/068731, The International Bureau of WIPO, dated Jun. 30, 2011.
Nickitas-Etienne, Athina, International Preliminary Report on Patentability,PCT/US2008/077741, The Internationa Bureau of WIPO, dated Mar. 30, 2010.
Nickitas-Etienne, Athina. International Preliminary Report on Patentability for PCT/US2009/068849, dated Jun. 30, 2011.
Nickitas-Etienne, Athina, International Preliminary Report on Patentability and Written Report, Application No. PCT/US2015/021090, dated Sep. 20, 2016.
Niu et al., 'Synthesis and structural characterization of the one dimensional polymers [Rh2(OAc)4(NCPhCN)S, S=CH3COCH3, CH30H, C2H50H, C4H80, and C6H6,' Polyhedron 17(23-24):4079-89 (1998).
Ni et al., 'Porous Metal-Organic Truncated Octahedron Constructed from Paddle-Wheel Squares and Terthiophene Links,' J. Am. Chem. Soc. 127:12752-12753 (2005).
Novoa, Carlos, International Search Report and Written Opinion for PCT/US2010/021201, European Patent Office, dated Apr. 27, 2010.
O'Keefe et al., 'Germanate Zeolites: Contrasting the Behavior of Germanate and Silicate Structures Built from Cubic T8O20 units (T=Si or Ge),' Chem. Eur. J., May 1999, 2796-2801.
O'Keeffe et al., 'Deconstructing the Crystal Structures of Metal-Organic Frameworks and Related Materials into Their Underlying Nets,' Chem. Rev. 112(2):675-702 (Feb. 8, 2012).
O'Keeffe et al., 'Frameworks for Extended Solids: Geometrical Design Principles,' J. Solid State Chem. 152:3-20 (2000).

O'Keeffe et al., 'The Reticular Chemistry Structure Resource (RCSR) Database of, and Symbols for, Crystal Nets,' Am. Chem. Res. 41:1782-1789 (2008).
Meneses, Ociel Esau Andrade, First Office Action, Mexican Application No. MX/a/2013/00469, Mexican Institute of Industrial Property (IMPI), dated Jan. 26, 2015.
Ockwig et al., 'Reticular Chemistry: Occurrence and Taxonomy of Nets, and Grammar for the Design of Frameworks,' Acc. Chem. Res. 38:176-182 (2005).
Oisaki et al., "A Metal-Organic Framework with Covalently Bound Organometallic Complexes," J. of the Amer. Chem. Soc., pp. 9262-9264, vol. 132, No. 27, 2010.
Okeefffe et al., 'Reticular Chemistry—Present and Future Prospects—Introduction,' J. Solid State Chem.178:V-VI (2005).
Park, H. et al., 'Synthesis, Structure Determination and Hydrogen Sorption Studies of New Metal-Organic Frameworks Using Triazole and Naphthalenedicarboxylic Acid,' Chem. Natur. 19:1302-1308 (2007).
Park, Jae Woo. International Search Report for PCT/US2010/039123, Korean Intellectual Property Office, dated Feb. 24, 2011.
Park, Jae Woo. International Search Report for PCT/US2010/039123, dated Feb. 24, 2011.
Park, Kyo Sung et al., 'Exceptional chemical and thermal stability of zeolitic imidazolate frameworks,' Proc. Natl. Acad. Sci., Jul. 5, 2006, vol. 103, No. 27, pp. 10186-10191.
Dietzel, Pascal D. C., et. al., "Application of metal-organic frameworks with coordinatively unsaturated metal sites in storage and separation of methane and carbon dioxide", Journal of Materials Chemistry, (Aug. 21, 2009), vol. 19, No. 39, doi:10.1039/b911242a, ISSN 0959-9428, pp. 7362-7370, XP055197279.
Patteux, Claudine, International Search Report and Written Opinion, Application No. PCT/US2010/043373, dated Oct. 6, 2010.
Patteux, Claudine. International Search Report for PCT/US2010/043373, dated Oct. 10, 2010.
Pawsey et al., 'Hyperpolarized 129Xe Nuclear Magnetic Resonance Studies of Isoreticular Metal-Organic Frameworks,' Phys. Chem. 111:6060-6067 (2007).
Peng et al., 'Methane Storage in Metal-Organic Frameworks: Current Records, Surprise Findings, and Challenges', Journal of the American Chemical Society, vol. 135, No. 2, Aug. 14, 2013, pp. 11887-11894.
Choi et al., 'Heterogeneity within Order in Crystals of a Porous Metal Organic Framework,' J. Am. Chem. Soc. 133:11920-11923 (2011).
Choi et al., 'Reversible Interpenetration in a Metal-Organic Framework Triggered by Ligand Removal and Addition,' Angew. Chem. Int. Ed. 51:8791-8795 (2012).
Chun et al., 'Concomitant Formation of N-Heterocyclic Carbene-Copper Comlexies within a Supramolecular Network in the Self-Assembly of Immidzolium Dicarboxylate with Metal Ions,' Inorganic Chemistry, Jul. 20, 2009, pp. 6353-6355, vol. 48, No. 14.
Chun et al., 'Cu20: A versatile Reagent for Base-Free Direct Synthesis of NHC-Copper Complexes and Decoration of 3D-MOF with Coordinatively Unsaturated NHC-Copper Species,' Organometallics, Mar. 16, 2010, pp. 1518-1521, vol. 29, No. 7.
Cordero Garcia, Marcela M. Nonfinal Office Action for U.S. Appl. No. 12/680,141, dated Nov. 2, 2012.
Corma et al., 'A large-cavity zeolite with wide pore windows and potential as an oil refining catalyst,' Nature, vol. 418, pp. 514-517 (Aug. 2002).
Coskun et al., 'Metal-Organic Frameworks Incorporating Copper-Complexed Rotaxanes,' Angew. Chem. Int. Ed., 51:2160-2163 (2012).
Costa ("Chemical Modification of a Bridging Ligand Inside a Metal-Organic Framework while Maintaining the 3D Structure" Eur. J. Inorg. Chem (2008) 10, 1551-1554).
Costa et al., 'Chemical Modification of a Bridging Ligand Inside a Metal-Organic Framework while Maintaining the 3D Structure,' Eur. J. Inorg. Chem. 10:1539-1545 (2008).
Cote et al., 'Porous, Crystalline, Covalent Organic Frameworks,' Science 310:1166-1170 (2005).

(56) References Cited

OTHER PUBLICATIONS

Crees et al., 'Synthesis of a Zinc(II) Imidazolium Dicarboxylate Logand Metal-Organic Framework (MOF): a Potential Precursor to MOF-Tethered N-Heterocyclic Carbene Compounds,' Inorganic Chemistry, Jan. 19, 2010, vol. 49, No. 4, pp. 1712-1719.
Cui et al., 'In Situ Hydrothermal Growth of Metal-Organic Framework 199 Films on Stainless Steel Fibers for Solid-Phase Microextraction of Gaseous Benzene Homologues,' Anal. Chem. 81(23):9771-9777 (2009).
Czaja et al., 'Industrial applications of metal-organic frameworks,' Chemical Society Reviews 38(5):1284-1293 (2009).
Day et al., "A New Structure Type in Polyoxoanion Chemistry: Synthesis and Structure of the V5O143-Anion", J. Am. Chem. Soc. 1989, 111, 4518-4519.
Day et al., "Synthesis and Characterization of a Soluble Oxide Inclusion Complex, [CH3CNC(V12O324-)]", J. Am. Chem. Soc. 1989, 111, 5959-5961.
Delgad0-Friedrichs et al., 'Three-Periodic Nets and Tilings: Semiregular Nets,' Acta Cryst. A59:515-525 (2003).
Delgado-Friedrichs et al. 'Three-Periodic Nets and Tilings: Edge-Transitive Binodal Structures,' Acta Cryst. 62:350-355 (2006).
Delgado-Friedrichs et al. 'What Do We Know About Three-Periodic Nets?,' J. Solid State Chem. 178:2533-2554 (2005).
Delgado-Friedrichs et al., 'Taxonomy of Periodic Nets and the Design of Materials,' Phys. Chem. 9:1035-1043 (2007).
Delgado-Friedrichs et al., 'The CdSO4, Rutile, Cooperate and Quartz Dual Nets: Interpenetration and Catenation,' Solid State Sciences 5:73-78 (2003).
Delgado-Friedrichs et al., 'Three-Periodic Nets and Tilings: Regular and Quasiregular Nets,' Acta Cryst. A59:22-27 (2003).
Demessence, A et al., 'Strong CO2 Bnding in a Water-Stable, Triazolate-Bridged Metal-Organic Framework Functionalized with Ethylenediamine,' J. Am. Chem. Soc. 131:8784-8786 (2009).
Demir et al., 'Role of Copper Species in the Oxidative Dimerization of Arylboronic Acids: Synthesis of Symmetrical Biaryls,' Journal of Organic Chemistry 68(26):10130-10134 (2003).
Deng et al., 'Large-Pore Apertures in a Series of Metal-Organic Frameworks,' Science 336:1018-1023 (May 25, 2012).
Deng et al., 'Multiple Functional Groups of Varying Ratios in Metal-Organic Frameworks', Science, vol. 327, No. 5967, Feb. 12, 2010, pp. 846-850.
Deng et al., 'Robust dynamics' Nature Chem. 2:439-443 (2010).
Deng, H. et al., "Large-Pore Apertures in a Series of Metal-Organic Frameworks," Science, vol. 336, No. 6084, May 12, 2012, pp. 1018-1023.
Deska, Malgorzata, "Donor-acceptor rotaxanes with tetracationic cyclophane ring", ARKIVOC, 2013, i, 185-242.
Deska, Malgorzata, "Rotaxanes and pseudorotaxanes with threads containing viologen units", ARKIVOC, 2013, i, 66-100.
Dhakshinamoorthy et al., "Metal-organic frameworks as heterogeneous catalysts for oxidation reactions", Catal. Sci. Technol., Apr. 28, 2011, 1, 856-867.
Doonan et al., 'Exceptional ammonia uptake by a covalent organic framework,' Nature Chem. 2:235-238 (2010).
Doonan et al., 'Hydrogen Storage in Metal-Organic Frameworks', Annual Merit Review Proceedings of DOE Hydrogen Program, May 22, 2009, pp. 1-27.
Doonan et al., 'Isoreticular Metalation of Metal-Organic Frameworks,' J. Am. Chem. Soc. 131:9492-9493 (2009).
Du et al., "Direction of unusual mixed-ligand metal-organic frameworks: a new type of 3-D polythreading involving 1-D and 2-D structural motifs and a 2-fold interpenetrating porous network", Chem. Commun., 2005, 5521-5523.
Dugan et al., 'Covalent modification of a metal-organic framework with isocyanates: probing substrate scope and reactivity,' 29:3366-3368 (2008).
Duren et al., 'Design of New Materials for Methane Storage,' Langmuir 20:2683-2689 (2004).
Eberhard, Michael, Extended European Search Report, EP11810321, dated Jan. 14, 2014.
Eberhard, Michael, International Search Report and Written Opinion, PCT/US2012/059877, European Patent Office, dated Oct. 15, 2013.
McDonald, Thomas M. et al., 'Capture of Carbon Dioxide from Air and Flue Gas in the Alkylamine-Appended Metal-Organic Framework mmen-Mg 2 (dobpdc)', Journal of the American Chemical Society, vol. 134, No. 16, Apr. 4, 2012, pp. 7056-7065.
Eddaoudi et al., 'Cu2[o-Br-C6H3(C02)2]2(H20)2-(DMF)8(H20)2: A Framework Deliberately Designed to have the NbO Structure Type,' J. Am. Chem. Soc.124:376-377 (2002).
Eddaoudi et al., 'Design and Synthesis of Metal-Organic Frameworks with Permanent Porosity,' In Topics in Catalysis, G. A. Somorjai and J. M. Thomas, Eds., 9:105 (1999).
Eddaoudi et al., 'Geometric Requirements and Examples of Important Structures in the Assembly of Square Building Blocks,' Proc. Natl. Acad. Sci. 99:4900-4904 (2002).
Eddaoudi et al., 'Highly Porous and Stable Metal-Organic Framework: Structure Design and Sorption Properties,' J. Am. Chem. Soc. 121:1391-1397 (2000).
Eddaoudi et al., 'Modular Chemistry: Secondary Building Units as a Basis for the Design of Highly Porous and Robust Metal-Organic Carboxylate Frameworks' Acc. Chem. Res. 34:319-330 (2001).
Eddaoudi et al., 'Porous Metal-Organic Polyhedra: 25 A Cuboctahedron Constructed from Twelve Cu2(CO2)4 Paddle-Wheel Building Blocks,' J. Am. Chem. Soc. 123:4368-4369 (2001).
Eddaoudi et al., 'Systematic Design of Pore Size and Functionality in Isoreticular Metal-Organic Frameworks and Application in Methane Storage,' Science 295:469-472 (2002): Featured in (1) Chemical and Engineering News, Jan. 21, 2002, and (2) Chemical Insight magazine, Nov. 15, 2002.
Eddaoudi, M et al., "Systematic Design of Pore Size and Functionality in Isoreticular MOFs and Their application in Methane Storage" Science, (2002), vol. 295, pp. 469-472.
Eiichiro Mizushima, Notice of Reasons for Rejection, Japanese Patent Application No. 2012-516363, dated Aug. 26, 2014.
El-Kaderi et al., "Supporting Online Material for Designed Synthesis of 3D Covalent Organic Frameworks", Science 316, 268 (2007).
Fang et al. A Metal-Organic Framework with the Zeolite MTN Topology Containing Large Cages of vol. 2.5 nm3. Ang Chem Int Ed 2005, vol. 44, pp. 3845-3848.
El-Kaderi et al., 'Designed Synthesis of 3D Covalent Organic Frameworks,' Science 316:268-272 (2007).
El-Kaderi, Hani M., et al., "Designed Synthesis of 3D Covalent Organic Frameworks", Science 316, 268 (Published Apr. 13, 2007), S1-S75.
Howe, Patrick, International Search Report and Written Opinion, Application No. PCT/US2009/068849, dated Jun. 4, 2010.
"IUPAC Gold Book-cryptand", http://goldbook.iupac.org/C01426.html, accessed Jan. 30, 2014.
"IUPAC Gold Book-macrocycle". http://goldbook.iupac.org/M03662.html, accessed Jan. 30, 2014.
Adkins, Chinessa T. Final Office Action for U.S. Appl. No. 12/524,205, dated Sep. 27, 2012.
Adkins, Chinessa T. Nonfinal Office Action for U.S. Appl. No. 12/524,205, dated Apr. 17, 2012.
Akporiaye et al., 'Combinatorial Approach to the Hydrothermal Synthesis of Zeolites,' Angew. Chemie 37(5):609-611 (1998).
Ashton, Peter R. et al., 'Hydrogen-Bonded Complexes of Aromatic Crown Ethers with (9-Anthracenyl) methylammonium Derivatives' J. Am. Chem. Soc., 1997, 119 (44), pp. 10641-10651.
Baharlou, Simin, International Preliminary Report on Patentability for PCT/US2009/043373, The International Bureau of WIPO, dated Feb. 9, 2012.
Baharlou, Simin, International Preliminary Report on Patentability for PCT/US2009/046463, The International Bureau of WIPO, dated Dec. 16, 2010.
Baharlou, Simin, International Preliminary Report on Patentability for PCT/US2011/024671, The International Bureau of WIPO, dated Aug. 23, 2012.
Bai, Lingfei, International Preliminary Report on Patentability and Written Opinion, The International Bureau of WIPO, PCT/US2012/022114 dated Jul. 23, 2013.

(56) References Cited

OTHER PUBLICATIONS

Banerjee et al., 'Control of Pore Size and Functionality in Isoreticular Zeolitic Imidazolate Frameworks and their Carbon Dioxide Selective Capture Properties,' J. Am. Chem. Soc. 131:3875-3877 (2009).
Banerjee et al., 'High-Throughput Synthesis of Zeiolitic Imidazolate Frameworks and Application to CO2 Capture,' Science, 2008, pp. 939-943, vol. 319.
Barman et al., 'Azulene Based Metal-Organic Frameworks for Strong Adsorption of H2,' Chem. Commun. 46:7981-7983 (2010).
Barman et al., 'Incorporation of active metal sites in MOFs via in situ generated ligand deficient metal-linker complexes' Chem. Commun. 47:11882-11884 (Oct. 11, 2011).
Barman et al., "Incorporation of active metal sites in MOFs via in situ generated ligand deficient metal-linker complexes", Chem. Comm., 2011, pp. 1-3.
Barton et al., 'Tailored Porous Materials,' Chem. Mater. 11:2633-2656 (1999).
Becamel, Philippe, International Preliminary Report on Patentability, PCT/US2012/023516, The International Bureau of WIPO, dated Aug. 6, 2013.
Becamel, Philippe, International Preliminary Report on Patentability, PCT/US2012/059877, The International Bureau of WIPO, dated Sep. 18, 2014.
Bhakta et al., 'Metal organic frameworks as templates for nanoscale NaAlH4', Journal of American Chemical Society, vol. 131, No. 37, Sep. 23, 2009, pp. S1-S14.
Chen, Binling, et. al., "Zeolitic imidazolate framework materials: recent progress in synthesis and applications", Journal of Materials Chemistry A: Materials for Energy and Sustainability, GB, (Jul. 17, 2014), vol. 2, No. 40, doi:10.1039/C4TA02984D, ISSN 2050-7488, pp. 16811-16831, XP055337959.
Bjai, Lingfei, International Preliminary Report on Patentability and Written Opinion, PCT/US2015/021107, The International Bureau of WIPO, dated Sep. 20, 2016.
Bloch et al., 'Metal Insertion in a Microporous Metal-Organic Framework Lined with 2,2'-Bipyridine' J. Am. Chem. Soc. 132:14382-14384 (2010).
Bork, Ana-Marie., International Search Report for PCT/US2011/24671, European Patent Office, dated Nov. 30, 2011.
Braun et al., '1,4-Benzenedicarboxylate Derivatives as Links in the Design of Paddle-Wheel Units and Metal-Organic Frameworks,' Chem. Commun. 24:2532-2533 (2001).
Britt et al., 'Highly efficient separation of carbon dioxide by a metal-organic framework replete with open metal sites,' Proc. Natl. Acad. Sci. USA 106:20637-20640 (2009).
Britt et al., 'Ring-Opening Reactions Within Metal-Organic Frameworks,' Inorg. Chem. 49:6387-6389 (2010).
Britt et al., "Metal-Organic frameworks with high capacity and selectivity for harmful gases", PNAS, 2008, vol. 105, No. 33, pp. 11623-11627.
Burrows et al., 'Post-Synthetic Modification of Tagged MOFs,' Angew. Chem. Int. Ed. 47:8482-8486 (2008).
Burrows, Andrew D., 'Mixed-component metal-organic frameworks (MC-MOFs): enhancing functionality through solid solution formation and surface modifications', Crystengcomm, vol. 13, No. 11, Jan. 1, 2011, pp. 3623-3642.
Carlucci et al., 'Nanoporous three-dimensional networks topologically related to cooperite from the self-assembly of copper(I)centres and 1,2,4,5-tetracyanobenzene,' New J. Chem. 23(23):397-401 (1999).
Carlucci, Lucia et al., 'Polycatenation, polythreading and polyknotting in coordination network chemistry' Coordination Chemistry Reviews 246, 2003, pp. 247-289.
Caskey et al., 'Dramatic Tuning of CO2 Uptake via Metal Substitution in a Coordination Polymer with Cylindrical Pores,' JACS 130(33):10870-10871 (2008).
Caskey et al., 'Selected Applications of Metal-Organic Frameworks in Sustainable Energy Technologies,' Material Matters 4.4:111 (2009).
Centrone et al., 'Raman Spectra of Hydrogen and Deuterium Adsorbed on a Metal-Organic Framework,' Chem. Phys. Lett. 411:516-519 (2005).
Chae et al., 'A Route to High Surface Area, Porosity and Inclusion of Large Molecules in Crystals,' Nature427, 523-527 (2004); Featured in (1) Chemical & Engineering News magazine, Feb. 9, 2004, (2) BBC World Service, Feb. 2004, (3) New Scientist, Feb. 2004.
Chae et al., 'Design of Frameworks with Mixed Triangular and Octahedral Building Blocks Exemplified by the Structure of [Zn4O(TCA)2] Having the Pyrite Topology,' Angew. Chem. Int. Ed. 42:3907-3909 (2003).
Chae et al., 'Tertiary Building Units: Synthesis, Structure, and Porosity of a Metal-Organic Dendrimer Framework (MODF-1),' J. Am. Chem. Soc, 2001, 123, 11482-11483.
Chambron, Jean-Claude, "Interlacing molecular threads on transition metals", Pure and Applied Chemistry, 1990, 62(6), 1027-1034.
Che et al., "Mono- and Diprotonation of the [(n5-C5H5)Ti(W5O18)]3- and [(n5-C5Me5)Ti(W5O18)]3-Anions," Inorg. Chem. 1992, 31, 2920-2928.
Chen et al. "Photoluminescent Metal-Organic Polymer Constructed from Trimetallic Clusters and Mixed Carboxylates", Inorg. Chem. 2003, 42, 944-946.
Chen et al., 'A Microporous Metal-Organic Framework for Gas-Chomatographic Separation of Alkanes,' Angew. Chem. Int. Ed. 45:1390-1393 (2006).
Chen et al., 'Cu2(ATC) 6H20: Design of Open Metal Sites in Porous Metal-Organic Crystals (ATC: 1,3,5,7-adamantane tetracarboxylate),' J. Am. Chem. Soc, 2000,122,11559-11560.
Chen et al., 'High H2 Adsorption in a Microporous Metal-Organic Framework with Open-Metal Sites,' Angew. Chem. Int. Ed. 44:4745-4749 (2005).
Chen et al., 'Interwoven Metal-Organic Framework on a Periodic Minimal Surface with Extra-Large Pores,' Science, 2001, 291,1021-1023: Featured in Chemical and Engineering News, Feb. 21, 2001.
Chen et al., 'Noncovalently Netted, Photoconductive Sheets with Extremely High Carrier Mobility and Conduction Anisotropy from Triphenylene-Fused Meetal Trigon Conjugates,' In. J. Am. Chem. Soc. 131:7287-7297 (2009).
CHen et al., 'Transformation of a Metal-Organic Framework from the NbO to PtS Net,' Inorg. Chem. 41:181-183 (2005).
Cho et al., 'A metal-organic framework material that functions as an enantioselective catalyst for olefin epoxidation,' Chem. Comm. 24:2563-2565 (2006).
Peterson et al., 'Ammonia Vapor Removal by Cu3(BTC)2 and its Characterization by MAS NMR,' J. Phys. Chem. C. 113(32):13906-13917 (2009).
Phan et al., 'Metal-Organic Frameworks of Vanadium as Catalysts for Conversion of Methane to Acetic Acid,' Inorg. Chem. 50:7388-7390 (2011).
Phan et al., 'Synthesis, Structure, and Carbon Dioxide Capture Properties of Zeolitic Imidazolate Frameworks,' Acc. Chem. Res 43:58-67 (2009).
Plevert et al., 'A Flexible Germanate Structure Containing 24-Ring Channels With Very Low Framework Density,' J. Am. Chem. Soc, 2001, 123, 12706-12707.
Plevert et al., 'Layered Structures Constructed from New Linkages of Ge7(0,OH,F)19 Clusters,' Chem. Mater. 15:714-718(2003).
Plevert et al., 'Synthesis and Characterization of Zirconogermanates,' Inorg. Chem., 42:5954-5959 (2003).
Prajapati et al., "Metal-organic frameworks (MOFs) constructed from ZnII/CdII-2,2'-bipyridines and polycarboxylic acids: Synthesis, characterization and microstructural studies", Polyhedron 28 (2009) 600-608.
Qiu, Xiaowei, Chinese Application No. 201180056905.5, Second Office Action, dated Feb. 3, 2015.
Queen et al., 'Site-Specific C02 Adsorption and Zero Thermal Expansion in an Anisotropic Pore Network,' J. Phys. Chem. C, 115:24915-24919 (Nov. 8, 2011).
Reineke et al., 'A Microporosity of Lanthanide-Organic Frameworks,' Angew. Chem. Int. Ed. 38:2590-2594 (1999).
Reineke et al., 'From Condensed lanthanide Coordination Solids to Microporous Frameworks having Accessible Metal Sites,' J. Am. Chem. Soc, 1999, 121, 1651-1657.

(56) References Cited

OTHER PUBLICATIONS

Reineke et al., 'Large Free Volume in Interpenetrating Networks: The Role of Secondary Building Units Exemplified by Tb2(ADB)3[(CH3)2SO]4-16[(CH3)2SO],' J. Am. Chem. Soc, 2000, 122, 4843-4844: Featured in Science Magazine, Editors Choice, Nov. 2000.
Ren Shi-Bin et al, "The variety of conformational isomerism of a flexible organic linker induced by the position and amounts of aromatic carboxylic groups", Polyhedron, (Jun. 4, 2014), vol. 83, doi:10.1016/J.POLY.2014.05.069, ISSN 0277-5387, pp. 130-136, XP029080831.
Richter, Herbert, Supplementary European Search Report, European Patent Application No. 11848340.3, European Patent Office, dated Feb. 6, 2014.
Rinkel, Bert. Extended European Search Report for European Patent Application EP08713961, dated Jan. 2, 2012.
Rosi et al., 'Advances in the Chemistry of Metal-Organic Frameworks,' CrystEngComm, Apr. 2002, 401-404.
Rosi et al., 'Infinite Secondary Building Units and Forbidden Catenation in Metal-Organic Frameworks,' Angew. Chem. Int. Ed. 41:294-297 (2002).
Rosi et al., 'Rod-Packings and Metal-Organic Frameworks Constructed from Rod-Shaped Secondary Building Units,' J. Am. Chem. Soc. 127:1504-1518 (2005).
Rosi et al., 'Hydrogen Storage in Microporous Metal-Organic Frameworks,' Science 300:1127-1129 (2003); Featured in (1) Chemical & Engineering News magazine, May 19, 2004, and (2) Technology Research News Magazine, May 21, 2003.
Rouseau-Jager, Nadia, International Search Report and Written Opinion, PCT/US2011/024671, European Patent Office, dated Dec. 13, 2011.
Rowsell et al., 'Characterization of H2 Binding sites in prototypical metal-organic frameworks by inelastic neutron scattering,' J. Am. Chem. Soc. 127:14904-14910 (2005).
Rowsell et al., 'Effects of Functionalization, Catenation, and Variation of the Metal Oxide and Organic Linking Units on the Low-Pressure Hydrogen Adsorption Properties of Metal-Organic Frameworks,' J. Am. Chem. Soc. 128: 1304-1315(2006).
Rowsell et al., 'Gas Adsorption Sites in a Large-Pore Metal-Organic Framework,' Science 309:1350-1354 (2005).
Rowsell et al., 'Hydrogen Sorption in Functionalized Metal-Organic Frameworks,' J. Am. Chem. Soc.126: 5666-5667 (2004).
Rowsell et al., 'Metal-Organic Frameworks: A New Class of Porous Materials,' Microporous Mesoporous Mater. 73:3-14 (2004).
Rowsell et al., 'Strategies for Hydrogen Storage in Metal-Organic Frameworks,' Angew. Chem. Int. Ed. 44: 4670-4679 (2005).
Burrows, Andrew D., et al., "Post-Synthetic Modification of Tagged MOFs", Angewa. Chem. Int . Ed., (Oct. 20, 2008), vol. 47, pp. 8482-8486, XP008150669.
Seo et al., 'A homochiral metal-organic porous material for enantioselective separation and catalysis,' Nature 404:982-986 (2000).
Shi-Jie et al., "Synthesis and Structural Characterization of a New 3D Lead Coordination Polymer with a Tetrazole-1-acetate Ligand", Chinese J. Struct. Chem., vol. 30, No. 7, 2011, pp. 1049-1053.
Siberio-Perez, 'Raman Spectroscopic Investigation of CH4 and N2 Adsorption in Metal-Organic Frameworks,' Chem. Mater 19:3681-3685 (2007).
Sigma-Aldrich, Basolite C300 (MOF-199), catalog No. 688614; http://www.sigmaaldrich.com/catalog/ProductDetail.do?D7=0&N5=SEARCH.sub.--CONCAT.sub.-PNO%7CBRAND.sub.-KEY&N4=688614%7CALDRICH&N25=0&QS=ON&F=SPEC-, obtained online in 2014.
Sigma-Aldrich, Basolite C300 (MOF-199), catalog No. 688614; Copyright 2014.
Sines, Brian J. Nonfinal Office Action for U.S. Appl. No. 13/142,564, dated Jul. 9, 2012.
Smaldone et al., 'Metal-Organic Frameworks from Edible Nature Products,' Angew. Chem. Int. Ed. 49:8630-8634 (2010).

Song et al., 'A Multiunit Catalyst with Synergistic Stability and Reactivity: A PolyoxometalateMetal Organic Framework for Aerobic Decontamination,' J. Am. Chem. Soc. 133(42):16839-16846 (Sep. 13, 2011).
Song et al., 'Hydrothermal Synthesis and Structural Characterization of Three-dimensional Metal-organic Framework [Zn3(C2H2N3)2(C7H5O2)4],' Chem. Res. Chinese Universities 25(1):1-4 (2009).
Spencer et al., 'Determination of the Hydrogen Absorption Sites in Zn4O(1,4-benzenedicarboxylate) by Single Crystal Neutron Diffraction,' Chem. Commun. 3:278-280 (2006); Epub Dec. 6, 2005.
Spitler et al., 'Lewis acid-catalysed formation of two-dimensional phthalocyanine covalent organic frameworks', Nature Chemistry, vol. 2, Aug. 2010, pp. 672-677.
Stallmach et al., 'NMR Studies on the Diffusion of Hydrocarbons on the Metal-Organic Framework Material MOF-5,' Angew. Chem. Int. Ed. 45:2123-2126 (2006).
Sudik et al., 'A Metal-Organic Framework with a Hierarchical System of Pores and Tetrahedral Bbuilding Blocks,' Angew. Chem. Int. Ed. 45:2528-2533 (2006).
Sudik et al., 'Design, Synthesis, Structure, and Gas (N2, Ar, CO2, CH4 and H2) Sorption Properties of Porous Metal-Organic Tetrahedral and Heterocuboidal Polyhedra,' J. Am. Chem. Soc. 127:7110-7118 (2005).
Sudik et al., 'Metal-Organic Frameworks Based on Trigonal Prismatic Building Blocks and the New 'acs' Topology,' Inorg. Chem. 44:2998-3000 (2005).
Szeto et al., "A Thermally Stable PtN-Based Metal-Organic Framework: Exploring the Accessibility of the Metal Centers with Spectroscopic Methods Using H2O, CH3OH, and CH3CN as Probes", J. Phys. Chem. B, 2006, 110, 21509-21520.
Szeto et al., "Characterization of a New Porous Pt-Containing Metal-Organic Framework Containing Potentially Catalytically Active Sites: Local Electronic Structure at the Metal Centers", Chem. Mater., 2007, 19, 211-220.
Tanabe et al., 'Systematic Functionalization of a Metal-Organic Framework via a Postsynthetic Modification Approach,' J. Am. Chem. Soc. 130(26):8508-8517 (2008).
Tilford et al., 'Facile Synthesis of a Highly Crystalline, Covalently Porous Boronate Network,' 18(22):5296-5301 (Oct. 11, 2006).
Tranchemontagne et al. 'Metal-Organic Frameworks with High Capacity and Selectivity for Harmful Gases,' Proc. Natl. Acad. Sci. USA 105:11623-11627 (2008).
Tranchemontagne et al. 'Secondary Building Units, Nets and Bonding in the Chemistry of Metal-Organic Frameworks,' Chem. Soc. Rev. 38:1257-1283 (2009).
Tranchemontagne et al., 'Hydrogen Storage in New Metal-Organic Frameworks,' J. Phys. Chem. C 116(24):13143-13151 (May 24, 2012).
Tranchemontagne et al., 'Reticular Chemistry of Metal-Organic Polyhedra,' Angew. Chem. Int. Ed., 2008, 47:5136-5147 (2008).
Tranchemontagne et al., 'Room Temperature Synthesis of Metal-organic Frameworks: MOF-5, MOF-74, MOF-177, MOF-199, and IRMOF-0,' Tetrahedron 64:8553-8557 (2008).
Uribe-Romo et al., 'A Crystalline Imine-Linked 3-D Porous Covalent Organic Framework,' J. Am. Chem. Soc. 131:4570-4571 (2009).
Uribe-Romo et al., 'Crystalline Covalent Organic Frameworks with Hydrazone Linkages,' J. Am. Chem. Soc. 133: 11478-11481 (2011).
Vairaprakash et al., 'Synthesis of Metal-Organic Complex Arrays,' J. Am. Chem. Soc. 133:759-761 (2011).
Valente et al., 'Metal-organic Frameworks with Designed Chiral Recognition Sites,' Chem. Commun. 46:4911-4913 (2010).
Vitillo et al., 'Role of Exposed Metal Sites in Hydrogen Storage in MOFs,' J. Am. Chem. Soc. 130(26):8386-8396 (2008).
Vodak et al., 'Computation of Aromatic C3N4 Networks and Synthesis of the Molecular Precursor N(C3N3)3C16,' Chem. Eur. J. 9:4197-4201 (2003).
Vodak et al., 'Metal-Organic Frameworks Constructed from Pentagonal Antiprismatic and Cuboctahedral Secondary Building Units,' Chem. Commun. 2534-2535 (2001).
Vodak et al., 'One-Step Synthesis and Structure of an Oligo(spiro-orthocarbonate),' J. Am. Chem. Soc.124(18):4942-4943 (2002).

(56) References Cited

OTHER PUBLICATIONS

Walton et al., 'Understanding Inflections and Steps in Carbon Dioxide Adsorption Isotherms in Metal-Organic Frameworks,' J. Am. Chem. Soc.130:406-407 (2008).
Wan et al, 'A Belt-Shaped, Blue Luminescent, and Semiconducting Covalent Organic Framework.' Angew. Chem. Int. Ed. 47:8826-8830 (2008).
Wan et al., 'Covalent Organic Frameworks with High Charge Carrier Mobility,' Chem. Mater. 23:4094-4097 (Aug. 22, 2011).
Wang et al., 'Colossal Cages in Zeolitic Imidazolate Frameworks as Selective Carbon Dioxide Reservoirs,' Nature 453:207-211 (2008).
Wang et al., 'Postsynthetic Covalent Modification of a Neutral Metal-Organic Framework,' J. Am. Chem. Soc. 129(41):12368-12369 (2007).
Wang et al., 'Tandem Modification of Metal-Organic Frameworks by a Postsynthetic Approach,' Angew. Chem. Int. 47:4699-4702 (2008).
Wang, Yiting, First Office Action, Chinese Patent Application No. CN201080036940.6, dated Dec. 4, 2013.
Wang, Zhenqiang, et al., 'Postsynthetic Covalent Modification of a Neutral Metal—Organic Framework', J. Am. Chem. Soc., (2007), vol. 129, No. 41, pp. 12368-12369.
Wardencki et al. Green Chemistry—Current and Future Issues. Review. Polish Journal of Environmental Studies. 2005. vol. 14, No. 4, pp. 389-395.
Whitfield et al. Metal-organic frameworks based on iron oxide octahedral chains connected by benzendicarboxylate dianions. Solid State Sciences, 2005. vol. 7, pp. 1096-1103.
Wong-Foy, AG et al., 'Exceptional H2 Saturation uptake in microporous metal-organic frameworks' J. Am. Chem. Soc, 2006, 128, pp. 3494-3495.
Wu et al., 'Structural Study of New Hydrocarbon Nano-Crystals by Energy-Filtered Electron Diffraction,' Ultramicroscopy 98:145-150 (2004).
Jia, Xiao, The Third Office Action, Chinese Patent Application No. 201080021284.2, dated Aug. 19, 2014.
Qiu, Xiaowei, Chinese Patent Application No. 201180056905.5, First Office Action, dated Jul. 18, 2014.
Yaghi et al., 'A Molecular Railroad with Large Pores: Synthesis and Structure of Ni(4,4'-bpy)2.5(H20)2(Cl04)2.1.5(4,4'-bpy)2(H2O),' Inorg. Chem., 1997, 36, 4292-4293.
Yaghi et al., 'A Molecular World Full of Holes,' Chem. Innov. p. 3 (2000).
Yaghi et al., 'Construction of a New Open-Framework Solid from 1,3,5-Cyclohexanetricarboxylate and Zinc(II) Building Blocks,' J, Chem. Soc, Dalton Trans., 1997, 2383-2384.
Yaghi et al., 'Construction of Microporous Materials from Molecular Building Blocks,' Fundamental Materials Research, T. J. Pinnavaia and M. F. Thorpe, eds., vol. II, Plenum: New York, p. 111 (1995).
Yaghi et al., 'Construction of Porous Solids from Hydrogen-Bonded Metal Complexes of 1,3,5-Benzenetricarboxylic Acid,' J. Am. Chem. Soc, 1996, 118, 9096-9101.
Yaghi et al., 'Conversion of Hydrogen-Bonded Manganese(II) and Zinc(II) Squarate (C4042-) Molecules, Chains, and Sheets to 3-D Cage Networks,' J. Chem. Soc, Dalton Trans., 1995, 727-732.
Yaghi et al., 'Conversion of Molecules and Clusters to Extended 3-D Cage and Channel Networks,' Metal Containing Polymeric Materials, C. U. Pittman, C. E. Carraher, B. M. Culbertson, M. Zeldin, J. E. Sheets, Eds., Plenum: New York p. 219(1996).
Yaghi et al., 'Crystal Growth of Extended Solids by Nonaqueous Gel Diffusion,' Chem. Mater., Sep. 1997, 1074-1076.
Yaghi et al., 'Design of Solids Molecular Building Blocks: Golden Opportunities for Solid State Chemistry,' J. Solid State Chem. 152, 1-2 (2000).
Yaghi et al., 'Designing Microporosity in Coordination Solids,' Modular Chemistry, J. Michl (ed.), Kluwer Academic Publishers, p. 663-670 (1997).

Yaghi et al., 'Hydrothermal Synthesis of a Metal-Organic Framework Containing Large Rectangular Channels,' J. Am. Chem. Soc, 1995, 117, 10401-10402.
Yaghi et al., 'Metal-Organic Frameworks: A Tale of Two Entanglements,' Nature materials 6:92-93 (2007).
Yaghi et al., 'Mutually Interpenetrating Sheets and Channels in the Extended Structure of Cu(4,4'-Bipyridine)Cl,' Angew. Chem. Int. Ed. Engl., 1995, 34, No. 2, 207-209.
Yaghi et al., 'Open-Framework Solids with Diamond-Like Structures Prepared from Clusters and Metal-Organic Building Blocks,' Mater. Res. Soc. Symp. Proc, 1995, 371, 15.
Yaghi et al., 'Reticular Chemistry and Metal-Organic Frameworks for Clean Energy,' MRS Bulletin 34:682-690 (2009).
Yaghi et al., 'Reticular Synthesis and the Design of New Materials,' Nature 423:705-714 (2003).
Yaghi et al., 'Selective binding and removal of guests in a microporous metal-organic framework,' Nature, Dec. 1995, pp. 703-706, vol. 378.
Yaghi et al., 'Selective Guest Binding by Tailored Channels in a 3-D Porous Zinc(II)-1,3,5-Benzenetricarboxylate Network,' J. Am. Chem. Soc, 1997, 119, 2861-2868.
Yaghi et al., 'Synthesis and Structure of a Metal-Organic Solid Having the Cadmium (II) Sulfate Net,' Mater. Res. Soc. Symp. Proc. 453:127, (1997).
Yaghi et al., 'Synthetic Strategies, Structure Patterns, and Emerging Properties in the Chemistry of Modular Porous Solids,' Acc. Chem. Res. 31:474-484 (1998).
Yaghi et al., 'T-Shaped Molecular Building Units in the Porous Structure of Ag(4,4'-bpy) N03,' J. Am. Chem. Soc, 1996, 118, 295-296.
Yaghi et al., 'Transformation of Germanium Dioxide to 4-Connected Porous Gemianate Net,' J. Am. Chem. Soc, 20:10569-10570(1998).
Yaghi et al., "Directed Transformation of Molecules to Solids: Synthesis of a Microporous Sulfide from Molecular Germanium Sulfide Cages", J. Am. Chem. Soc. 1994, 116, 807-808.
Yaghi et al., "Preparation of Single Crystals of Coordination Solids in Silica Gels: Synthesis and Structure of CuII (1,4-C4H4N2)(C4O4)(OH2)4", Journal of Solid State Chemistry, 117, 256-260 (1995).
Yaghi et al., "Rhenium-Selenium-Chlorine Solid Phases: Cluster Excision and Core Substitution Reactions of Molecular Species", Inorg. Chem. 1992, 31, 4778-4784.
Yaghi, Omar, 'Hydrogen Storage in Metal-Organic Frameworks,' slide presentation to DOE Hydrogen Program 2007 Annual Merit Review, US Department of Energy, on May 15, 2007 at http://www.hydrogen.energy.gov/pdfs/review07/St_10_yaghi.pdf.
Yaghi, Omar., 'Porous Crystals for Carbon Dioxide Storage,' slide presentation at the Fifth Annual Conference on Carbon Capture & Sequestration, US Department of Energy on May 10, 2006 http://www.netl.doe.gov/publications/proceedings/06/carbon-seq/Tech.degre- e.20Session.degree.20193.pdf.
Yang et al. 'Two Novel Triazole-Based Metal-Organic Frameworks Consolidated by a Flexible Dicarboxylate Co-ligand: Hydrothermal Synthesis, Crystal Structure, and Luminescence Properties,' Australian Journal of Chemistry 61(10):813-820 (2008).
Yang et al., 'Four Novel Three-Dimensional Triazole-Based Zinc(II) Metal-Organic Frameworks Controlled by the Spacers of Dicarboxylate Ligands: Hydrothermal Synthesis, Crystal Structure, and Luminescence Properties,' Crystal Growth Design 7(10):2009-2015 (2007).
Young, Lee W., International Search Report and Written Opinion, Application No. PCT/US08/70149, dated Jan. 12, 2009.
Young, Jung Doo, International Search Report & Written Opinion, Korean Application No. PCT/US2011/044625, dated Feb. 24, 2012.
Young, Jung Doo, International Search Report and Written Opinion, Application No. PCT/US2010/050170, dated Jun. 8, 2011.
Young, Jung Doo, Written Opinion, PCT/US2011/053423, Korean Intellectual Property Office, dated Jul. 23, 2012.
Young, Jung Doo. International Search Report and Written Opinion for PCT/US2011/053423, dated Jul. 23, 2012.
Young, Jung Doo, International Search Report and Written Opinion, Application No. PCT/US2012/022114, dated Aug. 22, 2012.

(56) References Cited

OTHER PUBLICATIONS

Young, Lee W., 'International search Report and Written Opinion,' PCT/US08/06008, United States Patent & Trademark Office, dated Aug. 20, 2008.
Young, Lee W., International Search Report and Written Opinion, dated May 7, 2008, International Application No. PCT/US08/51859.
Young, Lee W., International Search Report and Written Opinion, dated Dec. 2, 2008, International Application No. PCT/US08/77741.
Young, Lee W., International Search Report and Written Opinion, dated Jan. 12, 2009, International Application No. PCT/US08/70149.
Zhang et al., 'Crystal engineering of binary metal imidazolate and triazolate frameworks,' Chem. Comm. 1689-1699 (2006).
Zhang et al., 'Syntheses, Structures, and Porous/Luminescent Properties of Silver 3-Alkyl-1,2,4-Triazolate Frameworks with Rare 3-Connected Topologies,' Crystal Growth and Design 11:796-802 (2011).
Zhang, J. et al., 'Exceptional Framework Flexibility and Sorption Behavior of a Multifunctional Porous Cuprous Triazolate Framework,' J. Am. Chem. Soc. 130:6010-6017 (2008).
Zhao et al., 'Rigid-Strut-Containing Crown Ethers and [2]Catenanes for Incorporation into Metal-Organic Frameworks,' Chem. Eur. J. 15:13356-13380 (2009).
Zhao, Office Action in Chinese Patent Application No. 20088031572, dated Aug. 5, 2011.
Zhao, Wei, First Office Action for Chinese Application No. 200880003157.2,The State Intellectual Property Office of the People's Republic of China, dated Aug. 5, 2011.
Zhaofu et al., 'A Nearly Planar Water Sheet Sandwiched between Strontium-Imidazolium Carboxylate Coordination Polymers,' Inorg. Chem. 44:5200-5202 (2005).
Zhou et al., 'Introduction to Metal-Organic Frameworks,' Chemical Reviews 112:673-674 (Jan. 26, 2012).
Zhou, X et al., 'Hydrothermal Syntheses and Structures of Three Novel Coordination Polymers Assembled from 1,2,3-Triazolate Ligands,' CrystEngComm. 11:1964-1970 (2009).
Zhu, A. et al., 'Isomeric Zinc(II) Triazolate Frameworks with 3-Connected Networks: Syntheses, Structures, and Sorption Properties,' Inorg. Chem. 48:3882-3889 (2009).
Zou et al., "Novel Eclipsed 2D Cadmium(II) Coordination Polymers with Open-Channel Structure Constructed from Terephthalate and 3-(2-Pyridyl)pyrazole: Crystal Structures, Emission Properties, and Inclusion of Guest Molecules", Inorg. Chem. 2004, 43, 5382-5386.
Fei et al., 'A Nearly Planar Water Sheet Sndwiched between Strontium-Imidazolium Carboxylate Coordination Polymers,' Inorg. Chem., 2005, pp. 5200-5202, vol. 44.
Ferragut et al., 'Positronium Formation in Porous Materials for Antihydrogen Production,' J. Phys. Conf. Ser. 225:1-8 (2010).
Finger, Gabriela, International Search Report and Written Opinion, PCT/US2010/043373, European Patent Office, dated Oct. 6, 2010.
Finger, Gabriela, International Search Report and Written Opinion, PCT/US2015/021107, European Patent Office, dated Aug. 17, 2015.
First Office Action issued in Chinese Patent Application No. 201180045210.8, dated Sep. 28, 2014.
Forster et al., 'A High-Throughput Investigation of the Role of pH, Temperature, Concentration, and Time on the Synthesis of Hybrid Inorganic-Organic Materials,' Angew. Chemie Int. Ed. 44(46):7608-7611 (2005).
Fracaroli et al., 'Isomers of Metal-Organic Complex Arrays,' Inorg. Chem. 51: 6437-6439 (Jun. 5, 2012).
Fracaroli, A.M. et al., Metal-Organic Frameworks with Precisely Designed Interior for Carbon Dioxide Capture in the Presence of Water, J. Am. Chem. Soc, Jun. 25, 2014, vol. 136, No. 25, pp. 8863-8866.

Furukawa et al., 'Control of Vertex Geometry, Structure Dimensionality, Functionality, and Pore Metrics in the Reticular Synthesis of Crystalline Metal-Organic Frameworks and Polyhedra,' J. Am. Chem. Soc.130:11650-11661 (2008).
Furukawa et al., 'Crystal Structure, Dissolution, and Deposition of a 5 nm Functionalized Metal-Organic Great Rhombicuboctahedron,' J. Am. Chem. Soc. 128:8398-8399 (2006).
Furukawa et al., 'Independent verification of the saturation hydrogen uptake in MOF-177 and establishment of a benchmark for hydrogen adsorption in metal-organic frameworks,' J. Mater. Chem. 17:3197-3204 (2007).
Furukawa et al., 'Isoreticular Expansion of MetalOrganic Frameworks with Triangular and Square Building Units and the Lowest Calculated Density for Porous Crystals,' Inorg. Chem. 50:9147-9152 (2011).
Furukawa et al., 'Storage of Hydrogen, Methane, and Carbon Dioxide in Highly Porous Covalent Organic Frameworks for Clean Energy Applications,' J. Am. Chem. Soc. 25:8876-8883 (2009).
Furukawa et al., 'Ultra-High Porosity in Metal-Organic Frameworks,' Science 239:424-428 (2010).
Furukawa et al., "Water Adsorption in Porous Metal-Organic Frameworks and Related Materials," J. of the Amer. Chem. Soc, vol. 136, No. 11, pp. 4369-4381, Published: Mar. 3, 2014.
Gadzikwa, T. et al., 'Selective Bifunctional Modification of a Non-catenated Metal-Organic Framework Material via Click Chemistry,' J. Am. Chem. Soc. 131:13613-13615 (2009).
Galli et al., 'Adsorption of Harmful Organic Vapors by Flexible Hydrophobic Bis-pyrazolate Based MOFs,' Chem. Mater. 22(5):1664-1672 (2010).
Gandara, Felipe, et al., "Crystallography of metal-organic frameworks", IUCRJ, vol. 1, No. 6, Oct. 28, 2014, pp. 563-570.
Gandara et al., 'High Methane Storage Capacity in Aluminum Metal-Organic Frameworks', Journal of the American Chemical Society, vol. 136, No. 14, Mar. 21, 2014, pp. 5271-5274.
Gandara et al., 'Porous, Conductive Metal-Triazolates and Their Structural Elucidation by the Charge-Flipping Method,' Chem. Eur. J. 18:10595-10601 (2012).
Gassensmith et al., 'Strong and Reversible Binding of Carbon Dioxide in a Green Metal-Organic Framework,' J. Am. Chem. Soc. 133:15312-15315 (Aug. 30, 2011).
Glover et al., 'MOF-74 building unit has a direct impact on toxic gas adsorption,' J. Chem. Eng. Sci. 66:163-170 (2011).
Goebel, Matthias, Supplemental European Search Report and Written Opinion for EP08754337. Date of Completion of Search and Written Opinion: Dec. 3, 2010.
Goebel, Matthias, Supplemental European Search Report and Written Opinion for EP08826913. Date of Completion of Search and Written Opinion: Nov. 10, 2010.
Gonzalez-Arellano et al., 'Homogeneous and heterogeneous Au(III) Schiff base-complexes as selective and general catalysts for self-coupling of aryl boronic acids,' Chem. Comm. 15:1990-1992 (2005).
Goto, Y et al., "Clickable Metal-Organic Framework," J. Am. Chem. Soc. 130:14354-14355 (2008).
Gould et al., "Amphidynamic Character of Crystalline MOF-5: Rotational Dynamics of Terephthalate Phenylenes in a Free-Volume, Sterically Unhindered Environment", J. Am. Chem. Soc. 130:3246-3247 (2008).
Grzesiak et al., 'Polymer-Induced Heteronucleation for the Discovery of New Extended Solids,' Angew. Chem. Int. Ed. 45:2553-2556 (2006).
Halper et al., 'Topological Control in Heterom etal lie Metal-Organic Frameworks by Anion templating and Metalloligand Design,' J. Am. Chem. Soc, 2006, pp. 15255-15268, vol. 128.
Han et al., 'Covalent Organic Frameworks as Exceptional Hydrogen Storage Materials,' J. Am. Chem. Soc. 130: 11580-11581 (2008).
Han, SS et al., 'Improved designs of metal-organic frameworks for hydrogen storage', Angew. Chem Int. Ed., 2007, 46, pp. 6289-6292.
Hassan et al., "Aryl-Aryl Bond Formation One Century After the Discovery of the Ullmann Reaction", Chem. Rev., Published on Web: Mar. 8, 2002, 102, 1359-1469.
Hayashi et al., 'Zeolite A Imidazolate Frameworks,' Nature Materials 6:501-506 (Jul. 2007).

(56) References Cited

OTHER PUBLICATIONS

Hexiang et al., 'Multiple Functional Groups of Varying Rations in Metal-Organic Frameworks,' Science 327(5967):846-850 (2010).
Hmadeh et al., 'New Porous Crystals of Extended Metal-Catecholates,' J. Chem. Mater. 24:3511-3513 (Aug. 28, 2012).
Holler et al., 'The first dinitrile frameworks of the rare earth elements: [LnCl3(1,4-Ph(CN)2] and [Ln2Cl6(1,4Ph(CN)2], Ln=Sm, Gd, Tb, Y; Access to novel metal-organic frameworks by solvent free synthesis in molten 1,4-benodinitrile,' Inorganic Chemistry 47(21): 10141-9 (2008).
Holler et al., "The First Dintrile Frameworks of the Rare Earth Elements: 3[LnCL3(1,4-Ph(CN2)] and 3[Ln2CL6(1,4-Ph(CN)2)], Ln=Sm, Gd, Tb, Y; Access to Novel Metal-Organic Frameworks by Solvent Free Synthesis in Molten 1,4-Benzodinitrile," Inorganic Chemistry, 2008, pp. 10141-10149, vol. 47, No. 21.
Honda, Masashi, International Preliminary Report on Patentability for PCT/US2008/051859, dated Jul. 28, 2009.
Howe, Patrick, International Search Report and Written Opinion, Application No. PCT/US2010/022777, dated Jun. 7, 2010.
Huang et al., 'Ligand-Directed Strategy for Zeolite-Type Metal-Organic Frameworks: Zinc(ii) Imidazolates with Unusual Zeolitic Topologies,' Angew. Chem. Int. Ed. 45:1557-1559 (2006).
Huang et al., 'Thermal Conductivity of Metal-Organic Framework 5 (MOF-5): Part II Measurement,' Int. J. Heat Mass Transfer 50:405-411 (2007).
Hunt et al., 'Reticular Synthesis of Covalent Organic Borosilicate Frameworks,' J. Am. Chem. Soc. 130: 11872-11873 (2008).
Duval, Eric, International Search Report and Written Opinion, Application No. PCT/US2015/023173, dated Apr. 11, 2016.
Ingleson et al., 'Framework fractionalization triggers metal complex binding,' Chem. Comm. 23:2680-2682 (2008).
Isaeva et al., 'Metal-organic frameworks-new materials for hydrogen storage,' Russian Journal of General Chemistry 77(4):721-739(2007).
Jeong et al., 'Asymmetric Catalytic Reactions by NbO-Type Chiral Metal-Organic Frameworks,' Chem. Sci. 2:877-882 (2011).
Jones, Christopher. Nonfinal Office Action for U.S. Appl. No. 12/598,855, dated Oct. 12, 2012.
Jones, Christopher. Nonfinal Office Action for U.S. Appl. No. 12/598,855, dated Jun. 14, 2012.
Kaye et al., 'Impact of Preparation and Handling on the Hydrogen Storage Properties of Zn4O(1,4-benzenedicarboxylate)3 (MOF-5),' J. Am. Chem. Soc. 129:14176-14177 (2007).
Kim et al., 'Assembly of Metal-Organic Frameworks from Large organic and Inorganic Secondary Building Units: New Examples and Simplifying Principles for Complex Structures,' J. Am. Chem. Soc, 2001, 123, 8239-8247.
Fang et al., "A multifunctional metal-organic open framework with a bcu topology constructed from undecanuclear clusters", Angewandte Chemie, International Edition, 2006, 45(37), 6126-6130.
Samizo, Shigeyoshi, Office Action, Application No. 2016-552975, Japanese Patent Office, dated Oct. 23, 2018.
Bourghida, E., Office Action, Application No. 15707499.8, European Patent Office, dated Sep. 3, 2018.
Shahroosvand, Hashem et al., "Synthesis, characterization and optical properties of novel N, donor ligands-chelated zirconium (IV) complexes", Optical Materials, vol. 35, Aug. 25, 2012, pp. 79-84.
Shahroosvand, Hashem et al., "Red-yellow electroluminescence, yellow-green photoluminescence of novel N, O donor ligands-chelated zirconium (IV) complexes", Journal of Luminesence, vol. 135, Sep. 26, 2012, pp. 339-344.

\* cited by examiner

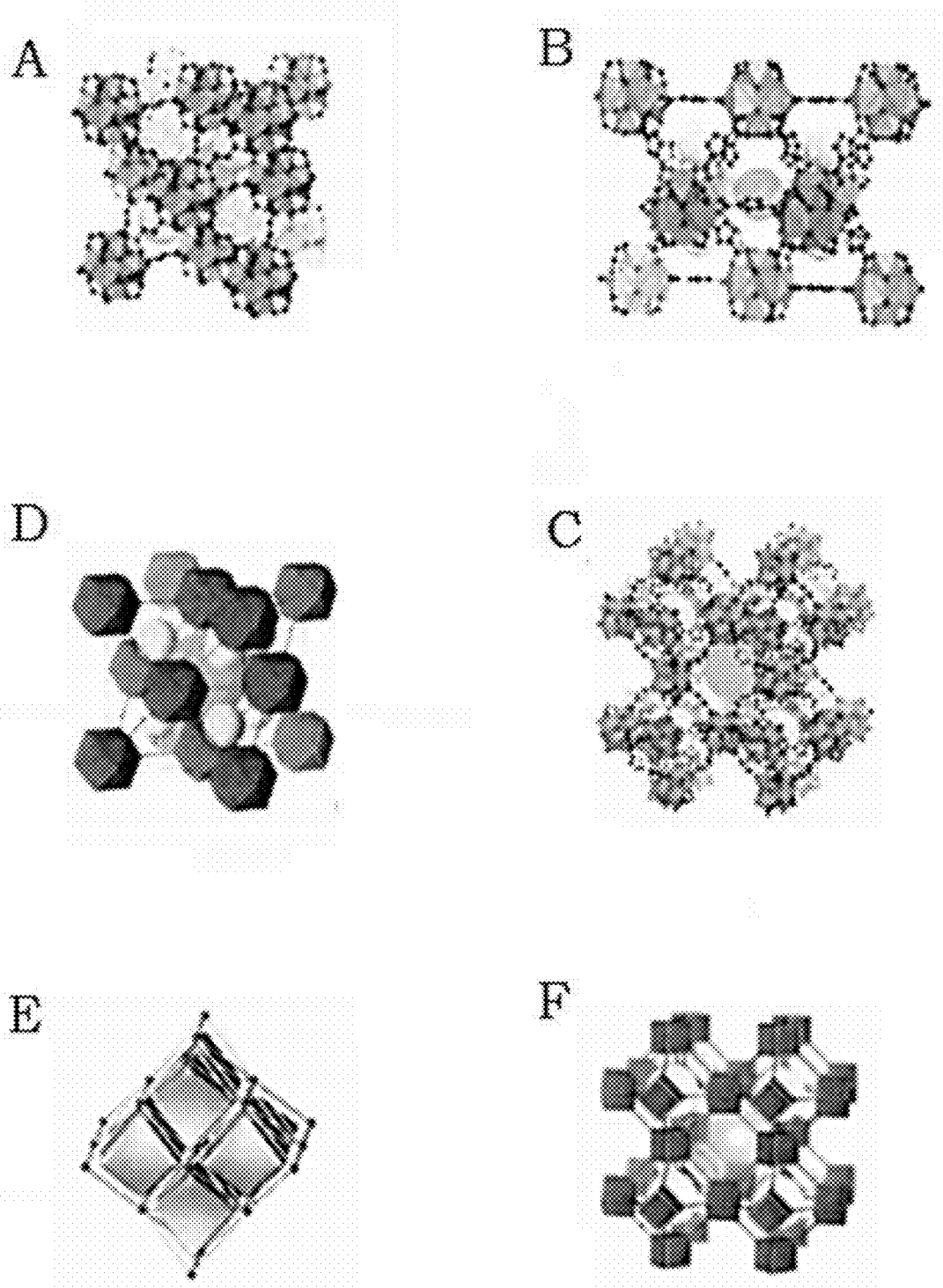
FIGURE 2A-F

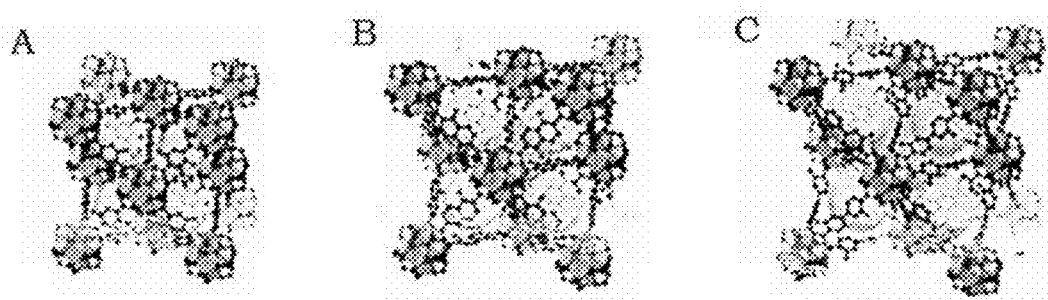
FIGURE 3A-C
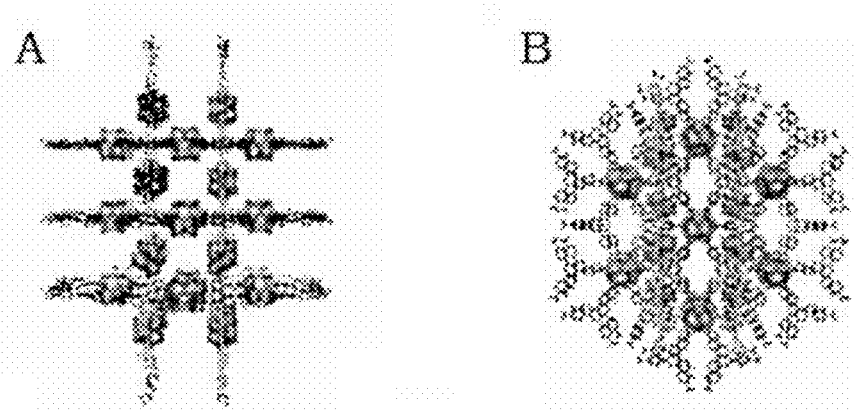
FIGURE 4A-B
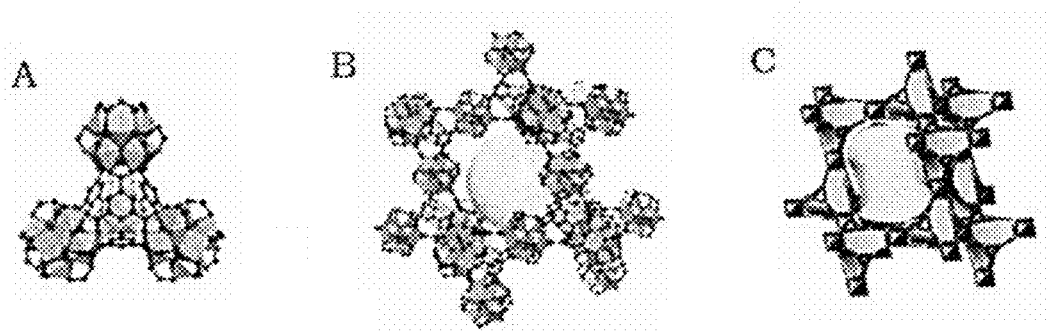
FIGURE 5A-C

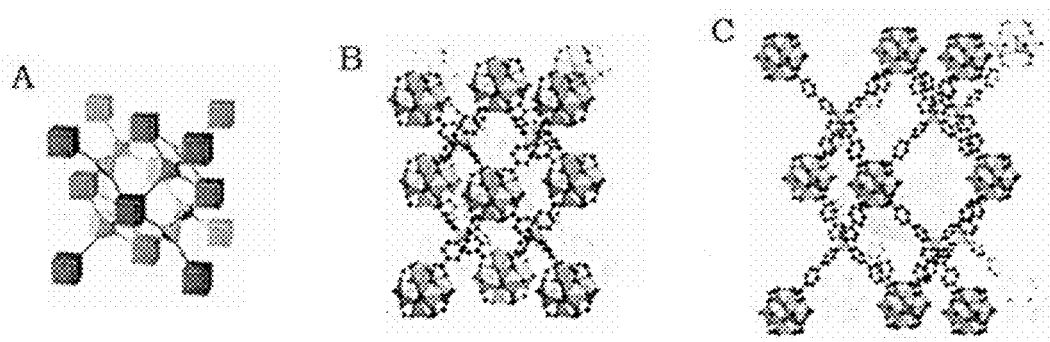
FIGURE 6A-C
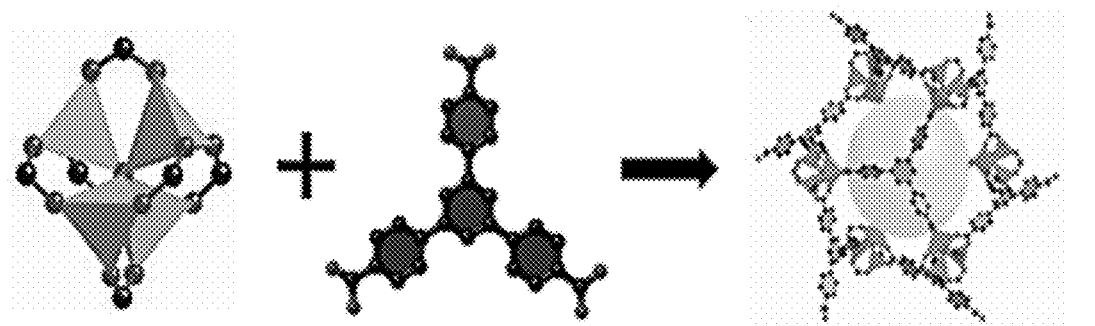
MOF-177
BET surface area, 4500m²/g
FIGURE 7

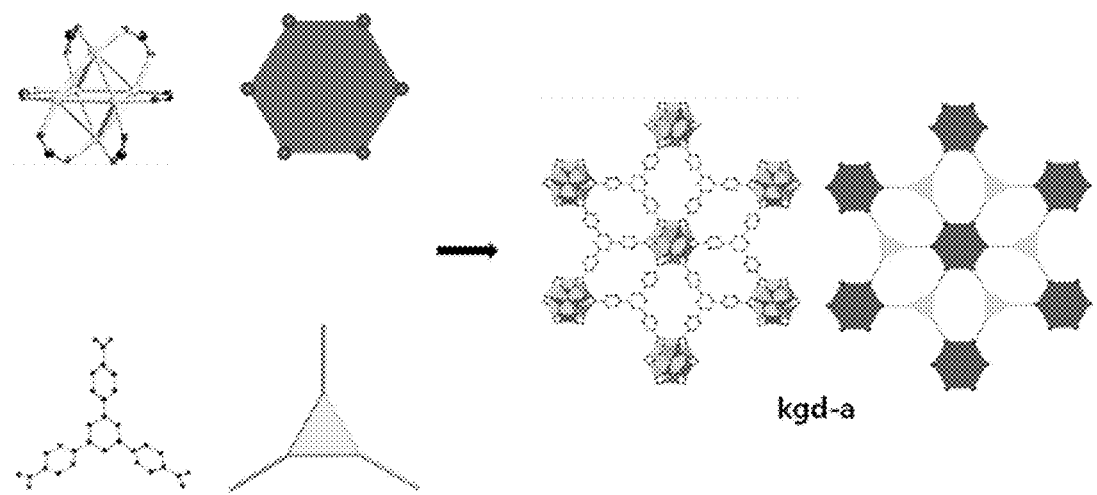
FIGURE 12
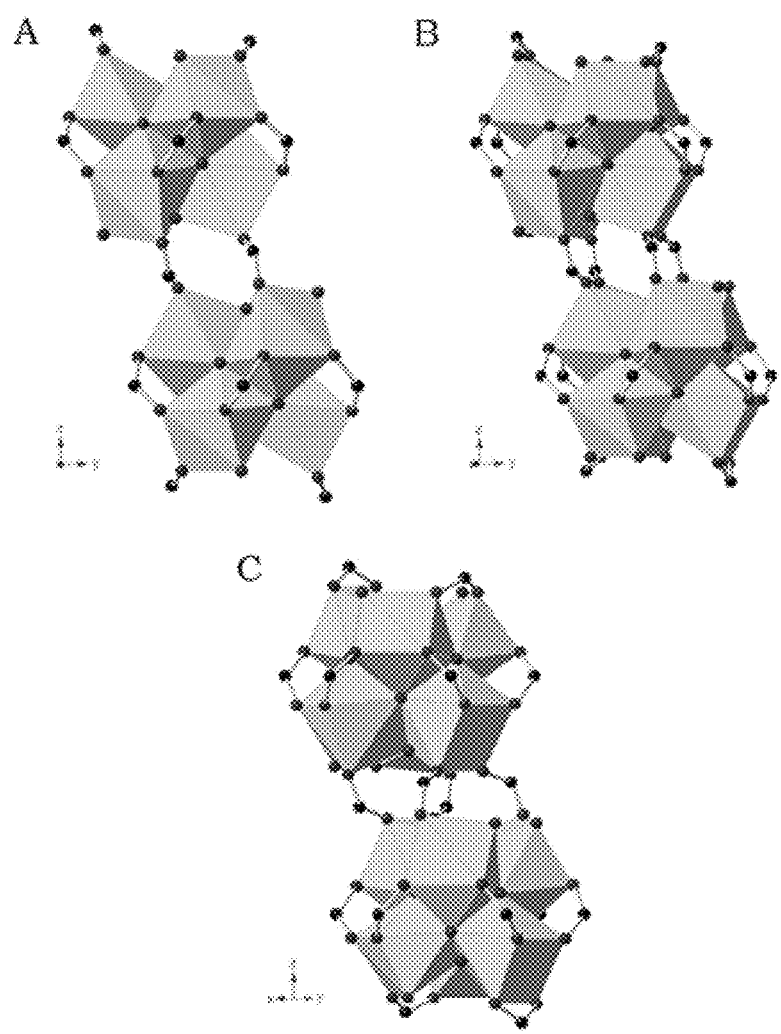
FIGURE 13A-C

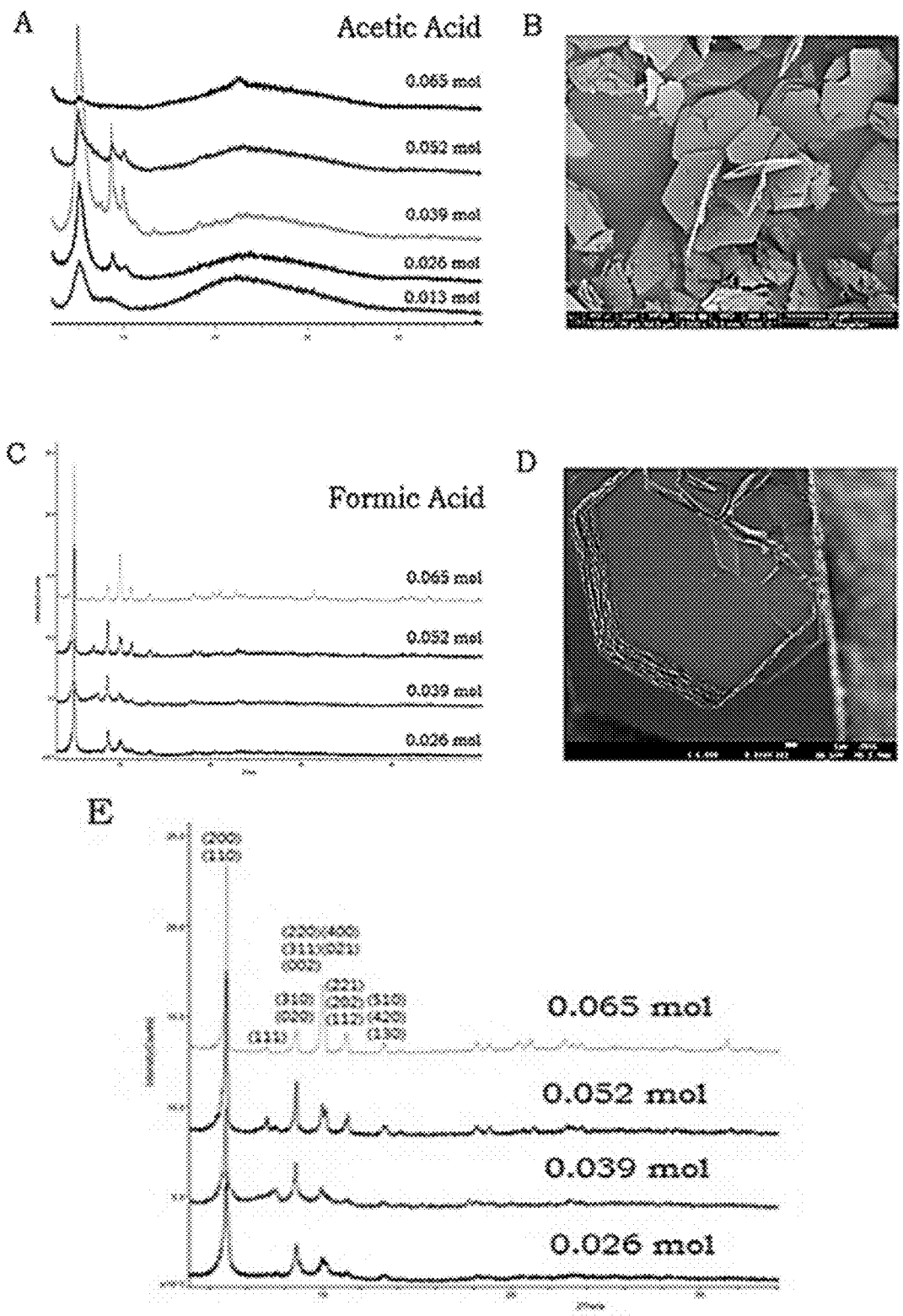
FIGURE 14A-E

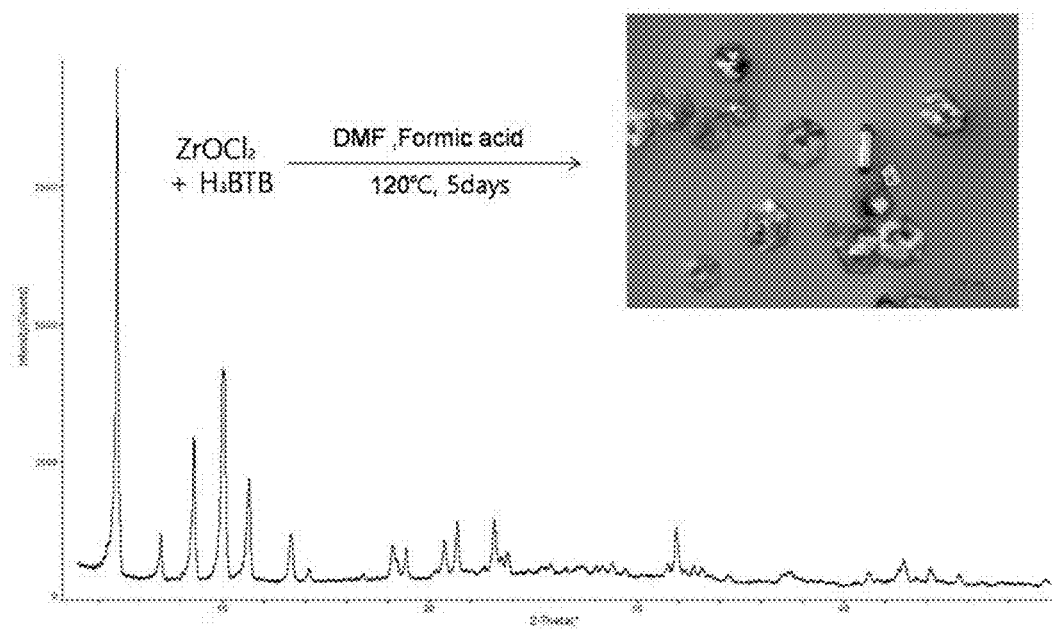
FIGURE 15
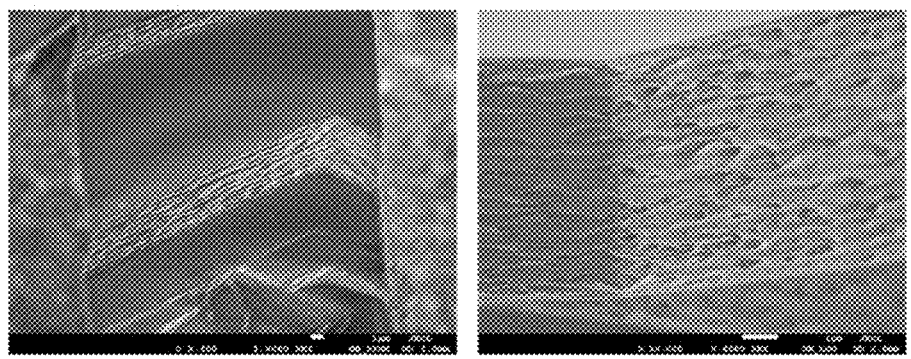
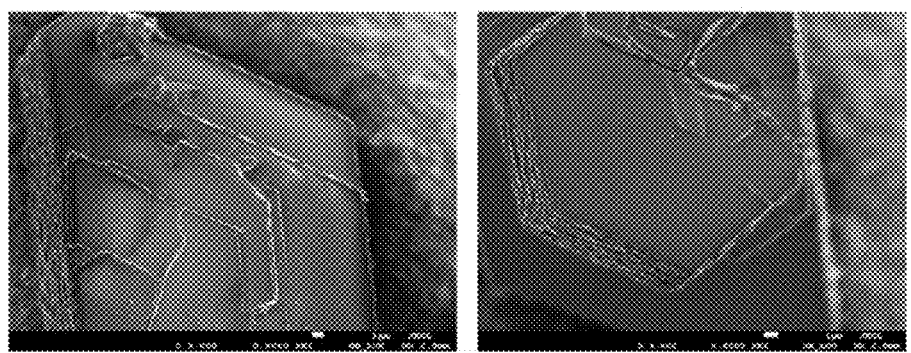
FIGURE 16

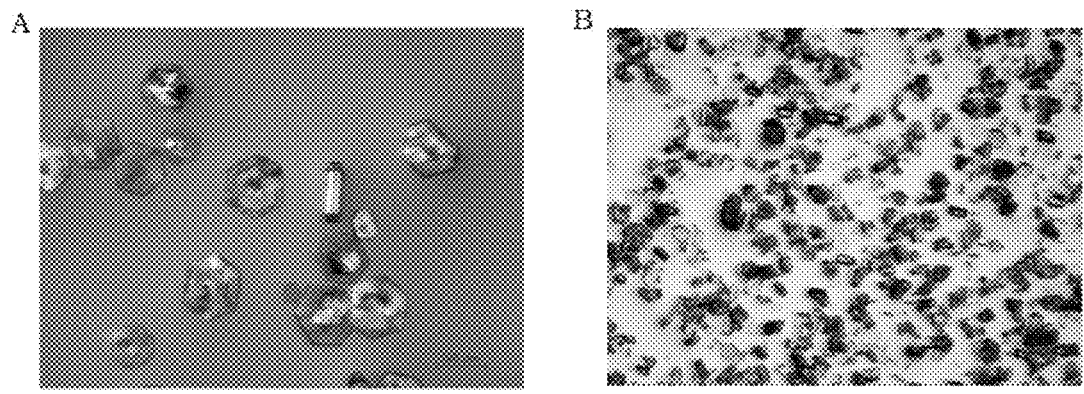
FIGURE 17A-B
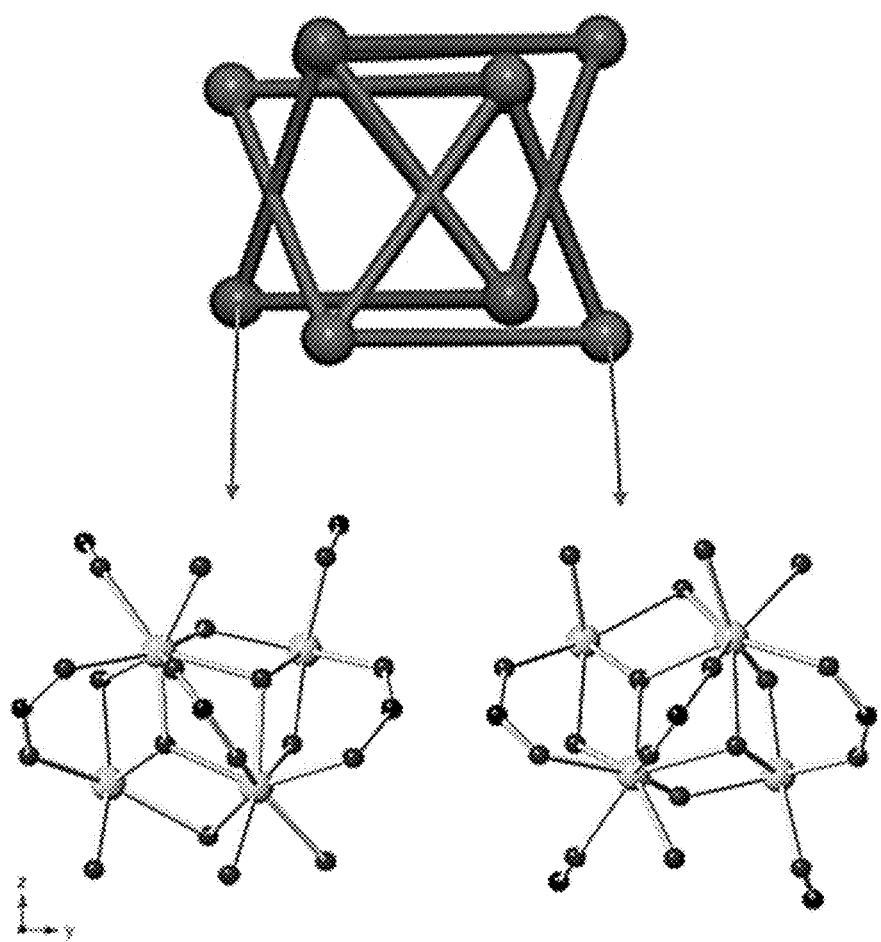
FIGURE 18

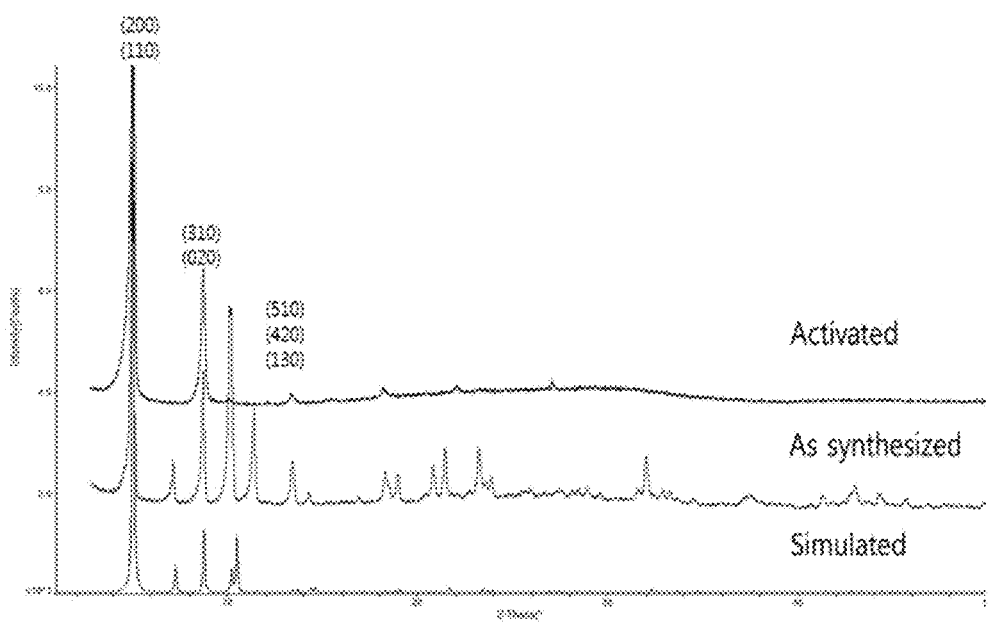
FIGURE 21
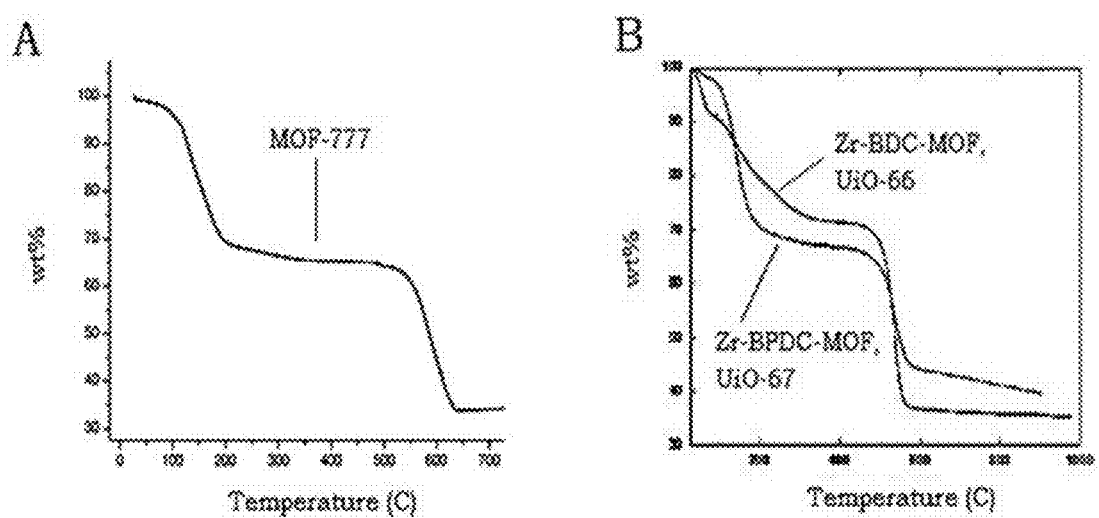
FIGURE 22A-B

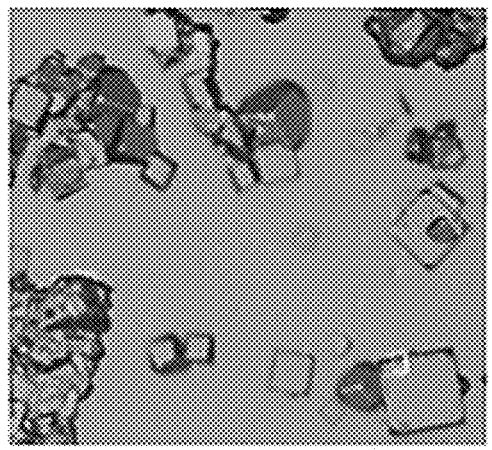
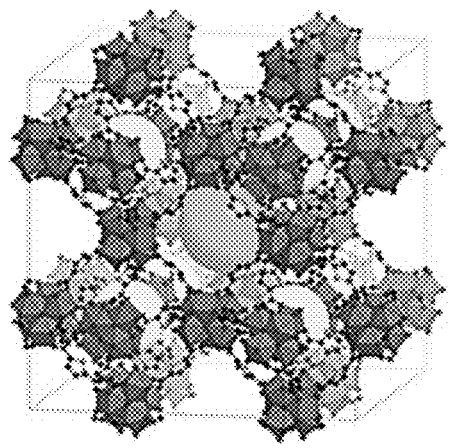
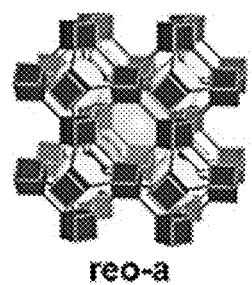
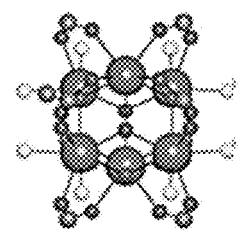
FIGURE 46

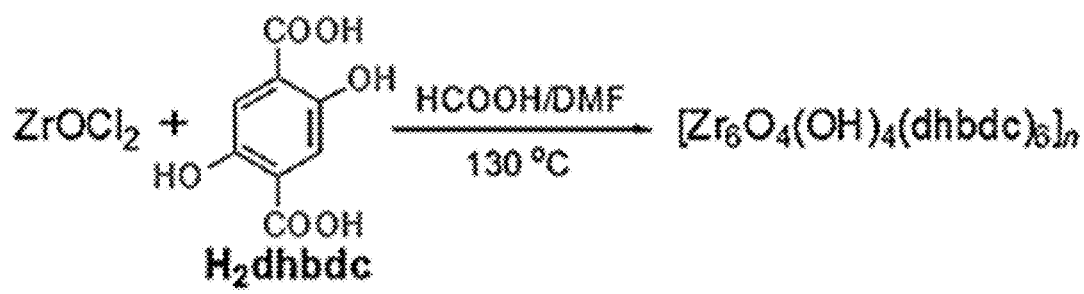
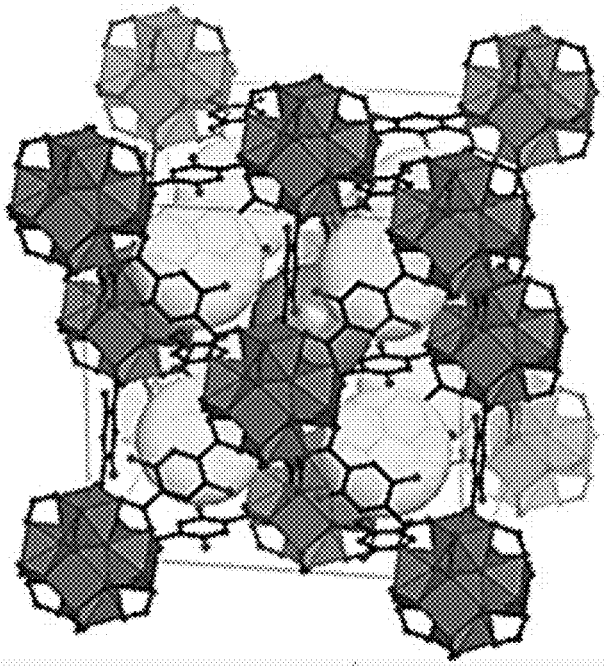
| | |
|---|---|
| Cubic $F23$ | $d = 1.45$ g·cm$^{-3}$ |
| $a = 20.391$ Å | $Void = 40.1\%$ |
| $V = 8478.31$ Å$^3$ | $V_p = 0.28$ cm$^3$·g$^{-1}$ |
FIGURE 53

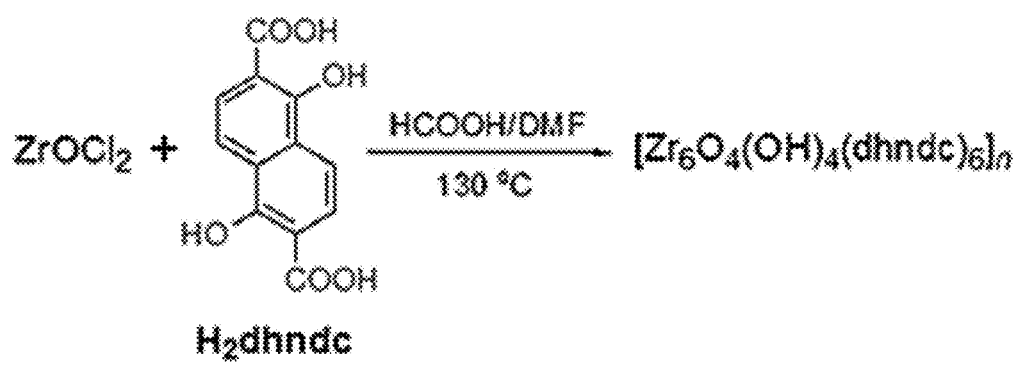
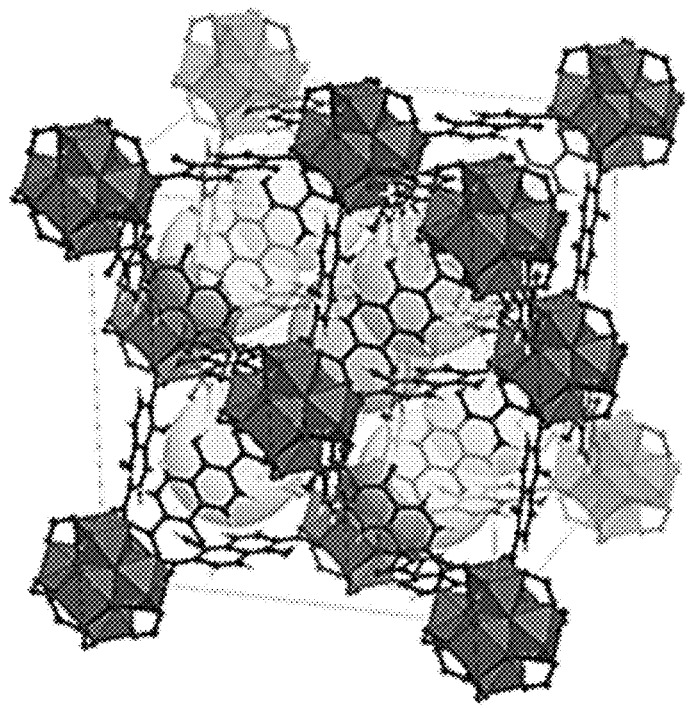
FIGURE 60

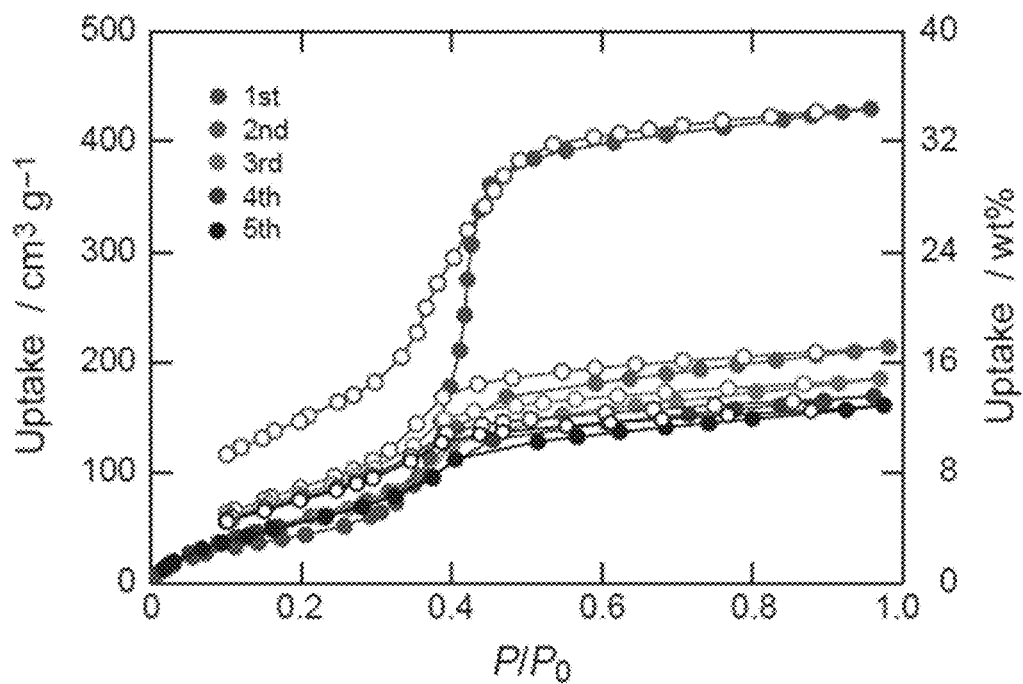
FIGURE 69
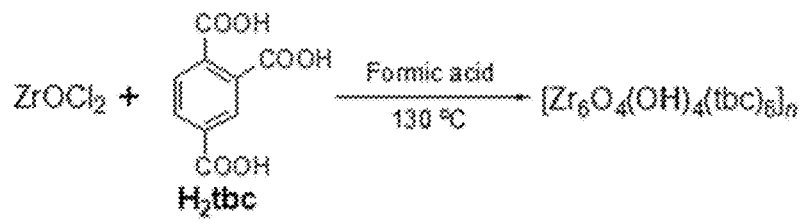
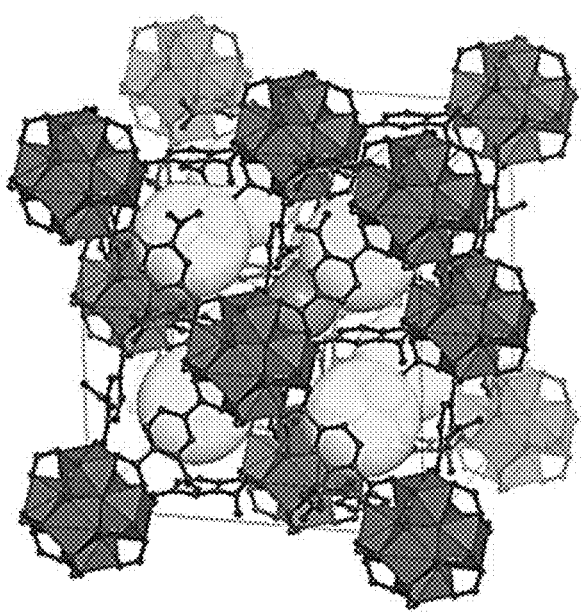
FIGURE 70

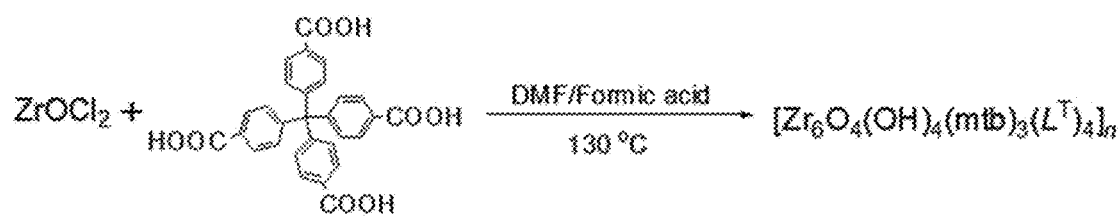
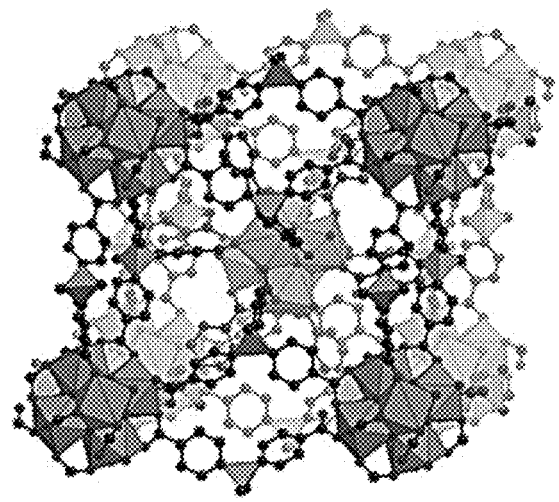
| Monoclinic $C2/c$ | |
|---|---|
| $a = 23.965(2)$ Å | $V = 12105.8$ Å$^3$ |
| $b = 29.284(2)$ Å | $d = 1.2162$ g·cm$^{-3}$ |
| $c = 17.355(1)$ Å | Void = 44.9 % |
| $\beta = 96.301(2)$ Å | $V_p = 0.37$ cm$^3$·g$^{-1}$ |
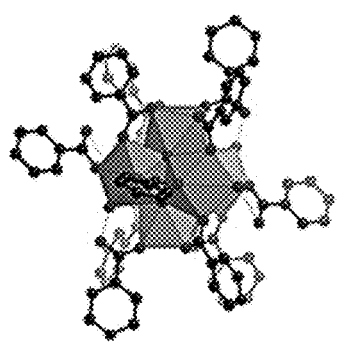
12-c. Cuboctahedron
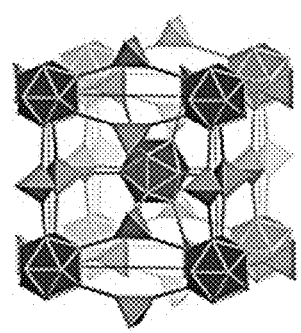
ith-a net
FIGURE 75

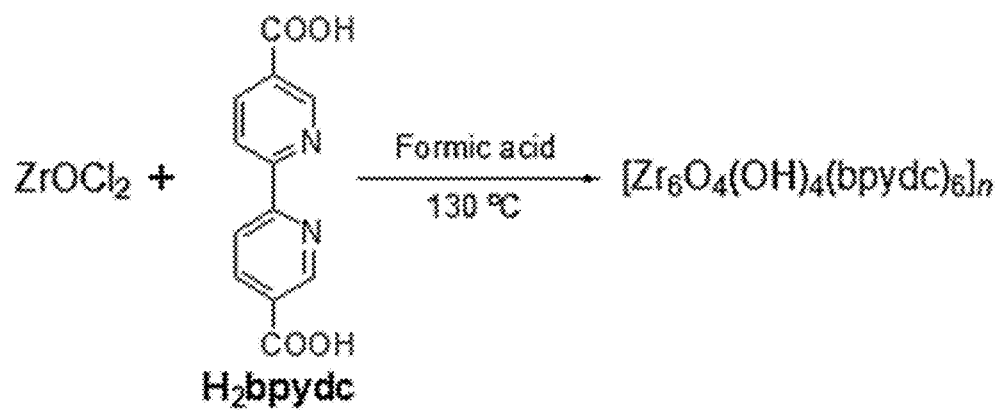
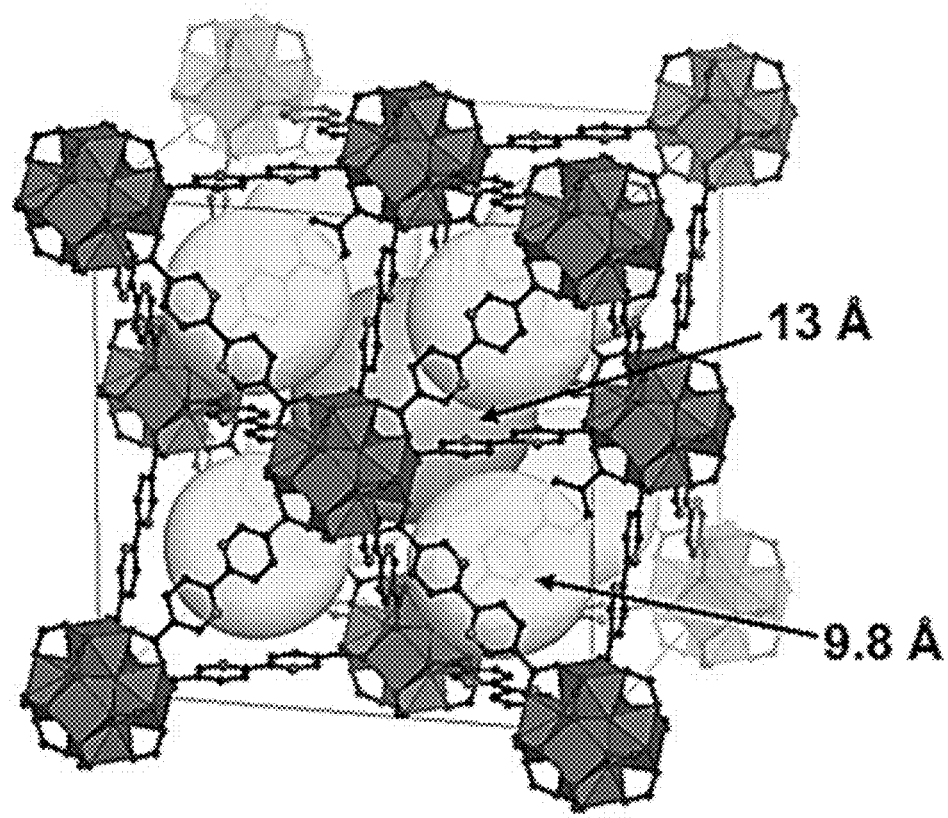
FIGURE 87

ACID, SOLVENT, AND THERMAL RESISTANT METAL-ORGANIC FRAMEWORKS

CROSS REFERENCE TO RELATED APPLICATIONS

This application is a U.S. National Stage Application filed under 35 U.S.C. § 371 and claims priority to International Application No. PCT/US2015/016555, filed Feb. 19, 2015, which application claims priority under 35 U.S.C. § 119 from Provisional Application Ser. No. 61/941,791, filed Feb. 19, 2014, the disclosures of which are incorporated herein by reference.

STATEMENT REGARDING FEDERAL SPONSORED RESEARCH

This invention was made with government support under Grant Nos. DE-AC02-05CH11231 and DE-SC000105 awarded by the U.S. Department of Energy. The U.S. government has certain rights in the invention.

TECHNICAL FIELD

This disclosure provides for acid, solvent, and/or thermal resistant Metal-Organic Frameworks (MOFs), including solid-acid MOFs (sa-MOFs), and the use of the MOFs for gas adsorption, gas separation, and catalysis.

BACKGROUND

Metal-organic frameworks (MOFs) are porous crystalline materials that are constructed by linking metal clusters called Secondary Binding Units (SBUs) and organic linking moieties. MOFs have high surface area and high porosity which enable them to be utilized in diverse fields, such as gas storage, catalysis, and sensors.

SUMMARY

The disclosure provides for metal-organic frameworks (MOFs) that are acid, solvent, and/or thermal resistant. The MOFs of the disclosure can be used in a variety of applications and environments that cannot be addressed by using conventional framework materials. The MOFs of the disclosure comprise metals (e.g., titanium, zirconium, and hafnium) coordinated to carboxylate clusters of organic linking ligands. The disclosure further provides for controlling metal-carboxylate cluster extensions and topologies of the MOFs by using the methods disclosed herein. The MOFs of the disclosure are comprised of organic linking moieties having various geometries, multivariate functionalities and metalation. Further, isomorphous analogues of the MOFs disclosed herein can be created by replacing framework metal ions with alternate metal ions. Accordingly, the disclosure provides for a new series of MOFs that feature: acid, solvent, and/or thermal resistance; designable topologies; multivariate framework components; controllable pore metrics; and tunable pore environments. The disclosure further provides for MOFs comprised of Zr-carboxylate SBUs linked to various organic linking ligands (e.g., MOF-801, MOF-802, MOF-803, MOF-804, MOF-805, MOF-806, MOF-807, MOF-808, MOF-812, MOF-841, and MOF-841).

The disclosure also provides for a framework comprising zirconium and benzene-tribenzoic acid (BTB)-based organic linking moieties (e.g., MOF-777). MOF-777 is thermally stable up to 550° C., and is resistant to common acids, bases, organic solvents and water. MOF-777 has a unique tfz-d type 3D topology that is based on stacking kgd-a type 2D structures which is built around hexagonal SBUs and triangle BTB-based linkers. The topology of MOF-777 is unique and the first of its kind in the field. Therefore, MOF-777 represents an entirely new class of MOFs which substructure allows for exfoliation. The disclosure additionally provides for variations of the MOF-777 framework which comprise substituting zirconium metal ions with alternate metal ions, substituting the BTB organic linking ligand with alternate organic linking ligands which have trigonal planar geometries, and/or substituting formate anions with alternate linking anions.

As the MOFs of the disclosure are typically acid resistant they can be also be modified to be strong solid-acids, by (1) modifying linking anions used to synthesize the frameworks with acidic site precursors capable of becoming Bronstead and/or Lewis acids (e.g., sulfate, and halide anions); (2) complexing open metal sites or other portions (e.g., pore) of the MOFs disclosed herein with acidic site precursors; and (3) exchanging anions coordinated to the metal, metal ions, or metal containing complexes of the MOFs with acidic site precursors. Further, due to the highly adsorptive nature of the MOFs disclosed herein, MOFs that are strong solid-acids are capable of being superacids.

The disclosure further provides that the MOFs disclosed herein can be used in variety of applications and devices, including, for use in fluid storage, fluid separation, thin films, catalysis, sensors, adsorbents (e.g., radioactive isotopes, and for harmful chemicals), conductors, and in the manufacture fertilizers, batteries, dyes, paints, drugs and explosives.

The disclosure provides a thermal, acid, and/or solvent resistant metal organic framework (MOF) comprising a plurality of linked M-O-L secondary binding units (SBUs), wherein M is a metal, metal ion, or metal containing complex; O is an oxygen atom of a carboxylate based linking cluster; and L is an organic linking ligand comprising one or more structures of Formula I-XII:

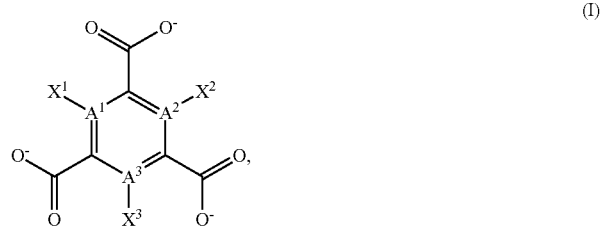
(I)

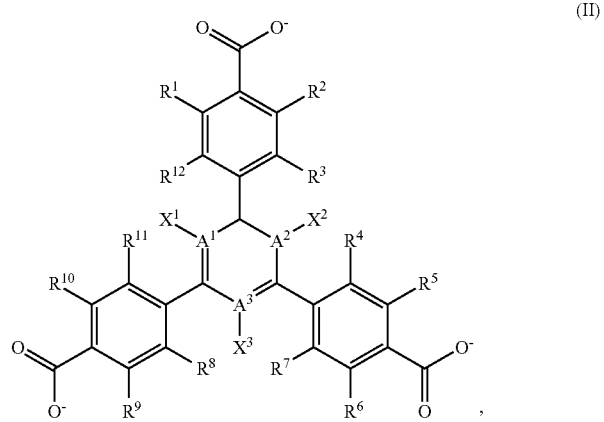
(II)

(III)
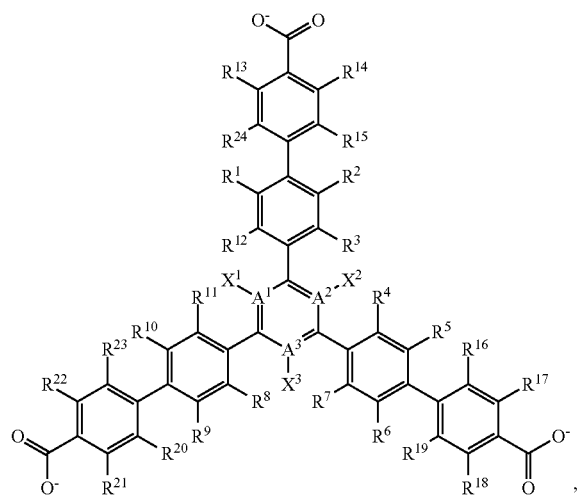
(IV)
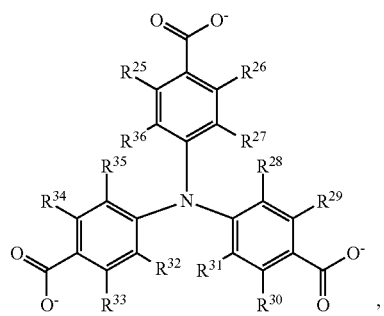
(V)
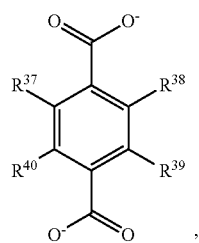
(VI)
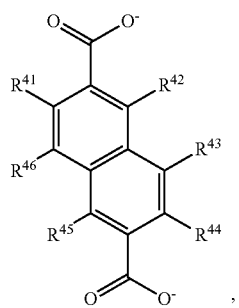
(VII)
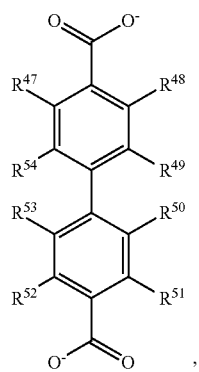
(VIII)
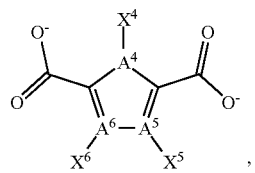
(IX)
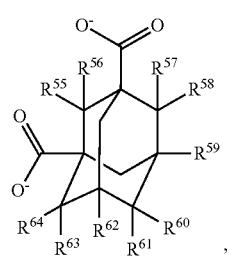
(X)
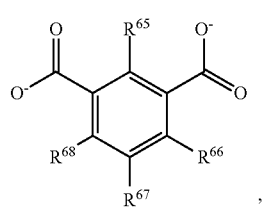

-continued
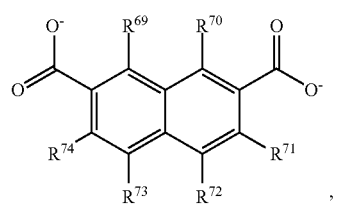
(X)
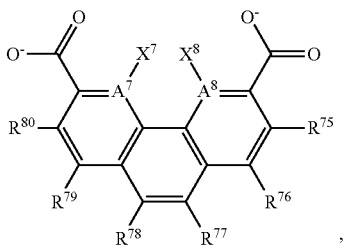
(XI)
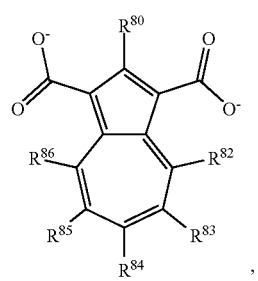
(XII)
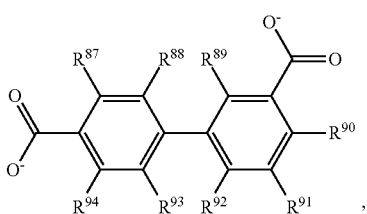
(XIII)
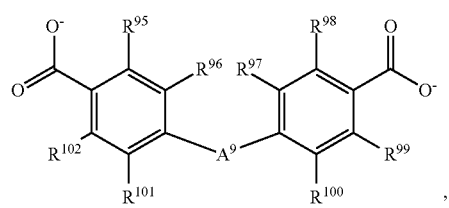
(XIV)
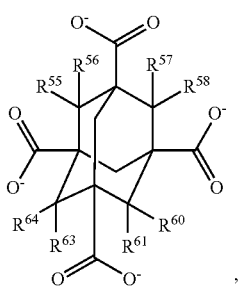
(XV)
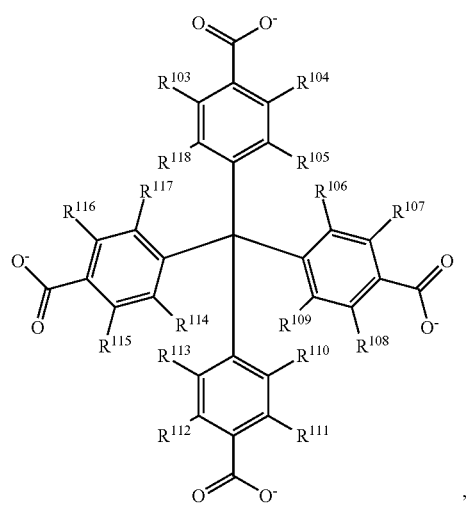
(XVI)
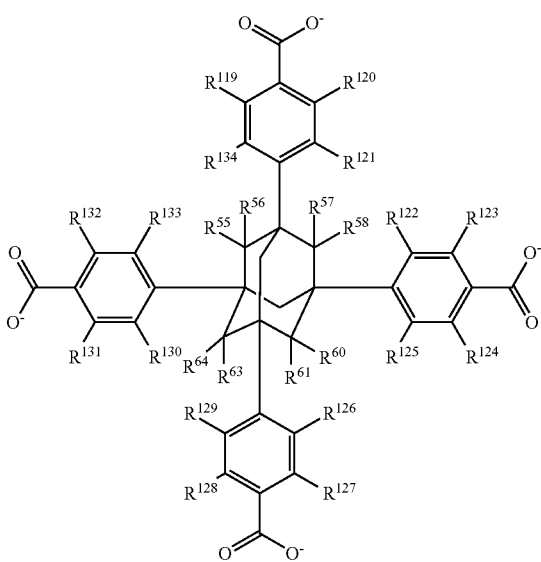
(XVII)
(XVIII)

-continued
(XIX)
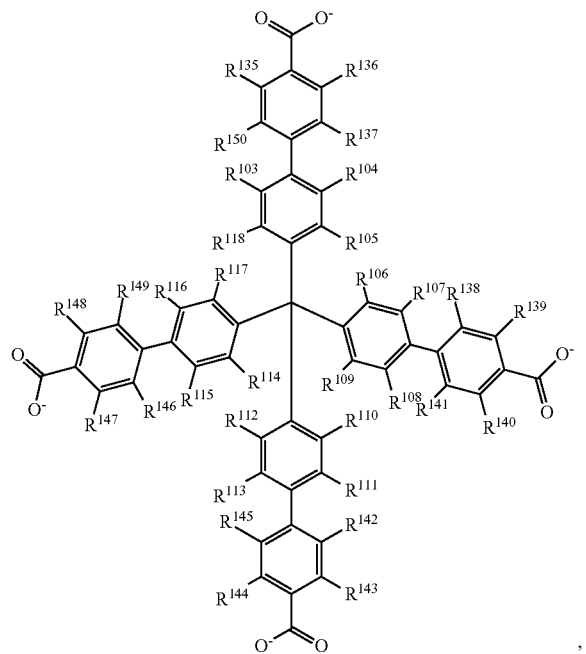
(XX)
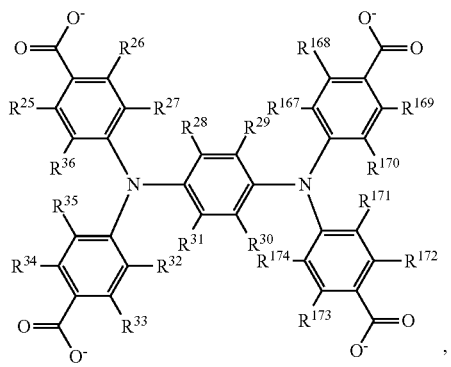
,
(XXI)
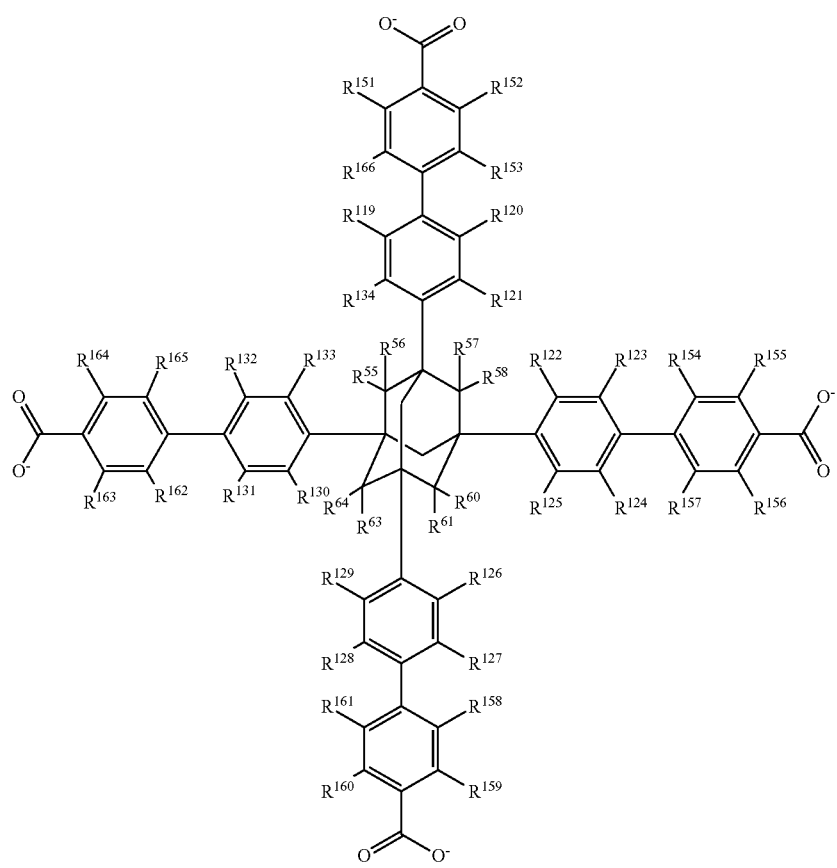
, and

-continued

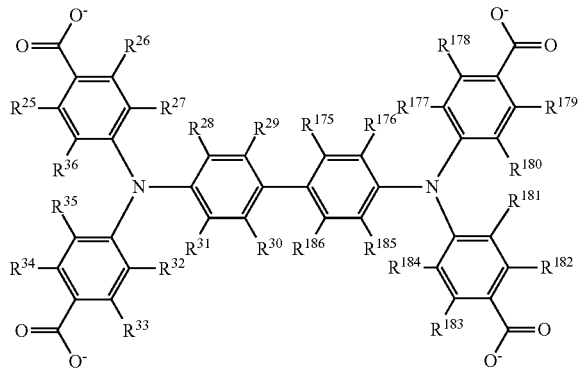

wherein, $A^1$-$A^8$ are independently a C, N, O, or S; $A^9$ is selected from

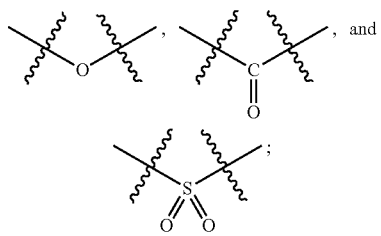

$X^1$-$X^8$ are independently selected from H, D, optionally substituted FG, optionally substituted ($C_1$-$C_{20}$)alkyl, optionally substituted ($C_1$-$C_{19}$)heteroalkyl, optionally substituted ($C_1$-$C_{20}$)alkenyl, optionally substituted ($C_1$-$C_{19}$)heteroalkenyl, optionally substituted ($C_1$-$C_{19}$)alkynyl, optionally substituted ($C_1$-$C_{19}$)heteroalkynyl, optionally substituted ($C_1$-$C_{19}$)cycloalkyl, optionally substituted ($C_1$-$C_{19}$) cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system; and $R^1$-$R^{186}$ are independently selected from H, D, optionally substituted FG, optionally substituted ($C_1$-$C_{20}$)alkyl, optionally substituted ($C_1$-$C_{19}$)heteroalkyl, optionally substituted ($C_1$-$C_{20}$) alkenyl, optionally substituted ($C_1$-$C_{19}$)heteroalkenyl, optionally substituted ($C_1$-$C_{19}$)alkynyl, optionally substituted ($C_1$-$C_{19}$)heteroalkynyl, optionally substituted ($C_1$-$C_{19}$) cycloalkyl, optionally substituted ($C_1$-$C_{19}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system; and wherein the framework is thermally stable when exposed to a temperature between 50° C. to 525° C., and/or the framework is chemically stable in the presence of a solvent and/or an acid. In another embodiment, L is a linear diptopic organic linking ligand comprising one or more structures of Formula V-VII:

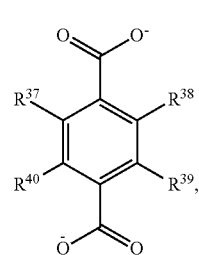

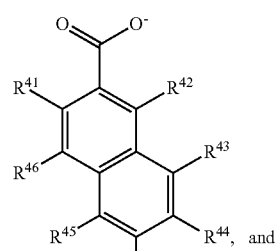

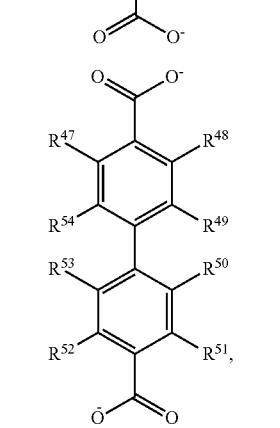

wherein, $R^{37}$-$R^{54}$ are independently selected from H, D, optionally substituted FG, optionally substituted ($C_1$-$C_{20}$) alkyl, optionally substituted ($C_1$-$C_{19}$)heteroalkyl, optionally substituted ($C_1$-$C_{20}$)alkenyl, optionally substituted ($C_1$-$C_{19}$) heteroalkenyl, optionally substituted ($C_1$-$C_{19}$)alkynyl, optionally substituted ($C_1$-$C_{19}$)heteroalkynyl, optionally substituted ($C_1$-$C_{19}$)cycloalkyl, optionally substituted ($C_1$-$C_{19}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system. In yet another embodiment, L is a linear diptopic organic linking ligand comprising one or more structures of Formula V(a), VI(a), VI(b) and VII(a):
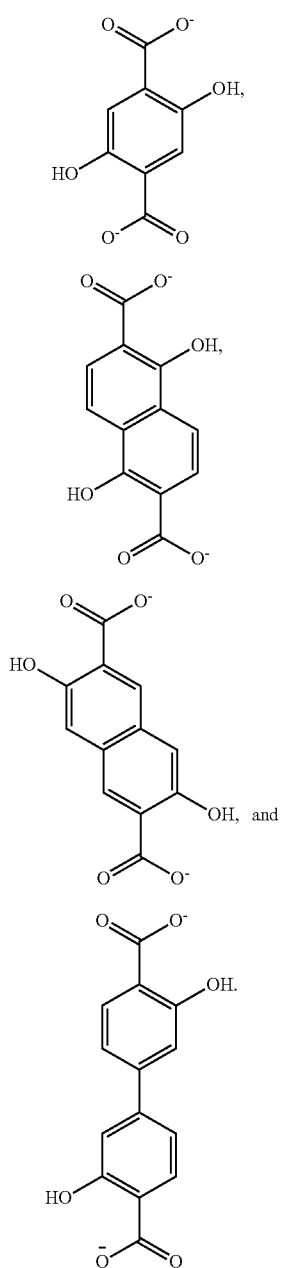
In another embodiment, L is a bent diptopic organic linking ligand comprising one or more structures of Formula VIII-XV:
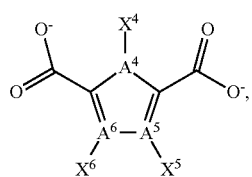
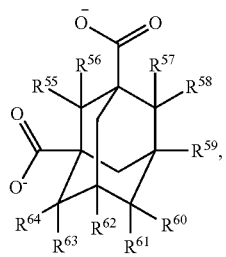
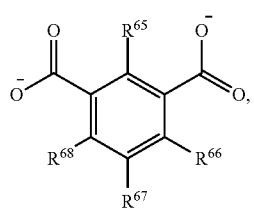
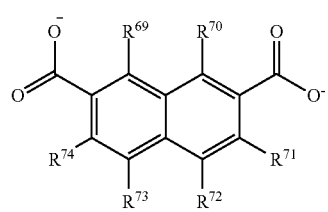
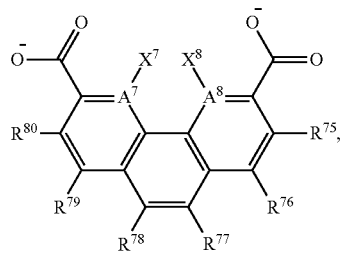
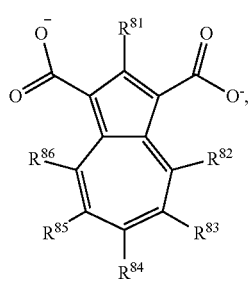
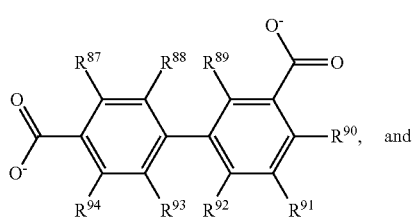

(XV)

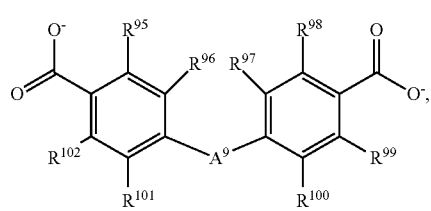

wherein, $A^4$-$A^8$ are independently a C, N, O, or S; $A^9$ is selected from

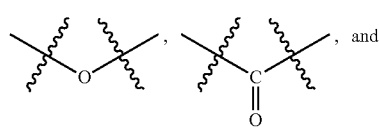, and

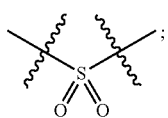;

$X^4$-$X^8$ are independently selected from H, D, optionally substituted FG, optionally substituted $(C_1$-$C_{20})$alkyl, optionally substituted $(C_1$-$C_{19})$heteroalkyl, optionally substituted $(C_1$-$C_{20})$alkenyl, optionally substituted $(C_1$-$C_{19})$heteroalkenyl, optionally substituted $(C_1$-$C_{19})$alkynyl, optionally substituted $(C_1$-$C_{19})$heteroalkynyl, optionally substituted $(C_1$-$C_{19})$cycloalkyl, optionally substituted $(C_1$-$C_{19})$cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system; and $R^{55}$-$R^{102}$ are independently selected from H, D, optionally substituted FG, optionally substituted $(C_1$-$C_{20})$alkyl, optionally substituted $(C_1$-$C_{19})$heteroalkyl, optionally substituted $(C_1$-$C_{20})$alkenyl, optionally substituted $(C_1$-$C_{19})$heteroalkenyl, optionally substituted $(C_1$-$C_{19})$alkynyl, optionally substituted $(C_1$-$C_{19})$heteroalkynyl, optionally substituted $(C_1$-$C_{19})$cycloalkyl, optionally substituted $(C_1$-$C_{19})$cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system. In yet a further embodiment, L is a bent diptopic organic linking ligand comprising one or more structures of Formula VIII(a), VIII(b), VIII(c), VIII(d), VIII(e), VIII(f), VIII(g), VIII(h), IX(a), X(a), XI(a), XII(a), XIII(a), XIV(a), XV(a), XV(b), and XV(c):

VIII(a)

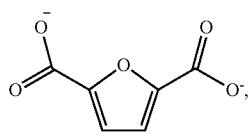

VIII(b)

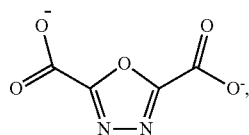

VIII(c)

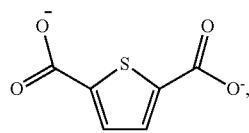

VIII(d)

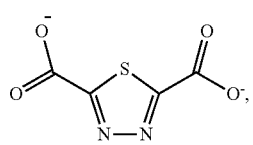

VIII(e)

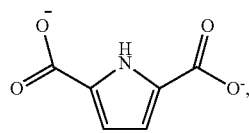

VIII(f)

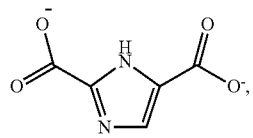

VIII(g)

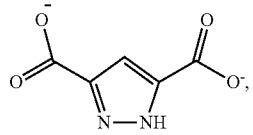

VIII(h)

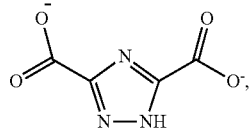

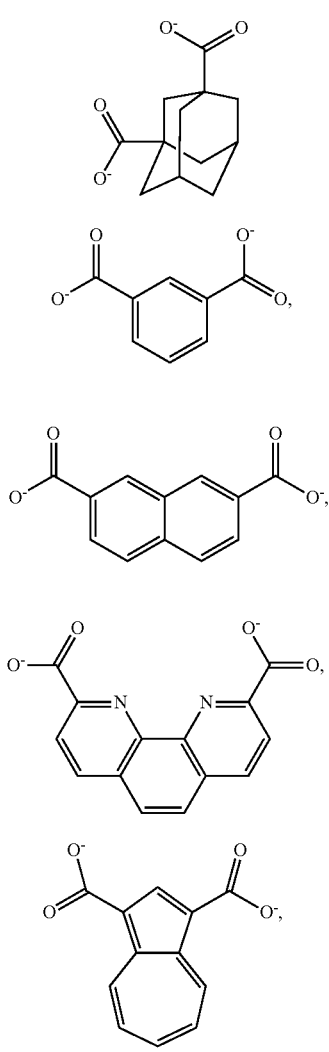
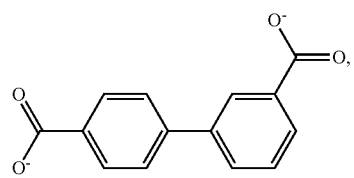
Ix(a)
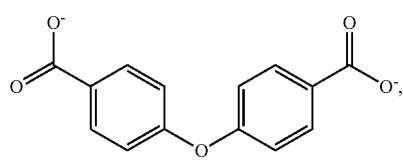
X(a)
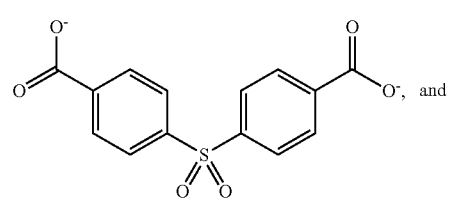
XI(a)
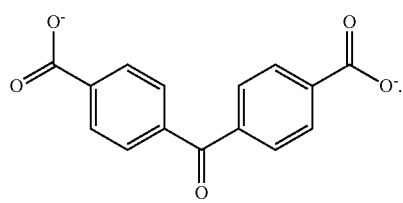
XII(a)
XIII(a)
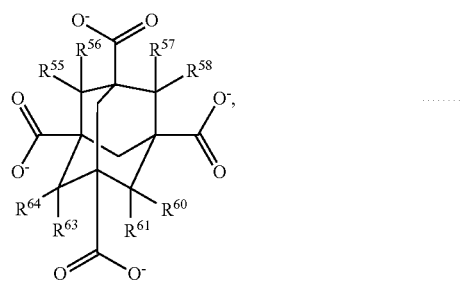
XIV(a)
XV(a)
XV(b)
XV(c)
In another embodiment, L is a tetratopic organic linking ligand comprising one or more structures of Formula XVI-XXII:
(XVI)
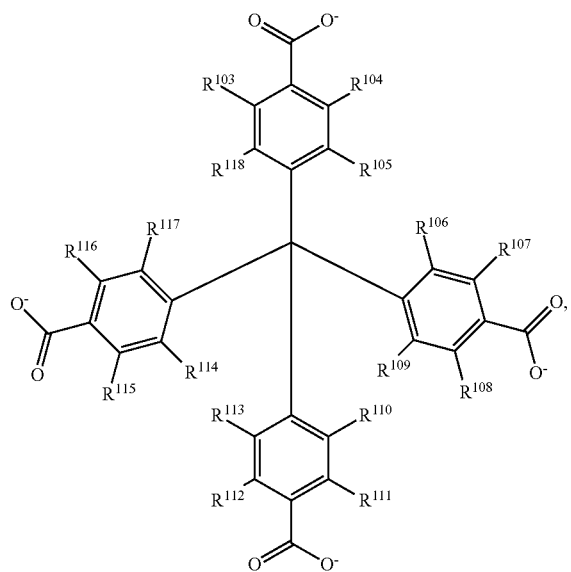
(XVII)

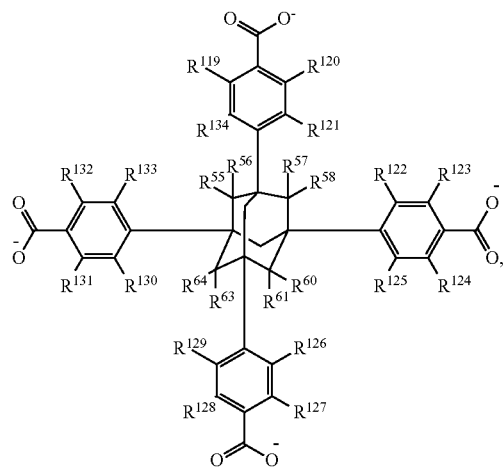
(XVIII)
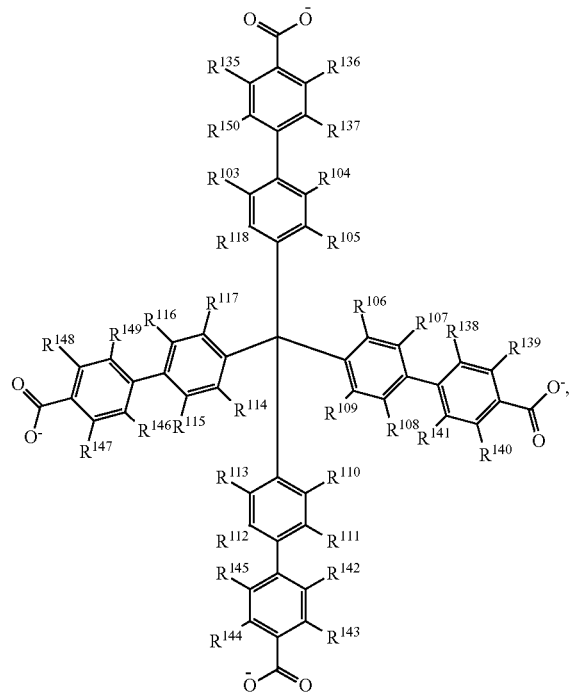
(XIX)
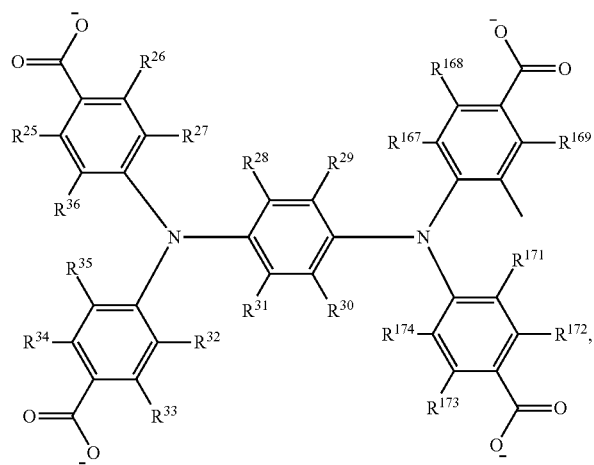
(XX)

-continued
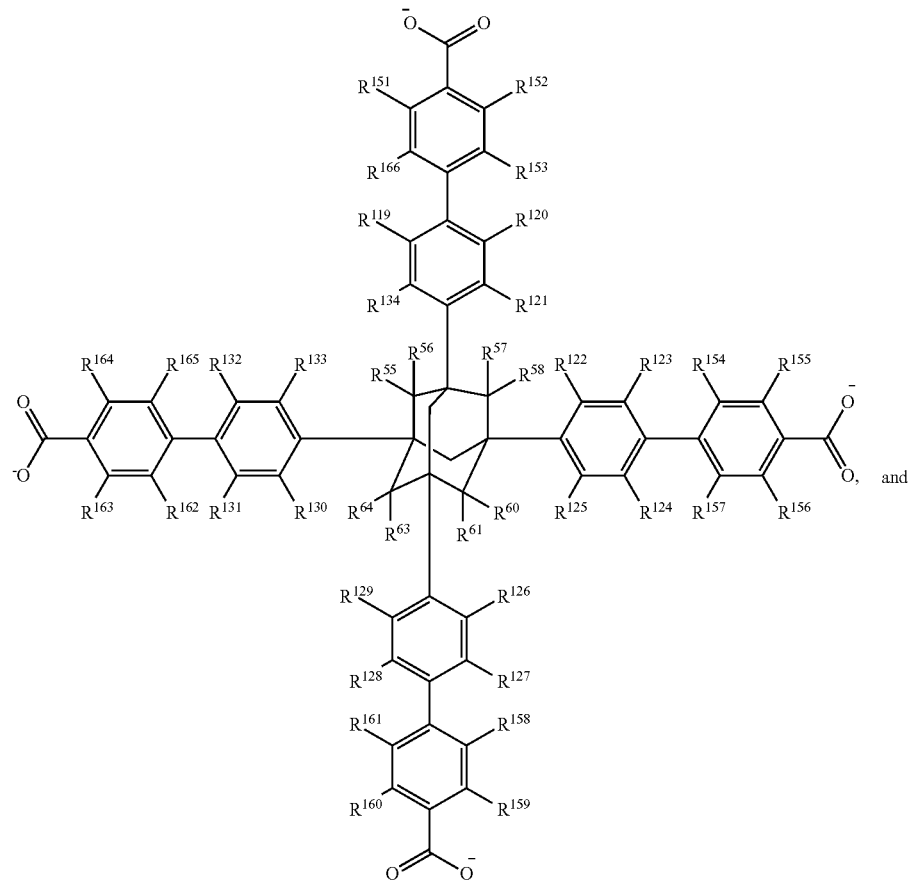
(XXI)
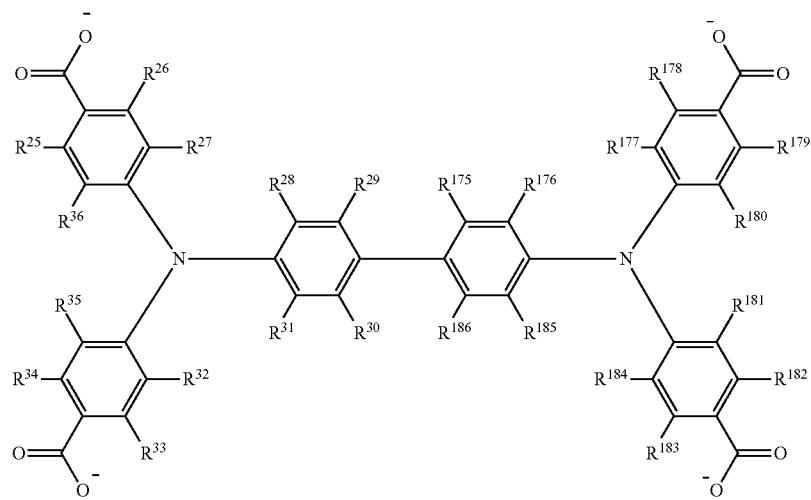
(XXII)

wherein, $R^{25}$-$R^{36}$, $R^{55}$-$R^{58}$, $R^{60}$, $R^{61}$, $R^{63}$, $R^{64}$, $R^{103}$-$R^{186}$ are independently selected from H, D, optionally substituted FG, optionally substituted ($C_1$-$C_{20}$)alkyl, optionally substituted ($C_1$-$C_{19}$)heteroalkyl, optionally substituted ($C_1$-$C_{20}$)alkenyl, optionally substituted ($C_1$-$C_{19}$)heteroalkenyl, optionally substituted ($C_1$-$C_{19}$)alkynyl, optionally substituted ($C_1$-$C_{19}$)heteroalkynyl, optionally substituted ($C_1$-$C_{19}$)cycloalkyl, optionally substituted ($C_1$-$C_{19}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system. In an further embodiment, L is a tetratopic organic linking ligand comprising one or more structures of Formula XVI(a), XVII(a), XVIII(a), XIX(a), XX(a), XXI(a) and XXII(a):

XVI(a)

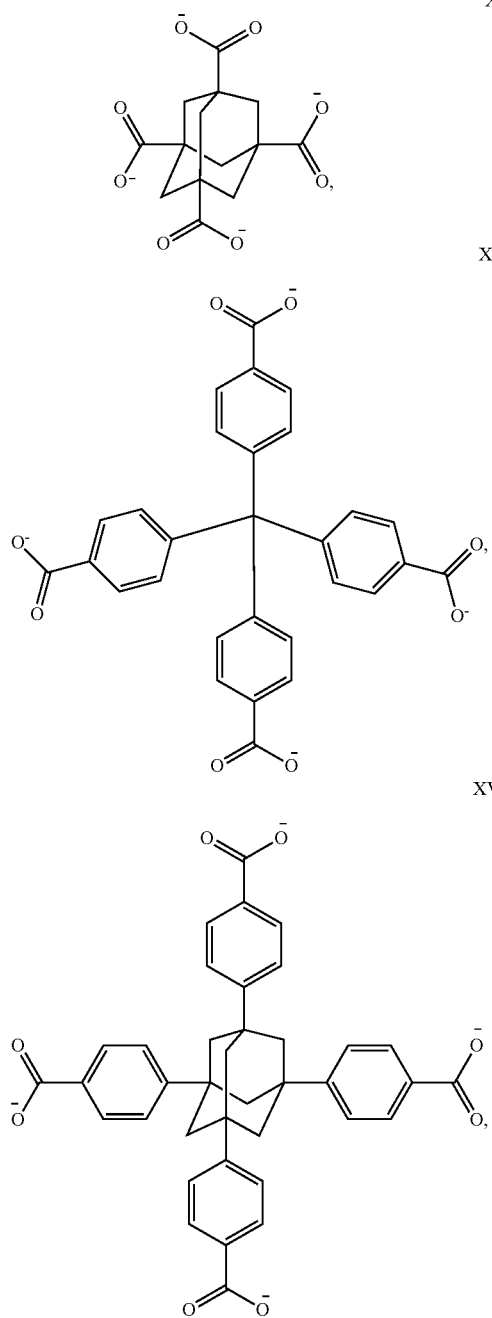

XVII(a)

XVIII(a)

XIX(a)

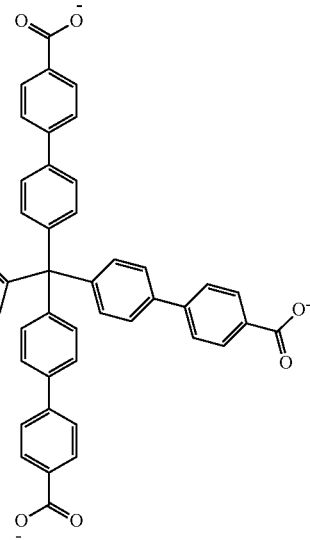

XX(a)

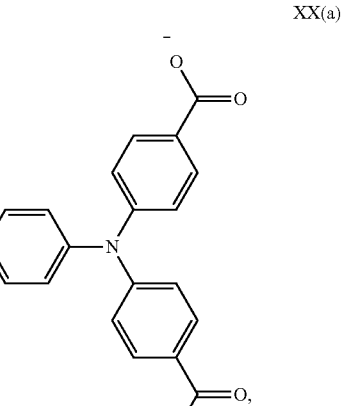

XXI(a)

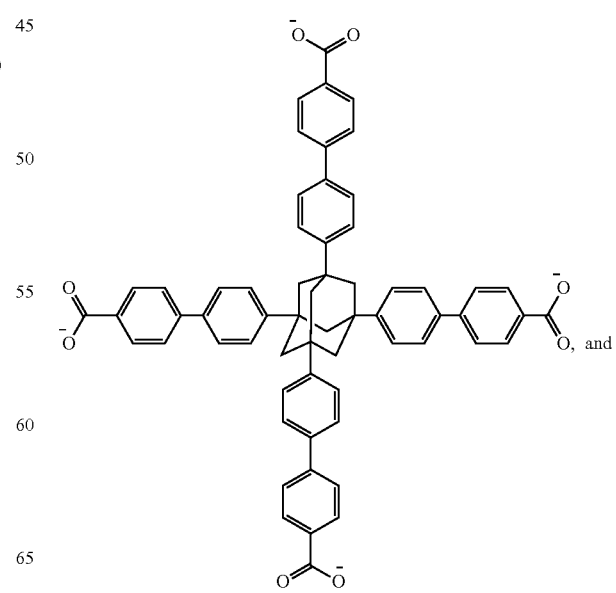

O, and

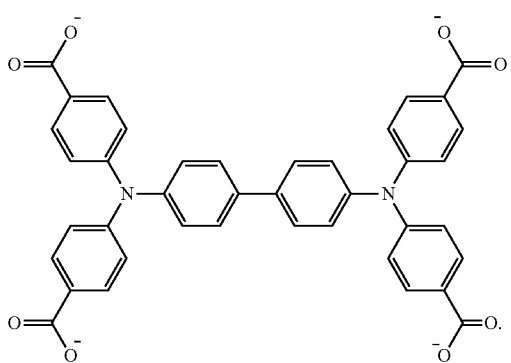

XXII(a)

In another embodiment, L is a tritopic organic linking ligand having one or more structures of Formula I-IV:

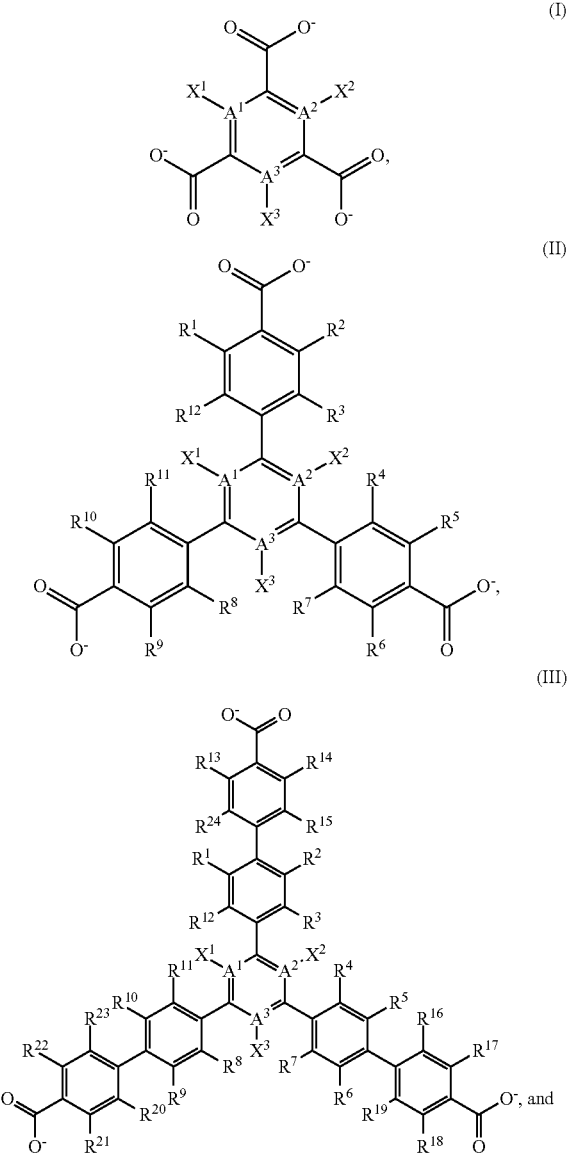

(I)

(II)

(III)

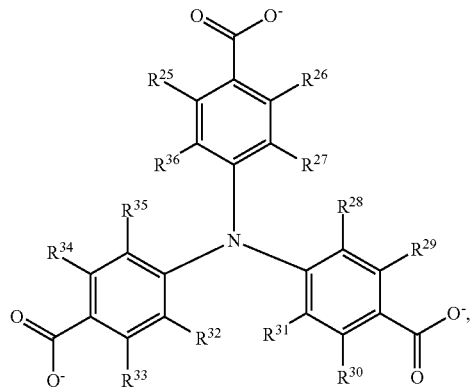

(IV)

wherein, $A^1$-$A^3$ are independently a C, N, O, or S; $X^1$-$X^3$ are independently selected from H, D, optionally substituted FG, optionally substituted $(C_1$-$C_{20})$alkyl, optionally substituted $(C_1$-$C_{19})$heteroalkyl, optionally substituted $(C_1$-$C_{20})$alkenyl, optionally substituted $(C_1$-$C_{19})$heteroalkenyl, optionally substituted $(C_1$-$C_{19})$alkynyl, optionally substituted $(C_1$-$C_{19})$heteroalkynyl, optionally substituted $(C_1$-$C_{19})$cycloalkyl, optionally substituted $(C_1$-$C_{19})$cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system; and $R^1$-$R^{36}$ are independently selected from H, D, optionally substituted FG, optionally substituted $(C_1$-$C_{20})$alkyl, optionally substituted $(C_1$-$C_{19})$heteroalkyl, optionally substituted $(C_1$-$C_{20})$alkenyl, optionally substituted $(C_1$-$C_{19})$heteroalkenyl, optionally substituted $(C_1$-$C_{19})$alkynyl, optionally substituted $(C_1$-$C_{19})$heteroalkynyl, optionally substituted $(C_1$-$C_{19})$cycloalkyl, optionally substituted $(C_1$-$C_{19})$cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system. In another embodiment, L is a tritopic organic linking ligand comprising one or more structures of any one of Formula I-IV:

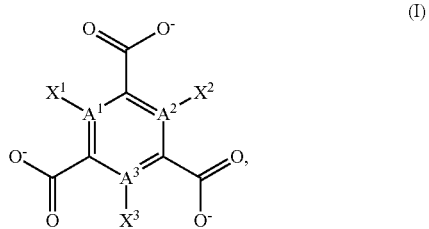

(I)

-continued

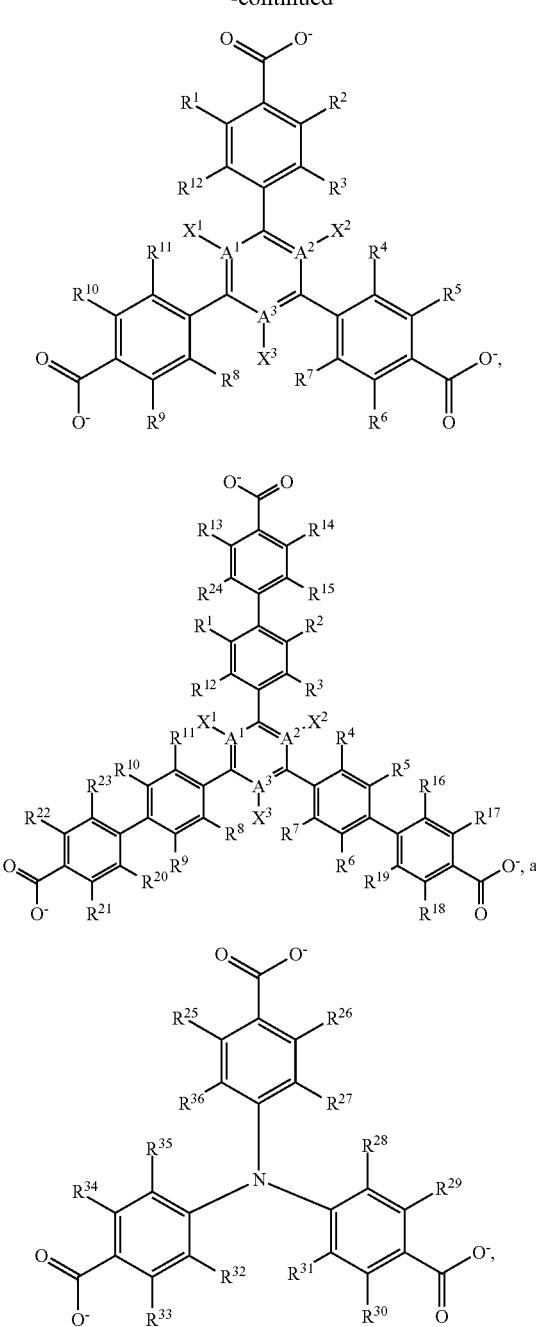

(II)

(III)

(IV)

wherein, $A^1$-$A^3$ are independently a C, N, O, or S; $X^1$-$X^3$ are independently selected from H, D, optionally substituted FG, optionally substituted ($C_1$-$C_{20}$)alkyl, optionally substituted ($C_1$-$C_{19}$)heteroalkyl, optionally substituted ($C_1$-$C_{20}$) alkenyl, optionally substituted ($C_1$-$C_{19}$)heteroalkenyl, optionally substituted ($C_1$-$C_{19}$)alkynyl, optionally substituted ($C_1$-$C_{19}$)heteroalkynyl, optionally substituted ($C_1$-$C_{19}$) cycloalkyl, optionally substituted ($C_1$-$C_{19}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system; and $R^1$, $R^3$-$R^5$, $R^7$-$R^9$, $R^{11}$-$R^{13}$, $R^{15}$-$R^{17}$, $R^{19}$-$R^{21}$, $R^{23}$-$R^{25}$, $R^{27}$-$R^{29}$, $R^{31}$-$R^{33}$, $R^{35}$-$R^{36}$ are H; and $R^2$, $R^6$, $R^{10}$, $R^{14}$, $R^{18}$, $R^{22}$, $R^{26}$, $R^{30}$ and $R^{34}$ are independently selected from amino, methyl, hydroxyl, =O, =S, halo, optionally substituted aryl, optionally substituted aryloxy, alkoxy, —O—($CH_2$)$_n$—$CH_3$, and —O—($CH_2$)$_2$—O—$CH_2$—$CH_3$, wherein n is an integer from 2 to 5. In a further embodiment, L is a tritopic organic linking ligand comprising one or more structures of Formula I(a), II(a), III(a) and IV(a):

I(a)

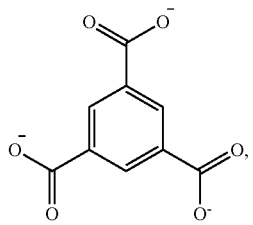

II(a)

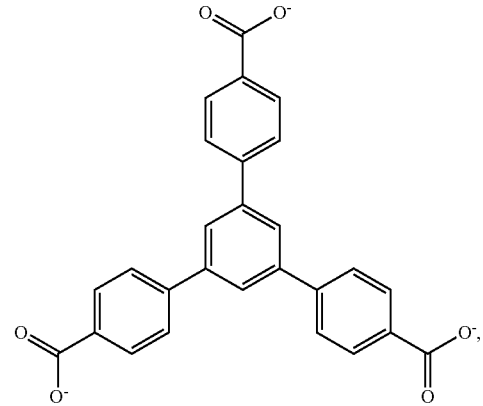

III(a)

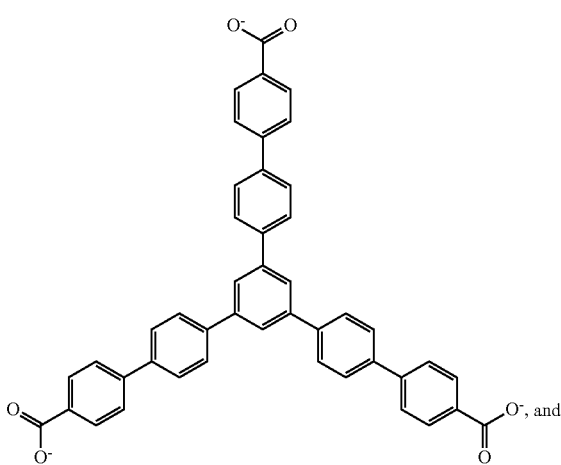

IV(a)

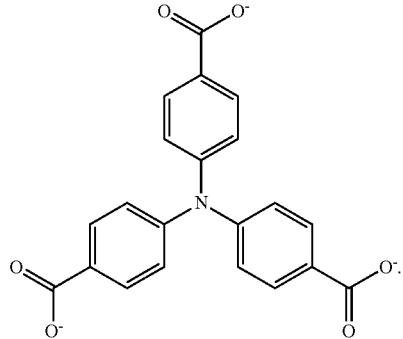

In another embodiment of any of the foregoing M is a metal or metal ion selected from Li$^+$, Na$^+$, K$^+$, Rb$^+$, Cs$^+$, Be$^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $Mo$, $W^{6+}$, $W^{5+}$, $W^{4+}$, $W^{3+}$, $W^{2+}$, $W^+$, $W$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Zn$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, $Ge$, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^2$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, and combinations thereof, including any complexes which contain the metals or metal ions listed above, as well as any corresponding metal salt counteranions. In a further embodiment, M is a metal or metal ion selected from $Li^+$, $Mg^{2+}$, $Ca^{2+}$, $Al^{3+}$, $Al^{2+}$, $Al^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, and combinations thereof, including any complexes which contain the metal ions listed, as well as any corresponding metal salt counteranions. In yet another embodiment of any of the foregoing embodiments, the MOF is MOF-778 (hf-MOF-777). In a further embodiment, M is a zirconium metal or zirconium metal ion, including any complexes which contain zirconium, as well as any corresponding metal salt counteranions. In another embodiment, the plurality of linked M-O-L SBUs are zirconium carboxylate clusters that have 3-c, 4-c, 6-c, 8-c, 9-c, 10-c, or 12-c extensions. In yet a further embodiment, the MOF is MOF-801, MOF-802, MOF-803, MOF-804, MOF-805, MOF-806, MOF-807, MOF-808, MOF-812, MOF-841, MOF-842 or MOF-867. In another embodiment, the plurality of linked M-O-L SBUs are hexagonal zirconium carboxylate clusters linked by benzene-tribenzoic acid (BTB)-based organic linking moieties. In a further embodiment, the MOF has tfz-d type 3D topology that is based upon the stacking of kgd-a type 2D layers. In yet another embodiment, the layers are connected to each other via linking anions. In yet a further embodiment, the linking anions are selected from formate, acetate, phthalate, lactate, oxalate, citrate, fumurate, adipate, anthranilate, ascorbate, benzoate, butyrate, lactate, malate, malonate, tatrate, succinate, sorbate, cinnamate, glutamate, gluconate, propionate, pavalate, and valerate. In another embodiment, the linking anion is formate. In yet another embodiment, the MOF is MOF-777. In another embodiment, the linking anions comprise acid site precursors. In yet a further embodiment, the acid site precursors are selected from $F^-$, $Cl^-$, $ClO^-$, $ClO_2^-$, $ClO_3^-$, $ClO_4^-$, $Br^-$, $BrO^-$, $I^-$, $IO_3^-$, $IO_4^-$, $NO_3^-$, $S_2^-$, $HS^-$, $HSO_3^-$, $SO_3^{2-}$, $SO_4^{2-}$, $HSO_4^-$, $H_2PO_4^{2-}$, $PO_4^{3-}$, $CO_3^{2-}$, $HCO_3^-$, $H_3BO_3$, $SiO_3^{2-}$, $PF_6^-$, $CF_3CO_2^-$ and $CF_3SO_3^-$. In yet another embodiment, the acid site precursor is $HSO_3^-$. In another embodiment, the MOF is a strong solid-acid (sa-MOF).

The disclosure also provides a method for producing a strong solid acid MOF (sa-MOF) comprising reacting the organic linking ligand as described above with a zirconium or hafnium metal or metal ion at an elevated temperature for at least 2 hours, in the presence of an acid site precursor. In one embodiment, the acid site precursor compound is selected from $F^-$, $Cl^-$, $ClO^-$, $ClO_2^-$, $ClO_3^-$, $ClO_4^-$, $Br^-$, $BrO^-$, $I^-$, $IO_3^-$, $IO_4^-$, $NO_3^-$, $S_2^-$, $HS^-$, $HSO_3^-$, $SO_3^{2-}$, $SO_4^{2-}$, $HSO_4^-$, $H_2PO_4^{2-}$, $PO_4^{3-}$, $CO_3^{2-}$, $HCO_3^-$, $H_3BO_3^-$, $SiO_3^{2-}$, $PF_6^-$, $CF_3CO_2^-$ and $CF_3SO_3^-$. In another embodiment, the organic linking ligand comprises a structure of Formula I(a), II(a), III(a), or IV(a):

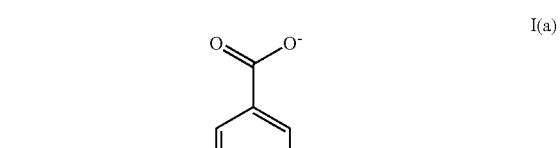

I(a)

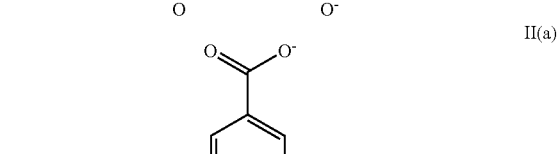

II(a)

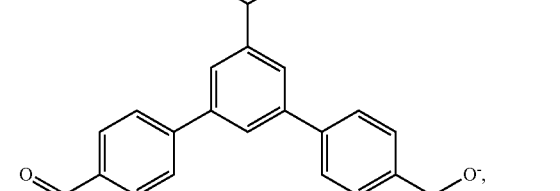

III(a)

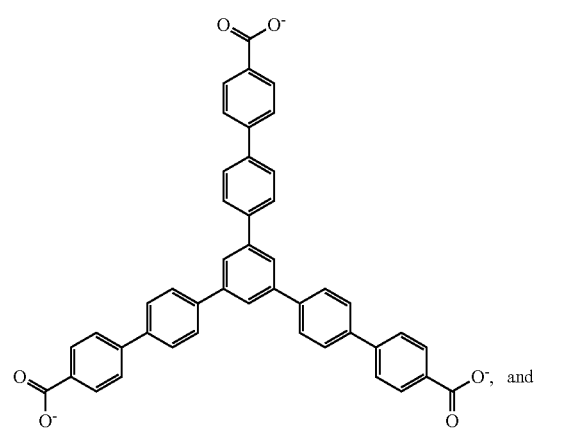

IV(a)

The disclosure also provides a sa-MOF produced by a method described above.

The disclosure also provides a gas storage and/or separation device comprising a MOF of the disclosure.

The disclosure also provides a device comprising a thin film or membrane of a MOF of the disclosure.

The disclosure also provides a catalytic device comprising a sa-MOF of the disclosure.

DESCRIPTION OF DRAWINGS

FIG. 2A-F provides examples of Zr-MOFs by incorporating short/bent linkers with extensions of 12-c. $Zr_6O_4(OH)_4(CO_2)_{12}$ SBU, 10-c. $Zr_6O_6(OH)_2(CO_2)_{10}$ and 8-c. $Zr_6O_8(CO_2)_8$ SBUs. (A) Crystal structure of MOF-801 with octahedral cages (pore fixed size of 7.0 Å) and tetrahedral cages (pore fixed size of 5.4 Å); (B) Crystal structure of MOF-802 with octahedral cages (pore fixed size of 5.6 Å) and tetrahedral cages (pore fixed size of 4.0 Å); (C) Crystal structure of MOF-804 with truncated cubic cages (pore fixed size of 13.6 Å) and octahedral cages (pore fixed size of 8.8 Å); (D) Underlying topology of MOF-801 termed fcu-net; (E) Underlying topology of MOF-802 termed bet-net; and (F) Underlying topology of MOF-803 termed reo-net.

FIG. 3A-C provides examples of hydroxyl-functionalized MOFs by incorporating linear ditopic linkers with extended 12-c. $Zr_6O_4(OH)_4(CO_2)_{12}$ SBUs. (A) Crystal structure of MOF-804 with octahedral cages (pore fixed size of 6.8 Å) and tetrahedral cages (pore fixed size of 7.2 Å); (B) Crystal structure of MOF-805 with octahedral cages (pore fixed size of 8.8 Å) and tetrahedral cages (pore fixed size of 8.6 Å); (C) Crystal structure of MOF-804 with octahedral cages (pore fixed size of 12.6 Å) and tetrahedral cages (pore fixed size of A).

FIG. 4A-B provides examples of incorporating triangle linkers with extended 6-c. $Zr_6O_4(OH)_4(HCOO)_6(CO_2)_6$ SBUs. (A) Crystal structures of MOF-777 and MOF-778 (isomorphous Hf version of MOF-777) in which hexagonal SBUs and the trigonal planar organic linking moiety forms kgd-layers bridged by formate into 3D tfz-d net; and (B) Perpendicular perinterpenetration of kgd-layers in MOF-778.

FIG. 5A-C provides examples of incorporating a square linker with extended 6-c. $Zr_6O_8(HCOO)_6(RCOO)_6$ SBUs. (A) Tetrahedral cage for a tetrahedral linker; (B) Crystal structure possessing a large adamantine-like cage; and (C) Underlying topology of the crystal structure is spn-net.

FIG. 6A-C provides examples of incorporating tetrahedral linkers with extended 8-c. $Zr_6O_8(RCOO)_8$ SBUs. (A) Underlying topology target of flu-net; (B) Crystal structure of MOF-841 which possess a rhombic dodecahedral cage; and (C) Crystal structure of MOF-842, an illustration of isoreticular expansion.

FIG. 7 provides a scheme to produce MOF-777 by linking hexagonal shaped zirconium building units with triangle shaped organic linking ligands.

FIG. 12 provides a schematic showing a top down view of MOF-777's kgd-a net structure showing the connection and placement of hexagonal Zr-SBUs and trigonal planar BTB organic linking moieties.

FIG. 13A-C provides close up views showing that the MOF-777 kgd-layers are linked by formate molecules. (A) X-axis directly out of the page; (B) 10 degree angled view; and (C) 90 degree side view FIG. 14A-E presents a graph showing (A) PXRD variation by increasing the amount of acetic acid; (B) SEM image of crystals formed by using acetic acid; (C) PXRD variation by increasing the amount of formic acid; (D) SEM image of crystals formed by using formic acid; and (E) PXRD variation by increasing amount of formic acid, and where individual peaks have been labeled.

FIG. 15 presents PXRD patterns of MOF-777 and optical microscope images of the crystals formed using the specified conditions.

FIG. 16 provides SEM images of various views of the MOF-777 framework.

FIG. 17A-B provides optical microscope images of MOF-777 using (A) low power magnification; and (B) high power magnification.

FIG. 18 shows disordered SBUs of MOF-777, where the SBUs are orientated 180° to each other.

FIG. 21 provides a comparison of the PRXD patterns for activated MOF-777, as-synthesized MOF-777, and simulated MOF-777.

FIG. 22A-B provides thermogravimetric (TGA) data for (A) MOF-777, and (B) UiO-66 and UiO-77.

FIG. 46 presents a scheme to synthesize MOF-803, an 8-extension Zr-carboxylate SBU. Also shown is an optical image of the crystals of MOF-803 and a depiction of the MOF-803 framework. The structural characteristics of MOF-803, reo-a net topology, and ball and stick model for the 8-extension SBU is further presented.

FIG. 53 presents a scheme to synthesize MOF-804, an OH functionalized Zr-carboxylate SBU. Also shown are a depiction of the MOF-803 framework and the structural characteristics of MOF-803.

FIG. 60 presents a scheme to synthesize MOF-805. A depiction of the MOF-805 framework is also shown.

FIG. 69 provides for the cycle performance of water uptake in MOF-806 at 298 K. The sample was evacuated for 2 h at 298 K between the cycles.

FIG. 70 presents a scheme to synthesize MOF-807. Also shown is a depiction of the MOF-807 framework.

FIG. 75 presents a scheme to synthesize MOF-812, a Zr-carboxylate SBU based upon a tetrahedral linker. Also shown is a depiction of the MOF-812 framework. The structural characteristics of MOF-812, ith-a net topology, and ball and stick model for the 12-c cuboctahedron SBU is further presented.

FIG. 87 presents a scheme to synthesize MOF-867, a Zr-carboxylate SBU based upon a linker which can be metallized. Also shown is a depiction of the MOF-867 framework.

DETAILED DESCRIPTION

Figure 1:
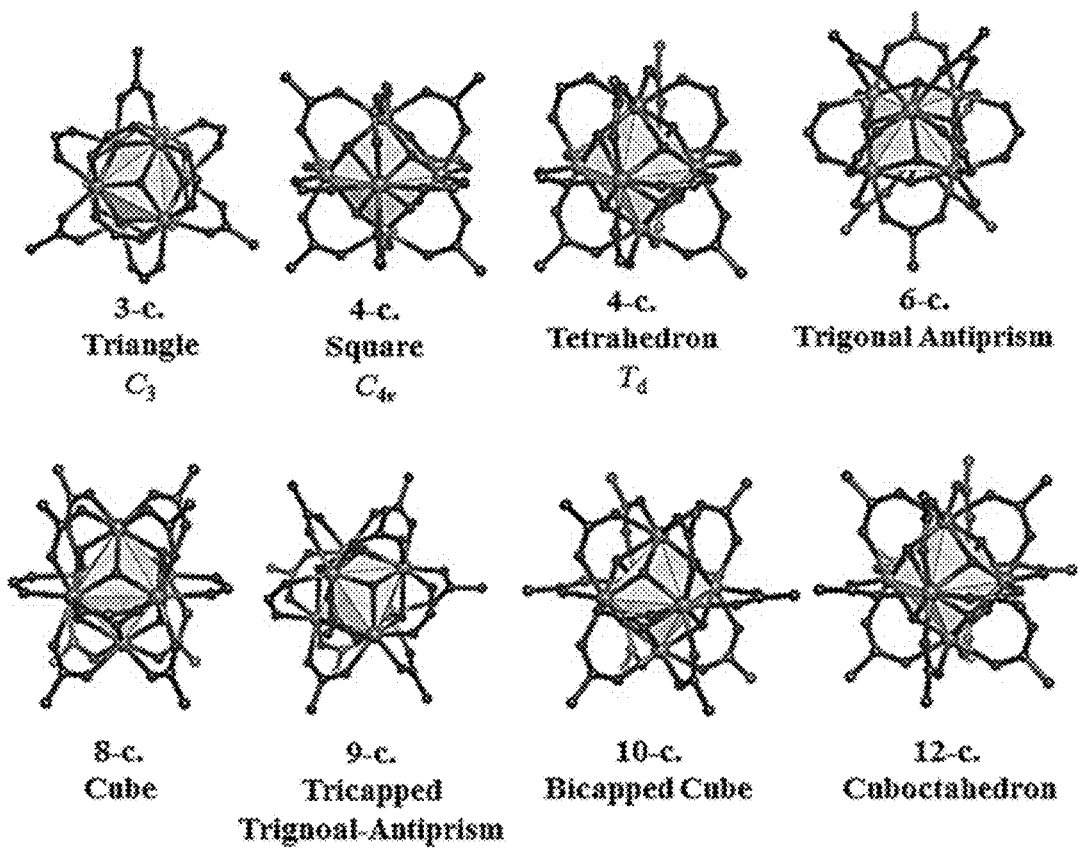
FIG. 1 provides examples of unsaturated zirconium-carboxylate SBUs with variable extension numbers, including a (12-c.) cuboctahedron SBU, a (10-c.) bicapped cube SBU, a (9-c.) tricapped trigonal-antiprism SBU, a (8-c.) cube SBU, a (6-c.) trigonal antiprism SBU, a (4-c.) square SBU, a (4-c.) Tetrahedron SBU, and a (3-c.) triangle SBU. Zr-carboxylate based SBUs have, at the least, the following advantages: high-symmetry, diverse geometries, robustness, and structural prediction.

As used herein and in the appended claims, the singular forms "a," "and," and "the" include plural referents unless the context clearly dictates otherwise. Thus, for example, reference to "an organic linking ligand" includes a plurality of such linking ligands and reference to "the metal ion" includes reference to one or more metal ions and equivalents thereof known to those skilled in the art, and so forth.

Unless defined otherwise, all technical and scientific terms used herein have the same meaning as commonly understood to one of ordinary skill in the art. Although many methods and reagents similar or equivalent to those described herein, the exemplary methods and materials are presented herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

The term "alkyl", refers to an organic group that is comprised of carbon and hydrogen atoms that contain single covalent bonds between carbons. Typically, an "alkyl" as used in this disclosure, refers to an organic group that contains 1 to 30 carbon atoms, unless stated otherwise. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

The term "alkenyl", refers to an organic group that is comprised of carbon and hydrogen atoms that contains at least one double covalent bond between two carbons. Typically, an "alkenyl" as used in this disclosure, refers to organic group that contains 1 to 30 carbon atoms, unless stated otherwise. While a $C_1$-alkenyl can form a double bond to a carbon of a parent chain, an alkenyl group of three or more carbons can contain more than one double bond. It certain instances the alkenyl group will be conjugated, in other cases an alkenyl group will not be conjugated, and yet other cases the alkenyl group may have stretches of conjugation and stretches of nonconjugation. Additionally, if there is more than 1 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise.

The term "alkynyl", refers to an organic group that is comprised of carbon and hydrogen atoms that contains a triple covalent bond between two carbons. Typically, an "alkynyl" as used in this disclosure, refers to organic group that contains 1 to 30 carbon atoms, unless stated otherwise. While a $C_1$-alkynyl can form a triple bond to a carbon of a parent chain, an alkynyl group of three or more carbons can contain more than one triple bond. Where if there is more than 1 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "cycloalkyl", as used in this disclosure, refers to an alkyl that contains at least 3 carbon atoms but no more than 12 carbon atoms connected so that it forms a ring. A "cycloalkyl" for the purposes of this disclosure encompass from 1 to 12 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof.

The term "cycloalkenyl", as used in this disclosure, refers to an alkene that contains at least 3 carbon atoms but no more than 12 carbon atoms connected so that it forms a ring. A "cycloalkenyl" for the purposes of this disclosure encompass from 1 to 12 cycloalkenyl rings, wherein when the cycloalkenyl is greater than 1 ring, then the cycloalkenyl rings are joined so that they are linked, fused, or a combination thereof. A cycloalkenyl may be substituted or unsubstituted, or in the case of more than one cycloalkenyl ring, one or more rings may be unsubstituted, one or more rings may be substituted, or a combination thereof.

The term "aryl", as used in this disclosure, refers to a conjugated planar ring system with delocalized pi electron clouds that contain only carbon as ring atoms. An "aryl" for the purposes of this disclosure encompass from 1 to 12 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof.

The term "heterocycle", as used in this disclosure, refers to ring structures that contain at least 1 noncarbon ring atom. A "heterocycle" for the purposes of this disclosure encompass from 1 to 12 heterocycle rings wherein when the heterocycle is greater than 1 ring the heterocycle rings are joined so that they are linked, fused, or a combination thereof. A heterocycle may be a hetero-aryl or nonaromatic, or in the case of more than one heterocycle ring, one or more rings may be nonaromatic, one or more rings may be hetero-aryls, or a combination thereof. A heterocycle may be substituted or unsubstituted, or in the case of more than one heterocycle ring one or more rings may be unsubstituted, one or more rings may be substituted, or a combination thereof. Typically, the noncarbon ring atom is N, O, S, Si, Al, B, or P. In case where there is more than one noncarbon ring atom, these noncarbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1] heptane.

The terms "heterocyclic group", "heterocyclic moiety", "heterocyclic", or "heterocyclo" used alone or as a suffix or prefix, refers to a heterocycle that has had one or more hydrogens removed therefrom.

The term "hetero-" when used as a prefix, such as, hetero-alkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain. Examples of such non-carbon atoms include, but are not limited to, N, O, S, Si, Al, B, and P. If there is more than one non-carbon atom in the hetero-based parent chain then this atom may be the same element or may be a combination of different elements, such as N and O.

The term "mixed ring system" refers to optionally substituted ring structures that contain at least two rings, and wherein the rings are joined together by linking, fusing, or a combination thereof. A mixed ring system comprises a combination of different ring types, including cycloalkyl, cycloalkenyl, aryl, and heterocycle.

The term "unsubstituted" with respect to hydrocarbons, heterocycles, and the like, refers to structures wherein the parent chain contains no substituents.

The term "substituted" with respect to hydrocarbons, heterocycles, and the like, refers to structures wherein the parent chain contains one or more substituents.

The term "substituent" refers to an atom or group of atoms substituted in place of a hydrogen atom. For purposes of this disclosure, a substituent would include deuterium atoms.

The term "hydrocarbons" refers to groups of atoms that contain only carbon and hydrogen. Examples of hydrocarbons that can be used in this disclosure include, but are not limited to, alkanes, alkenes, alkynes, arenes, and benzyls.

The term "functional group" or "FG" refers to specific groups of atoms within molecules that are responsible for the characteristic chemical reactions of those molecules. While the same functional group will undergo the same or similar chemical reaction(s) regardless of the size of the molecule it is a part of, its relative reactivity can be modified by nearby functional groups. The atoms of functional groups are linked to each other and to the rest of the molecule by covalent bonds. Examples of FG that can be used in this disclosure, include, but are not limited to, substituted or unsubstituted alkyls, substituted or unsubstituted alkenyls, substituted or unsubstituted alkynyls, substituted or unsubstituted aryls, substituted or unsubstituted hetero-alkyls, substituted or unsubstituted hetero-alkenyls, substituted or unsubstituted hetero-alkynyls, substituted or unsubstituted cycloalkyls, substituted or unsubstituted cycloalkenyls, substituted or unsubstituted hetero-aryls, substituted or unsubstituted heterocycles, halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitriles, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, $Si(OH)_3$, $Ge(OH)_3$, $Sn(OH)_3$, $Si(SH)_4$, $Ge(SH)_4$, $AsO_3H$, $AsO_4H$, $P(SH)_3$, $As(SH)_3$, $SO_3H$, $Si(OH)_3$, $Ge(OH)_3$, $Sn(OH)_3$, $Si(SH)_4$, $Ge(SH)_4$, $Sn(SH)_4$, $AsO_3H$, $AsO_4H$, $P(SH)_3$, and $As(SH)_3$.

The term "acidic site precursor" or "acid site precursor" as used herein refers to ligands possessing functional groups capable of becoming Bronsted and/or Lewis acids. Further, "acidic site precursors" can be used in preparing strong solid-acid MOFs (sa-MOFs). Examples of acidic site precursors, include but are not limited to, $F^-$, $Cl^-$, $ClO^-$, $ClO_2^-$, $ClO_3^-$, $ClO_4^-$, $Br^-$, $BrO^-$, $I^-$, $IO_3^-$, $IO_4^-$, $NO_3^-$, $S_2^-$, $HS^-$, $HSO_3^-$, $SO_3^{2-}$, $SO_4^{2-}$, $HSO_4^-$, $H_2PO_4^-$, $PO_4^{3-}$, $CO_3^{2-}$, $HCO_3^-$, $H_3BO_3^-$, $SiO_3^{2-}$, $PF_6^-$ and organic acid anions, such as $CF_3CO_2^-$ and $CF_3SO_3^-$.

As used herein, a wavy line intersecting another line that is connected to an atom indicates that this atom is covalently bonded to another entity that is present but not being depicted in the structure. A wavy line that does not intersect a line but is connected to an atom indicates that this atom is interacting with another atom by a bond or some other type of identifiable association.

Metal-organic frameworks (MOFs) are porous crystalline materials that are constructed by linking metal clusters called Secondary Binding Units (SBUs) and organic linking moieties. MOFs have high surface area and high porosity which enable them to be utilized in diverse fields, such as gas storage, catalysis, and sensors. However, MOFs which are chemically and thermally stable are rare. Further, very few MOFs have been reported to be water resistant and thus capable of absorbing water. Accordingly, MOFs have been generally restricted in their use to gaseous environments and mild environmental conditions (i.e., at temperatures less than 50° C.). However, many industrial and environmental processes are performed under much harsher and variable environments that utilize not only high heat but also solvents.

MOFs comprised of SBUs that comprise metal, metal ions, or metal containing complexes that can form very strong bonds with oxygen atoms from carboxylate based organic linking moieties having specific geometries were found to have high thermal stabilities and resistance to solvents and acids. Accordingly, the MOFs of the disclosure are capable of being utilized under harsh reaction conditions and environments. For example, the MOFs disclosed herein can serve as adsorbents in adsorptive heat transformation processes using aqueous or organic solvents; as proton conducting materials in acidic environments; as strong solid-acid materials; and as catalysts in high temperature and high pressure industrial processes.

The synthesis methods provided herein allow for the production of single-crystal MOFs that are large enough to be characterized by X-ray diffraction, and are generally applicable to allow for the characterization of many new types MOFs which comprise various metals, and linkers varying by length, shapes/geometry, and/or functionality. The syntheses methods disclosed herein allow for control over the extension (e.g., 12, 10, 8, 6 and 4) of metal-carboxylate SBU clusters and can produce MOFs with linear ditopic organic linking moieties, bent ditopic organic linking moieties, tritopic organic linking moieties, square organic linking moieties or tetrahedral organic linking moieties. The MOFs of the disclosure can comprise multivariate metal ratios and functionalities in order to tune the MOFs to have specific adsorption proprieties and pore dynamics. The MOFs of the disclosure are related by being thermal, solvent and/or acid resistant.

Further, due to the acid resistant properties of the MOFs disclosed herein, the MOFs of the disclosure can be synthesized as strong solid-acids, or be modified post synthesis to be strong solid-acids. Strong solid-acids are important catalytic materials that can be used in various industries. For example, solid acid catalysis is heavily used in oil refining and the chemical industry. Although in most cases the nature of the active sites of solid acids are known and its chemical behavior can be modeled or theorized, industries can benefit from solid acid materials that have higher efficiencies, selectivities, stabilities, and environmental friendliness as well as having lower costs. The MOFs disclosed herein are ideally suited as solid-acid substrates. The MOFs acid resistant properties along with a highly ordered structure provide a platform to study and simulate sites for acid precursor incorporation. Moreover, by using various organic linking moieties and metal ions, the MOFs disclosed herein are highly tunable and can be tailored so as to provide suitable solid-acid catalytic environments for particular applications. For example, the solid-acid MOFs (sa-MOFs) disclosed herein can be used to catalyze a variety of reactions including alkylations, isomerizations, condensations, etherifications, acylations, esterifications, nitrations, oligomerizations, Fischer-Tropsch reactions, cracking, and methane oxidative coupling reactions.

In a particular embodiment, the disclosure provides for thermal, acid, and/or solvent resistant metal organic frameworks comprising a plurality of linked M-O-L secondary binding units (SBUs), wherein M is a metal, metal ion, or metal containing complex; O is an oxygen atom of a carboxylate based linking cluster; and L is an organic linking ligand comprising an optionally substituted ($C_1$-$C_{20}$) alkyl, optionally substituted ($C_1$-$C_{20}$) alkenyl, optionally substituted ($C_1$-$C_{20}$) alkynyl, optionally substituted ($C_1$-$C_{20}$) hetero-alkyl, optionally substituted ($C_1$-$C_{20}$) hetero-alkenyl, optionally substituted ($C_1$-$C_{20}$) hetero-alkynyl, optionally substituted ($C_3$-$C_{12}$) cycloalkyl, optionally substituted ($C_3$-$C_{12}$) cycloalkenyl, optionally substituted aryl, optionally substituted heterocycle or optionally substituted mixed ring system, wherein the linking ligand comprises at least two or more carboxylate linking clusters.

In a certain embodiment, the disclosure provides for thermal, acid, and/or solvent resistant metal organic frameworks comprised of a plurality of linked M-O-L secondary binding units (SBUs), wherein M is a metal, metal ion, or metal containing complex; O is an oxygen atom of a carboxylate based linking cluster; and L is an organic linking ligand comprising one or more structures of Formula I-XII:
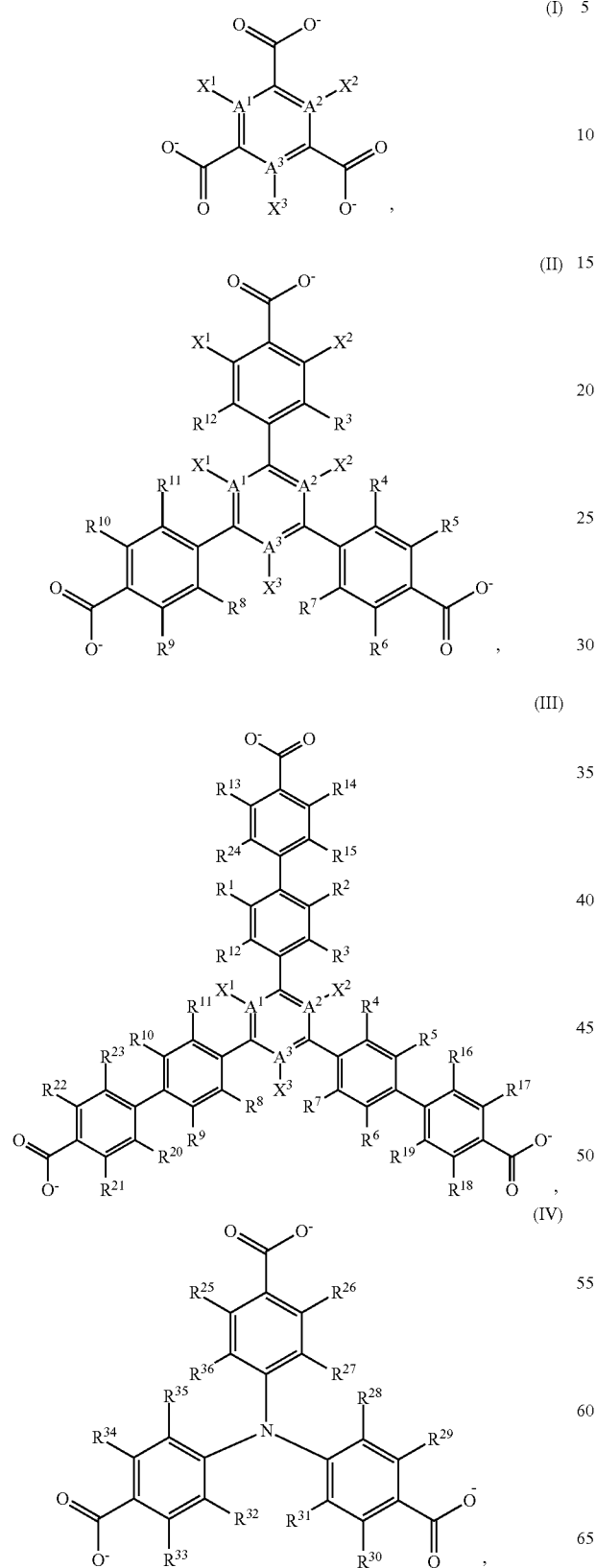
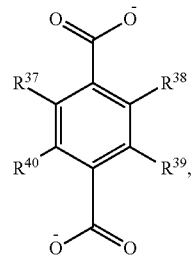

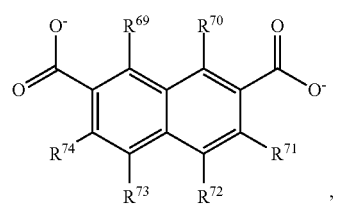
(XI)
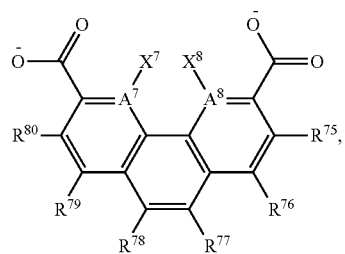
(XII)
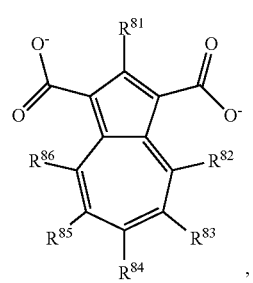
(XIII)
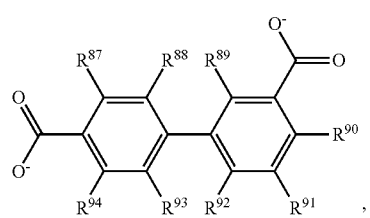
(XIV)
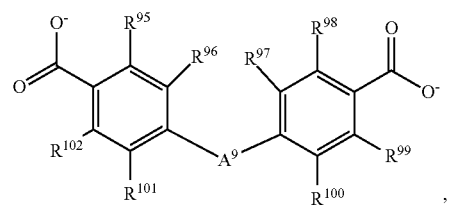
(XV)
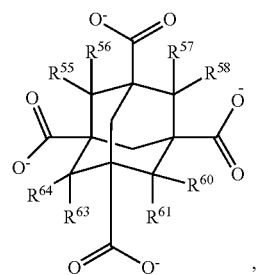
(XVI)
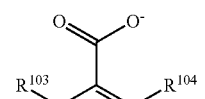
(XVII)
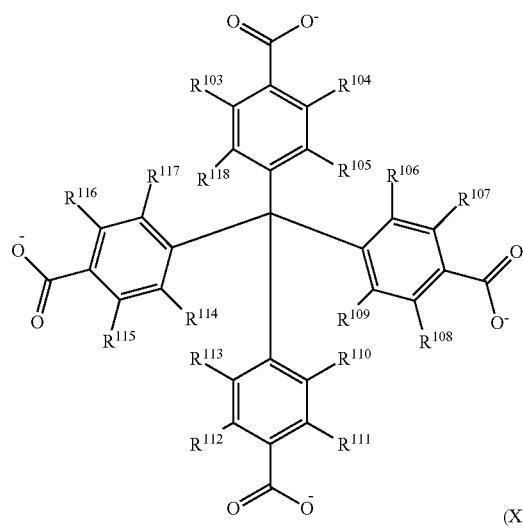
(XVIII)
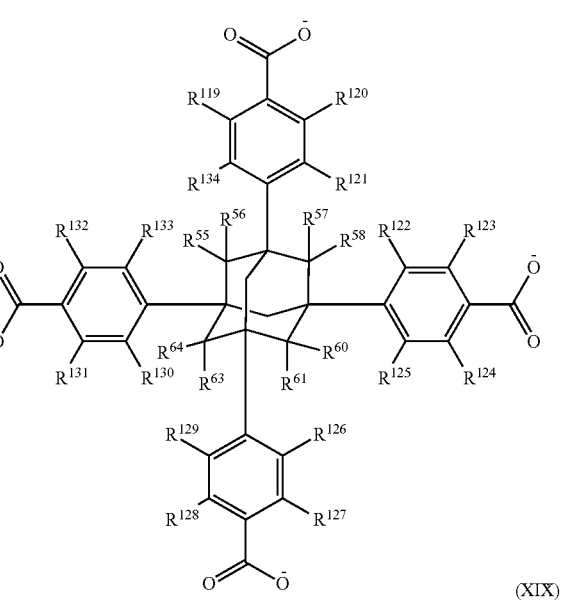
(XIX)
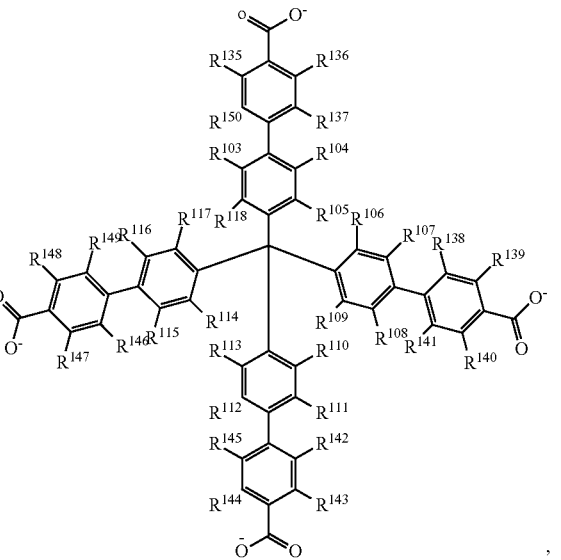

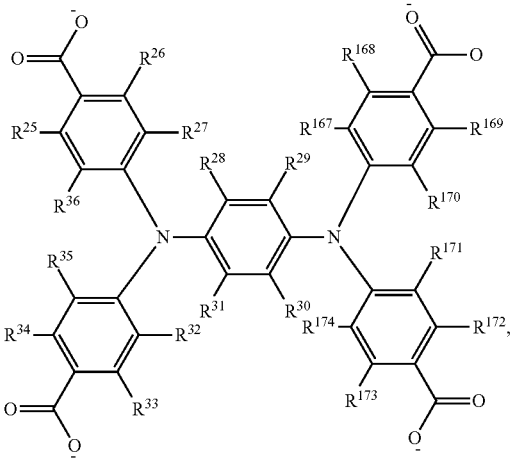

(XX)

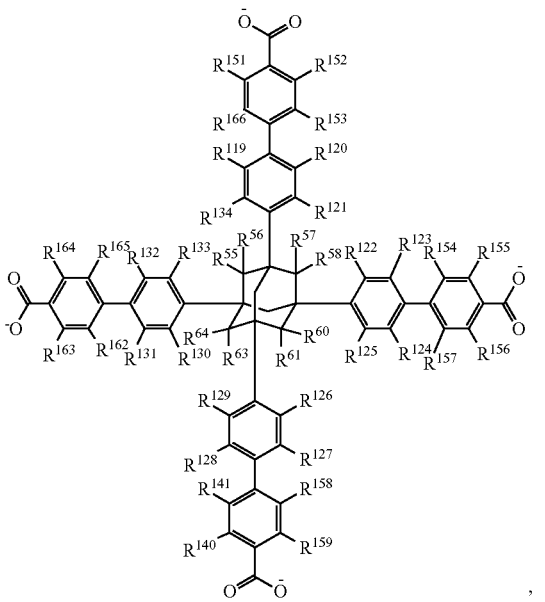

, and (XXI)

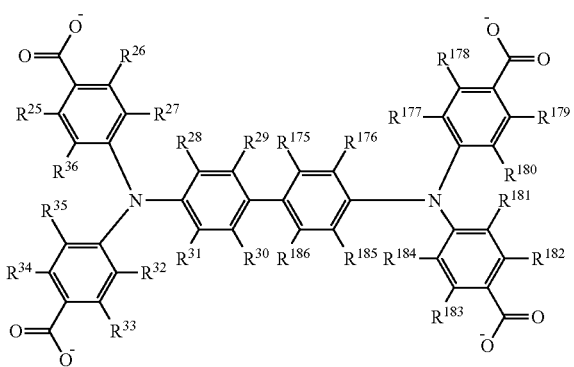

(XXII)

wherein, $A^1$-$A^8$ are independently a C, N, O, or S;
$A^9$ is selected from

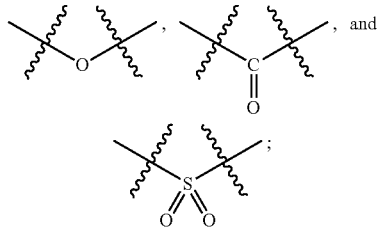

, and

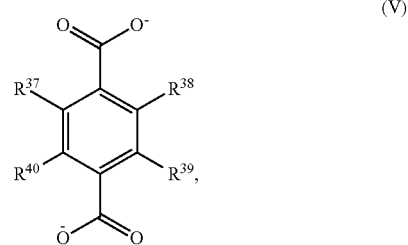

;

$X^1$-$X^8$ are independently selected from H, D, optionally substituted FG, optionally substituted $(C_1$-$C_{20})$alkyl, optionally substituted $(C_1$-$C_{19})$heteroalkyl, optionally substituted $(C_1$-$C_{20})$alkenyl, optionally substituted $(C_1$-$C_{19})$heteroalkenyl, optionally substituted $(C_1$-$C_{19})$alkynyl, optionally substituted $(C_1$-$C_{19})$heteroalkynyl, optionally substituted $(C_1$-$C_{19})$cycloalkyl, optionally substituted $(C_1$-$C_{19})$cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system; and $R^1$-$R^{16}$ are independently selected from H, D, optionally substituted FG, optionally substituted $(C_1$-$C_{20})$alkyl, optionally substituted $(C_1$-$C_{19})$heteroalkyl, optionally substituted $(C_1$-$C_{20})$alkenyl, optionally substituted $(C_1$-$C_{19})$heteroalkenyl, optionally substituted $(C_1$-$C_{19})$alkynyl, optionally substituted $(C_1$-$C_{19})$heteroalkynyl, optionally substituted $(C_1$-$C_{19})$cycloalkyl, optionally substituted $(C_1$-$C_{19})$cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system. It should be noted that a carboxylate is depicted in embodiments of the linking ligands depicted herein. These carboxylates undergo condensation with, e.g., a metal or metal ion to form a M-O bond, wherein M is the metal or metal ion and O is the oxygen of the carboxylate.

In another embodiment, the disclosure provides for thermal, acid, and/or solvent resistant metal organic frameworks comprised of a plurality of linked M-O-L secondary binding units (SBUs), wherein M is a metal, metal ion, or metal containing complex; O is an oxygen atom of a carboxylate based linking cluster; and L is a linear diptopic organic linking ligand comprising one or more structures of Formula V-VII:

(V)

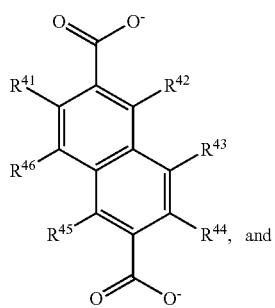
(VI)

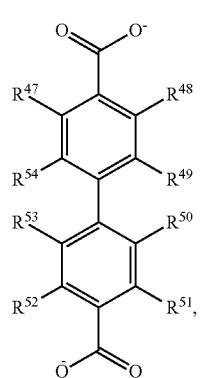
(VII)

wherein, $R^{37}$-$R^{54}$ are independently selected from H, D, optionally substituted FG, optionally substituted $(C_1$-$C_{20})$alkyl, optionally substituted $(C_1$-$C_{19})$heteroalkyl, optionally substituted $(C_1$-$C_{20})$alkenyl, optionally substituted $(C_1$-$C_{19})$heteroalkenyl, optionally substituted $(C_1$-$C_{19})$alkynyl, optionally substituted $(C_1$-$C_{19})$heteroalkynyl, optionally substituted $(C_1$-$C_{19})$cycloalkyl, optionally substituted $(C_1$-$C_{19})$cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system.

In yet another embodiment, the disclosure provides for thermal, acid, and/or solvent resistant metal organic frameworks comprised of a plurality of linked M-O-L secondary binding units (SBUs), wherein M is a metal, metal ion, or metal containing complex; O is an oxygen atom of a carboxylate based linking cluster; and L is a linear diptopic organic linking ligand comprising one or more structures of Formula V(a), VI(a), VI(b) and VII(a):

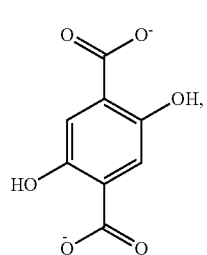
V(a)

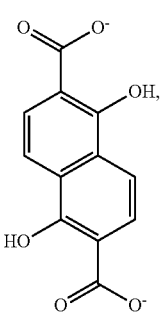
VI(a)

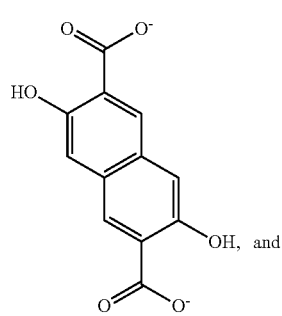
VI(b)

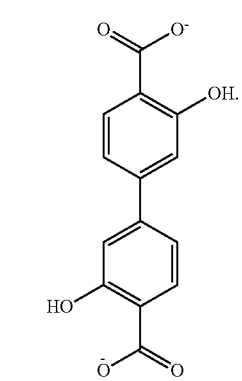
VII(a)

In a particular embodiment, MOFs disclosed herein are based upon extending a 12-carbon cuboctahedral $X_6(\mu_3$-$O/OH)_8(COO)_{12}$ clusters (where X is a metal ion) with linear ditopic linkers, resulting in 3D frameworks which possess tetrahedral cages and octahedral cages in fcu net topology.

In an alternate embodiment, the disclosure provides for thermal, acid, and/or solvent resistant metal organic frameworks comprised of a plurality of linked M-O-L secondary binding units (SBUs), wherein M is a metal, metal ion, or metal containing complex; O is an oxygen atom of a carboxylate based linking cluster; and L is a bent diptopic organic linking ligand comprising one or more structures of Formula VIII-XV:

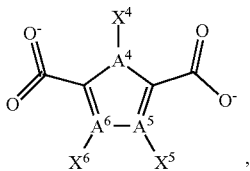
(VIII)

-continued (IX) 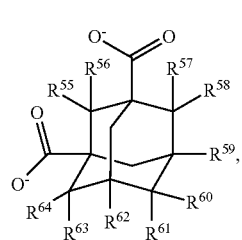

(X) 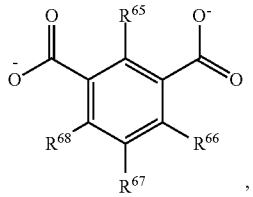

(XI) 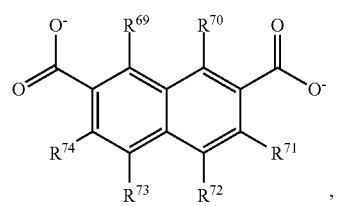

(XII) 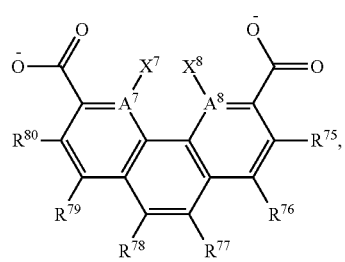

(XIII) 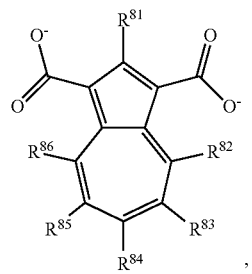

(XIV) 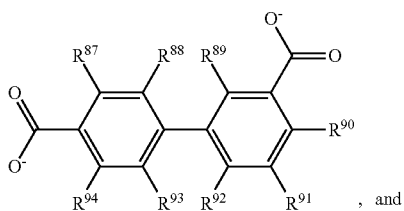, and (XV) 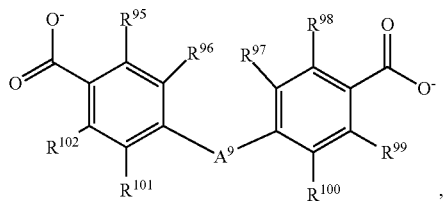

wherein, $A^4$-$A^8$ are independently a C, N, O, or S;

$A^9$ is selected from

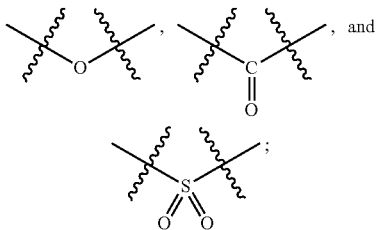, and ;

$X^4$-$X^8$ are independently selected from H, D, optionally substituted FG, optionally substituted ($C_1$-$C_{20}$)alkyl, optionally substituted ($C_1$-$C_{19}$)heteroalkyl, optionally substituted ($C_1$-$C_{20}$)alkenyl, optionally substituted ($C_1$-$C_{19}$)heteroalkenyl, optionally substituted ($C_1$-$C_{19}$)alkynyl, optionally substituted ($C_1$-$C_{19}$)heteroalkynyl, optionally substituted ($C_1$-$C_{19}$)cycloalkyl, optionally substituted ($C_1$-$C_{19}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system; and $R^{55}$-$R^{102}$ are independently selected from H, D, optionally substituted FG, optionally substituted ($C_1$-$C_{20}$)alkyl, optionally substituted ($C_1$-$C_{19}$)heteroalkyl, optionally substituted ($C_1$-$C_{20}$)alkenyl, optionally substituted ($C_1$-$C_{19}$)heteroalkenyl, optionally substituted ($C_1$-$C_{19}$)alkynyl, optionally substituted ($C_1$-$C_{19}$)heteroalkynyl, optionally substituted ($C_1$-$C_{19}$)cycloalkyl, optionally substituted ($C_1$-$C_{19}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system.

In a further embodiment, the disclosure provides for thermal, acid, and/or solvent resistant metal organic frameworks comprised of a plurality of linked M-O-L secondary binding units (SBUs), wherein M is a metal, metal ion, or metal containing complex; O is an oxygen atom of a carboxylate based linking cluster; and L is a bent diptopic organic linking ligand comprising one or more structures of Formula VIII(a), VIII(b), VIII(c), VIII(d), VIII(e), VIII(f), VIII(g), VIII(h), IX(a), X(a), XI(a), XII(a). XIII(a), XIV(a), XV(a), XV(b), and XV(c):

VIII (a)
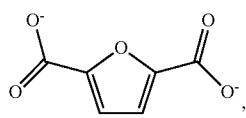

VIII (b)
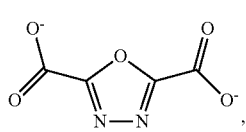

VIII (c)
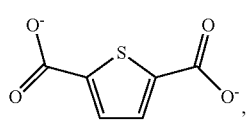

VIII (d)
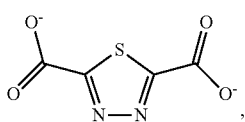

VIII (e)
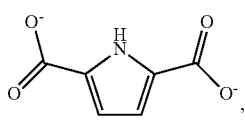

VIII (f)
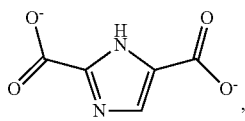

VIII (g)
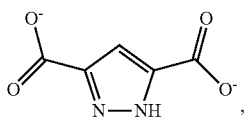

VIII (h)
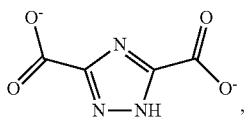

IX (a)
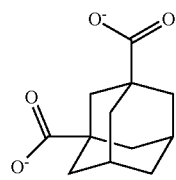

X (a)
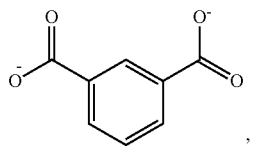

XI (a)
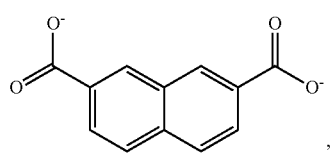

XII (a)
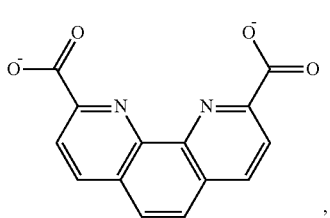

XIII (a)
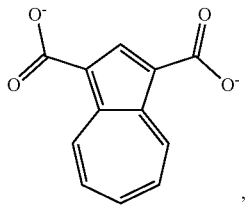

XIV (a)
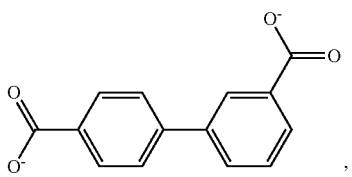

XV (a)
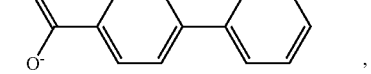

XV (b)
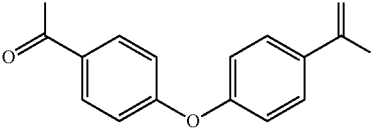

, and

XV (c)
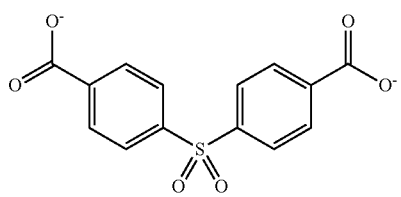

In another embodiment, the disclosure provides for thermal, acid, and/or solvent resistant metal organic frameworks comprised of a plurality of linked M-O-L secondary binding units (SBUs), wherein M is a metal, metal ion, or metal containing complex; O is an oxygen atom of a carboxylate based linking cluster; and L is an organic linking ligand comprising a tetratopic organic linking ligand comprising one or more structures of Formula XVI-XXII:

(XVI)
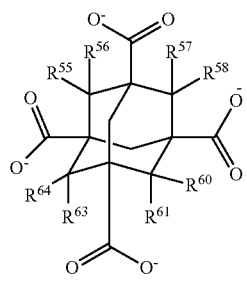

,

51
-continued
(XVII)
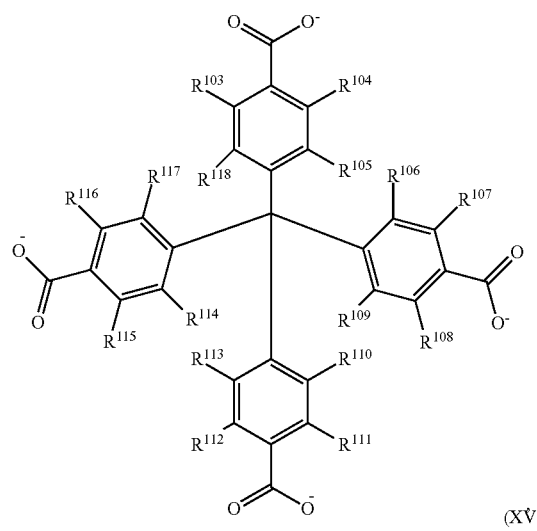
(XVIII)
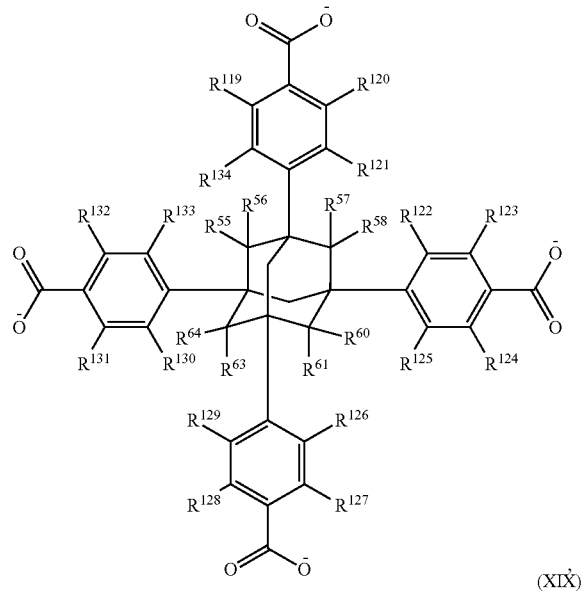
(XIX)
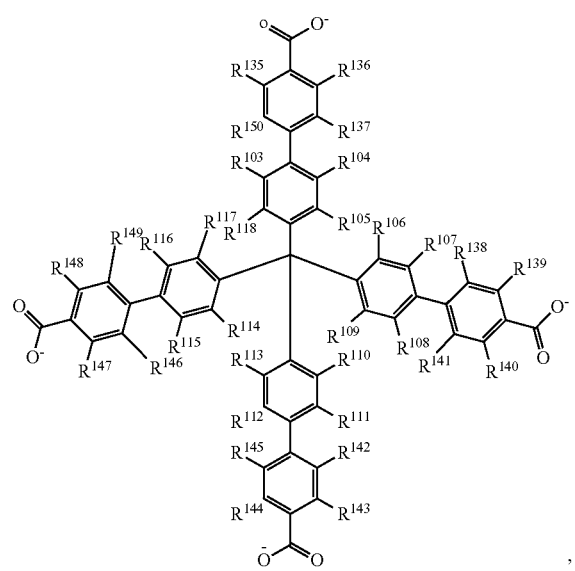
52
-continued
(XX)
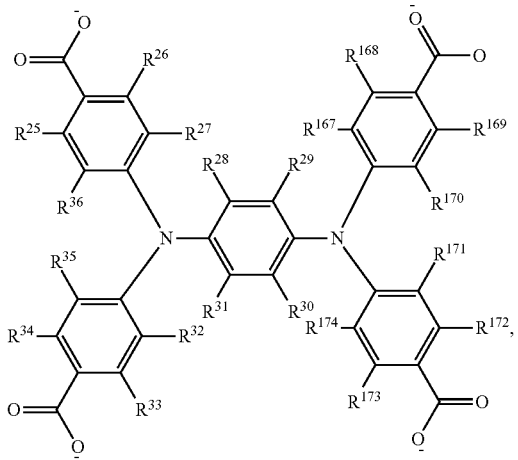
(XXI)
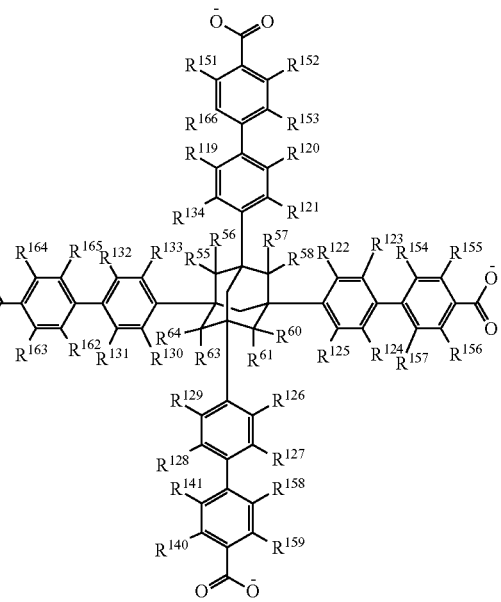
, and
(XXII)
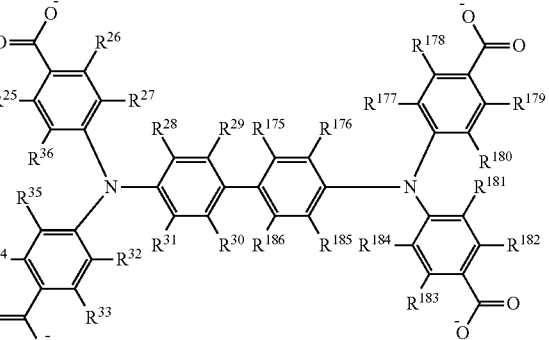
wherein,
$R^{25}$-$R^{36}$, $R^{55}$-$R^{58}$, $R^{60}$, $R^{61}$, $R^{63}$, $R^{64}$, $R^{103}$-$R^{186}$ are independently selected from H, D, optionally substituted FG, optionally substituted $(C_1$-$C_{20})$alkyl, optionally substituted $(C_1$-$C_{19})$heteroalkyl, optionally substituted $(C_1$-$C_{20})$alkenyl, optionally substituted $(C_1$-$C_{19})$heteroalkenyl, optionally substituted ($C_1$-$C_{19}$)alkynyl, optionally substituted ($C_1$-$C_{19}$)heteroalkynyl, optionally substituted ($C_1$-$C_{19}$)cycloalkyl, optionally substituted ($C_1$-$C_{19}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system.

In a further embodiment, the disclosure provides for thermal, acid, and/or solvent resistant metal organic frameworks comprised of a plurality of linked M-O-L secondary binding units (SBUs), wherein M is a metal, metal ion, or metal containing complex; O is an oxygen atom of a carboxylate based linking cluster; and L is an organic linking ligand comprising a tetratopic organic linking ligand comprising one or more structures of Formula XVI(a), XVII(a), XVIII(a), XIX(a), XX(a), XXI(a) and XXII(a):

XVI (a)

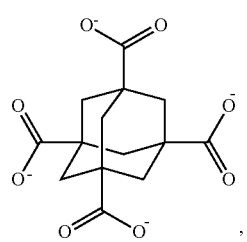

XVII (a)

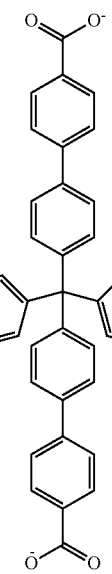

XVIII (a)

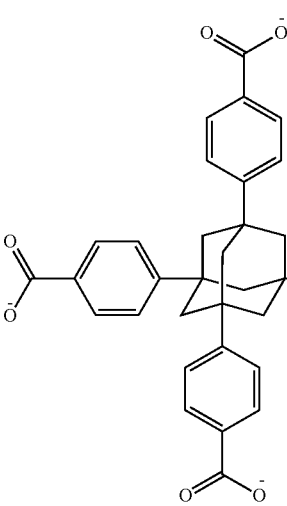

XIX (a)

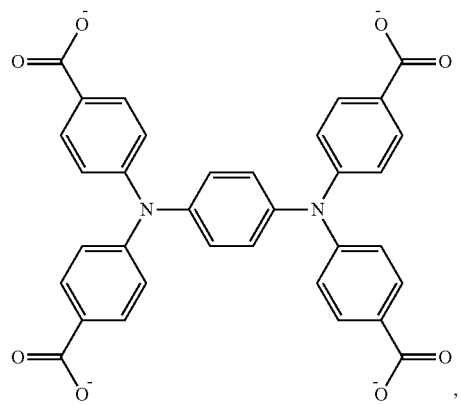

,

XX (a)

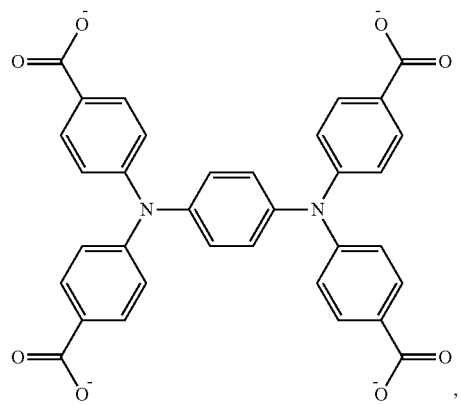

,

XXI (a)

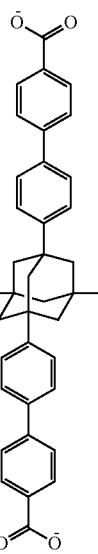

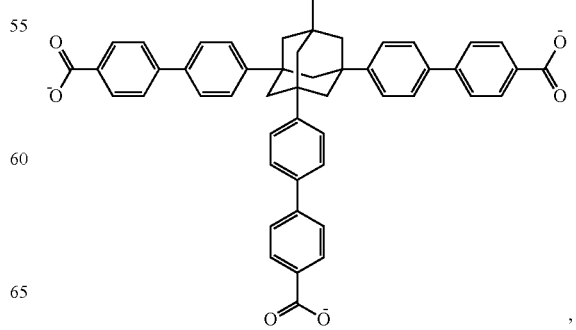

, and

XXII (a)

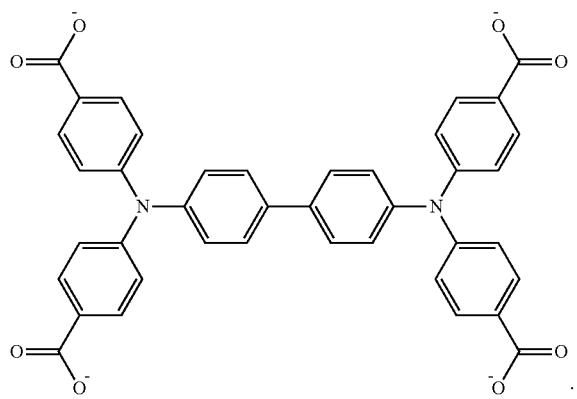

In another embodiment, the disclosure provides for thermal, acid, and/or solvent resistant metal organic frameworks comprised of a plurality of linked M-O-L secondary binding units (SBUs), a MOF of the disclosure comprises a plurality of linked M-O-L secondary binding units (SBUs), wherein M is a metal, metal ion, or metal containing complex; O is an oxygen atom of a carboxylate based linking cluster; and L is a tritopic organic linking ligand having one or more structures of Formula I-IV:

(I)

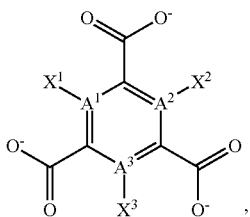

(II)

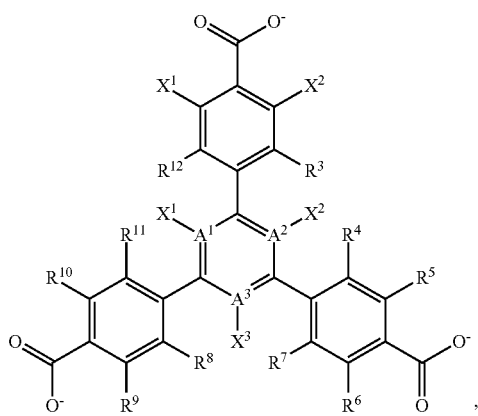

(III)

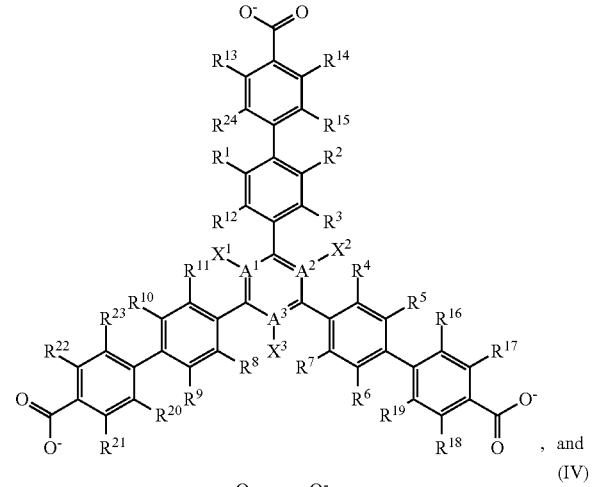

, and (IV)

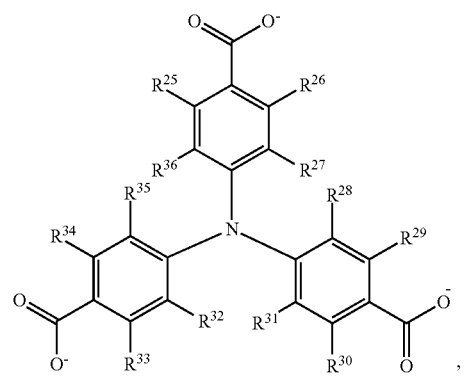

, wherein, $A^1$-$A^3$ are independently a C, N, O, or S;

$X^1$-$X^3$ are independently selected from H, D, optionally substituted FG, optionally substituted $(C_1$-$C_{20})$alkyl, optionally substituted $(C_1$-$C_{19})$heteroalkyl, optionally substituted $(C_1$-$C_{20})$alkenyl, optionally substituted $(C_1$-$C_{19})$heteroalkenyl, optionally substituted $(C_1$-$C_{19})$alkynyl, optionally substituted $(C_1$-$C_{19})$heteroalkynyl, optionally substituted $(C_1$-$C_{19})$cycloalkyl, optionally substituted $(C_1$-$C_{19})$cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system; and $R^1$-$R^{36}$ are independently selected from H, D, optionally substituted FG, optionally substituted $(C_1$-$C_{20})$alkyl, optionally substituted $(C_1$-$C_{19})$heteroalkyl, optionally substituted $(C_1$-$C_{20})$alkenyl, optionally substituted $(C_1$-$C_{19})$heteroalkenyl, optionally substituted $(C_1$-$C_{19})$alkynyl, optionally substituted $(C_1$-$C_{19})$heteroalkynyl, optionally substituted $(C_1$-$C_{19})$cycloalkyl, optionally substituted $(C_1$-$C_{19})$cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system.

In yet another embodiment, the disclosure provides for thermal, acid, and/or solvent resistant metal organic frameworks comprised of a plurality of linked M-O-L secondary binding units (SBUs), a MOF of the disclosure comprises a plurality of linked M-O-L secondary binding units (SBUs), wherein M is a metal, metal ion, or metal containing complex; O is an oxygen atom of a carboxylate based linking cluster; and L is a tritopic organic linking ligand comprising one or more structures of any one of Formula I-IV:

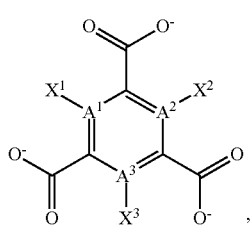
(I)

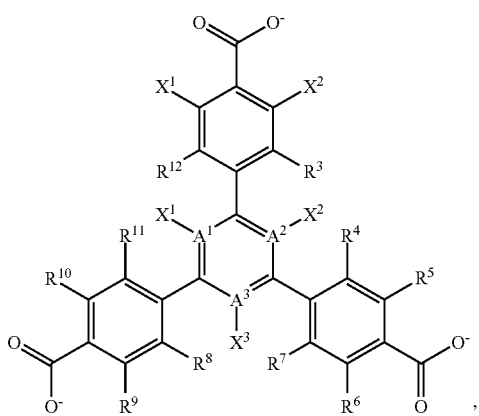
(II)

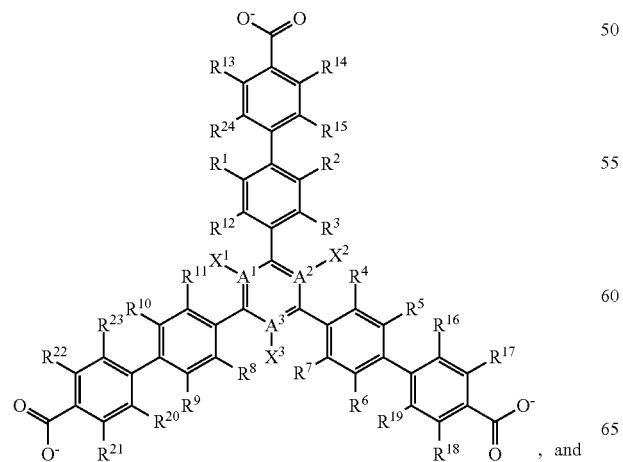
(III), and

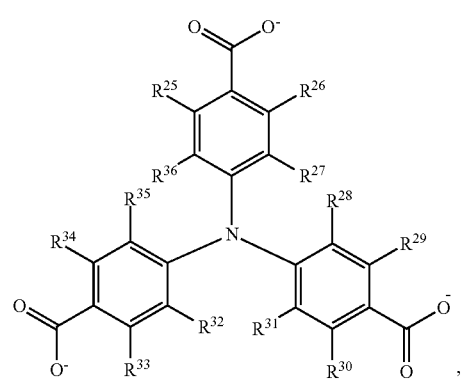
(IV)

wherein, $A^1$-$A^3$ are independently a C, N, O, or S;

$X^1$-$X^3$ are independently selected from H, D, optionally substituted FG, optionally substituted ($C_1$-$C_{20}$)alkyl, optionally substituted ($C_1$-$C_{19}$)heteroalkyl, optionally substituted ($C_1$-$C_{20}$)alkenyl, optionally substituted ($C_1$-$C_{19}$)heteroalkenyl, optionally substituted ($C_1$-$C_{19}$)alkynyl, optionally substituted ($C_1$-$C_{19}$)heteroalkynyl, optionally substituted ($C_1$-$C_{19}$)cycloalkyl, optionally substituted ($C_1$-$C_{19}$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system; and $R^1$, $R^3$-$R^5$, $R^7$-$R^9$, $R^1$-$R^{13}$, $R^{15}$-$R^{17}$, $R^{19}$-$R^{21}$, $R^{23}$-$R^{25}$, $R^{27}$-$R^{29}$, $R^{31}$-$R^{33}$, $R^{35}$-$R^{36}$ are H; and $R^2$, $R^6$, $R^{10}$, $R^{14}$, $R^{18}$, $R^{22}$, $R^{26}$, $R^{30}$ and $R^{34}$ are independently selected from amino, methyl, hydroxyl, =O, =S, halo, optionally substituted aryl, optionally substituted aryloxy, alkoxy, —O—($CH_2$)$_n$—$CH_3$, and —O—($CH_2$)$_2$—O—$CH_2$—$CH_3$, wherein n is an integer from 2 to 5.

In yet another embodiment, the disclosure provides for thermal, acid, and/or solvent resistant metal organic frameworks comprised of a plurality of linked M-O-L secondary binding units (SBUs), a MOF of the disclosure comprises a plurality of linked M-O-L secondary binding units (SBUs), wherein M is a metal, metal ion, or metal containing complex; O is an oxygen atom of a carboxylate based linking cluster; and L is a tritopic organic linking ligand comprising one or more structures of Formula I(a), II(a), III(a) and IV(a):

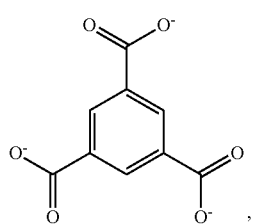
I(a)

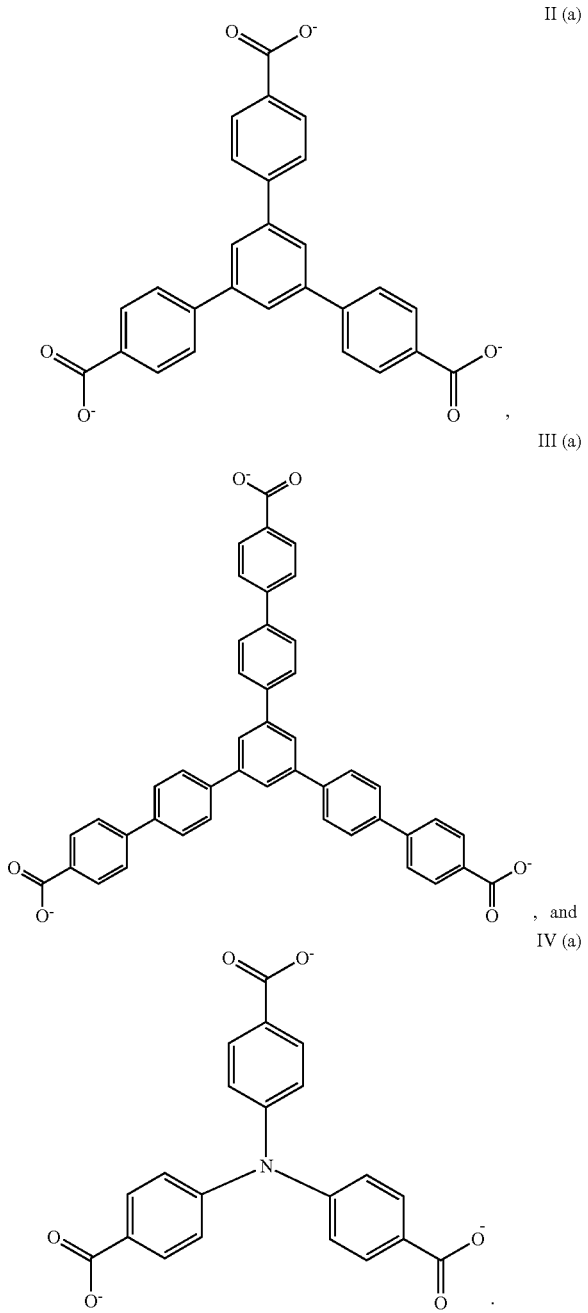

The disclosure further provides for thermal, acid, and/or solvent resistant MOFs that are based on tfz-d type 3D topology resulting from stacking kgd-type 2D structures of hexagonal M-O-L SBUs linked to trigonal planar tritopic organic ligands. In a further embodiment, MOFs disclosed herein have a tfz-d type 3D topology resulting from stacking kgd-type 2D structures of hexagonal M-O-L SBUs linked to trigonal planar tritopic organic ligands having a structure of Formula I-IV. In yet a further embodiment, the thermal, acid, and solvent resistant metal organic frameworks disclosed herein have a tfz-d type 3D topology resulting from stacking kgd-type 2D structures of hexagonal M-O-L SBUs linked to trigonal planar tritopic organic ligands having a structure of Formula I(a), II(a), III(a), or IV(a).

MOFs based on M-O-L SBUs linked to trigonal planar tritopic organic ligands (e.g., MOF-777) have a layer-like topology that allows for exfoliation of layers. So far, very few MOFs have been reported that can exfoliate layers, and most of these MOF either have no apertures or are not stable under ambient conditions. The layers of the kgd-type 2D structures are connected together via interactions with linking anions. For the purpose of this disclosure, "linking anions" are anionic molecules which can form a bond with one or more SBUs so as connect two or more SBUs together in a stacking like arrangement. Examples of "linking anions," include but are not limited to, formate, acetate, phthalate, lactate, oxalate, citrate, fumarate, adipate, anthranilate, ascorbate, benzoate, butyrate, lactate, malate, malonate, tatrate, succinate, sorbate, cinnamate, glutamate, gluconate, propionate, pavalate, and valerate. In a particular embodiment, MOFs comprising kgd-type 2D structures are connected together with linking anions to form 3D MOFs with tfz-d topology (e.g., MOF-777).

In a certain embodiment, one or more metals and/or metal ions, that can be used in the (1) synthesis of a thermal, acid, and/or solvent resistant MOF of the disclosure, (2) exchanged post synthesis of the MOF disclosed herein, and/or (3) added to a MOF disclosed herein by forming coordination complexes with post framework reactant linking clusters, include, but are not limited to, $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $Mo$, $W^{6+}$, $W^{5+}$, $W^{4+}$, $W^{3+}$, $W^{2+}$, $W^+$, $W$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Zn$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{3+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, $Ge$, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, and combinations thereof, including any complexes which contain the metals or metal ions listed above, as well as any corresponding metal salt counter-anions.

In a further embodiment, one or more metal ions, that can be used in the (1) synthesis of a thermal, acid, and/or solvent resistant MOF of the disclosure, (2) exchanged post synthesis of the MOF disclosed herein, and/or (3) added to a MOF disclosed herein by forming coordination complexes with post framework reactant linking clusters, include, but are not limited to, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $Mo$, $W^{6+}$, $W^{5+}$, $W^{4+}$, $W^{3+}$, $W^+$, $W$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Zn$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, $Ge$, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, and combinations thereof, including any complexes which contain the metal ions listed, as well as any corresponding metal salt counter-anions.

In another embodiment, one or more metal ions, that can be used in the (1) synthesis of a thermal, acid, and/or solvent resistant MOF of the disclosure, (2) exchanged post synthesis of the MOF disclosed herein, and/or (3) added to a MOF disclosed herein by forming coordination complexes with post framework reactant linking clusters, include, but are not limited to, $Mg^{2+}$, $Ca^{2+}$, $Al^{3+}$, $Al^{2+}$, $Al^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, and combinations thereof, including any complexes which contain the metal ions listed, as well as any corresponding metal salt counter-anions.

In yet another embodiment, one or more metal ions, that can be used in the (1) synthesis of a thermal, acid, and/or solvent resistant MOF of the disclosure, (2) exchanged post synthesis of the MOF disclosed herein, and/or (3) added to a MOF disclosed herein by forming coordination complexes with post framework reactant linking clusters, include, but are not limited to, $Ti^{4+}$, $Ti^{3+}$, $Ti^{2+}$, $Zr^{4+}$, $Zr^{3+}$, $Zr^{2+}$, $Hf^+$, $Hf^{3+}$, and combinations thereof, including any complexes which contain the metal ions, as well as any corresponding metal salt counter-anions.

In a preferred embodiment, one or more metal ions that can be used in the synthesis of a thermal, acid, and/or solvent resistant MOF of the disclosure comprise $Zr^{3+}$, $Zr^{2+}$, $Hf^+$, $Hf^{3+}$, and combinations thereof, including any complexes which contain the metal ions, as well as any corresponding metal salt counter-anions.

The MOFs of the disclosure may be generated by first utilizing a plurality of linking moieties having different functional groups, wherein at least one of these functional groups may be modified, substituted, or eliminated with a different functional group post-synthesis of the framework. In other words, at least one linking moiety comprises a functional group that may be post-synthesized reacted with a post framework reactant to further increase the diversity of the functional groups of the MOFs disclosed herein.

After MOFs of the disclosure are synthesized, the MOFs may be further modified by reacting with one or more post framework reactants that may or may not have denticity. In a certain embodiment, the MOFs as-synthesized are not reacted with a post framework reactant. In another embodiment, the MOFs as-synthesized are reacted with at least one post framework reactant. In yet another embodiment, the MOFs as-synthesized are reacted with at least two post framework reactants. In a further embodiment, the MOFs as-synthesized are reacted with at least one post framework reactant that will result in adding denticity to the framework.

The disclosure provides for chemical reactions that modify, substitute, or eliminate a functional group post-synthesis of a MOF disclosed herein with a post framework. These chemical reactions may use one or more similar or divergent chemical reaction mechanisms depending on the type of functional group and/or post framework reactant used in the reaction. Examples of chemical reaction include, but are not limited to, radical-based, unimolecular nucleophilic substitution (SN1), bimolecular nucleophilic substitution (SN2), unimolecular elimination (E1), bimolecular elimination (E2), E1cB elimination, nucleophilic aromatic substitution (SnAr), nucleophilic internal substitution (SNi), nucleophilic addition, electrophilic addition, oxidation, reduction, cycloaddition, ring closing metathesis (RCM), pericylic, electrocylic, rearrangement, carbene, carbenoid, cross coupling, and degradation.

All the aforementioned linking moieties that possess appropriate reactive functionalities can be chemically transformed by a suitable reactant post framework synthesis to add further functionalities to the pores. By modifying the organic links within the framework post-synthetically, access to functional groups that were previously inaccessible or accessible only through great difficulty and/or cost is possible and facile.

It is yet further contemplated by this disclosure that to enhance chemoselectivity it may be desirable to protect one or more functional groups that would generate unfavorable products upon a chemical reaction desired for another functional group, and then deprotect this protected group after the desired reaction is completed. Employing such a protection/deprotection strategy could be used for one or more functional groups.

Other agents can be added to increase the rate of the reactions disclosed herein, including adding catalysts, bases, and acids.

In another embodiment, a post framework reactant adds at least one effect to a MOF of the disclosure including, but not limited to, modulating the gas storage ability of the MOF; modulating the sorption properties of the MOF; modulating the pore size of the MOF; modulating the catalytic activity of the MOF; modulating the conductivity of the MOF; and modulating the sensitivity of the MOF to the presence of an analyte of interest. In a further embodiment, a post framework reactant adds at least two effects to the MOF of the disclosure including, but not limited to, modulating the gas storage ability of the MOF; modulating the sorption properties of the MOF; modulating the pore size of the MOF; modulating the catalytic activity of the MOF; modulating the conductivity of the MOF; and modulating the sensitivity of the MOF to the presence of an analyte of interest.

In one embodiment, a post framework reactant can be a saturated or unsaturated heterocycle.

In another embodiment, a post framework reactant has 1-20 carbons with functional groups including atoms such as N, S, and O.

In yet another embodiment, a post framework reactant is selected to modulate the size of the pores of the MOF disclosed herein.

In another embodiment, a post framework reactant is selected to increase the hydrophobicity of the MOF disclosed herein.

In yet another embodiment, a post framework reactant is selected to modulate gas separation of the MOF disclosed herein. In a certain embodiment, a post framework reactant creates an electric dipole moment on the surface of the MOF of the disclosure when it chelates a metal ion.

In a further embodiment, a post framework reactant is selected to modulate the gas sorption properties of the MOF of the disclosure. In another embodiment, a post framework reactant is selected to promote or increase greenhouse gas sorption of the MOF disclosed herein. In another embodiment, a post framework reactant is selected to promote or increase hydrocarbon gas sorption of the MOF of the disclosure.

In yet a further embodiment, a post framework reactant is selected to increase or add catalytic efficiency to the MOF disclosed herein.

In another embodiment, a post framework reactant is selected so that organometallic complexes can be tethered to the MOF of the disclosure. Such tethered organometallic complexes can be used, for example, as heterogeneous catalysts.

The MOFs disclosed herein may be modified to be strong solid-acids, by (1) modifying linking anions used to synthesize the frameworks with acidic site precursors capable of becoming Bronstead and/or Lewis acids (e.g., sulfate, and halide anions); (2) complexing open metal sites or other portions (e.g., pore) of the MOFs disclosed herein with acidic site precursors; and (3) exchanging anions coordinated to the metal, metal ions, or metal containing complexes of the MOFs with acidic site precursors. Further, due to the highly adsorptive nature of the MOFs disclosed herein, MOFs that are strong solid-acids are capable of being superacids. In a particular embodiment, a post framework reactant is an acid site precursor.

In a particular embodiment, the MOFs of the disclosure can be used for catalysis, adsorption and separation, energy gas storage (e.g., hydrogen, methane and other natural gases), greenhouse gas capture, respirator against toxic gas/vapor, adsorptive thermal battery, water supply and purification, proton conductor, photovoltaic device, and radioactive ion capture.

In one embodiment of the disclosure, a gas storage or separation material comprising a MOF of the disclosure is provided. Advantageously, the MOF includes one or more sites for storing and/or separating gas molecules. Gases that may be stored in the gas storage material of the disclosure include gas molecules which have high electron density for attachment to the one or more sites on the surface area of a pore or interpenetrating porous network. Such electron density includes molecules having multiple bonds between two atoms contained therein or molecules having a lone pair of electrons. Suitable examples of such gases include, but are not limited to, the gases comprising a component selected from the group consisting of ammonia, argon, carbon dioxide, carbon monoxide, hydrogen, and combinations thereof. In a particularly useful variation the gas storage material is a hydrogen storage material that is used to store hydrogen ($H_2$). In another particularly useful variation, the gas storage material is a carbon dioxide storage material that may be used to separate carbon dioxide from a gaseous mixture.

The disclosure provides an apparatus and method for separating one or more components from a multi-component gas using a separation system having a feed side and an effluent side separated by a MOF of the disclosure. The MOF may comprise a column separation format.

In an embodiment of the disclosure, a gas storage material comprising a MOF is provided. Gases that may be stored or separated by the methods, compositions and systems of the disclosure includes gas molecules comprising available electron density for attachment to the one or more sites. Such electron density includes molecules having multiple bonds between two atoms contained therein or molecules having a lone pair of electrons. Suitable examples of such gases include, but are not limited to, the gases comprising ammonia, argon, carbon dioxide, carbon monoxide, hydrogen, and combinations thereof. In particularly useful variation, the gas binding material is a carbon dioxide binding material that may be used to separate carbon dioxide from a gaseous mixture. Moreover, the MOFs of disclosure can be used in methods or in devices that have gases or gaseous mixtures that are at temperatures between 50° C. to 525° C., 100° C. to 500° C., 150° C. to 450° C., 200° C. to 400° C., or 250° C. to 350° C.; or at temperatures greater than 50° C., 65° C., 80° C., 100° C., 120° C., 150° C., 200° C., 300° C., or greater than 400° C.

In an embodiment, a gas separation material comprising one or more MOFs disclosed herein is provided. Advantageously, a MOF disclosed herein includes one or more open metal sites for sorption of one or more select gas molecules resulting in separation of these gas molecules from a multicomponent gas. Furthermore, gases that may be separated by one or more MOFs disclosed herein include gas molecules that have available electron density for attachment to the one or more open metal sites on the surface area of a pore or interpenetrating porous network. Such electron density includes molecules having multiple bonds between two atoms contained therein or molecules having a lone pair of electrons. Suitable examples of such gases include, but are not limited to, the gases comprising ammonia, argon, carbon dioxide, hydrogen sulfide, carbonyl sulfide, carbon disulfide, mercaptans, carbon monoxide, hydrogen, and combinations thereof. In a particular embodiment, one or more MOFs disclosed herein, can be used to separate one or more component gases from a multi-component gas mixture. In a certain embodiment, one or more MOFs disclosed herein can be used to separate one or more gases with high electron density from a gas mixture. In another embodiment, one or more MOFs disclosed herein can be used to separate one or more gases with high electron density from one or more gases with low electron density.

In a particular embodiment, one or more MOFs disclosed herein are part of a device. In another embodiment, a gas separation device comprises one or more MOFs of the disclosure. In a further embodiment, a gas separation device used to separate one or more component gases from a multi-component gas mixture comprises one or more MOFs disclosed herein. Examples of gas separation and/or gas storage devices include, but are not limited to, purifiers, filters, scrubbers, pressure swing adsorption devices, molecular sieves, hollow fiber membranes, ceramic membranes, cryogenic air separation devices, and hybrid gas separation devices. In a certain embodiment, a gas separation device used to separate one or more gases with high electron density from gas mixture comprises one or more MOFs of the disclosure. In a further embodiment, a gas separation device used to separate one or more gases with high electron density from one or more low density gases comprises one or more MOFs of the disclosure.

In a particular embodiment of the disclosure, a gas storage material comprises one more MOFs disclosed herein. A gas that may be stored or separated by the methods, compositions and systems of the disclosure includes gas molecules comprising available electron density for attachment to the one or more open metal sites. Such electron density includes molecules having multiple bonds between two atoms contained therein or molecules having a lone pair of electrons. Suitable examples of such gases include, but are not limited to, the gases comprising ammonia, argon, hydrogen sulfide, carbon dioxide, hydrogen sulfide, carbonyl sulfide, carbon disulfide, mercaptans, carbon monoxide, hydrogen, and combinations thereof. In particularly useful variation, a gas binding material is a carbon dioxide binding material that may be used to separate carbon dioxide from a gaseous mixture. In a particularly useful variation a gas storage material is a hydrogen storage material that is used to store hydrogen ($H_2$). In another particularly useful variation, a gas storage material is a carbon dioxide storage material that may be used to separate carbon dioxide from a gaseous mixture.

In yet a further embodiment, one or more MOFs disclosed herein can be used to separate and/or store one or more gases selected from the group comprising carbon monoxide, carbon dioxide, hydrogen sulfide, carbonyl sulfide, carbon disulfide, mercaptans, nitrous oxide, and ozone.

In another embodiment, one or more MOFs disclosed herein can be used to separate and/or store one or more gases selected from the group comprising carbon monoxide, carbon dioxide, hydrogen sulfide, carbonyl sulfide, carbon disulfide, and mercaptans.

In yet another embodiment, one or more MOFs disclosed herein can be used to separate and/or store carbon monoxide or carbon dioxide.

In a certain embodiment, one or more MOFs disclosed herein can be used to separate and/or store carbon dioxide.

In an embodiment, one or more MOFs disclosed herein can be used to separate and/or store hydrogen.

In another embodiment, a gas storage device comprises one or more MOFs disclosed herein. In a further embodiment, a gas storage device used to adsorb and/or absorb one or more component gases from a multi-component gas mixture comprises one or more MOFs disclosed herein. In a certain embodiment, a gas storage device used to adsorb and/or absorb one or more gases with high electron density from gas mixture comprises one or more MOFs disclosed herein. In a further embodiment, a gas storage device used to adsorb and/or absorb one or more gases with high electron density from one or more low density gases comprises one or more MOFs disclosed herein.

In a particular embodiment, the MOFs of the disclosure can be used as a porous thin film, a catalyst, or a smart membrane for gas separation. MOFs disclosed herein that are comprised of stacked layers (e.g., MOF-777) are particularly amendable as thin films or smart membranes in gas separation or gas storage devices.

In a certain embodiment, the MOFs of the disclosure can be used to store gases or other molecules in devices that operate at elevated temperatures, including at temperatures between 50° C. to 525° C., 100° C. to 500° C., 150° C. to 450° C., 200° C. to 400° C., or 250° C. to 350° C.; or at temperatures greater than 50° C., 65° C., 80° C., 100° C., 120° C., 150° C., 200° C., 300° C., or greater than 400° C.

In a another embodiment, the MOFs of the disclosure can be used to separate gases or other molecules in devices that operate at elevated temperatures, including at temperatures between 50° C. to 525° C., 100° C. to 500° C., 150° C. to 450° C., 200° C. to 400° C., or 250° C. to 350° C.; or at temperatures greater than 50° C., 65° C., 80° C., 100° C., 120° C., 150° C., 200° C., 300° C., or greater than 400° C.

In a certain embodiment, the MOFs of the disclosure can be used to store gases or other molecules in devices that operate in acidic environments, aqueous environments, or in the presence of organic solvents. In a further embodiment, the device is a water purification device, photovoltaic device, or radioactive ion capture device.

The disclosure also provides methods using MOFs disclosed herein. In a certain embodiment, a method to separate or store one or more gases comprises contacting one or more gases with one or more MOFs disclosed herein. In a further embodiment, a method to separate or store one or more gases from a mixed gas mixture comprises contacting the gas mixture with one or more MOFs disclosed herein. In yet a further embodiment, a method to separate or store one or more high electron density gases from a mixed gas mixture comprises contacting the gas mixture with one or more MOFs disclosed herein. In a certain embodiment, a method to separate or store one or more gases from a fuel gas stream comprises contacting the fuel gas stream with one or more MOFs disclosed herein. In a further embodiment, a method to separate or store one or more acid gases from a natural gas stream comprises contacting the natural gas stream with one or more MOFs disclosed herein. In yet another embodiment, a method to separate or store one or more gases from the exhaust of a combustion engine comprises contacting the exhaust with one or more MOFs disclosed herein. In a certain embodiment, a method to separate or store one or more gases from flue-gas comprises contacting the flue-gas with one or more MOFs disclosed herein. In a particular embodiment, for the methods provided herein the one or more gases are heated at temperature between 50° C. to 525° C., 100° C. to 500° C., 150° C. to 450° C., 200° C. to 400° C., or 250° C. to 350° C.; or at temperature greater than 50° C., 65° C., 80° C., 100° C., 120° C., 150° C., 200° C., 300° C., or greater than 400° C.

The MOFs of the disclosure can be used for removing contaminants from natural gas streams, including carbon dioxide, hydrogen sulfide, and water vapor. Moreover, due to the acid and water resistant properties of the MOFs disclosed herein, the MOFs of the disclosure are especially suited for natural gas separation and storage. "Natural gas" refers to a multi-component gas obtained from a crude oil well (associated gas) or from a subterranean gas-bearing formation (non-associated gas). The composition and pressure of natural gas can vary significantly. A typical natural gas stream contains methane as a significant component. The natural gas will also typically contain ethane, higher molecular weight hydrocarbons, one or more acid gases (such as carbon dioxide, hydrogen sulfide, carbonyl sulfide, carbon disulfide, and mercaptans), and minor amounts of contaminants such as water, nitrogen, iron sulfide, wax, and crude oil.

In a certain embodiment, one or more MOFs disclosed herein can be used to separate and/or store one or more gases from a natural gas stream. In another embodiment, one or more MOF disclosed herein can be used to separate and/or store one or more acid gases from a natural gas stream. In yet another embodiment, one or more MOFs disclosed herein can be used to separate and/or store one or more gases from a town gas stream. In yet another embodiment, one or more MOFs disclosed herein can be used to separate and/or store one or more gases of a biogas stream. In a certain embodiment, one or more MOFs disclosed herein can be used to separate and/or store one or more gases from a syngas stream.

Sorption is a general term that refers to a process resulting in the association of atoms or molecules with a target material. Sorption includes both adsorption and absorption. Absorption refers to a process in which atoms or molecules move into the bulk of a porous material, such as the absorption of water by a sponge. Adsorption refers to a process in which atoms or molecules move from a bulk phase (that is, solid, liquid, or gas) onto a solid or liquid surface. The term adsorption may be used in the context of solid surfaces in contact with liquids and gases. Molecules that have been adsorbed onto solid surfaces are referred to generically as adsorbates, and the surface to which they are adsorbed as the substrate or adsorbent. Adsorption is usually described through isotherms, that is, functions which connect the amount of adsorbate on the adsorbent, with its pressure (if gas) or concentration (if liquid). In general, desorption refers to the reverse of adsorption, and is a process in which molecules adsorbed on a surface are transferred back into a bulk phase.

MOFs of the disclosure can be used as standard compounds for sorption instruments, and obtained results would be helpful to improve various industrial plants (i.e. separation or recovery of chemical substance).

In a variation of this embodiment, the gaseous storage site comprises a MOF with a pore which has been functionalized with a group having a desired size or charge. In a refinement, this activation involves removing one or more chemical moieties (guest molecules) from the MOF disclosed herein. Typically, such guest molecules include species such as water, solvent molecules contained within the MOF disclosed herein, and other chemical moieties having electron density available for attachment.

The MOFs used in the embodiments of the disclosure include a plurality of pores for gas adsorption. In one variation, the plurality of pores has a unimodal size distribution. In another variation, the plurality of pores have a multimodal (e.g., bimodal) size distribution.

The disclosure further provides for catalyst comprising a MOF of the disclosure (e.g., sa-MOFs). The MOFs disclosed herein, as crystalline material, layered material, or as molding, can be used in the catalytic conversion of organic molecules. Reactions of this type are, for example, oxidations, the epoxidation of olefins, e.g. the preparation of propylene oxide from propylene and $H_2O_2$ the hydroxylation of aromatics, e.g. the preparation of hydroquinone from phenol and $H_2O_2$ or the conversion of toluene into cresol, the conversion of alkanes into alcohols, aldehydes and acids, isomerization, reactions, for example the conversion of epoxides into aldehydes.

The following examples are intended to illustrate but not limit the disclosure. While they are typical of those that might be used, other procedures known to those skilled in the art may alternatively be used.

EXAMPLES

Materials

Formic acid (purity >98%) was obtained from either Aldrich Chemical Co. or from EMD Millipore Chemicals. N,N-Dimethylformamide (DMF), and anhydrous methanol were obtained from EMD Millipore Chemicals; anhydrous acetone was obtained from Acros Organics; zirconium oxychloride octahydrate ($ZrOCl_2 \cdot 8H_2O$, purity ≥99.5%) and Sigmacote® siliconizing reagent were obtained from Sigma-Aldrich Co. Fumaric acid, 2,5-dihydroxy-1,4-benzenedicarboxylic acid [$H_2BDC$—$(OH)_2$], 3,3'-dihydroxy-4,4'-biphenyldicarboxylic acid [$H_2BPDC$—$(OH)_2$], thiophene-2,5-dicarboxylic acid ($H_2TDC$), 1H-pyrazole-3,5-dicarboxylic acid ($H_2PZDC$), hafnium tetrachloride ($HfCl_4$), acetic acid, and N,N-dimethylformamide (DEF) were purchased from Aldrich Chemical Co. obtained from Aldrich. 1,3,5-benzenetricarboxylic acid ($H_3BTC$) was obtained from either Aldrich Chemical Co. or from EMD Millipore Chemicals. 1,5-Dihydroxynaphthalene-2,6-dicarboxylic acid [$H_2NDC$—$(OH)_2$] was purchased from Sugai Chemical Industry (Japan). 4,4',4'',4'''-Methanetetrayltetrabenzoic acid ($H_4MTB$) was prepared according to the published procedure (Si). 4,4'-[(2,5-Dimethoxy-1,4-phenylene)bis(ethyne-2,1-diyl)] dibenzoic acid [$H_2$-PEDB—$(OMe)_2$] was kindly provided by Prof Stoddart group at Northwestern University. All starting materials and solvents, unless otherwise specified, were used without further purification.

General Procedure for Sample Preparation for MOF-801, MOF-802, MOF-803, MOF-804, MOF-805, MOF-806, MOF-807, MOF-808, MOF-812, MOF-841, MOF-842, and MOF-867:

To reduce nucleation in the growth of MOF single-crystals, the inner surface of glass containers were rinsed with Sigmacote® siliconizing reagent, washed three times with acetone, and dried in oven before use. Solvent exchange of the MOFs is performed by immersing the sample in anhydrous methanol or acetone for three days, during which the solvent was decanted and freshly replenished three times per day. For supercritical $CO_2$ activation, the solvent-exchanged MOFs were fully exchanged with liquid $CO_2$, kept under supercritical $CO_2$ atmosphere, and then bled using a Tousimis Samdri PVT-3D critical point dryer.

X-Ray Diffraction Analysis:

Single-crystal X-ray diffraction (SXRD) data were typically collected on a Bruker D8-Venture diffractometer equipped with Mo- ($\lambda$=0.71073 Å) and Cu-target ($\lambda$=1.54184 Å) micro-focus X-ray tubes and a PHOTON 100 CMOS detector, unless indicated otherwise. Additional data was collected using synchrotron radiation in the beamline 11.3.1 of the Advanced Light Source, LBNL.

Powder X-ray diffraction patterns (PXRD) were recorder using a Bruker D8 Advance diffractometer (Göbel-mirror monochromated Cu K$\alpha$ radiation $\lambda$=1.54056 Å). Room-temperature neutron powder diffraction data were collected on the high-resolution neutron powder diffractometer, BT1, at the National Institute of Standards and Technology (NIST) Center for Neutron Research using a Ge(311) monochromator ($\lambda$=2.0781 Å) and a 60 minute collimator.

Nuclear Magnetic Resonance (NMR) and Elemental Mircoanalysis (EA) Analysis:

Solution $^1H$ NMR spectra were acquired on a Bruker AVB-400 NMR spectrometer. EA were performed in the Microanalytical Laboratory of the College of Chemistry at UC Berkeley, using a Perkin Elmer 2400 Series II CHNS elemental analyzer. Attenuated total reflectance (ATR) FTIR spectra of neat samples were performed in-house on a Bruker ALPHA Platinum ATR-FTIR Spectrometer equipped with a single reflection diamond ATR module.

Thermal Gravimetric Analysis:

TGA curves were recorded in-house on a TA Q500 thermal analysis system under air flow.

Isotherm Analysis:

Low-pressure gas ($N_2$ and Ar) adsorption isotherms were recorded in-house on a Quantachrome Autosorb-1 volumetric gas adsorption analyzer. Liquid nitrogen and argon baths were used for the measurements at 77 and 87 K, respectively. Water isotherms were measured in-house on a BEL Japan BELSORP-aqua3, and the water uptake in weight percent (wt %) unit is calculated as [(adsorbed amount of water)/(amount of adsorbent)×100], consistent with the established procedures. Prior to the water adsorption measurements, water (analyte) was flash frozen under liquid nitrogen and then evacuated under dynamic vacuum at least five times to remove any gases in the water reservoir. The measurement temperature was controlled with a water circulator. Helium was used for the estimation of dead space for gas and water adsorption measurements. Ultra-high-purity grade $N_2$, Ar, and He gases (Praxair, 99.999% purity) were used throughout the experiments.

Synthesis of MOF-777 [$Zr_6O_4(OH)_4$](HCOO)$_4$ ($H_2O)_2(OH)_2$ $BTB_2$

In 20 mL vial, zirconium dichloride oxide octahydrate (12 mg, 0.037 mmol) and 1,3,5-tris(4-carboxyphenyl)benzene ($H_3BTB$, 10 mg, 0.023 mmol) were added to N,N-dimethylformamide (DMF, 4 mL). The solution was sonicated for ten minutes. Following the sonication, formic acid (2.5 mL) was added to the solution. The solution was heated at 130° C. in preheated oven for five days. The single crystals were collected and washed with DMF (5×10 mL) over three hour period. The DMF solvent was then replaced with methanol (9×20 mL) over three days period. The methanol was then removed in vacuo (30 mTorr) for 48 hrs.

Synthesis of Hf-MOF-777 [Hf$_6$O$_4$(OH)$_4$](HCOO)$_4$(OH)$_2$(H$_2$O)$_2$ BTB$_2$ In 20 mL vial, hafnium dichloride (12 mg, 0.037 mmol) and 1,3,5-tris(4-carboxyphenyl)benzene (H$_3$BTB, 10 mg, 0.023 mmol) were added to N,N-dimethylformamide (DMF, 4 mL). The solution was sonicated for ten minutes. Following the sonication, formic acid (2.5 ml) was added to the solution. The solution was heated at 130° C. in preheated oven for five days. The single crystals were collected and washed with DMF (5×10 mL) over three hour period. The DMF solvent was then replaced with methanol (9×20 mL) over three days period. The methanol was then removed in vacuo (30 mTorr) for 48 hrs.

Single Crystal Sample of Zr$_6$O$_4$(OH)$_4$(Fumarate)$_6$, MOF-801-SC.

A solvent mixture of fumaric acid (0.081 g, 0.70 mmol) and ZrOCl$_2$.8H$_2$O (0.23 g, 0.70 mmol) in a solvent mixture of DMF/formic acid (35 mL/5.3 mL) were placed in a 60-mL screw-capped glass jar, which was heated at 120° C. for one day. Octahedral colorless crystals were collected and quickly washed three times with 5 mL of fresh DMF (Yield: 0.10 g; 63% based on fumaric acid). $^1$H digested solution NMR of as-synthesized sample (400 MHz, DMSO-d$_6$, ppm): 8.103 (s, 0.5H, 0.5×HCOOH), 7.917 (s, 1H, 1×DMF), 6.621 (s, 2H, 1× Fumarate), 2.871 (s, 3H, 1×DMF), 2.714 (s, 3H, 1×DMF). EA of as-synthesized sample: Calcd. for [Zr$_6$O$_4$(OH)$_4$(C$_4$H$_2$O$_4$)$_6$](C$_3$H$_7$NO)$_6$(HCOOH)$_3$ (H$_2$O)$_{10}$: C, 25.49; H, 3.99; N, 3.96%. Found: C, 25.22; H, 3.19; N, 3.95%. ATR-FTIR (4000-400 cm$^{-1}$): 3151 (br), 1651 (m), 1566 (s), 1384 (s), 1200 (w), 1098 (w), 1062 (m), 984 (m), 793 (m), 739 (w), 640 (s), 483 (s).

As-synthesized MOF-801-SC was rinsed three times per day with 10 mL of DMF for three days and immersed in 10 mL of anhydrous methanol for three days, during which time the solvent was replaced three times per day. The solid was then evacuated at 150° C. for 24 hours to yield activated sample. EA of activated sample: Calcd. for Zr$_6$C$_{24}$H$_{28}$O$_{38}$=[Zr$_6$O$_4$(OH)$_4$(C$_4$H$_2$O$_4$)$_6$](H$_2$O)$_6$: C, 19.59; H, 1.92%. Found: C, 19.40; H, 1.77%. ATR-FTIR (4000-400 cm$^{-1}$): 3217 (br), 1574 (m), 1397 (s), 1212 (w), 983 (w), 795 (w), 653 (s), 490 (m).

Microcrystalline Powder Sample of Zr$_6$O$_4$(OH)$_4$(Fumarate)$_6$, MOF-801-P.

Fumaric acid (5.8 g, 50 mmol) and ZrOCl$_2$.8H$_2$O (16 g, 50 mmol) were dissolved in a solvent mixture of DMF/formic acid (200 mL/70 mL) in a 500-mL screw-capped jar, which was heated at 130° C. for 6 hours. The resulting white precipitate was filtrated using Nylon membrane filters (pore size 0.2-μm), and washed three times with 20 mL of fresh DMF and three times with 50 mL of methanol (Yield: 10 g; 90% based on fumaric acid). As-synthesized MOF-801-P was rinsed three times per day with 50 mL of DMF for three days, and immersed in 100 mL methanol for three days, during which time the methanol was replaced three times per day. The solid was then evacuated at 150° C. for 24 hours to yield activated sample. EA of activated sample: Calcd. for Zr$_6$C$_{24}$H$_{28}$O$_{38}$=[Zr$_6$O$_4$(OH)$_4$(C$_4$H$_2$O$_4$)$_6$](H$_2$O)$_6$: C, 19.59; H, 1.92%. Found: C, 19.25; H, 1.05%.

Zr$_6$O$_4$(OH)$_4$(PZDC)$_5$(HCOO)$_2$(H$_2$O)$_2$, MOF-802

1H-Pyrazole-3,5-dicarboxylic acid (H$_2$PZDC) (0.27 g, 1.5 mmol) and ZrOCl$_2$.8H$_2$O (0.40 g, 1.3 mmol) in a solvent mixture of DMF/formic acid (50 mL/35 mL) were placed in a 125-mL screw-capped glass jar, which was heated at 130° C. for three days. Block colorless crystals were collected and washed three times with 5 mL of fresh DMF (Yield: 0.12 g; 39% based on H$_2$PZDC). $^1$H digested solution NMR of as-synthesized sample (400 MHz, DMSO-d$_6$, ppm): 8.108 (s, 1H, 1×HCOOH), 7.924 (s, 0.8H, 0.8×DMF), 7.086 (s, 1H, 1×PZDC), 2.871 (s, 2.4H, 0.8×DMF), 2.714 (s, 2.4H, 0.8×DMF). EA of as-synthesized sample: Calcd. for Zr$_6$C$_{42}$H$_{66}$O$_{50}$N$_{14}$=[Zr$_6$O$_4$(OH)$_4$ (C$_5$H$_2$N$_2$O$_4$)$_5$(HCOO)$_2$(H$_2$O)$_2$](C$_3$H$_7$NO)$_4$(HCOOH)$_3$(H$_2$O)$_6$: C, 23.86; H, 3.15; N, 9.27%. Found: C, 23.52; H, 3.34; N, 9.18%. ATR-FTIR (4000-400 cm$^{-1}$): 3082 (br), 1653 (m), 1566 (s), 1503 (m), 1463 (m), 1432 (m), 1363 (s), 1196 (m), 1097 (m), 1059 (w), 996 (m), 865 (w), 823 (w), 780 (m), 739 (w), 649 (s), 598 (m), 537 (m), 475 (s).

As-synthesized MOF-802 was rinsed three times per day with 10 mL of DMF for three days, and immersed in 10 mL of anhydrous acetone for three days, during which time the solvent was replaced three times per day. Acetone-exchanged material was activated with a supercritical CO$_2$ activation protocol and evacuated at 120° C. for 24 hours to yield activated sample. EA of activated sample: Calcd. for Zr$_6$C$_{27}$H$_{20}$O$_{34}$N$_{10}$=[Zr$_6$O$_4$(OH)$_4$(C$_5$H$_2$N$_2$O$_4$)$_5$(HCOO)$_2$(H$_2$O)$_2$]: C, 20.58; H, 1.28; N, 8.89%. Found: C, 18.39; H, 0.72; N, 7.56%. ATR-FTIR (4000-400 cm$^{-1}$): 2870 (vw), 1656 (w), 1557 (m), 1462 (w), 1434 (w), 1360 (s), 1187 (w), 1095 (w), 1015 (w), 989 (w), 817 (w), 798 (w), 778 (w), 758 (w), 737 (w), 645 (s), 543 (w), 470 (s).

Zr$_6$O$_4$(OH)$_4$(TDC)$_4$(HCOO)$_4$, MOF-803

Benzene-1,2,4-tricarboxylic acid (H$_2$TDC) (0.069 g, 0.40 mmol) and ZrOCl$_2$.8H$_2$O (0.19 g, 0.60 mmol) in a solvent mixture of DMF/formic acid (20 mL/11 mL) were placed in a 60-mL screw-capped glass jar, which was heated at 130° C. for three days. Cubic colorless crystals were collected and washed three times with 10 mL of fresh DMF (Yield: 0.11 g, 73% based on H$_2$TDC). $^1$H digested solution NMR of activated sample (400 MHz, DMSO-d$_6$, ppm): 8.110 (s, 1H, 1×HCOOH), 7.927 (s, 2H, 2×DMF), 7.697 (s, 2H, 1×TDC), 2.873 (s, 6H, 2×DMF), 2.716 (s, 6H, 2×DMF). EA of as-synthesized sample: Calcd. for Zr$_6$C$_{52}$H$_{88}$O$_{48}$N$_8$S$_4$=[Zr$_6$O$_4$(OH)$_4$(C$_6$H$_2$O$_4$S)$_4$ (HCOO)$_4$](C$_3$H$_7$NO)$_8$ (H$_2$O)$_8$: C, 27.53; H, 3.91; N, 4.94; S, 5.65%. Found: C, 27.72; H, 4.01; N, 4.52; S, 5.34%. ATR-FTIR (4000-400 cm$^{-1}$): 3270 (br), 2928 (vw), 2859 (vw), 1650 (m), 1591 (m), 1562 (m), 1527 (m), 1436 (w), 1374 (s), 1252 (m), 1097 (m), 1061 (w), 1026 (w), 848 (w), 801 (w), 767 (s), 740 (m), 685 (m), 642 (s), 475 (s).

As-synthesized MOF-803 was rinsed three times per day with 10 mL of DMF for three days, and immersed in anhydrous acetone for three days, during which time the acetone was replaced three times per day. The acetone exchanged material then underwent a supercritical CO$_2$ activation protocol and evacuated at 120° C. for 24 hours to yield activated sample. EA of activated sample: Calcd. for Zr$_6$C$_{28}$H$_{26}$O$_{37}$S$_4$=[Zr$_6$O$_4$(OH)$_4$ (C$_6$H$_2$O$_4$S)$_4$(HCOO)$_4$](H$_2$O)$_5$: C, 20.63; H, 1.61, S, 7.87%. Found: C, 20.51; H, 1.27; S, 7.12%. ATR-FTIR (4000-400 cm$^{-1}$): 3233 (br), 1558 (m), 1527 (m), 1373 (s), 1323 (s), 1212 (w), 1125 (w), 1028 (w), 839 (w), 765 (s), 685 (m), 646 (s), 511 (m), 456 (s).

Zr$_6$O$_4$(OH)$_4$(BDC—(OH)$_2$)$_6$, MOF-804

2,5-Dihydroxy-terephthalic acid (H$_2$BDC—(OH)$_2$) (0.040 g, 0.20 mmol) and ZrOCl$_2$.8H$_2$O (0.064 g, 0.20 mmol) in a solvent mixture of DMF/formic acid (10 mL/4 mL) were placed in a 20-mL screw-capped glass vial, which was heated at 120° C. for one day. Yellow precipitate was then obtained by centrifuge, and washed with three times with 5 ml of fresh DMF (Yield: 0.051 g; 80% based on $H_2BDC-(OH)_2$). $^1H$ digested solution NMR of as-synthesized sample (400 MHz, DMSO-$d_6$, ppm): 8.106 (s, 0.3H, 0.3×HCOOH), 7.923 (s, 2H, 2×DMF), 7.267 (s, 2H, 1×BDC—(OH)$_2$), 2.871 (s, 6H, 2×DMF), 2.714 (s, 6H, 2×DMF). EA of as-synthesized sample: Calcd. for $Zr_6C_{86}H_{144}O_{74}N_{12}=[Zr_6O_4(OH)_4(C_8H_4O_6)_6](C_3H_7NO)_{12}$ $(HCOOH)_2(H_2O)_{14}$: C, 33.56; H, 4.72; N, 5.46%. Found: C, 32.53; H, 4.69; N, 5.77%. ATR-FTIR (4000-400 cm$^{-1}$): 3258 (br), 2931 (vw), 2873 (vw), 1651 (s), 1591 (s), 1487 (m), 1456 (m), 1382 (s), 1231 (s), 1099 (m), 1061 (w), 1002 (w), 904 (w), 868 (m), 806 (m), 788 (s), 654 (vs), 610 (m), 570 (s), 480 (s).

As-synthesized MOF-804 was rinsed three times per day with 10 mL of DMF for three days and exchanged solvent with anhydrous methanol for three days, during which time the methanol was replaced three times per day. The methanol exchanged material was then evacuated at 120° C. for 24 hours to yield activated sample. EA of activated sample: Calcd. for $Zr_6C_{48}H_{48}O_{54}=[Zr_6O_4(OH)_4(C_8H_4O_6)_6](H_2O)_{10}$: C, 28.31; H, 2.38%. Found: C, 28.01; H, 1.91%. ATR-FTIR (4000-400 cm$^{-1}$): 3256 (br), 1586 (m), 1489 (m), 1457 (s), 1382 (s), 1234 (s), 1119 (w), 870 (w), 805 (m), 788 (m), 659 (s), 608 (m), 572 (s), 481 (s).

$Zr_6O_4(OH)_4[NDC-(OH)_2]_6$, MOF-805

1,5-Dihydroxy-naphthalene-2,6-dicarboxylic acid ($H_2NDC-(OH)_2$) (0.012 g, 0.050 mmol) and $ZrOCl_2.8H_2O$ (0.032 g, 0.10 mmol) in a solvent mixture of DMF/formic acid (10 mL/2 mL) were placed in a 20-mL screw-capped glass vial, which was heated at 120° C. for one day. Yellow precipitate was then obtained by centrifuge, and washed three times with 3 mL of fresh DMF [Yield: 0.014 g, 78% based on $H_2NDC-(OH)_2$]. $^1H$ digested solution NMR of activated sample (400 MHz, DMSO-$d_6$, ppm): 8.109 (s, 0.25H, 0.25×HCOOH), 7.926 (s, 3H, 3×DMF), 7.811 (d, J=4.4 Hz, 2H, 1×NDC—(OH)$_2$), 7.732 (d, J=4.4 Hz, 2H, 1×NDC—(OH)$_2$), 2.872 (s, 9H, 3×DMF), 2.715 (s, 9H, 3×DMF). EA of as-synthesized sample: Calcd. for $Zr_6C_{127.5}H_{209}O_{85}N_{18}=[Zr_6O_4(OH)_4(C_{12}H_6O_6)_6]$ $(C_3H_7NO)_{18}(HCOOH)_{1.5}(H_2O)_{20}$: C, 39.25; H, 5.40; N, 6.46%. Found: C, 38.73; H, 5.02; N, 6.65%. ATR-FTIR (4000-400 cm$^{-1}$): 3139 (br), 2931 (w), 2874 (w), 1652 (s), 1581 (m), 1485 (m), 1417 (s), 1386 (m), 1334 (m), 1334 (m), 1285 (m), 1190 (m), 1095 (m), 1061 (m), 1016 (w), 896 (w), 866 (vw), 782 (s), 660 (s), 632 (s), 595 (s), 575 (w), 517 (w), 469 (s).

As-synthesized MOF-805 was rinsed three times per day with 5 mL of DMF for three days, and immersed in 5 mL of anhydrous methanol for three days, during which time the solvent was exchanged three times per day. Exchanged material was evacuated at 120° C. for 24 hours to yield activated sample. EA of activated sample: Calcd. for $Zr_6C_{72}H_{50}O_{49}=[Zr_6O_4(OH)_4(C_{12}H_6O_6)_6](H_2O)_5$: C, 38.49; H, 2.24%. Found: C, 38.36; H, 1.74%. ATR-FTIR (4000-400 cm$^{-1}$) 3153 (br), 1656 (w), 1582 (m), 1486 (m), 1420 (s), 1332 (w), 1285 (m), 1191 (m), 1101 (vw), 1025 (vw), 898 (w), 780 (s), 668 (s), 636 (m), 583 (w), 520 (w), 467 (s).

$Zr_6O_4(OH)_4(BPDC-(OH)_2)_6$, MOF-806

3,3'-Dihydroxy-biphenyl-4,4'-dicarboxylic acid ($H_2BPDC-(OH)_2$) (0.014 g, 0.050 mmol) and $ZrOCl_2.8H_2O$ (0.032 g, 0.10 mmol) in a solvent mixture of DMF/formic acid (10 mL/2 mL) were placed in a 20-mL screw-capped glass vial, which was heated at 120° C. for two days. Octahedral colorless crystals were collected and washed three times with 3 mL of fresh DMF [Yield: 0.012 g, 62% based on $H_2BPDC-(OH)_2$]. $^1H$ digested solution NMR of as-synthesized sample (400 MHz, DMSO-$d_6$, ppm): 8.108 (s, 1.25H, 1.25×HCOOH), 7.926 (s, 3H, 3×DMF), 7.877-7.855 (m, 2H, 1×BPDC—(OH)$_2$), 7.274-7.252 (m, 4H, 1×BPDC—(OH)$_2$), 2.874 (s, 9H, 3×DMF), 2.716 (s, 9H, 3×DMF). EA of as-synthesized sample: Calcd. for $Zr_6C_{145.5}H_{229}O_{95}N_{18}=[Zr_6O_4(OH)_4(C_{14}H_8O_6)_6]$ $(C_3H_7NO)_{18}(HCOOH)_{7.5}(H_2O)_{18}$: C, 40.66; H, 5.37; N, 5.87%. Found: C, 36.28; H, 4.83; N, 5.83%. ATR-FTIR (4000-400 cm$^{-1}$): 3226 (br), 2927 (vw), 2873 (vw), 1651 (m), 1604 (m), 1569 (m), 1434 (m), 1374 (s), 1314 (m), 1232 (w), 1165 (w), 1097 (m), 1062 (m), 1035 (w), 974 (w), 876 (m), 849 (vw), 785 (m), 762 (w), 707 (w), 647 (s), 614 (m), 570 (w), 478 (m), 434 (m).

As-synthesized MOF-806 was rinsed three times per day with 5 mL of DMF for three days, and immersed in 5 mL of anhydrous acetone for three days, during which time acetone was replaced three times per day. Acetone exchanged material was activated following a supercritical $CO_2$ activation protocol and evacuated at 120° C. for 24 hours to yield activated sample. EA of activated sample: Calcd. for $Zr_6C_{84}H_{72}O_{54}=[Zr_6O_4(OH)_4(C_{14}H_8O_6)_6](H_2O)_{10}$: C, 40.48; H, 2.91%. Found: C, 39.80; H, 2.34%. ATR-FTIR (4000-400 cm$^{-1}$): 3294 (br), 1632 (m), 1576 (s), 1507 (vw), 1487 (w), 1438 (s), 1375 (s), 1321 (w), 1224 (m), 1192 (w), 1164 (w), 1035 (w), 963 (w), 873 (m), 846 (w), 783 (s), 691 (m), 663 (s), 559 (w), 455 (s), 450 (s).

$Zr_6O_4(OH)_4(BTC)_2(HCOO)_6$, MOF-808

Benzene-1,3,5-tricarboxylic acid ($H_3BTC$) (0.11 g, 0.50 mmol) and $ZrOCl_2.8H_2O$ (0.16 g, 0.50 mmol) in a solvent mixture of DMF/formic acid (20 mL/20 mL) were placed in a 60-mL screw-capped glass jar, which was heated at 100° C. for seven days. Octahedral colorless crystals were collected and washed three times with 10 mL of fresh DMF (Yield: 0.098 g, 70% based on Zr). $^1H$ digested solution NMR of as-synthesized sample (400 MHz, DMSO-$d_6$, ppm): 8.630 (s, 3H, 1×BTC), 8.114 (s, 2H, 2×HCOOH), 7.928 (s, 5H, 5×DMF), 2.874 (s, 15H, 5×DMF), 2.716 (s, 15H, 5×DMF). EA of as-synthesized sample: Calcd. for $Zr_6C_{52}H_{94}O_{43}N_{10}=[Zr_6O_4(OH)_4(C_9H_3O_6)_2(HCOO)_4]$ $(C_3H_7NO)_{10}(H_2O)_5$: C, 29.82; H, 4.52; N, 6.69%. Found: C, 29.74; H, 5.13; N, 6.69%. ATR-FTIR (4000-400 cm$^{-1}$): 3381 (br), 2930 (vw), 2861 (vw), 1651 (m), 1614 (m), 1573 (m), 1497 (w), 1437 (m), 1372 (s), 1252 (m), 1099 (m), 1061 (w), 940 (w), 864 (w), 802 (w), 783 (w), 756 (m), 717 (w), 702 (w), 646 (s), 569 (w), 501 (w), 477 (m), 445 (s).

As-synthesized MOF-808 was rinsed three times per day with DMF for three days, and immersed in 10 mL of anhydrous acetone for three days, during which time the acetone was replaced three times per day. Acetone exchanged material was then applied with supercritical $CO_2$ activation protocol and evacuated at 150° C. for 24 hours to yield activated sample. EA of activated sample: Calcd. for $Zr_6C_{25.5}H_{21.5}O_{33.5}N_{0.5}=[Zr_6O_4(OH)_4 (C_9H_3O_6)_2 (HCOO)_6](C_3H_7NO)_{0.5}(H_2O)$: C, 21.59; H, 1.53, N, 0.49%. Found: C, 21.46; H, 1.46; N, 0.77%. ATR-FTIR (4000-400 cm$^{-1}$): 2867 (br), 1603 (m), 1583 (m), 1447 (m), 1379 (s), 1110 (w), 944 (w), 758 (w), 740 (w), 703 (m), 657 (s), 572 (w), 500 (m), 451 (s).

$Zr_6O_4(OH)_4(MTB)_3(H_2O)_2$, MOF-812

Methanetetrabenzoic acid ($H_4MTB$) (0.048 g, 0.1 mmol) and $ZrOCl_2 \cdot 8H_2O$ (0.064 g, 0.2 mmol) were dissolved in a solvent mixture of DMF/formic acid (10 mL/6 mL) in a 20-mL screw-capped glass vial, which was heated at 130° C. for one day.

$Zr_6O_4(OH)_4(MTB)_2(HCOO)_4(H_2O)_4$, MOF-841

$H_4MTB$ (0.12 g, 0.25 mmol) and $ZrOCl_2 \cdot 8H_2O$ (0.32 g, 1.0 mmol) in a solvent mixture of DMF/formic acid (40 mL/25 mL) were placed in a 125-mL screw-capped glass jar, which was heated at 130° C. for two days. Mother liquor of the reaction mixture was separated and further heated at 130° C. for another two days. Colorless block crystals were collected and washed three times with 5 mL of fresh DMF (Yield: 0.13 g, 55% based on $H_4MTB$). $^1H$ digested solution NMR of as-synthesized sample (400 MHz, DMSO-$d_6$, ppm): 8.111 (s, 2H, 2×HCOOH), 7.929 (s, 5H, 5×DMF), 7.883 (d, J=4.4 Hz, 8H, 1×MTB), 7.335 (d, J=4.4 Hz, 8H, 1×MTB), 2.875 (5s, 15H, 5×DMF), 2.717 (s, 15H, 5×DMF). EA of as-synthesized sample: Calcd. for $Zr_6C_{92}H_{134}O_{54}N_{10}=[Zr_6O_4(OH)_4(C_{29}H_{16}O_8)_2(HCOO)_4(H_2O)_4](C_3H_7NO)_{10}(H_2O)_8$: C, 39.58; H, 4.84; N, 5.02%. Found: C, 39.11; H, 4.91; N, 5.09%. ATR-FTIR (4000-400 $cm^{-1}$): 3382 (br), 2930 (vw), 2860 (vw), 1652 (m), 1602 (m), 1583 (m), 1564 (m), 1541 (m), 1407 (s), 1253 (m), 1191 (m), 1151 (w), 1096 (w), 1061 (w), 1017 (w), 860 (w), 837 (w), 772 (m), 743 (w), 719 (w), 695 (w), 646 (s), 523 (m), 454 (s).

As-synthesized MOF-841 was rinsed three times per day with 10 mL of DMF for three days and immersed in 10 mL of anhydrous acetone for three days, during which time the acetone was replaced three times per day. Acetone exchanged material was activated by first undergoing a supercritical $CO_2$ activation protocol and then being evacuated at 120° C. for 24 hours. EA of activated sample: Calcd. for $Zr_6C_{62}H_{48}O_{36}=[Zr_6O_4(OH)_4(C_{29}H_{16}O_8)_2(HCOO)_4(H_2O)_4]$: C, 38.86; H, 2.52%. Found: C, 39.15; H, 2.16%. ATR-FTIR (4000-400 $cm^{-1}$): 2858 (vw), 1596 (m), 1559 (m), 1407 (s), 1380 (m), 1366 (m), 1336 (m), 1194 (w), 1152 (w), 1019 (w), 839 (w), 771 (m), 751 (m), 719 (m), 664 (m), 570 (w), 525 (m), 457 (s).

Powdered X-Ray Diffraction (PXRD) of MOF-777:

Single-crystal X-ray diffraction data for MOF-777 were collected at 100 K using a Bruker Platinum 200 diffractometer with synchrotron radiation ($\lambda$=0.774900 Å) at Beamline 11.3.1 at the Advanced Light Source (ALS), Lawrence Berkeley National Laboratory. Powder X-ray diffraction data were collected using Rigaku D/MAX-RB (12 KW) diffractometer at 40 kV, 100 mA for $CuK_\alpha$ radiation ($\lambda$=1.5406 Å). For single crystal XRD measurement, 100 μm size of MOF-777 was used and for PXRD measurement, obtained as synthesized single crystal was washed with DMF solvent and grinded for sample preparations.

$N_2$ Isotherms for Surface Area of MOF-777:

Low-pressure gas adsorption isotherms were carried out volumetrically. $N_2$ isotherm of MOF-777 was measured using a Quadrasorp (Quantachrome Instruments). A liquid nitrogen sample bath (77 K) was used for $N_2$ measurements. The $N_2$ gas was UHP grade. For measurement of the surface areas, the BET method was applied using the adsorption branches of the $N_2$ isotherms assuming a $N_2$ cross sectional area of 16.2 $Å^2$/molecule. For activation process of MOF-777, the obtained crystals were washed with DMF for 3 days 9 times and DMF solvent was exchanged with methanol in the 20 mL vials for 3 days changing the methanol solvent 9 times. After drying the crystals at vacuum (30 mTorr) for 12 hrs, at room temperature. Finally, 98 mg of the crystals was transferred to glass tube and $N_2$ isotherm measurements were carried out. For the calculation of surface area correlation coefficient was 0.99997 and BET C-value was 2350.

Figure 8:
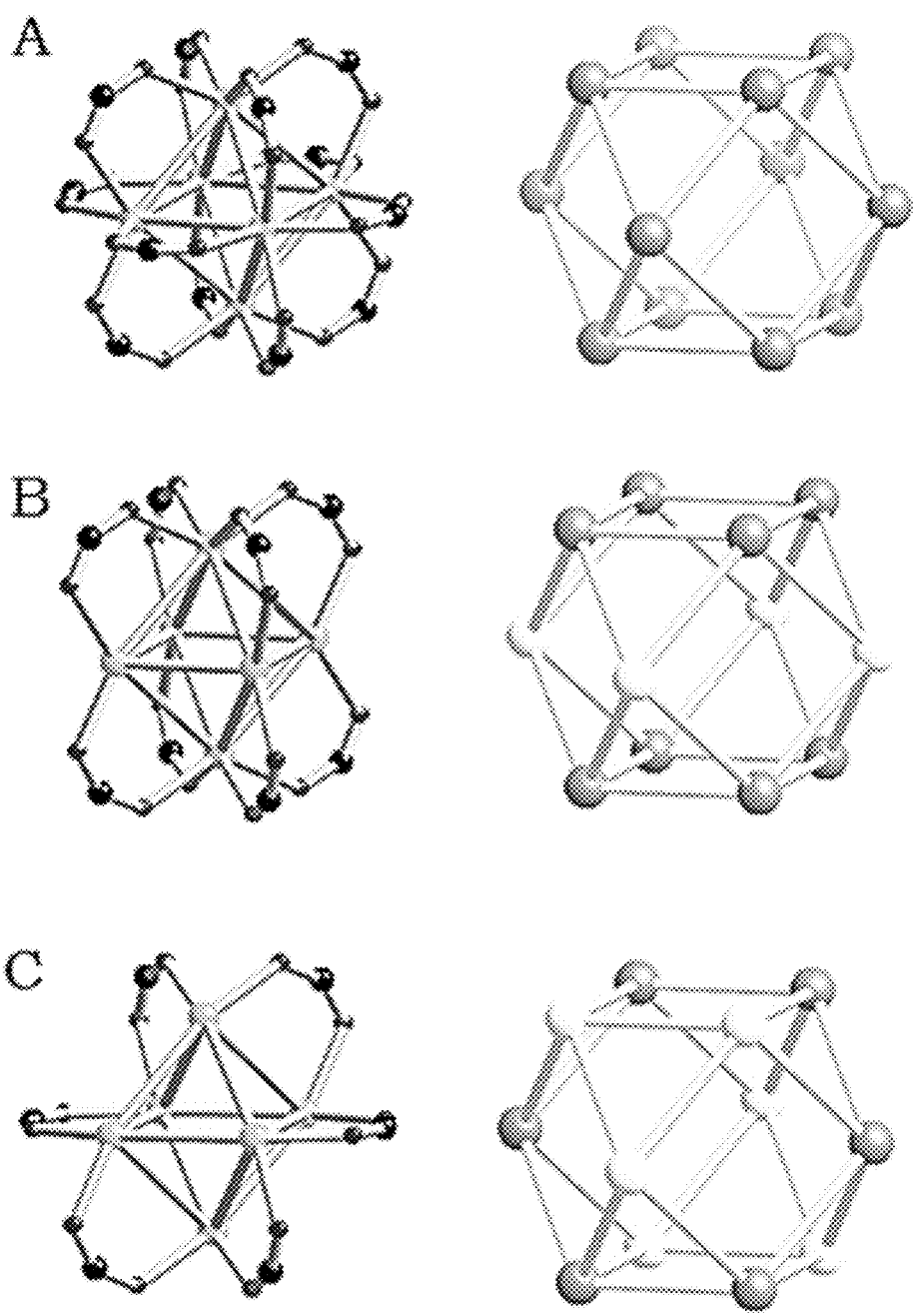
FIG. 8A-C demonstrates the difference in connectivity for Zr-carboxylate SBUs from different MOFs. Connectivity for (A) UiO-66; (B) MOF-545; and (C) MOF-777.

Secondary Building Unit (SBU) of MOF-777:

Six Zr atoms are arranged in octahedron shape and four oxygen atoms are coordinated on four faces of the octahedron in tetrahedral arrangement and four hydroxyl molecules are coordinated on the other four faces of the octahedron resulting in $[Zr_6O_4(OH)_4]^{12+}$ cluster. The six edges out of 12 edges of the octahedron are coordinated by carboxylate anion ($COO^-$) of BTB linker in hexagonal arrangement resulting in $[Zr_6O_4(OH)_4(COO)_6]^{6+}$. The rest of the 6+ charges is covered by four $HCOO^-$ and two $OH^-$ molecules resulting in $Zr_6O_4(OH)_4(HCOO)_4(OH)_2(COO)_6$. Finally adding four $H_2O$ molecules, the overall topology of the SBU was obtained, $Zr_6O_4(OH)_4(HCOO)_4(OH)_2(H_2O)_4(COO)_6$ (e.g., see FIG. 7 and FIG. 12). The hexagonal shape of the building unit was completely unexpected as no similar structure has been previously reported for Zr-based MOFs. For example, reported Zr SBUs based on the Zr oxy/hydroxyl cluster are 12-coordinated cuboctahedron and 8-coordinated cube for UiO-66 and MOF-545, respectively. Considering that the cuboctahedron, cube and hexagon shaped SBUs are all based on a similar Zr oxy/hydroxyl cluster, the results presented herein demonstrate that Zr clusters can generate diverse SBUs with different connectivity and geometry. By removing the four carboxylate anions from the cubooctahedron SBU of UiO-66, the cube shape SBU of MOF-545 can be obtained; and by removing the six carboxylate anions from the SBU of UiO-66, the hexagonal SBU of MOF-777 can be obtained (e.g., see FIG. 8A-C). It has been proposed that the Zr oxy/hydroxyl cluster flexibility is based upon symmetrical geometry and the number of possible coordination sites, twelve. As the twelve edges of the Zr cluster octahedron are high symmetry coordination sites that allow for the carboxylate anions to coordinate to the edges with proper geometries, the cuboctahedron, cube and hexagonal topologies are possible. Since no hexagonal shaped inorganic and organic building units have reported in any MOF structure, the hexagonal SBU of MOF-777 is a very unique. Moreover, combinations with this hexagonal building unit for synthesizing MOFs would generate additional structural diversity.

3D Structure of MOF-777 Based on a Stacked 2D Layered Structure.

Figure 9:
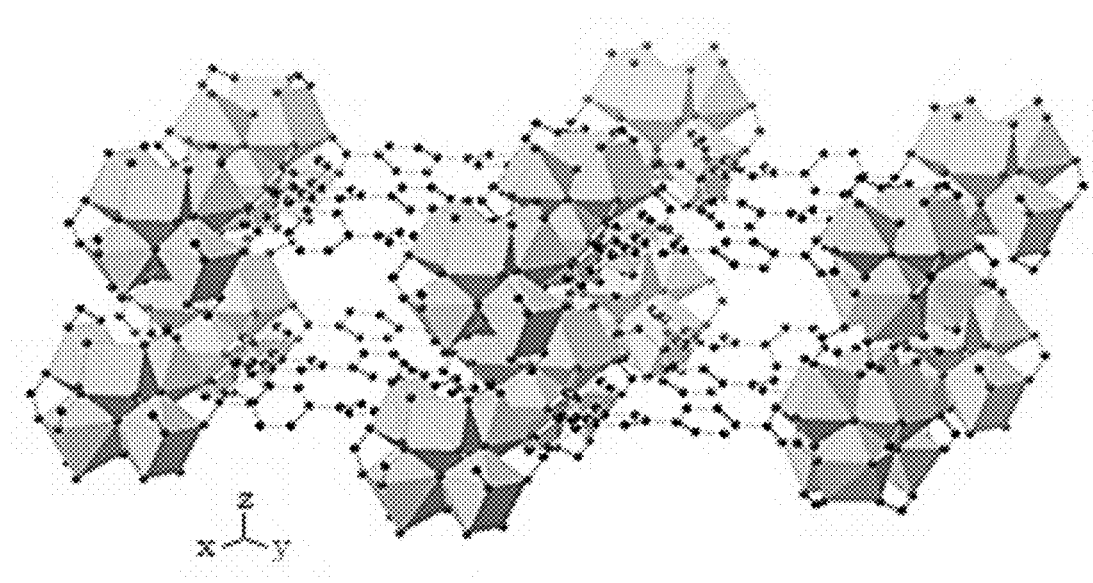
FIG. 9 presents the MOF-777 framework showing the connectivity between Zr-Carboxylate SBUs and BTB linking moieties. MOF-777 $[Zr_6O_4(OH)_4](HCOO)_4(OH)_2(H_2O)_4BTB_2]$. Crystal system: orthorhombic. Space group: Cmcm. Unit Cell: a=34.86 Å, b=20.13 Å, c=16.77 Å.
Figure 10:
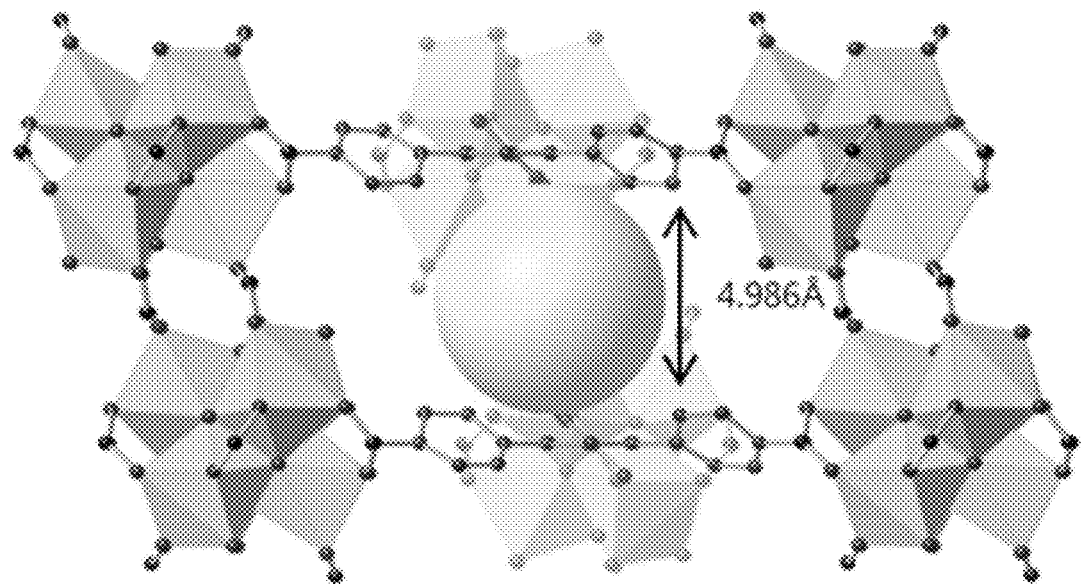
FIG. 10 presents a diagram of the MOF-777 framework. A pore of MOF-777 having a diameter of 4.986 Å is also indicated.
Figure 11:
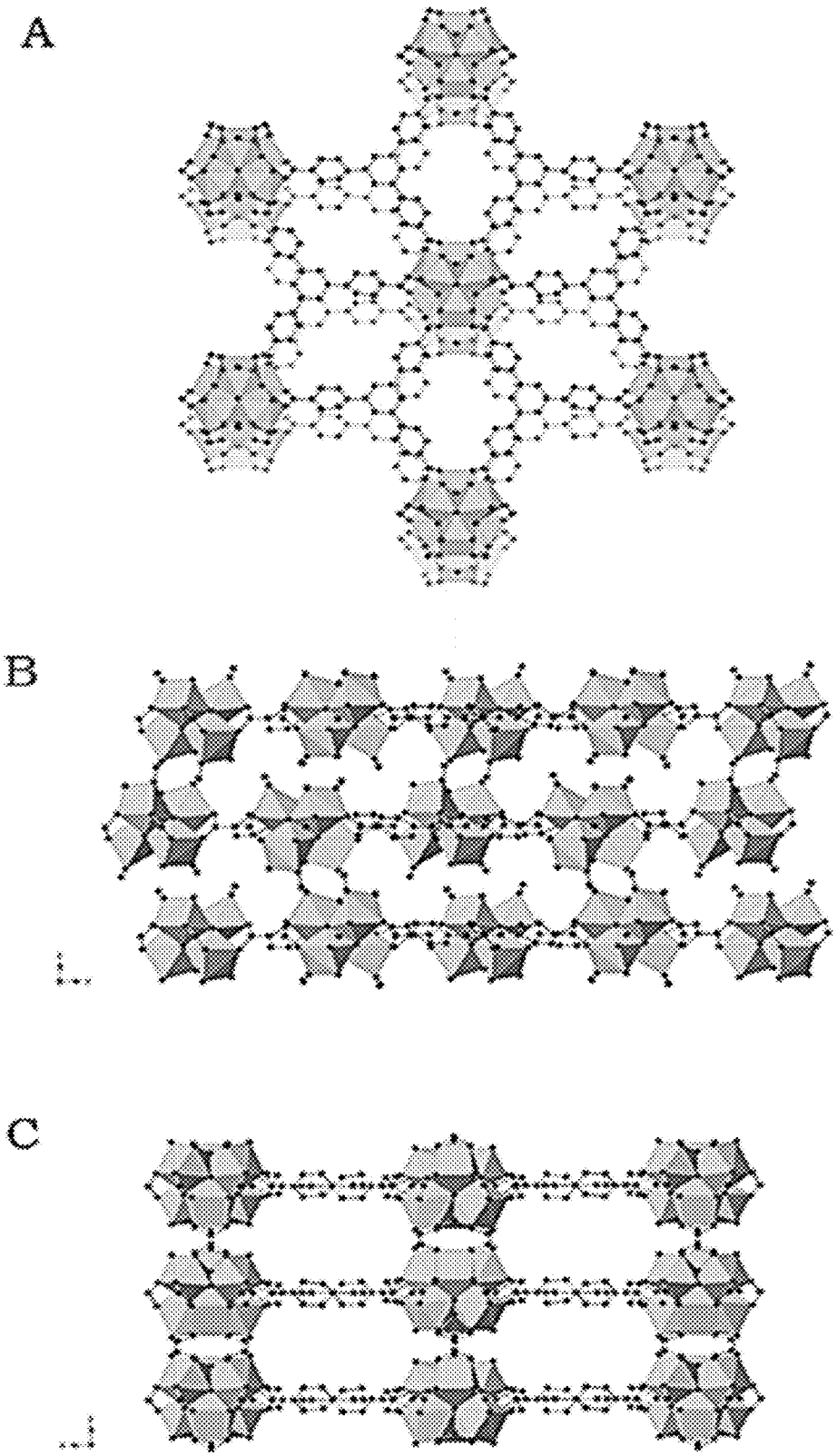
FIG. 11A-C provides the crystal structure of MOF-777 from (A) top down view; (B) angled view; and (C) side view.
Figure 19:
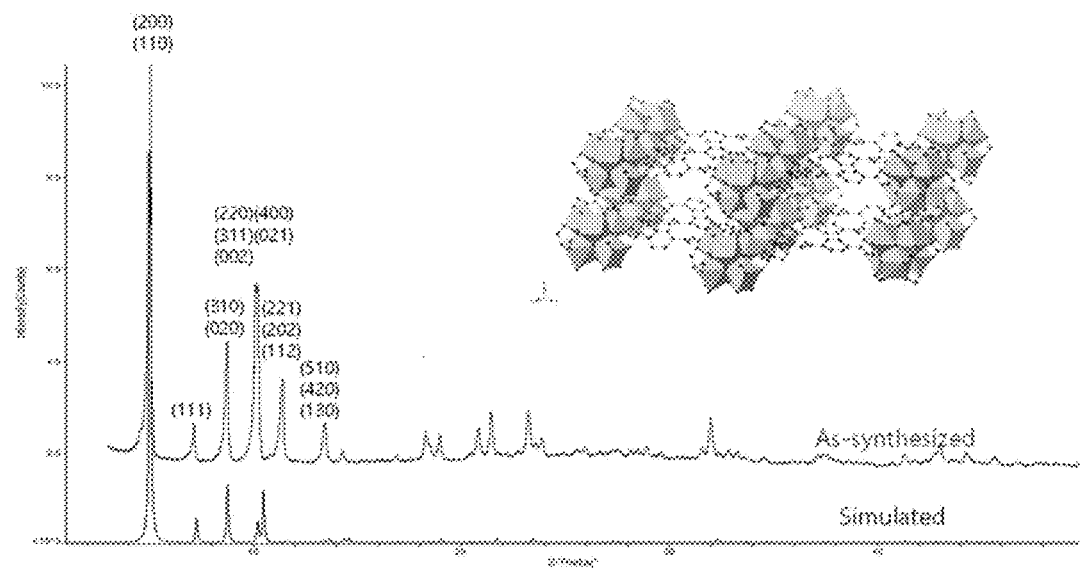
FIG. 19 presents the as-synthesized PXRD patterns for MOF-777 versus the simulated PXRD pattern for MOF-777.

The structure of MOF-777 was obtained from single crystal XRD analysis. MOF-777 has a tfz-d type 3D structure. The crystal system is orthorhombic and the space group is Cmcm. Unit cell parameters are a=34.86 Å, b=20.13 Å, c=16.77 Å and a pore diameter of 4.986 Å was obtained from the calculation (e.g., see FIG. 9 and FIG. 10). The 3D structure of MOF-777 is comprised of stacked 2D layers (e.g., see FIG. 11). The 2D layers are comprised of hexagonal Zr SBUs and triangle BTB linkers having a 2D kgd-a type structure (e.g., see FIG. 12). Stacking these layers occurs through the z axis. The tfz-d type 3D structure of MOF-777 is formed by connecting the layers through z axis with formate molecules, which bind to vacant coordination sites on the Zr SBUs (e.g., see FIG. 13A-C). As can be seen in the SEM images of MOF-777, the layered structures are discernable (e.g., see FIG. 16). When the single crystal XRD data was obtained, the SBUs of MOF-777 were found to be disordered with two different orientations. The SBUs were rotated 180° to each other SBUs (e.g., see FIG. 18). To rectify this issue, SBUs were positioned so as to be adjacent to the other type of SBUs in the layer. From which, the ordered structure of MOF-777 was generated. Based upon this structure, the PXRD pattern of MOF-777 was simulated and compared with the experimental PXRD pattern of MOF-777 to confirm that the structure was equivalent. The PXRD pattern of the simulated structure was shown to be equivalent to the experimental PXRD pattern for MOF-777 (e.g., see FIG. 19).

Crystal Growth and Morphology of Single Crystals of MOF-777.

The images of single crystals of MOF-177 were obtained using an optimal microscope. The crystals were ~100 μm in size and had a thickness ~10 μm. The crystals were found to be homogeneous with hexagonal plate morphology (e.g., see FIG. 17A-B). In order to obtain crystals that had sufficient thickness for PXRD studies, the amount of formic acid had to be adjusted. By adding increasing amounts of formic acid, the intensity and sharpness of the peaks related to the stacking of the layers increased along with the thickness (up to ~10 μm) of single crystals (e.g., see FIG. 14C-E). The results indicate that the thickness of the crystals can be controlled by varying the amount of formate molecules. As the layers are connected by formate molecules, the results are understandable.

One of the distinguishing characteristics of MOF-777 in comparison to other Zr-MOFs, is MOF-777's layered structure. While other Zr-MOFs have rigid 3D structures, MOF-777's 3D structure results from stacking interactions between hexagonal plate morphologies that have 2D topologies. Therefore, the unique hexagonal plate morphology of MOF-777 SBUs, combined with controllable thickness and high stability, indicate that MOF-777 can be used as a thin film. Relatively few studies have been conducted with MOF films and have been limited to the following: MOF-5, MOF-199 (HKUST-1), [$Zr_2bdc_2$(dabco)] (dabco=1,4-diazabicyclo[2,2,2]octane), [Mn(HCOO)], MIL-53(Fe) and MIL-88B. MOF-777 has several advantages over the MOFs mentioned above. By MOF-777 having plate shape morphology, MOF-777 is far more conducive for growing and covering the surface of substrate. MOF-777 is very stable, while the MOFs mentioned above, except for MOF-199 (HKUST-1), are known for being relatively unstable. The stability of MOF-777, therefore, provides an additional practical advantage for creating a thin film material. A 1 cm² scaled thin film material comprising MOF-777 was created on top of glass substrate.

Characterization of MOF-777 Surface Area.

Figure 20:
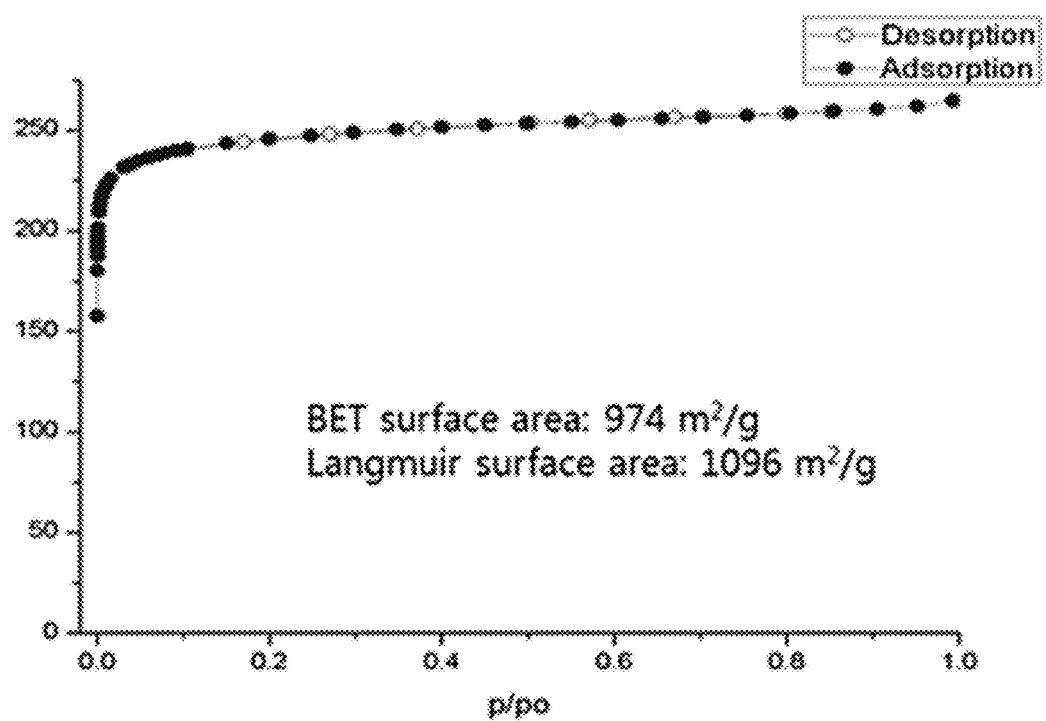
FIG. 20 presents $N_2$ isotherm data for MOF-777.

Activated MOF-777 crystals were used for $N_2$ isotherms. The BET surface area of the activated sample was 974 m²/g and Langmuir surface area was 1096 m²/g. Those two values are quite lower than the calculated solvent accessible surface area (2330 m²/g) using a materials studio program. The experimental values are lower than the calculated surface area is due to a loss of crystallinity along z axis during activation. After the activation, the PXRD pattern of the sample was obtained and it showed that the peaks related to stacking of the layers disappeared such as (111), (311), (021), (221), (202) and (112), while the other peaks such as (200), (110), (310), and (020) remained still sharp and strong (e.g., see FIG. 20) indicating that the crystals lost the crystallinity along z axis.

Inductively Coupled Plasma (ICP) and Elemental Analysis (EA) of MOF-777.

Four measurements were carried out with four different samples. The wt % of each element of the activated samples was obtained from ICP and EA (e.g., see TABLE 1).

TABLE 1

Experimental wt % values of MOF-777 from ICP and EA.

| wt % | From EA | | | | | | From ICP |
|---|---|---|---|---|---|---|---|
| | C | O | H | N | S | Zr + O | Zr |
| 1 | 37.36 | 15.75 | 2.730 | 0.059 | 0.015 | 44.51 | 27.51 |
| 2 | 38.06 | 15.58 | 2.715 | 0.059 | 0.013 | 43.57 | 27.21 |
| 3 | 38.77 | 14.81 | 2.657 | 0.065 | 0.009 | 43.68 | 27.42 |
| 4 | 38.51 | 14.81 | 2.604 | 0.068 | 0.011 | 43.99 | 28.21 |

All measurements showed similar values and the first row was chosen for the experimental value. The molecular formula from the experimental value, $Zr_6C_{60.7}O_{40.1}H_{53.7}$ reasonably matches with the molecular formula of MOF-777, $Zr_6C_{58}O_{38}H_{48}$. Although the oxygen and hydrogen ratios are slightly higher in experimental value, this discrepancy can be explained by the experimental having one or two water molecules within the pores.

Testing the Thermal and Chemical Stability of MOF-777.

A thermal stability test was carried out by using thermal gravimetric analysis (TGA). The first significant weight loss was from the evaporation of the solvent from the pores, while a second significant weight loss was around 550° C. was, indicating decomposition of the structure (e.g., see FIG. 22). This result shows that MOF-777 is thermally stable up to ~550° C.

Figure 23:
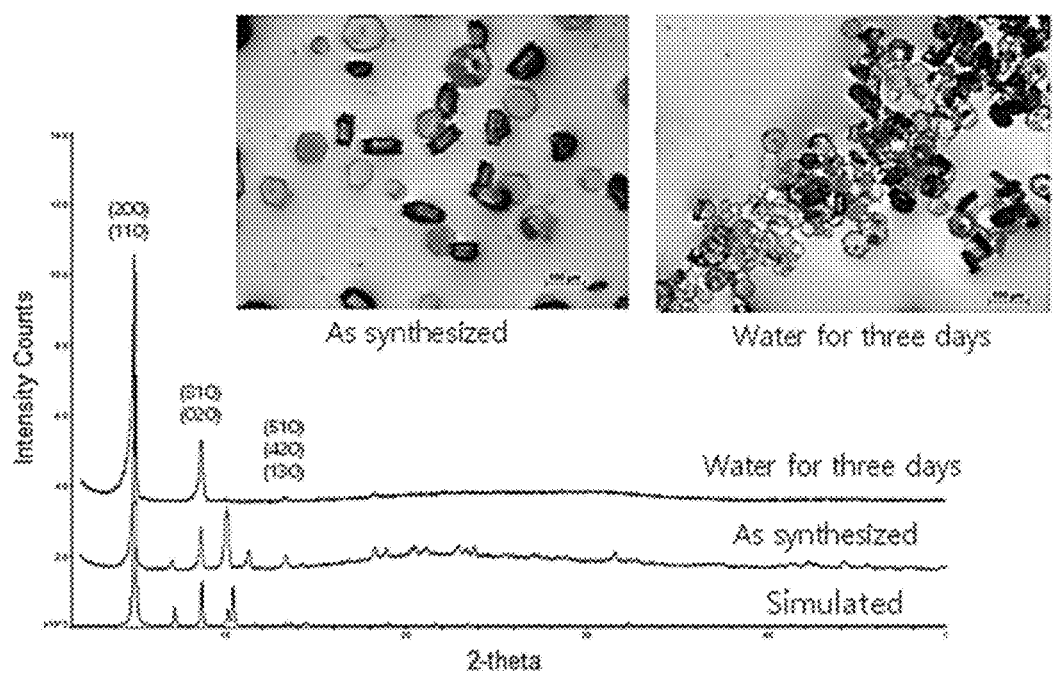
FIG. 23 provides optical microscope images of MOF-777 (top) and variation of the PXRD pattern for MOF-777 (bottom) when MOF-777 is immersed in water or methanol for 3 days.

A chemical stability test of MOF-777 was carried out against water. The PXRD pattern of as-synthesized MOF-777 was compared against the PXRD pattern of MOF-777 immersed in water for 3 days (e.g., see FIG. 23). After MOF-777 was immersed in water for three days, the peaks related to the stacking of the layers disappeared, while the other peaks remained. Considering (200), (110) peaks were still sharp as those from the as-synthesized MOF-777 sample, the layers of MOF-777 are chemically stable against water.

MOF-777 has several interesting characteristics. Outside of MOF-777, no hexagonal shape inorganic and organic building units have been reported for MOFs. MOF-777's hexagonal building units therefore provide for new geometries for constructing MOFs. Also the layered structure enables MOF-777 to grow as thin layers. With the thermally and chemically stable properties of MOF-777 layers, this morphology of MOF-777 has an advantage to being used as porous thin film materials.

Figure 24:
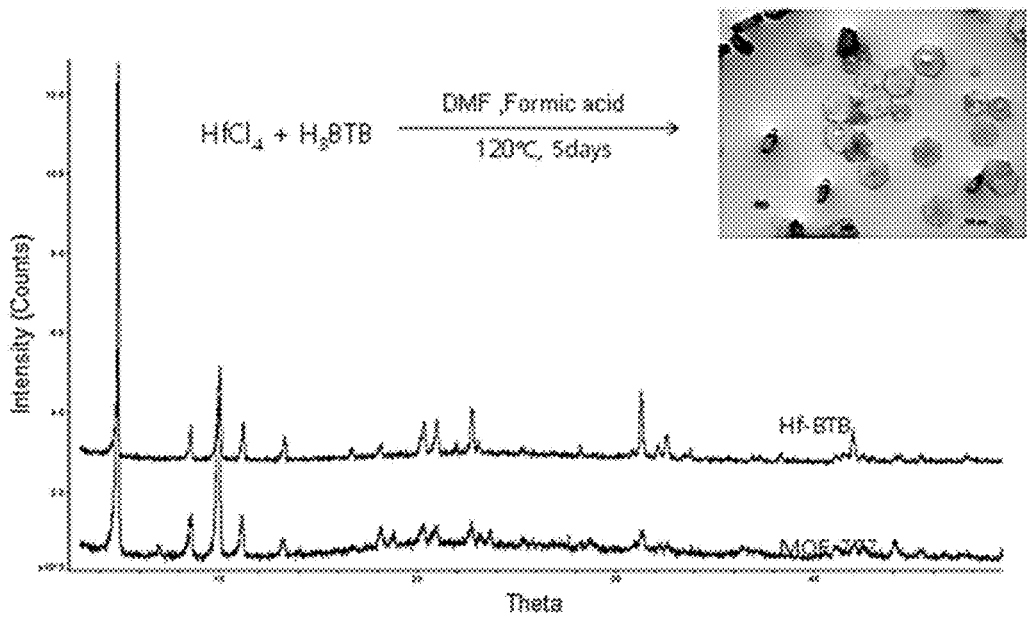
FIG. 24 presents PXRD patterns of MOF-778 and optical microscope images of the crystals formed using the specified conditions.
Figure 25:
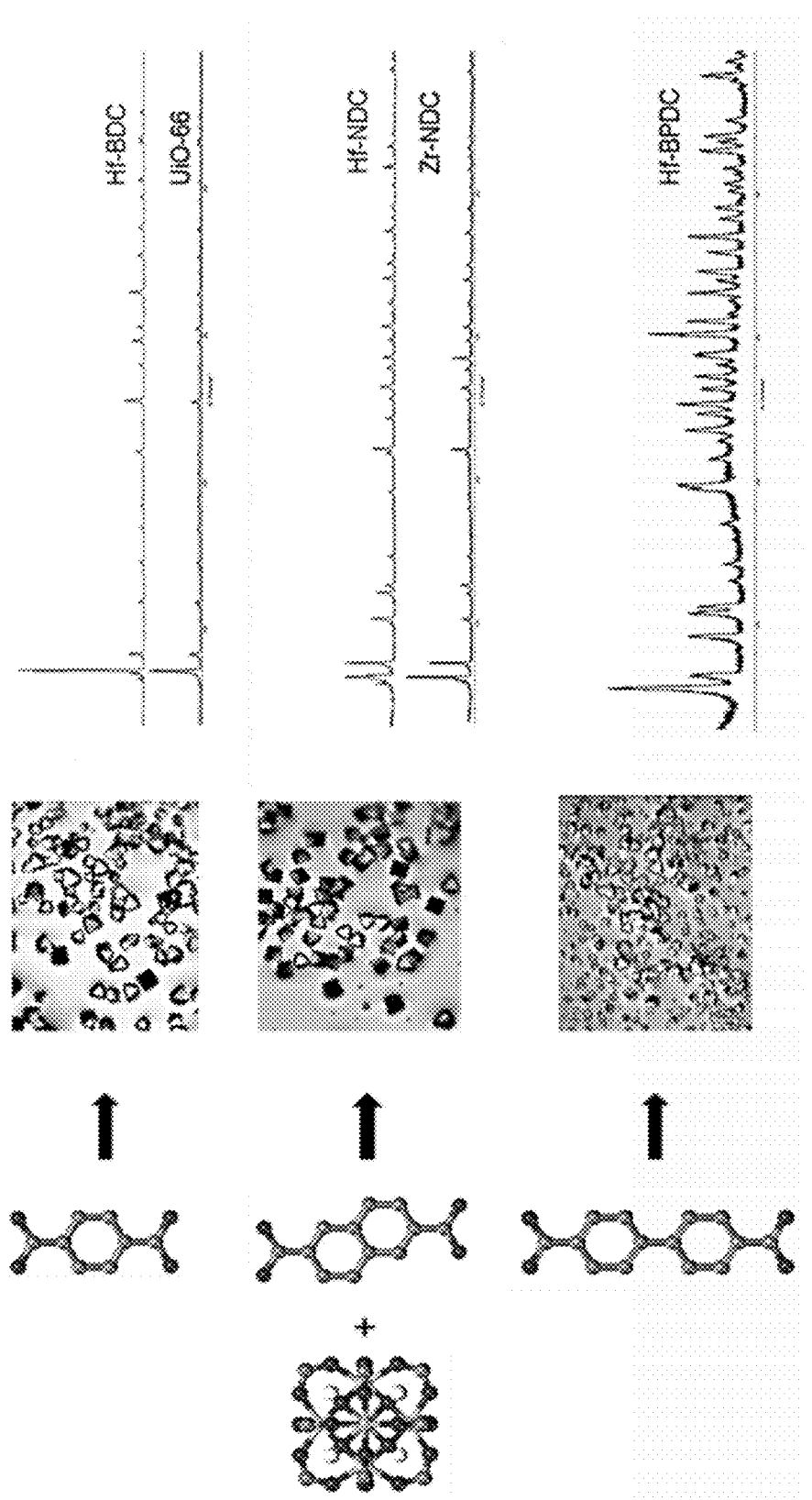
FIG. 25 presents PXRD patterns and optical microscope images of MOFs comprising the indicated Hf-SBUs and organic linking moieties.
Figure 26:
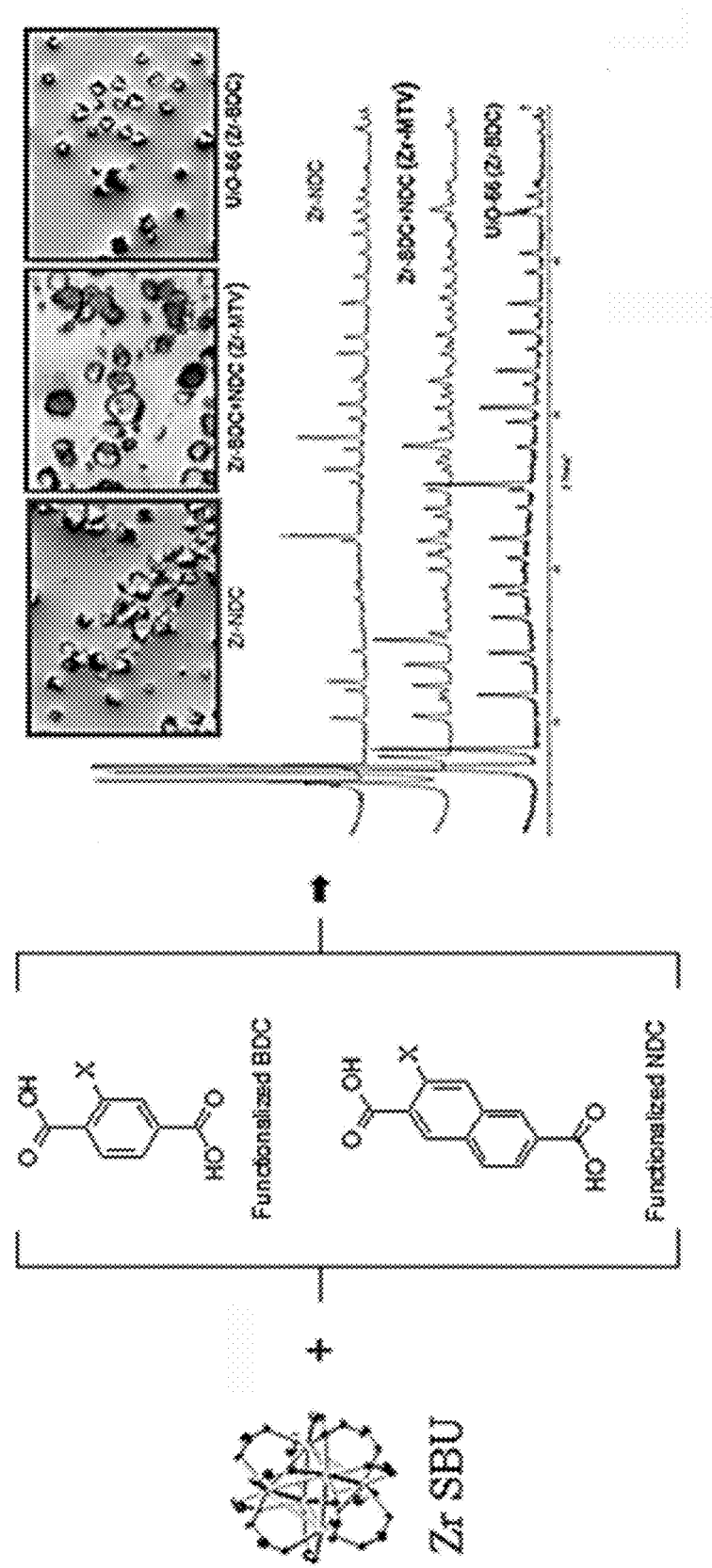
FIG. 26 presents PXRD patterns and optical microscope images of MOFs comprising the indicated Zr-SBUs and organic linking moieties.
Figure 27:
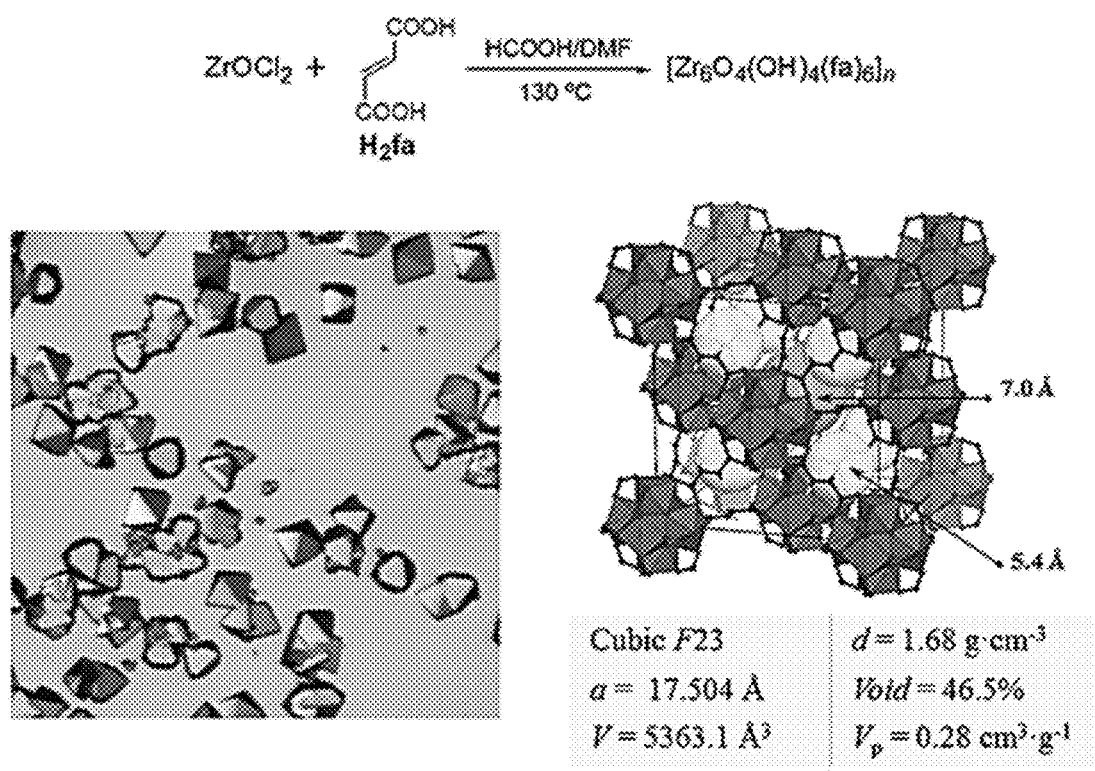
FIG. 27 presents a scheme to synthesize MOF-801, a 12-extension Zr-carboxylate SBU. Also shown is an optical image of the octahedral crystals of MOF-801 and a depiction of the MOF-801 framework. Structural characteristics and pore sizes for MOF-801 are also indicated.
Figure 28:
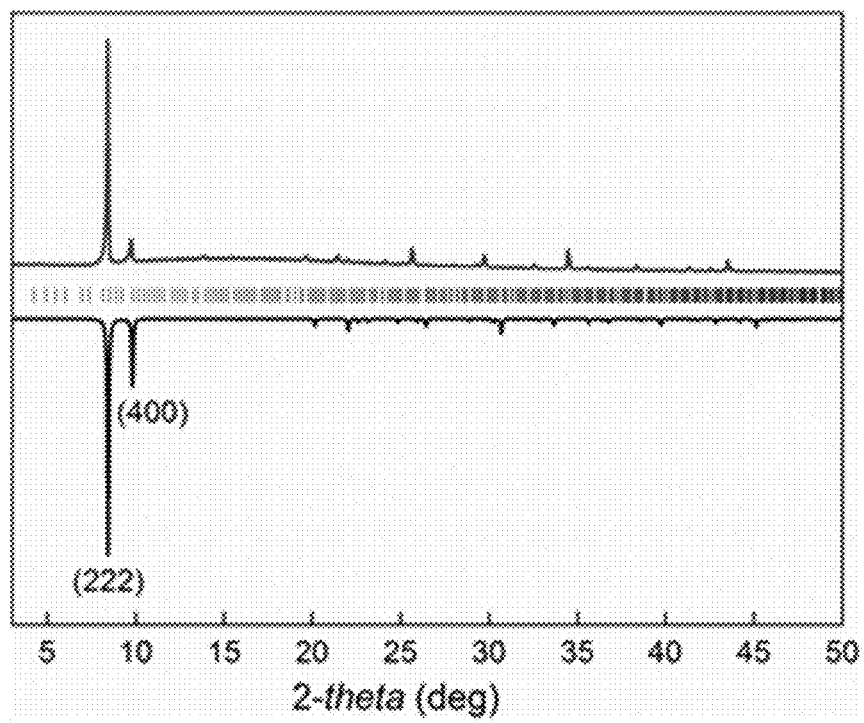
FIG. 28 provides a comparison of the experimental PXRD patterns of MOF-801(SC): as-prepared (top) and simulated pattern (bottom) from single-crystal X-ray data.
Figure 29:
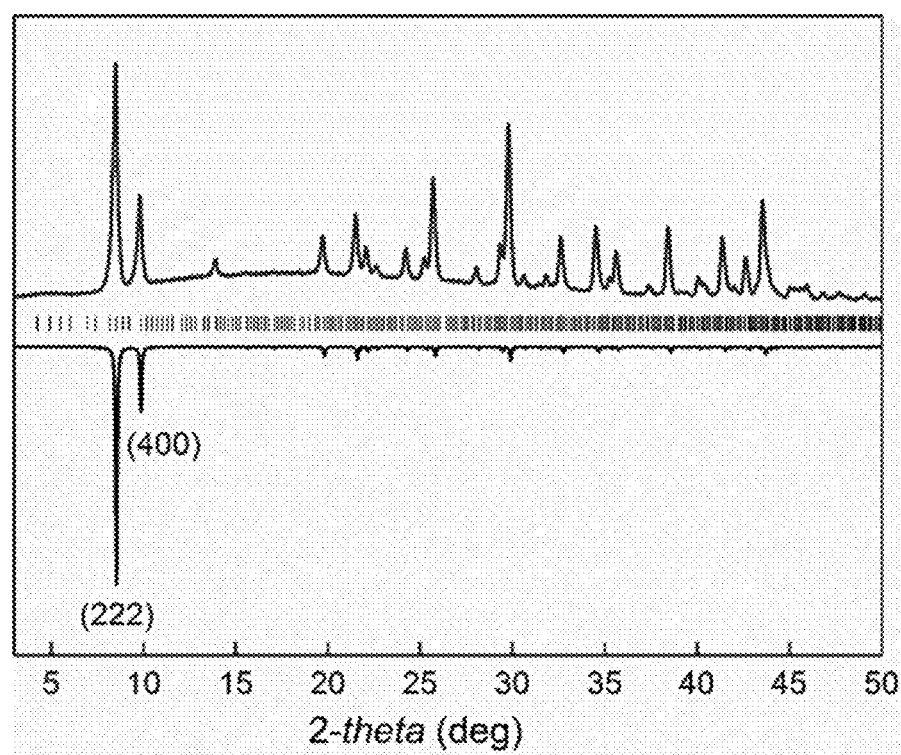
FIG. 29 provides a comparison of the experimental PXRD patterns of MOF-801(P): as-prepared (top) and simulated pattern (bottom) from single-crystal X-ray data.
Figure 30:
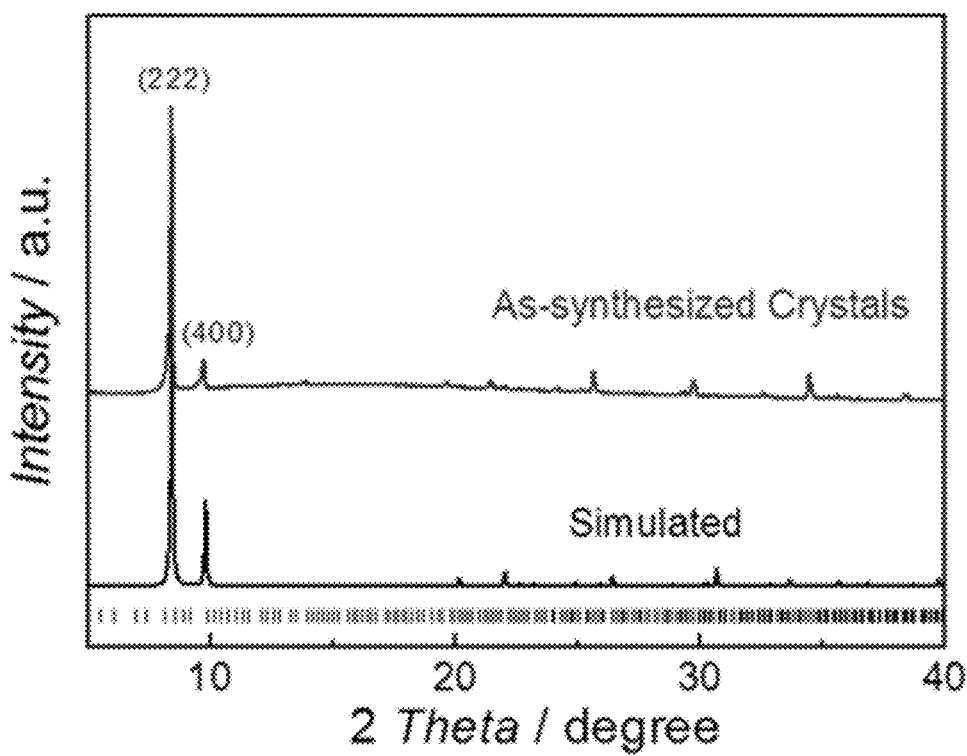
FIG. 30 provides a comparison of the experimental PXRD patterns of MOF-801: as-prepared (top) and simulated pattern (bottom) from single-crystal X-ray data.
Figure 31:
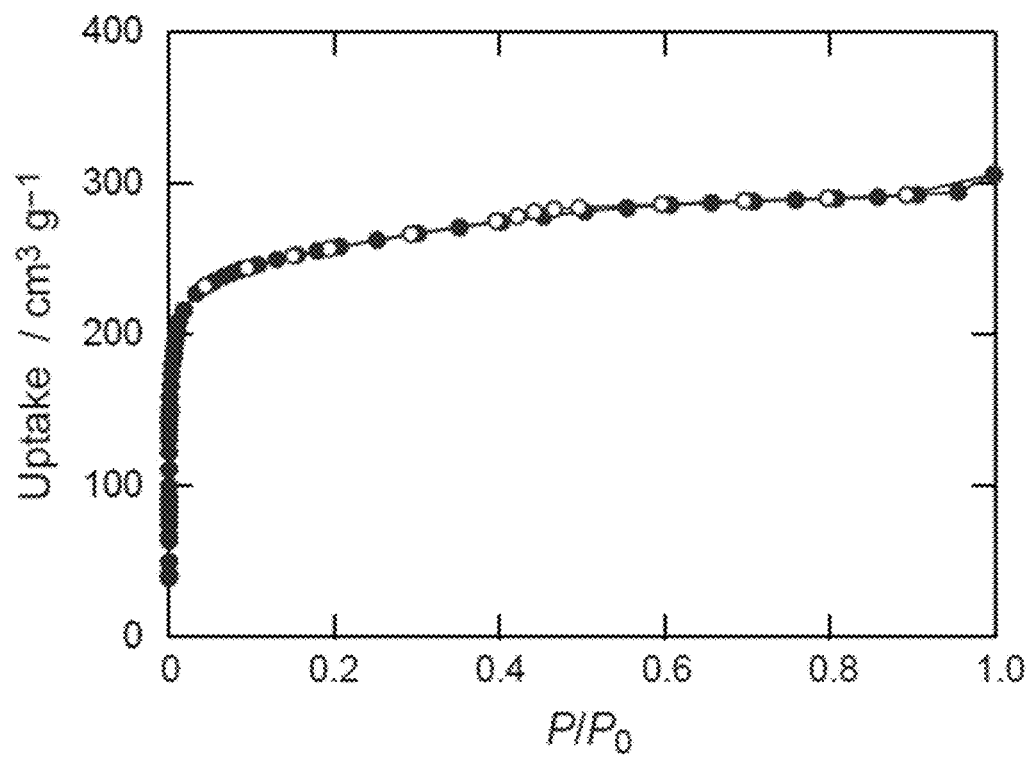
FIG. 31 presents a $N_2$ isotherm of MOF-801(P) at 77 K.
Figure 32:
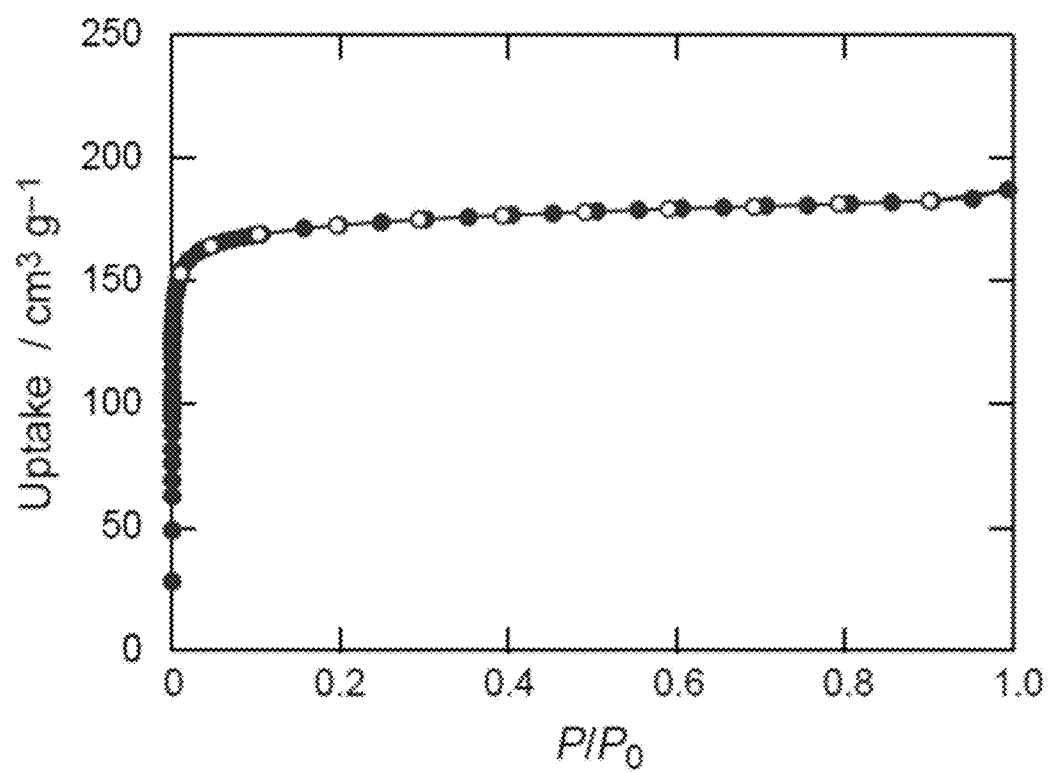
FIG. 32 presents a $N_2$ isotherm of MOF-801(SC) at 77 K.
Figure 33:
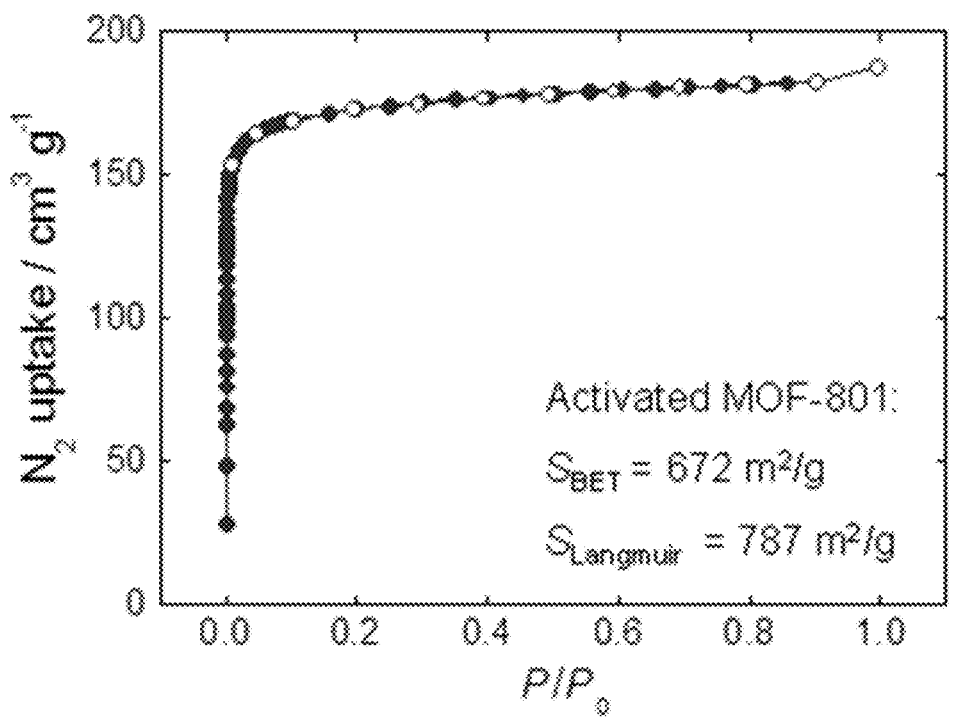
FIG. 33 presents a $N_2$ isotherm of activated MOF-801 at 77 K. The surface area is of MOF-801 is also indicated.
Figure 34:
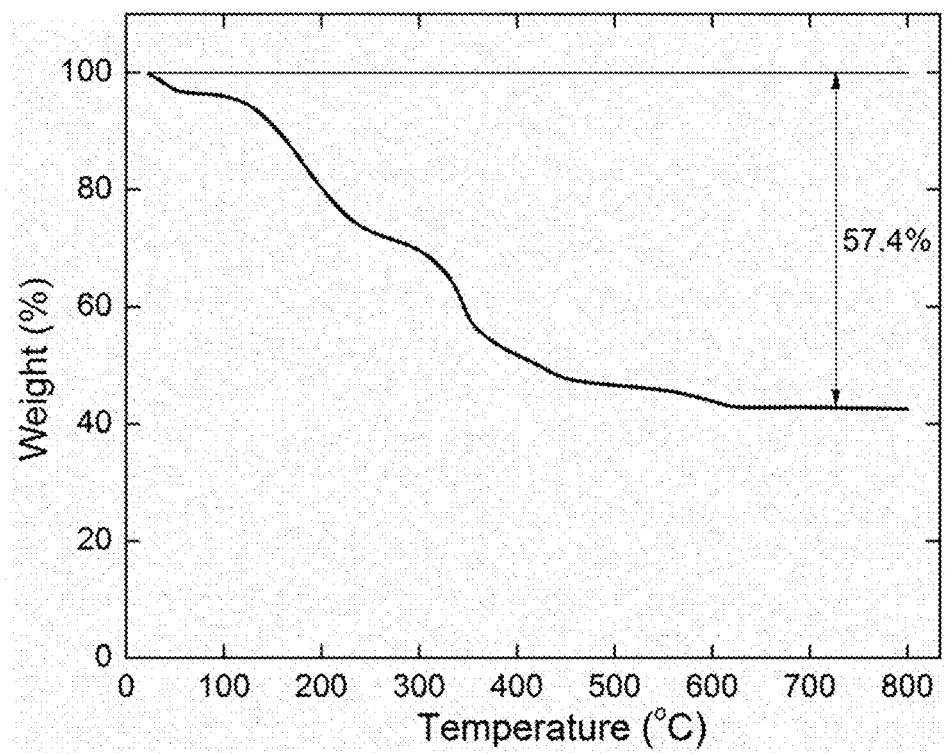
FIG. 34 presents a TGA trace for as-prepared MOF-801 (SC), heating rate: 5° C. $min^{-1}$ in air.
Figure 35:
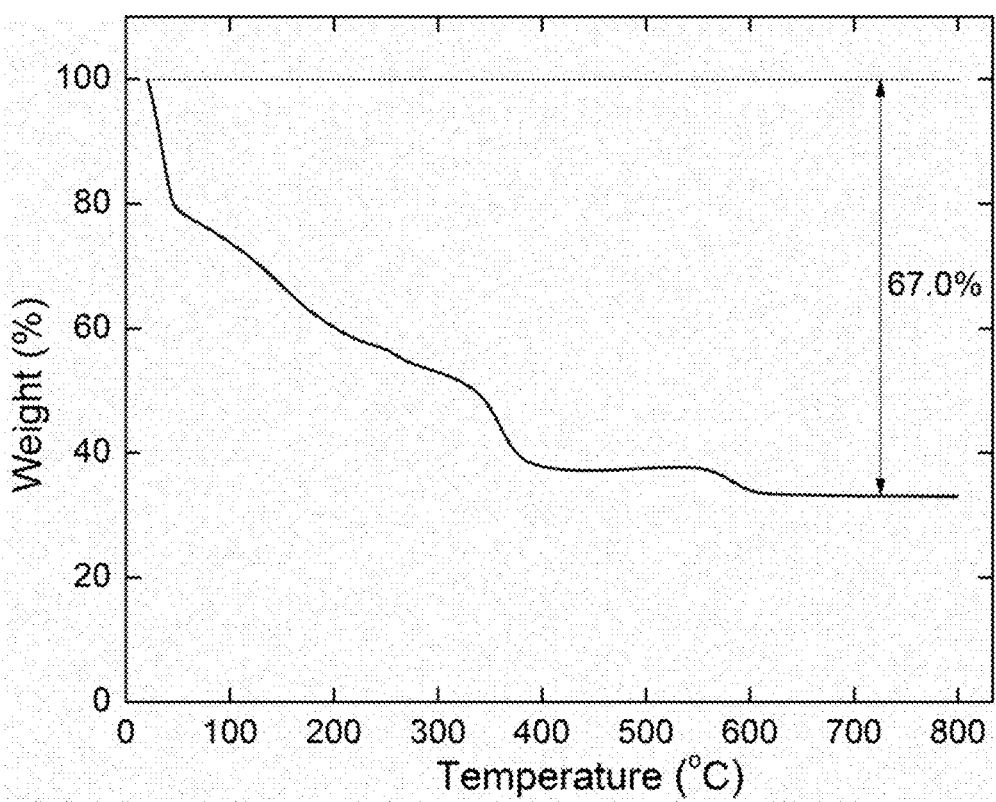
FIG. 35 presents a TGA trace for as-prepared MOF-801 (P), heating rate: 5° C. $min^{-1}$ in air.
Figure 36:
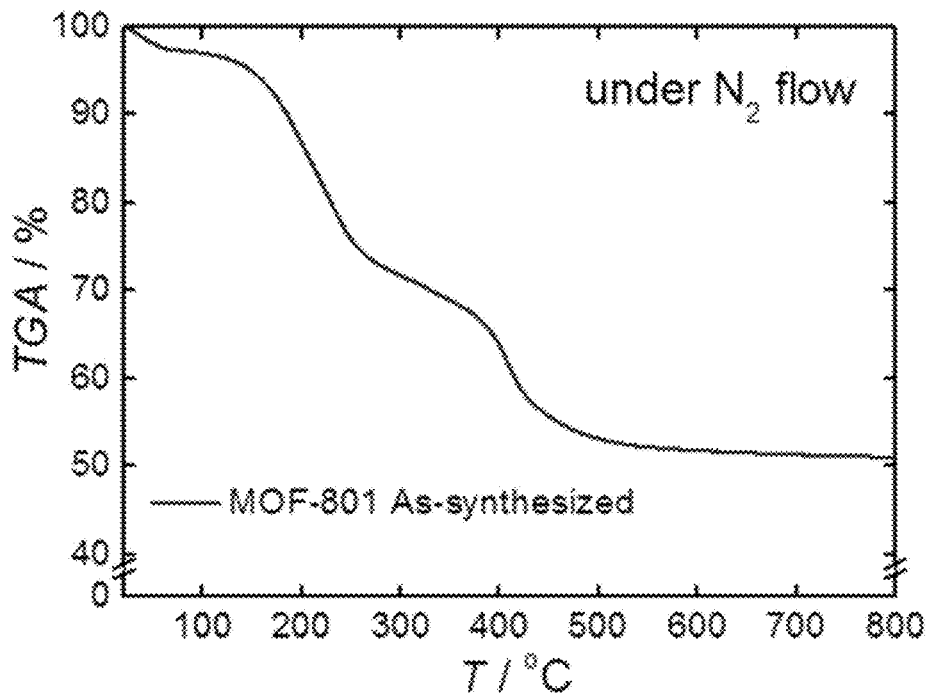
FIG. 36 presents a TGA trace for as-prepared MOF-801, heating rate: 5° C. $min^{-1}$ in air. The TGA analysis indicates that MOF-801 is stable up to 400° C.
Figure 37:
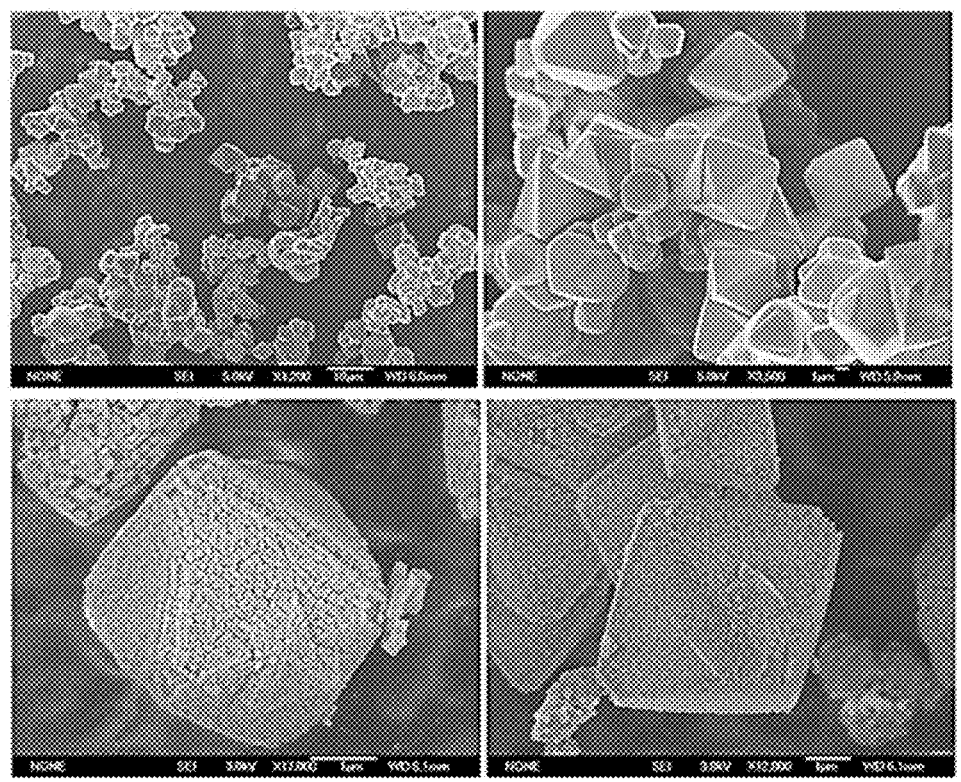
FIG. 37 provides SEM images of as synthesized MOF-801 (top) and activated MOF-801 (bottom). The small pores seen on the surface of activated MOF-801 are due to solvent molecules escaping during activation.
Figure 38:
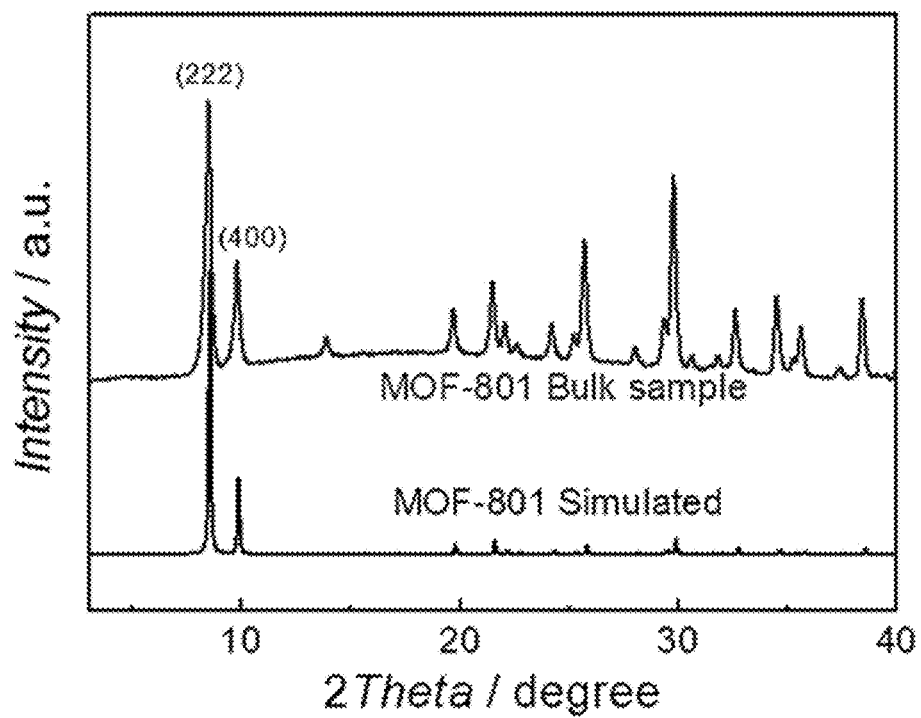
FIG. 38 provides a comparison of the experimental PXRD patterns for a large scale bulk sample of MOF-801: as-prepared (top) and simulated pattern (bottom) from single-crystal X-ray data.
Figure 39:
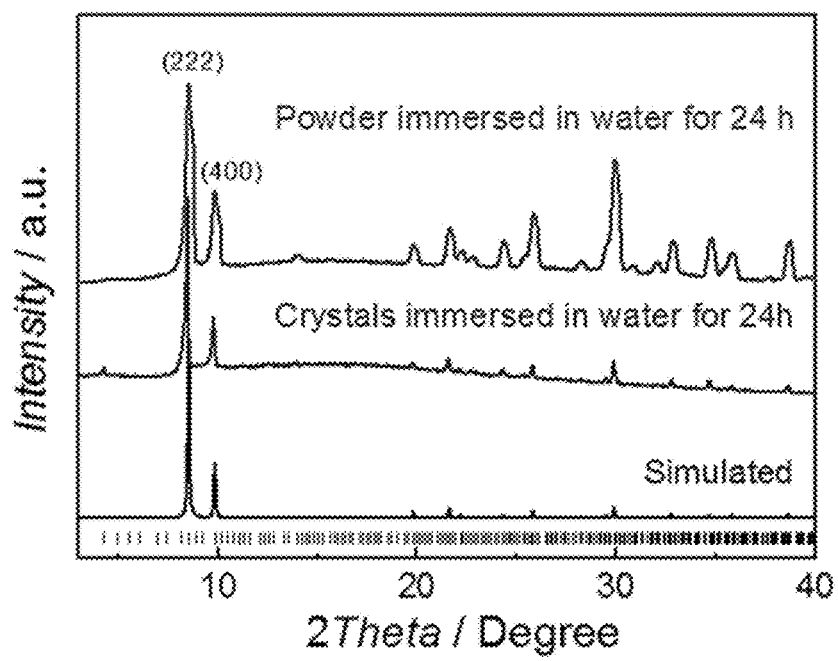
FIG. 39 demonstrates the water resistant properties of MOF-801 by comparing the PXRD patterns of experimental MOF-801 (top) after being immersed in water for 24 hours with the simulated pattern (bottom) from single-crystal X-ray data.
Figure 40:
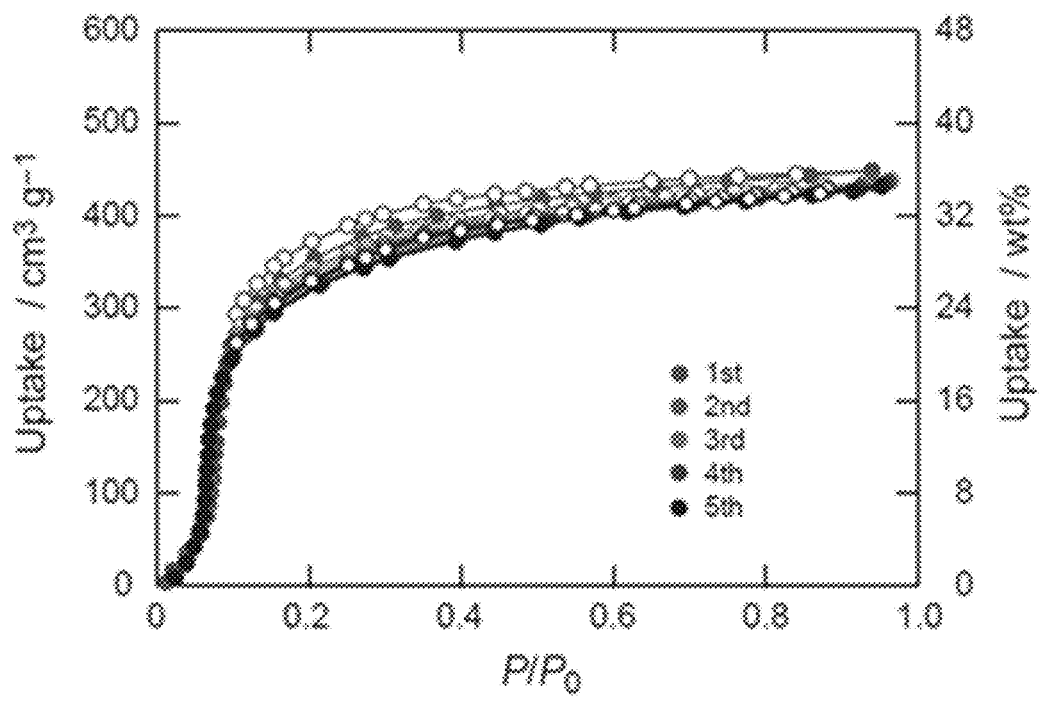
FIG. 40 provides for the cycle performance of water uptake in MOF-801(P) at 298 K. The sample was evacuated for 2 h at 298 K between the cycles.
Figure 41:
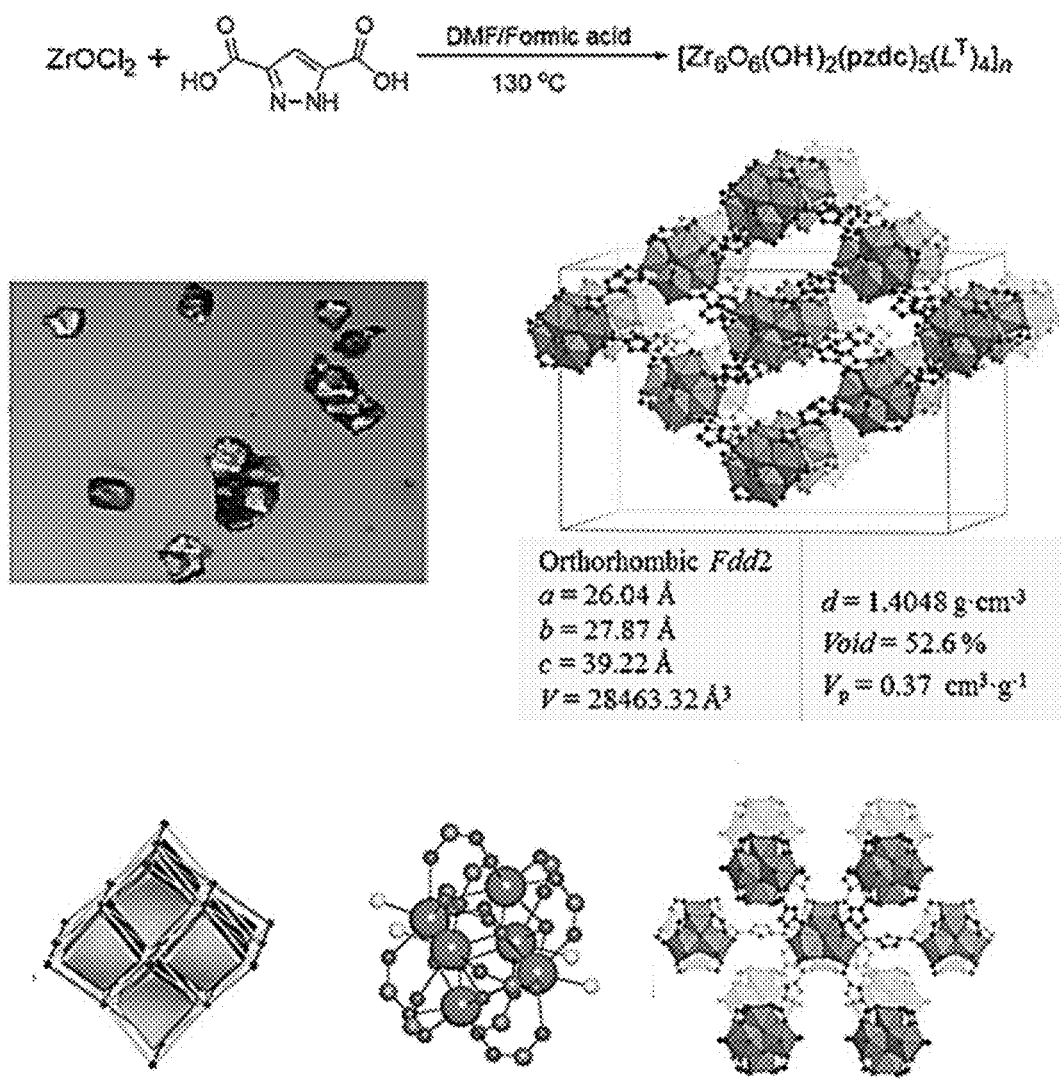
FIG. 41 presents a scheme to synthesize MOF-802, a 10-extension Zr-carboxylate SBU. Also shown is an optical image of the crystals of MOF-802 and a depiction of the MOF-802 framework. The structural characteristics of MOF-802, btc net topology, and ball and stick model for the 10-extension SBU is further presented.
Figure 42:
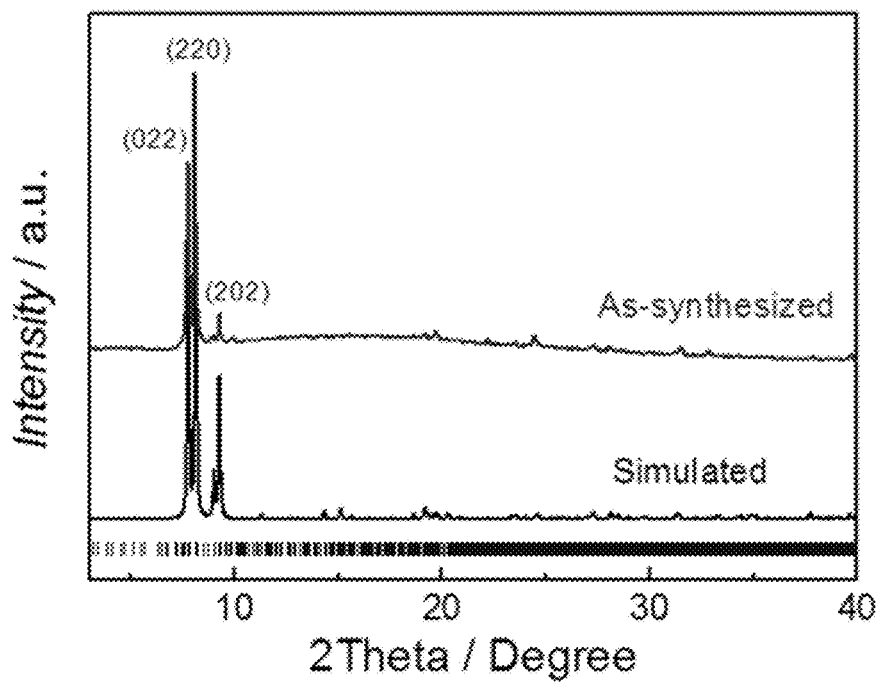
FIG. 42 provides a comparison of the experimental PXRD patterns for MOF-802: as-prepared (top) and simulated pattern (bottom) from single-crystal X-ray data.
Figure 43:
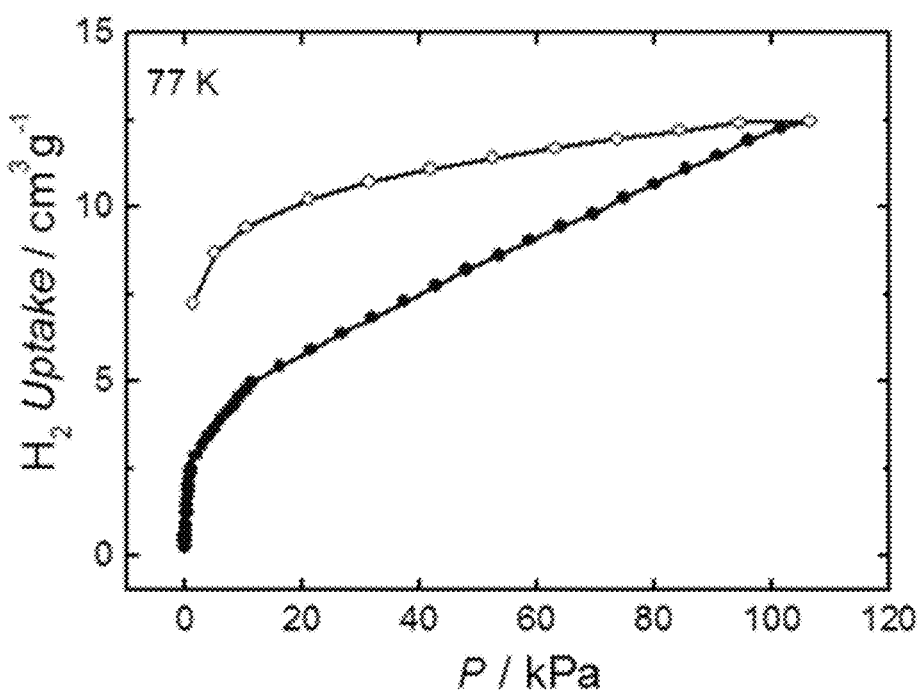
FIG. 43 presents a $H_2$ isotherm of MOF-802 at 77 K. The pores of MOF-802 (~4 Å) are too small for a $N_2$ sorption measurement at 77 K.
Figure 44:
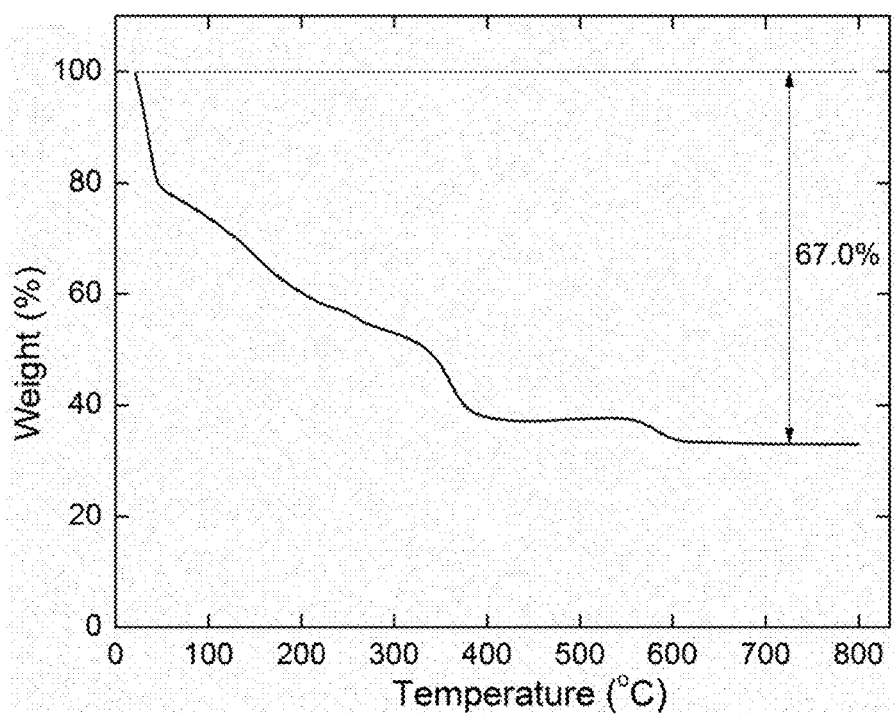
FIG. 44 presents a TGA trace for as-prepared MOF-802, heating rate: 5° C. $min^{-1}$ in air.
Figure 45:
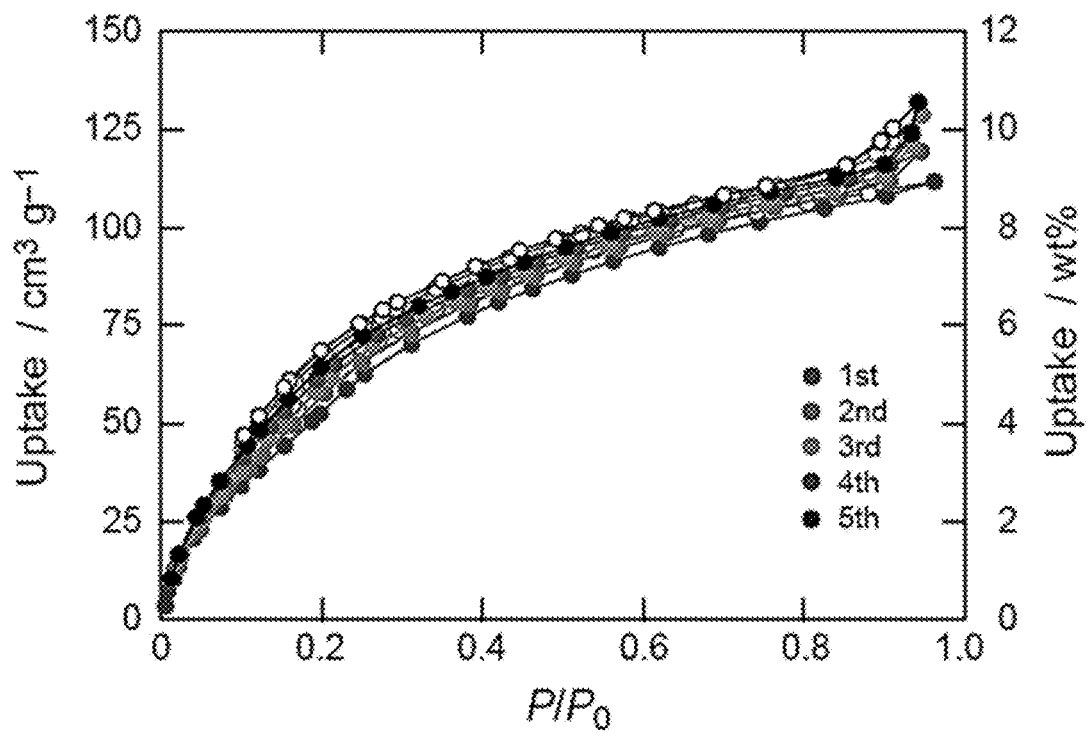
FIG. 45 provides for the cycle performance of water uptake in MOF-802 at 298 K. The sample was evacuated for 2 h at 298 K between the cycles.
Figure 47:
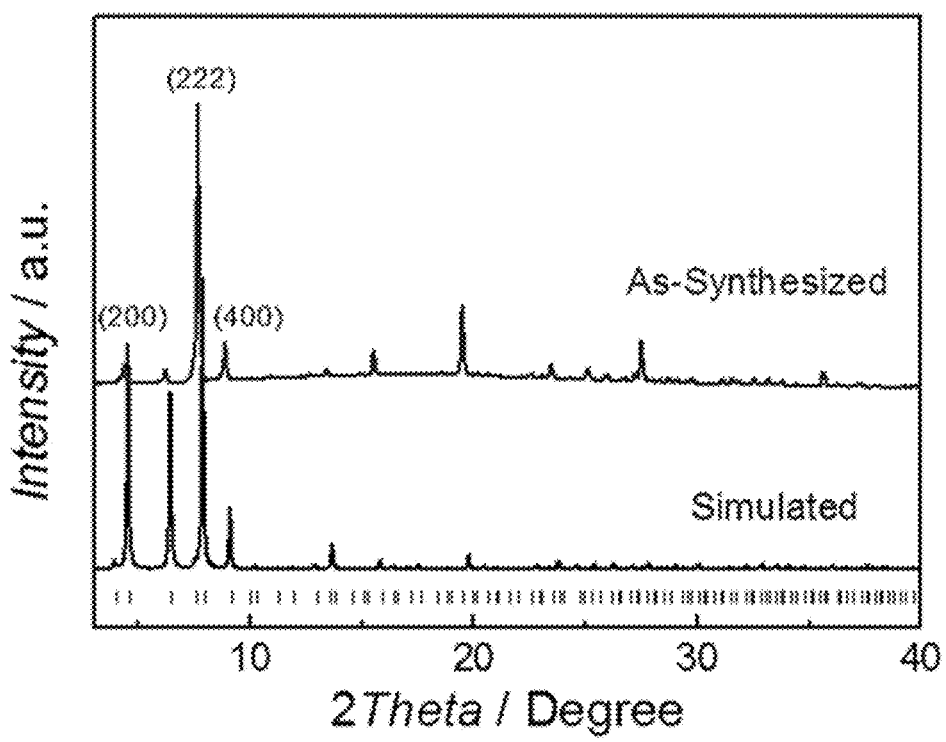
FIG. 47 provides a comparison of the experimental PXRD patterns for MOF-803: as-prepared (top) and simulated pattern (bottom) from single-crystal X-ray data.
Figure 48:
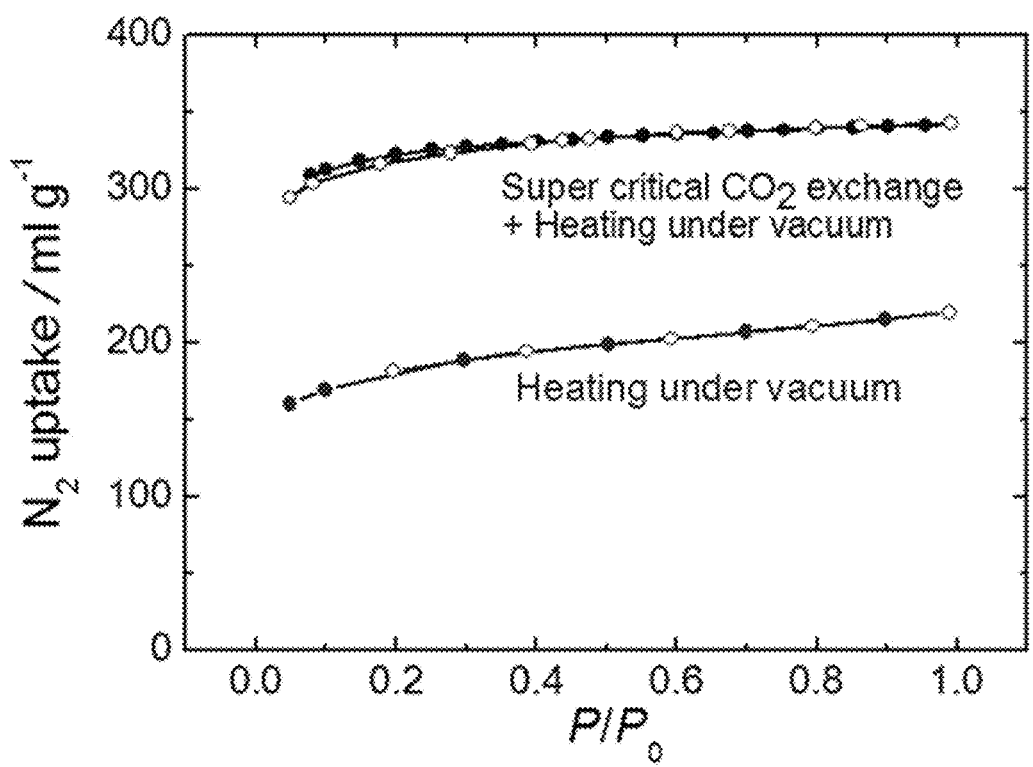
FIG. 48 provides that MOF-803 can be partially activated by heating under vacuum, while can be fully activated by using super-critical $CO_2$ procedure and heating under vacuum.
Figure 49:
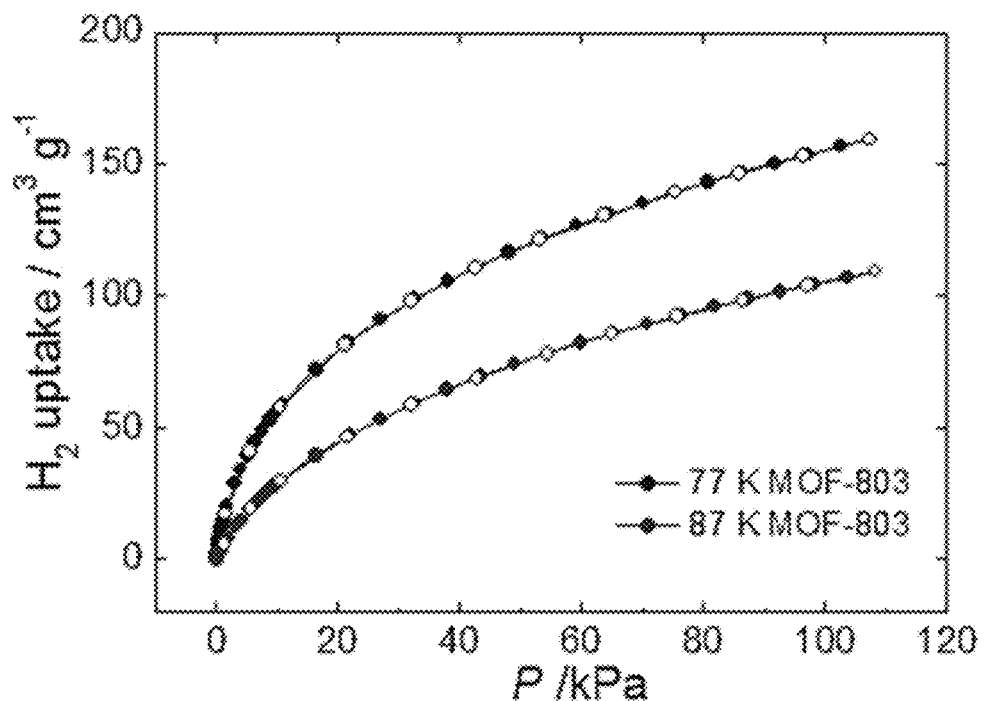
FIG. 49 presents a $H_2$ isotherm of MOF-803 at 77 K and 87 K.
Figure 50:
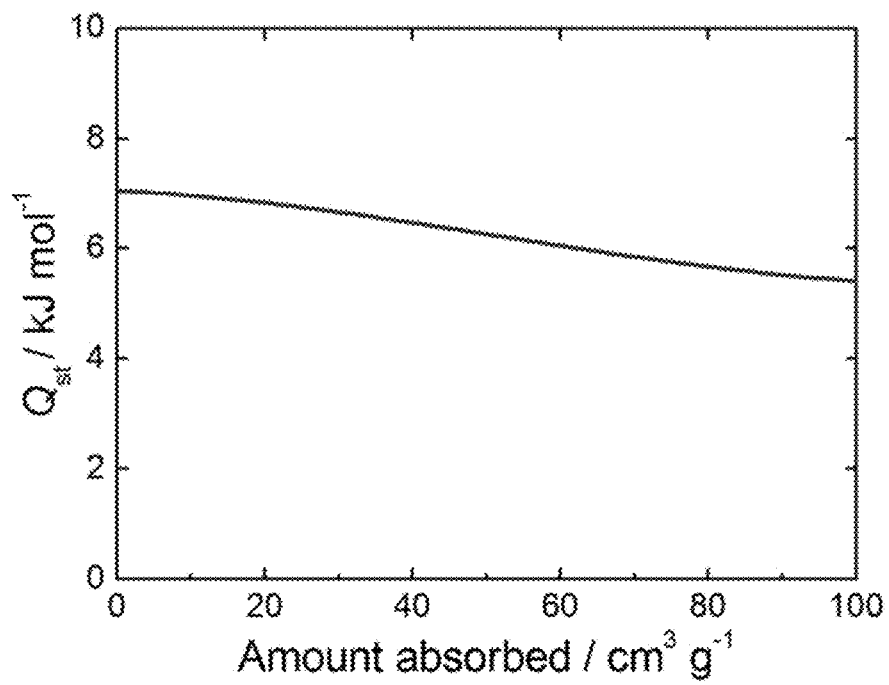
FIG. 50 provides a sorption curve for $H_2$ by MOF-803. $Q_{st}$=7.05 kJ/mol at zero uptake.
Figure 51:
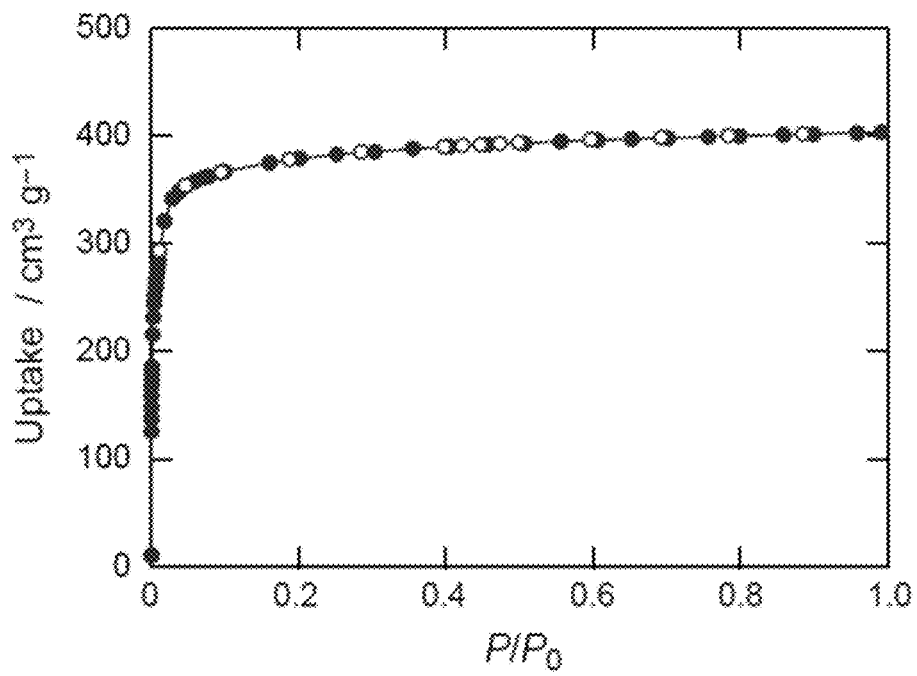
FIG. 51 presents a $N_2$ isotherm of MOF-803 at 77 K.
Figure 52:
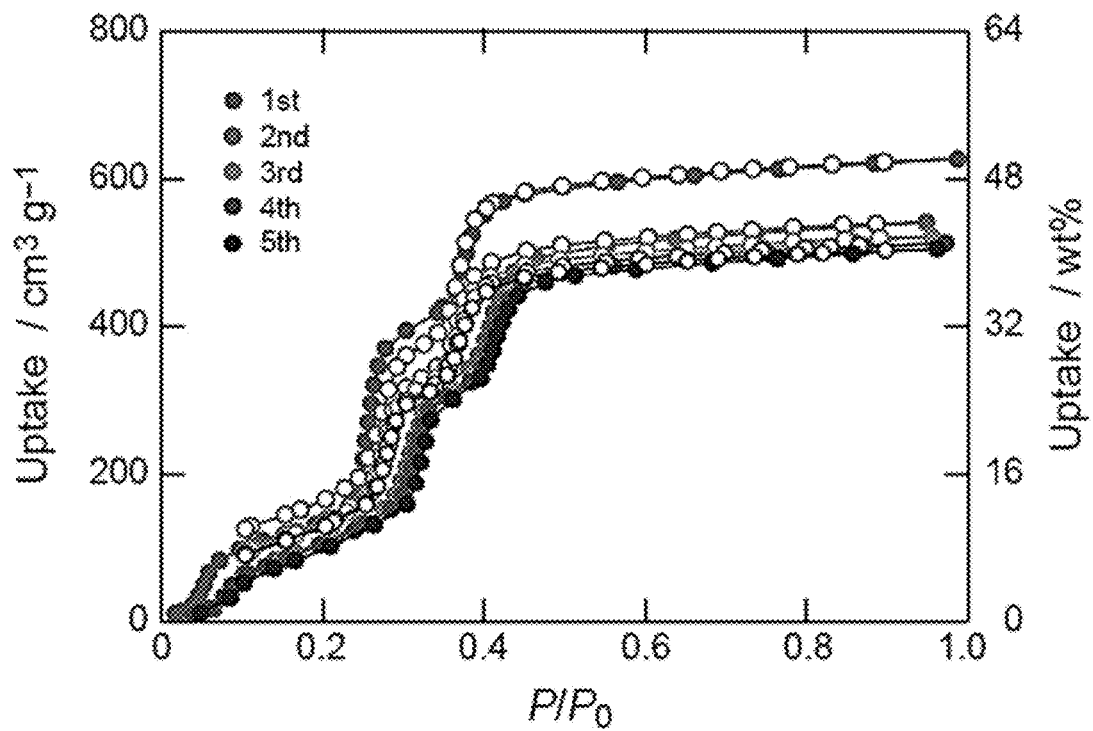
FIG. 52 provides for the cycle performance of water uptake in MOF-803 at 298 K. The sample was evacuated for 2 h at 298 K between the cycles.
Figure 54:
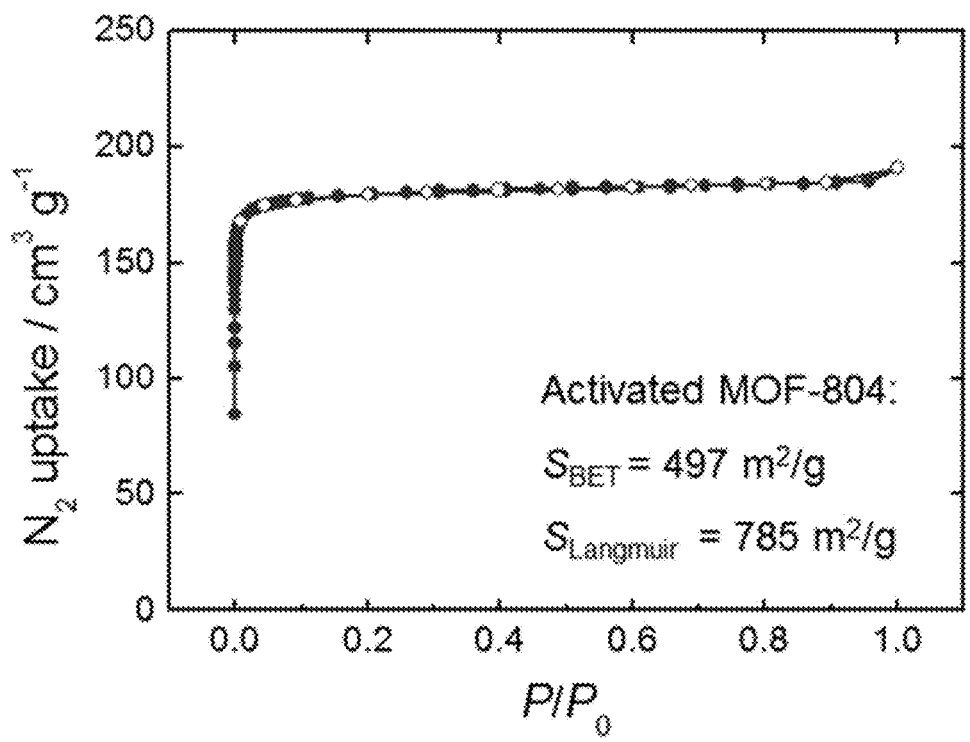
FIG. 54 presents a $N_2$ isotherm of MOF-804 at 77 K.
Figure 55:
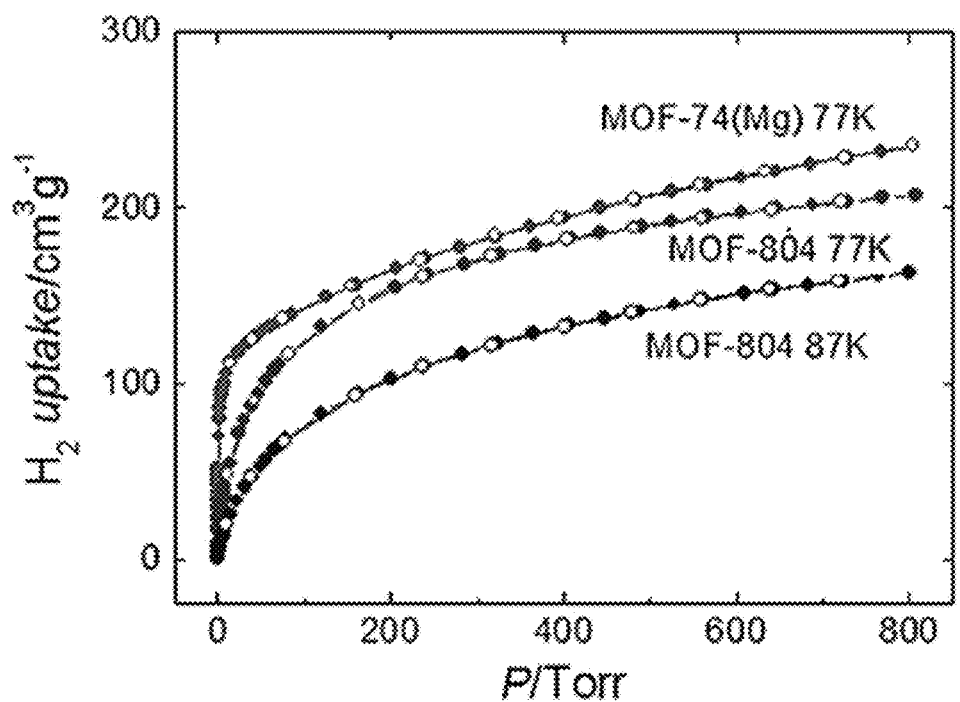
FIG. 55 provides a comparison of $H_2$ isotherms for MOF-804 and MOF-75 (Mg) at 77 K, and MOF-804 at 87 K.
Figure 56:
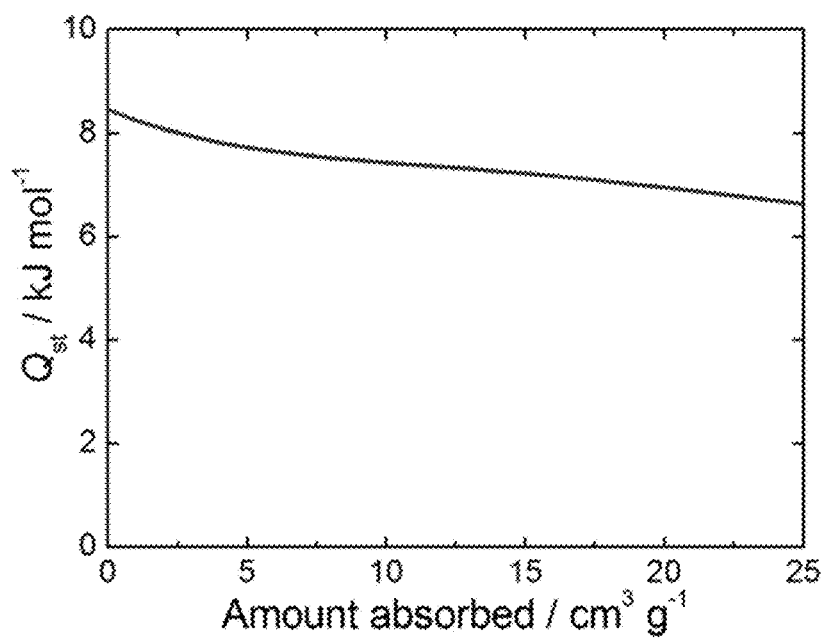
FIG. 56 provides a sorption curve for $H_2$ by MOF-804. $Q_{st}$=8.45 kJ/mol at zero uptake.
Figure 57:
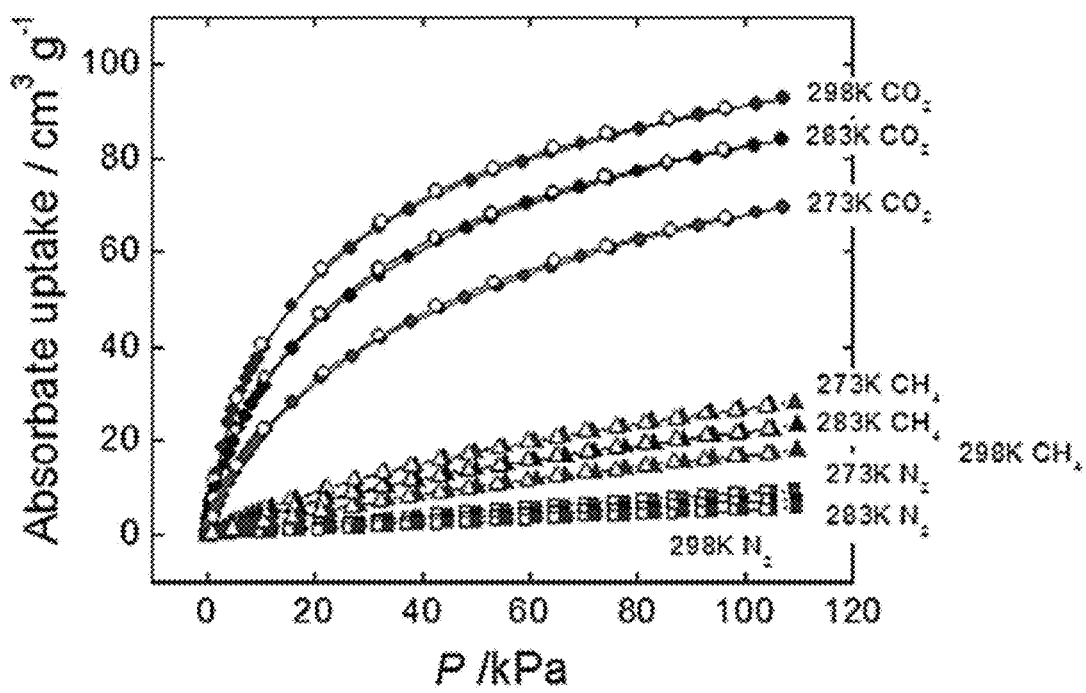
FIG. 57 provides absorbance uptake curves for $CO_2$, $N_2$ and $CH_4$ by MOF-804 at 298 K, 283 K, and 273 K under increasing gas pressures.
Figure 58:
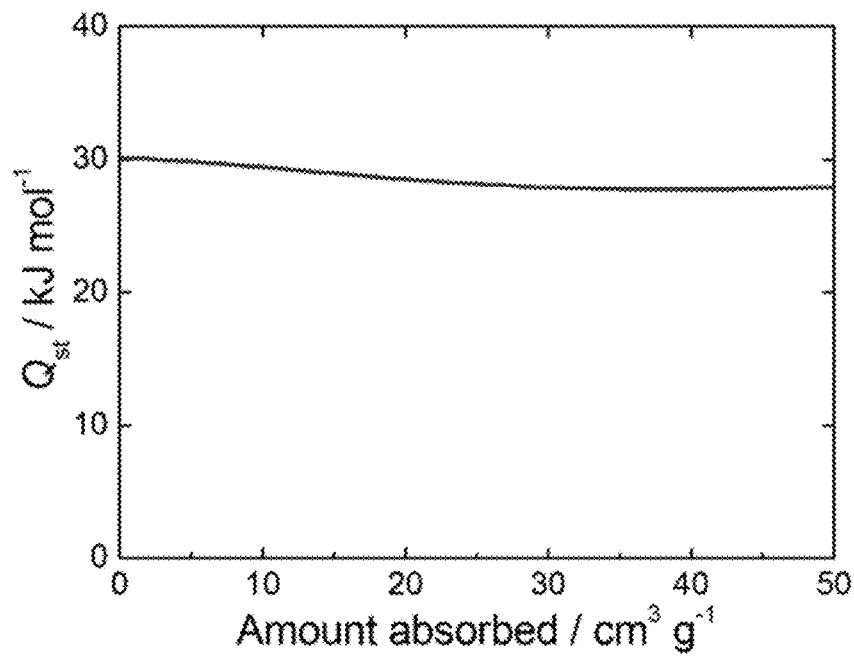
FIG. 58 provides a sorption curve for $CO_2$ by MOF-804. $Q_{st}(CO_2)$=30.2 kJ/mol at zero uptake.
Figure 59:
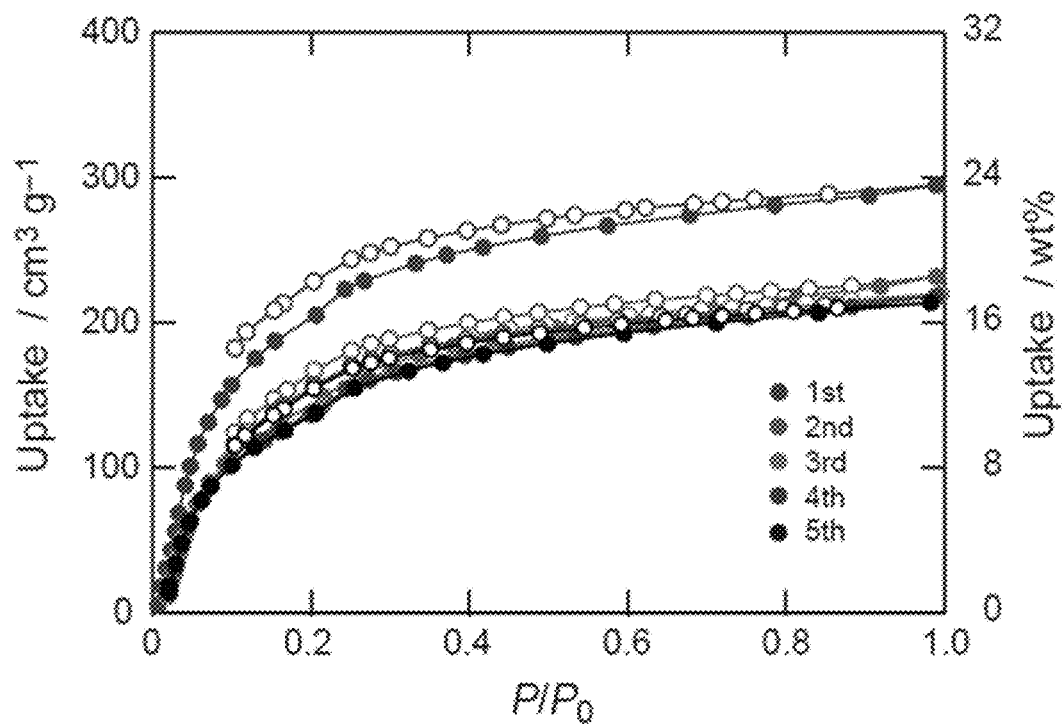
FIG. 59 provides for cycle performance of water uptake in MOF-804 at 298 K. The sample was evacuated for 2 h at 298 K between the cycles.
Figure 61:
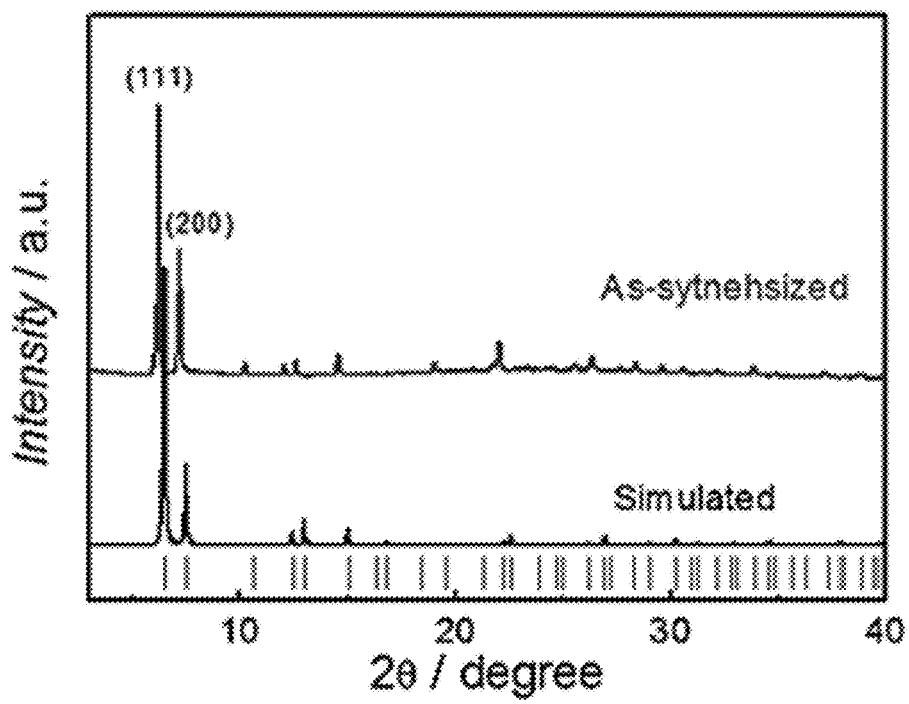
FIG. 61 provides a comparison of the experimental PXRD patterns for MOF-805: as-prepared (top) and simulated pattern (bottom) from single-crystal X-ray data.
Figure 62:
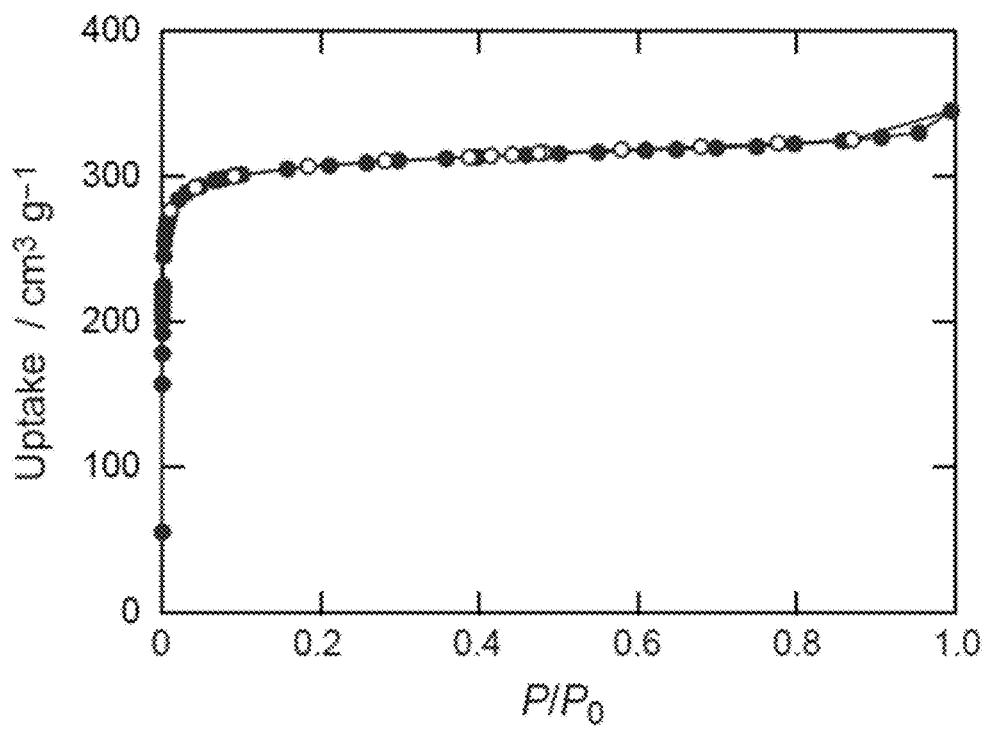
FIG. 62 presents a $N_2$ isotherm of MOF-805 at 77 K.
Figure 63:
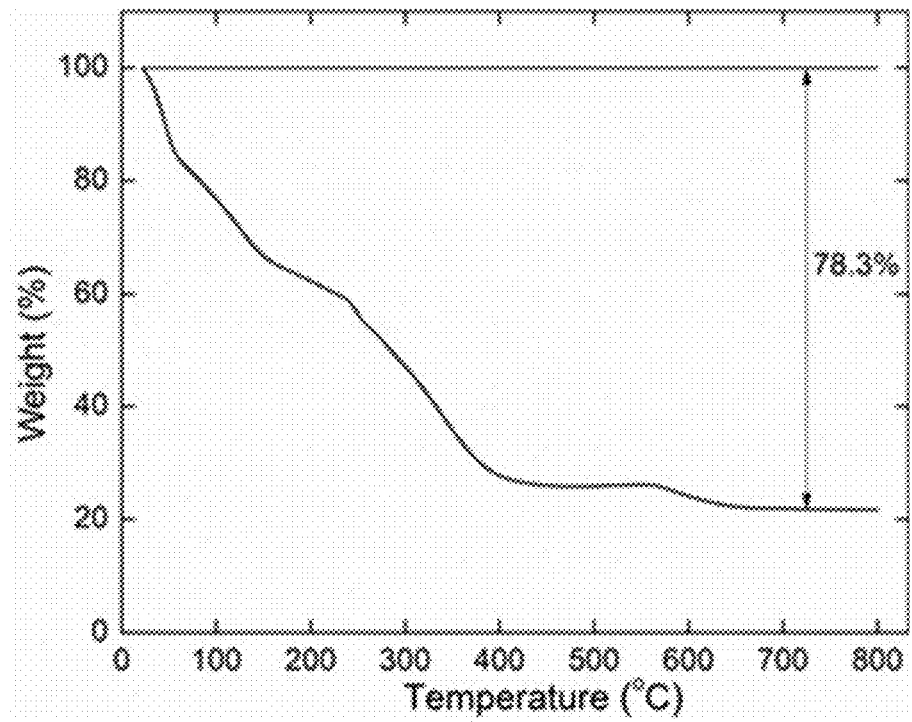
FIG. 63 presents a TGA trace for as-prepared MOF-805, heating rate: 5° C. $min^{-1}$ in air.
Figure 64:
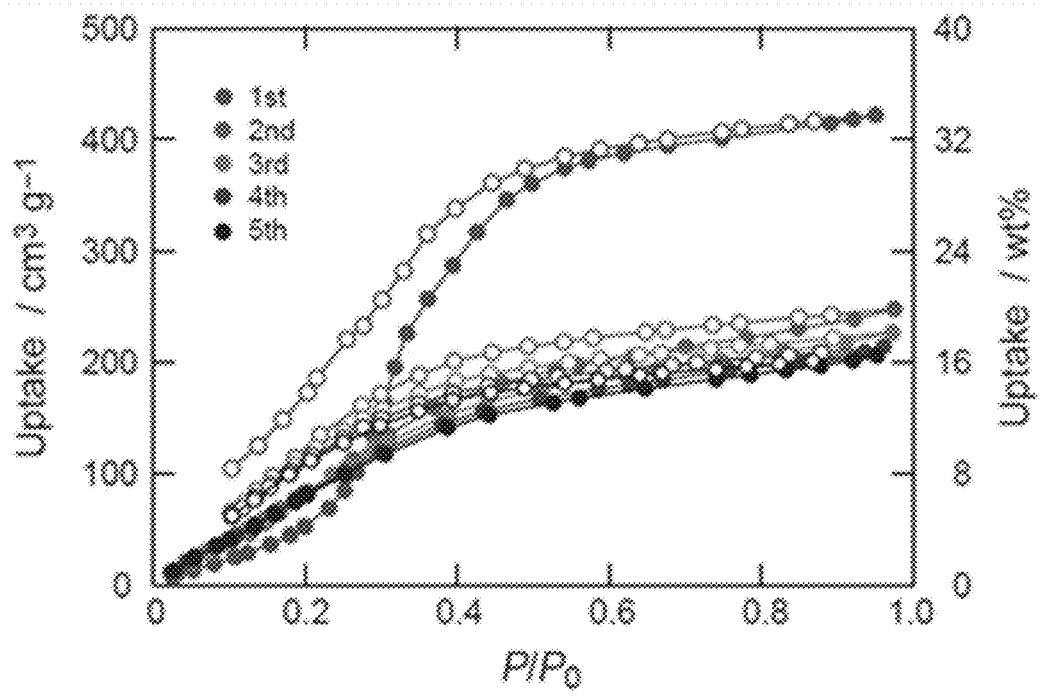
FIG. 64 provides for the cycle performance of water uptake in MOF-805 at 298 K. The sample was evacuated for 2 h at 298 K between the cycles.
Figure 65:
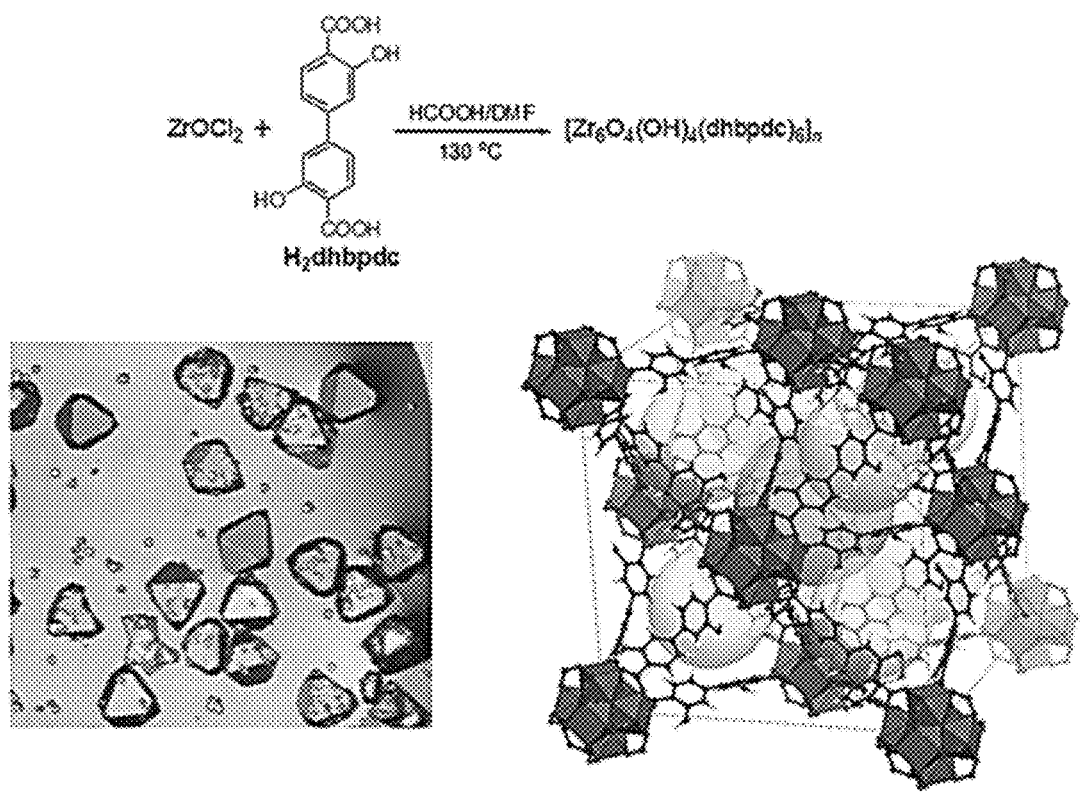
FIG. 65 presents a scheme to synthesize MOF-806. Also shown is an optical image of the crystals of MOF-806 and a depiction of the MOF-806 framework.
Figure 66:
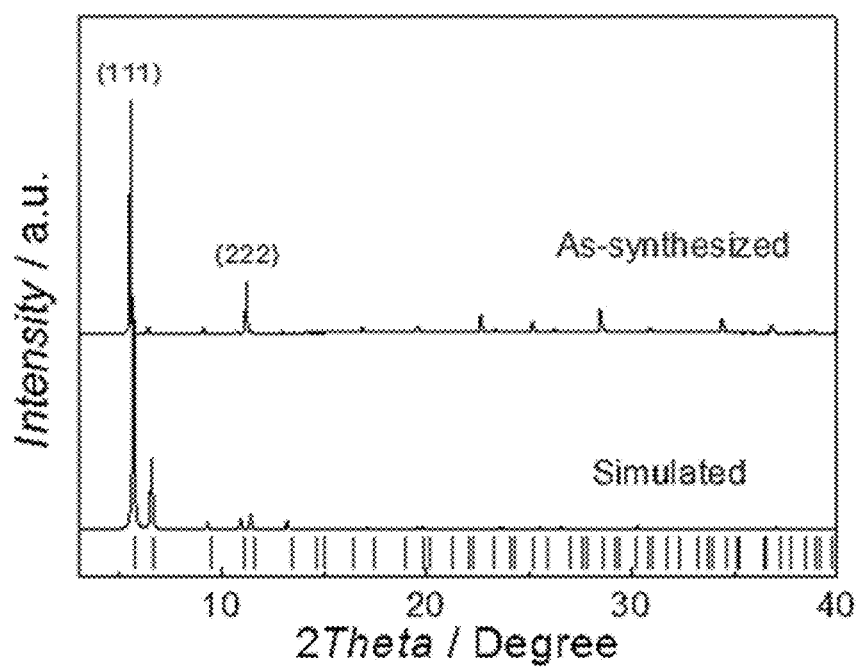
FIG. 66 provides a comparison of the experimental PXRD patterns for MOF-806: as-prepared (top) and simulated pattern (bottom) from single-crystal X-ray data.
Figure 67:
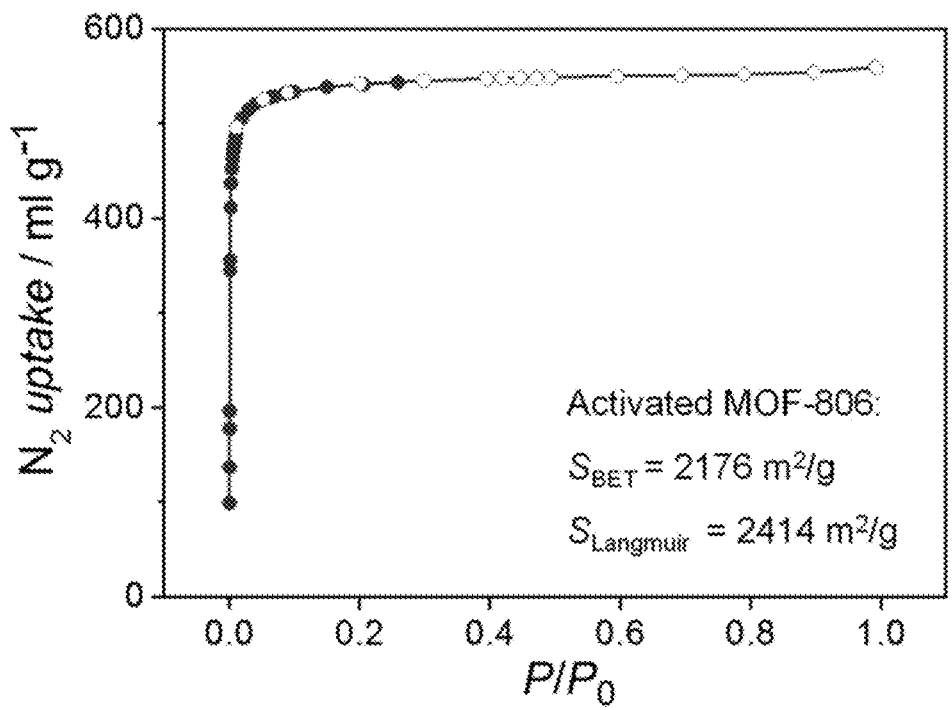
FIG. 67 presents a $N_2$ isotherm of MOF-806 at 77 K.
Figure 68:
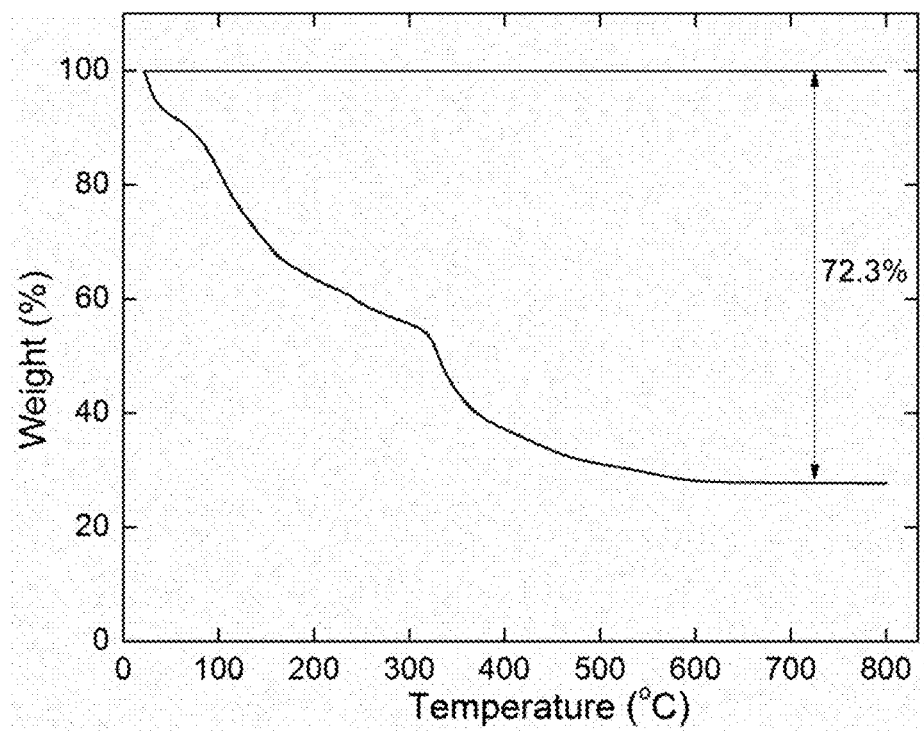
FIG. 68 provides a TGA trace for as-prepared MOF-806, heating rate: 5° C. $min^{-1}$ in air.
Figure 71:
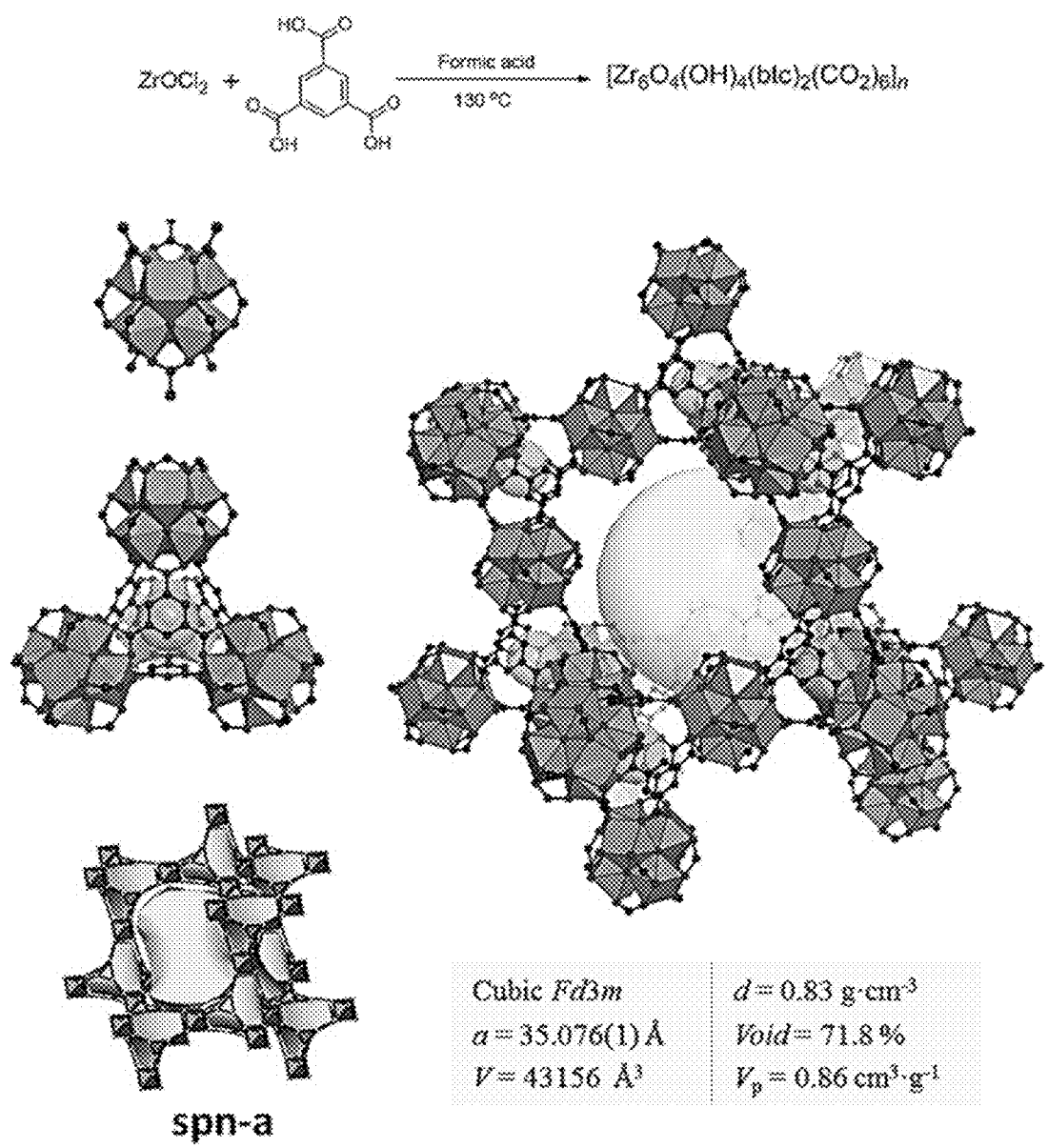
FIG. 71 presents a scheme to synthesize MOF-808. Also shown is a depiction of the MOF-808 framework and a close up of the 6c-extension of the SBU. The structural characteristics of MOF-808 and spn-a net topology is further presented.
Figure 72:
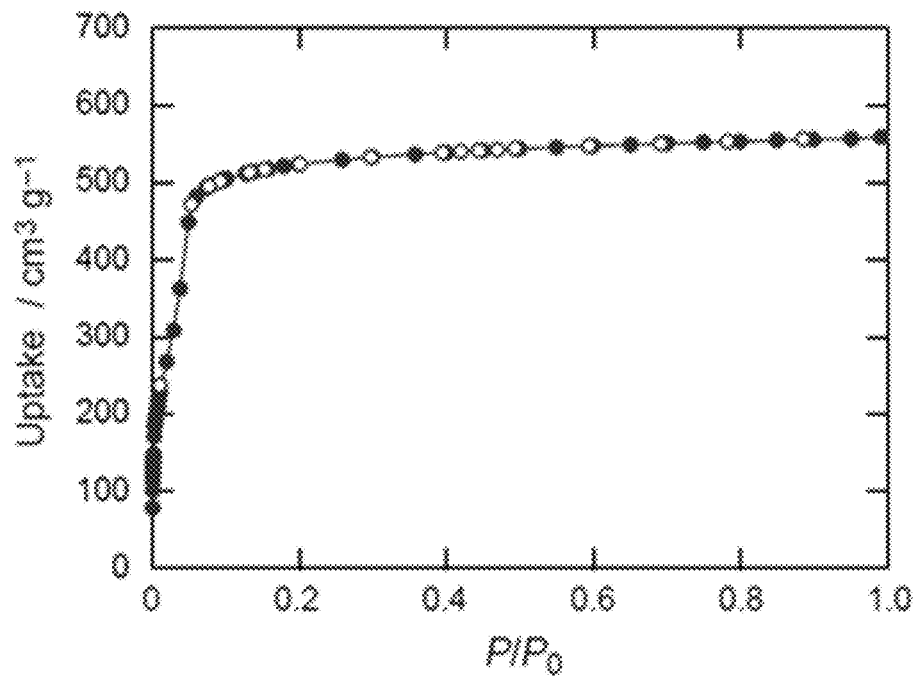
FIG. 72 presents a $N_2$ isotherm of MOF-808 at 77 K.
Figure 73:
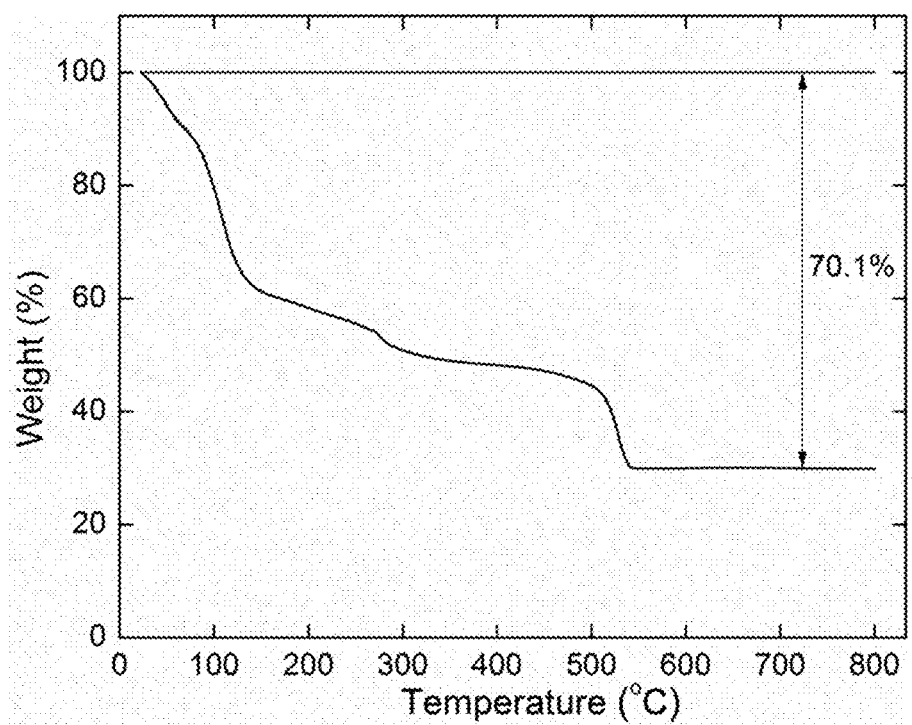
FIG. 73 provides a TGA trace for as-prepared MOF-808, heating rate: 5° C. $min^{-1}$ in air.
Figure 74:
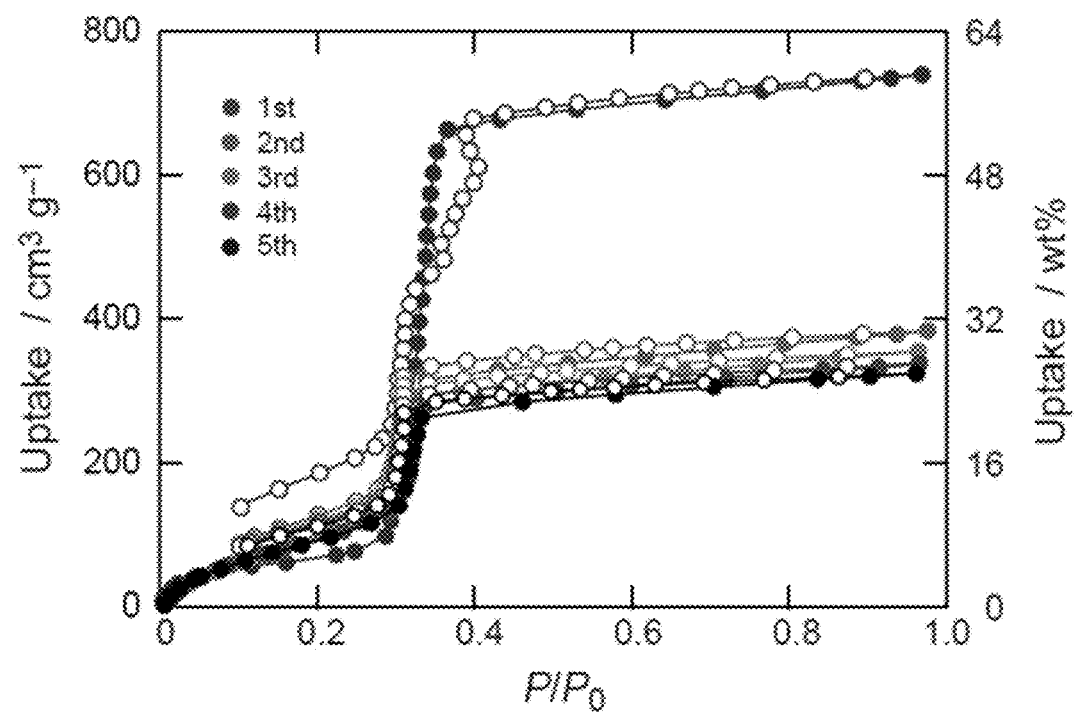
FIG. 74 provides for the cycle performance of water uptake in MOF-808 at 298 K. The sample was evacuated for 2 h at 298 K between the cycles.
Figure 76:
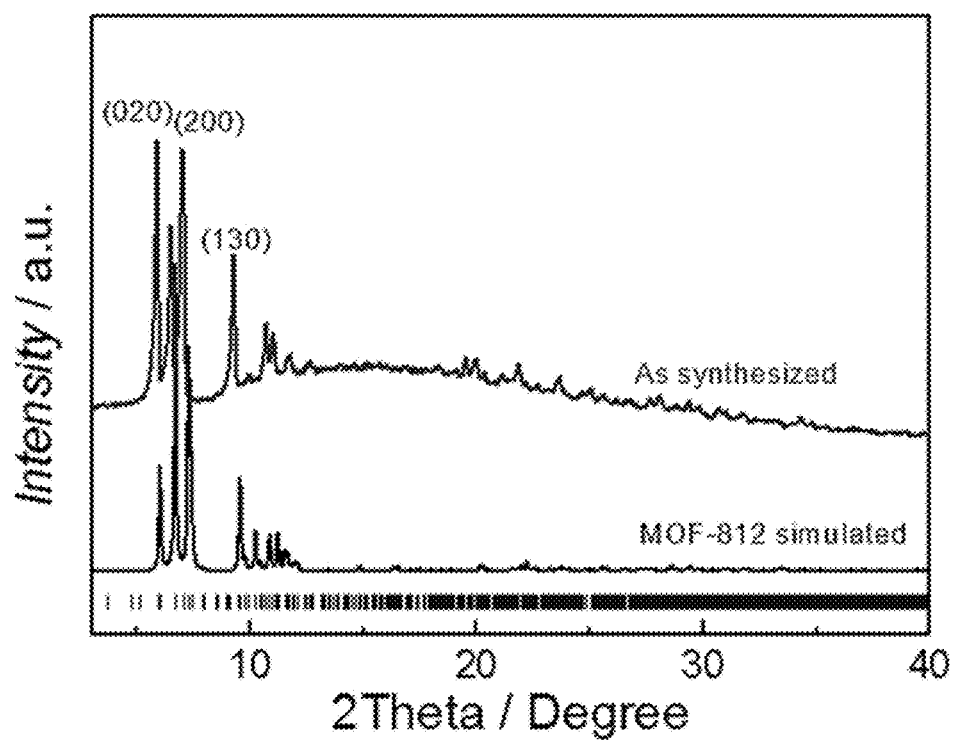
FIG. 76 provides a comparison of the experimental PXRD patterns of MOF-812: as-prepared (top) and simulated pattern (bottom) from single-crystal X-ray data.
Figure 77:
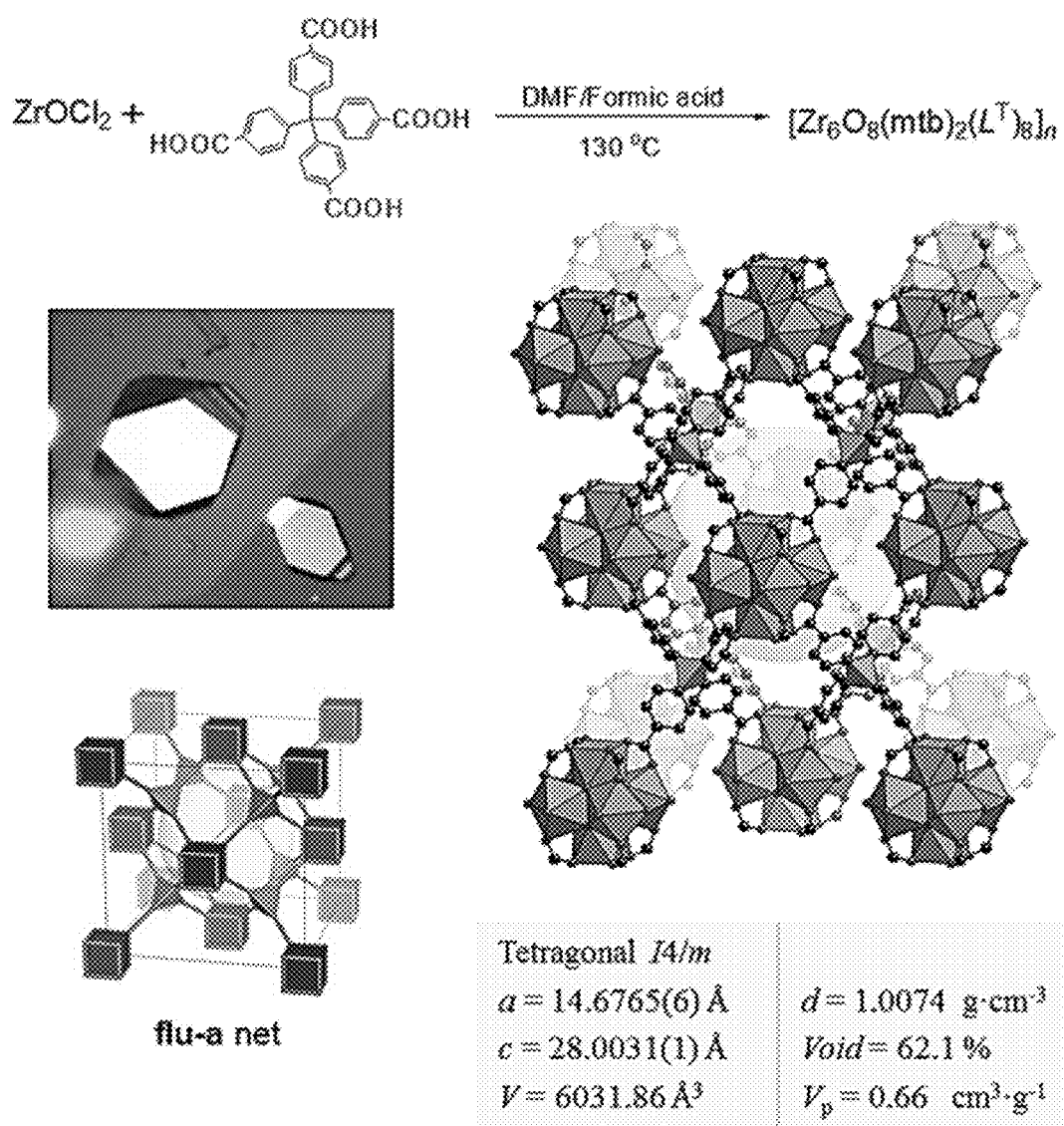
FIG. 77 presents a scheme to synthesize MOF-841, a Zr-carboxylate SBU based upon a tetrahedral linker. Also shown is an optical image of the crystals of MOF-841 and a depiction of the MOF-841 framework. The structural characteristics of MOF-841 and the flu-a net topology is further presented.
Figure 78:
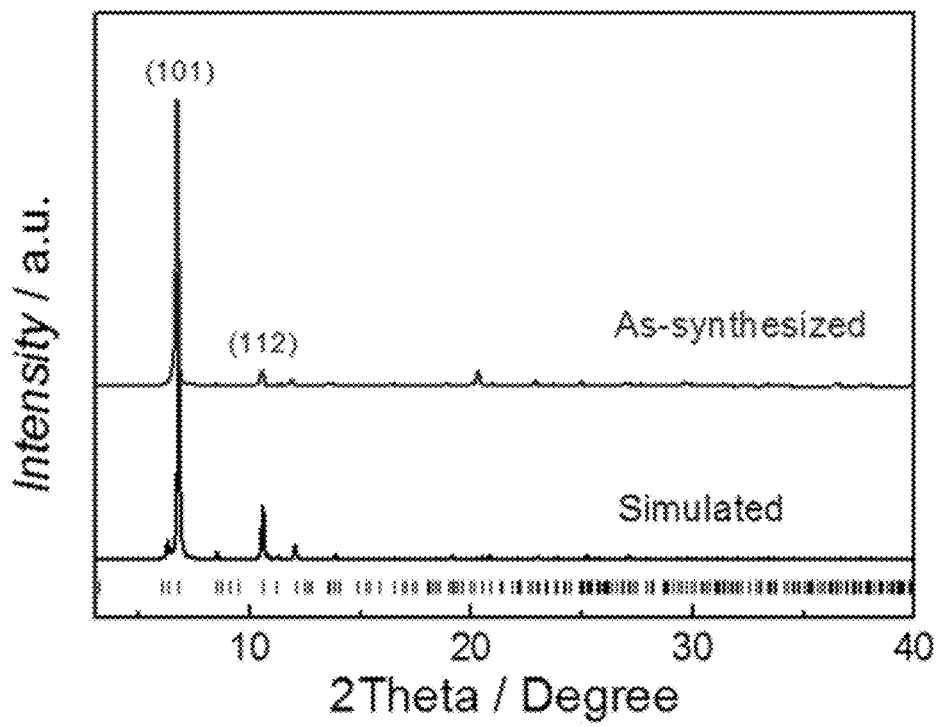
FIG. 78 provides a comparison of the experimental PXRD patterns of MOF-841: as-prepared (top) and simulated pattern (bottom) from single-crystal X-ray data.
Figure 79:
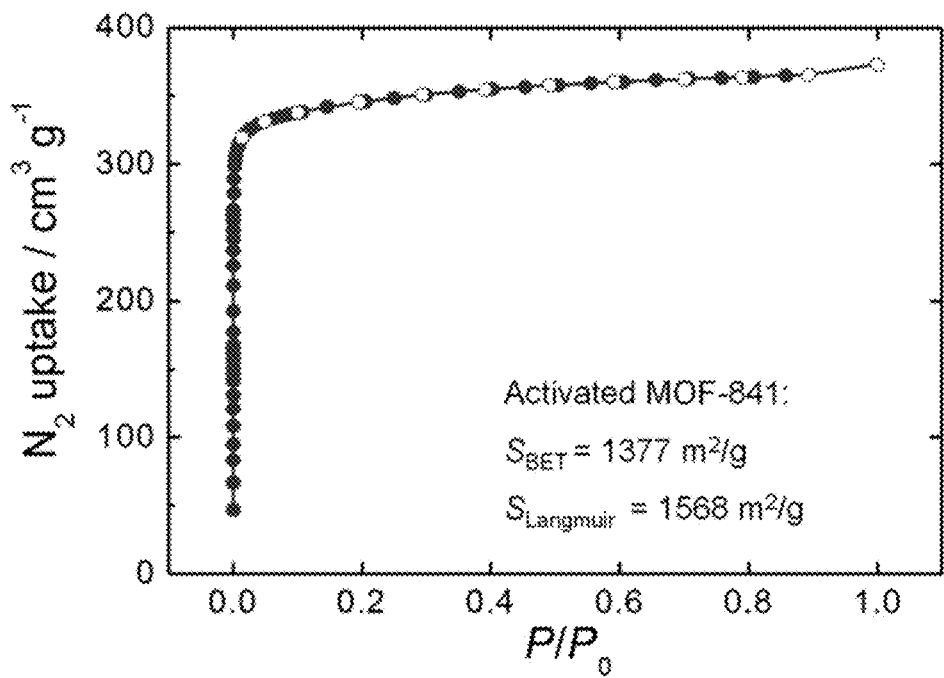
FIG. 79 presents a $N_2$ isotherm of MOF-841 at 77 K.
Figure 80:
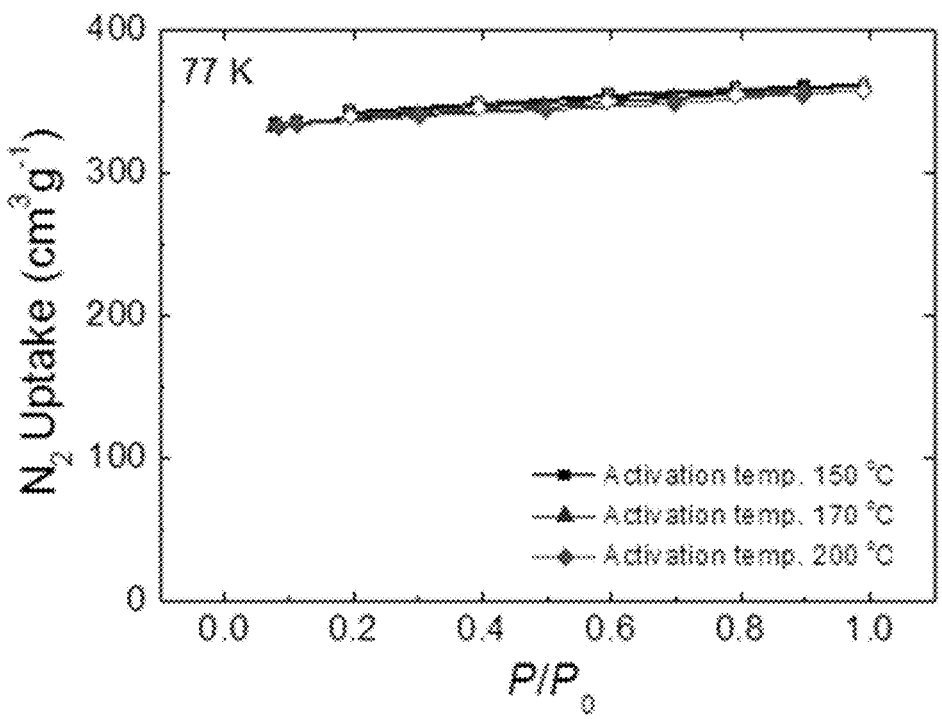
FIG. 80 presents a $N_2$ isotherm of activated MOF-841 at 77 K.
Figure 81:
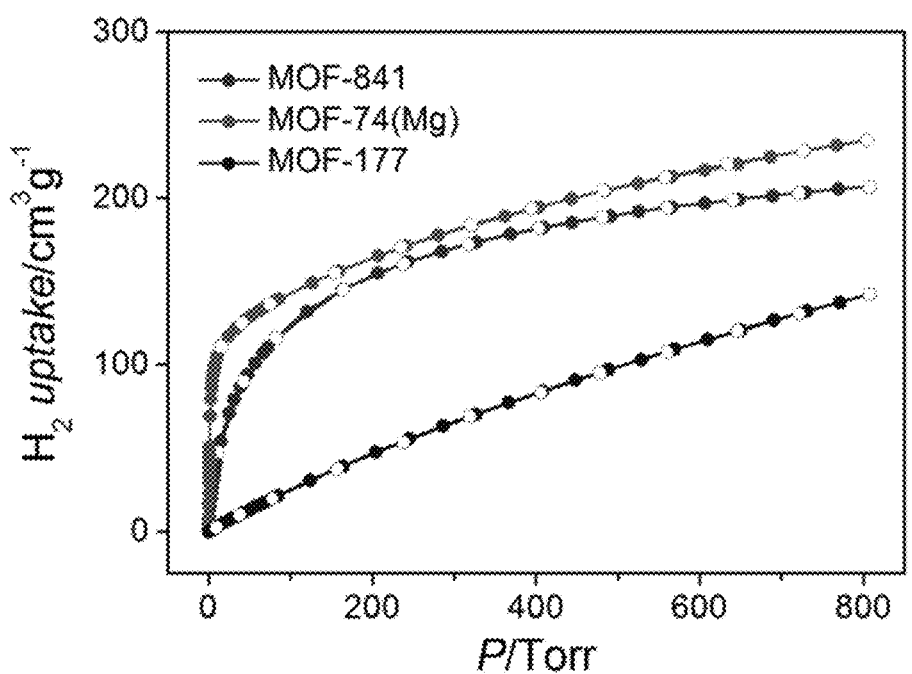
FIG. 81 provides a comparison of $H_2$ isotherms of MOF-841, MOF-74 (Mg) and MOF-177 at 77 K.
Figure 82:
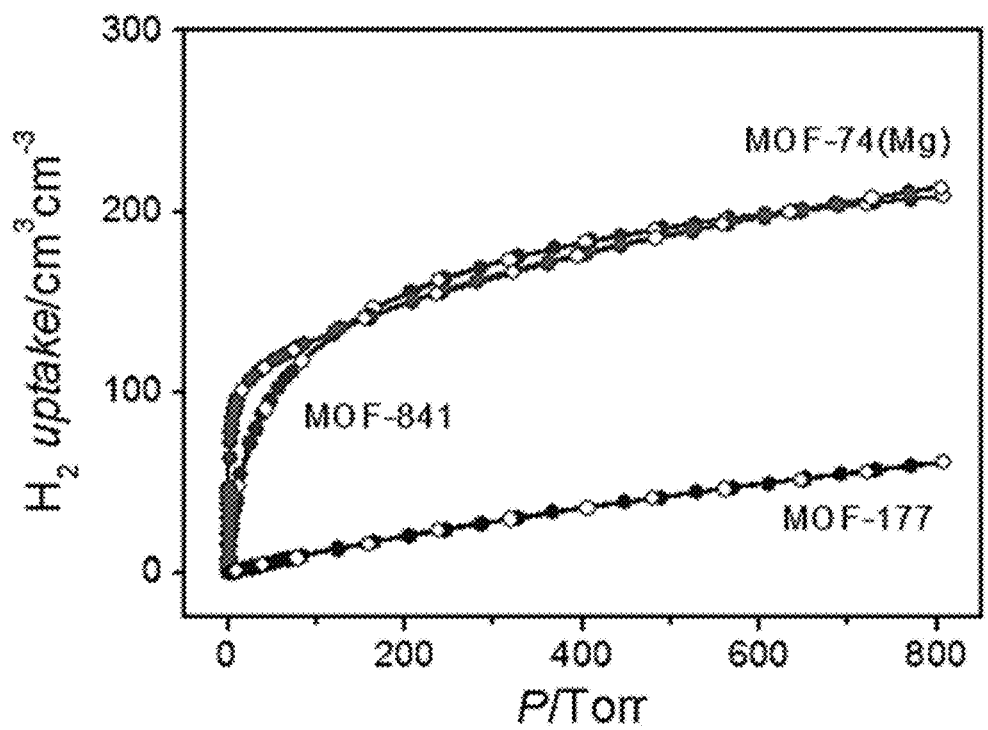
FIG. 82 provides a comparison of $H_2$ isotherms of MOF-841, MOF-74 (Mg) and MOF-177 at ambient temperature.
Figure 83:
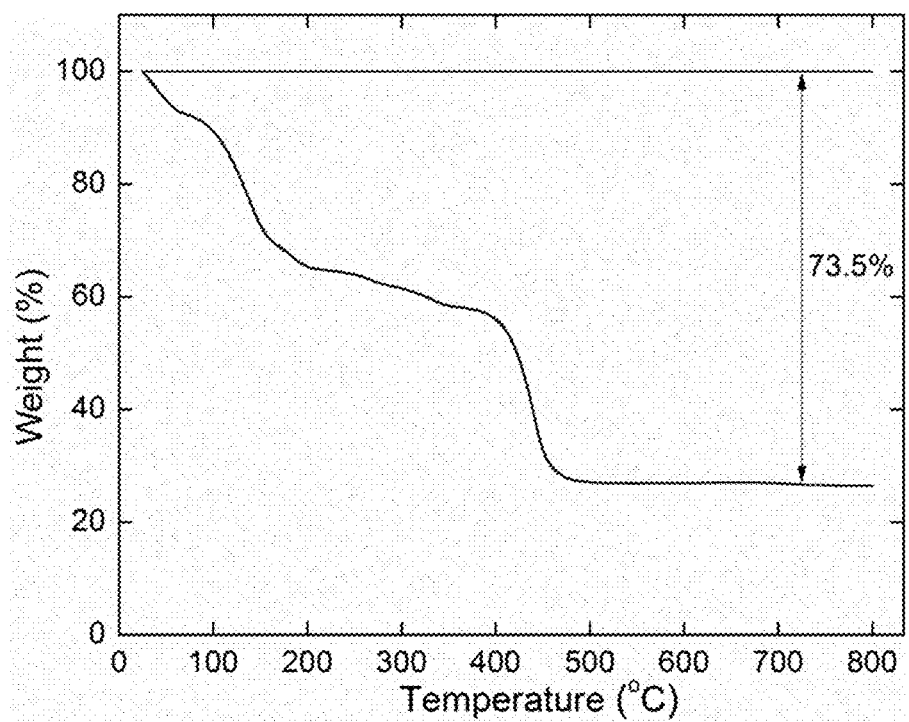
FIG. 83 presents a TGA trace for as-prepared MOF-841, heating rate: 5° C. $min^{-1}$ in air.
Figure 84:
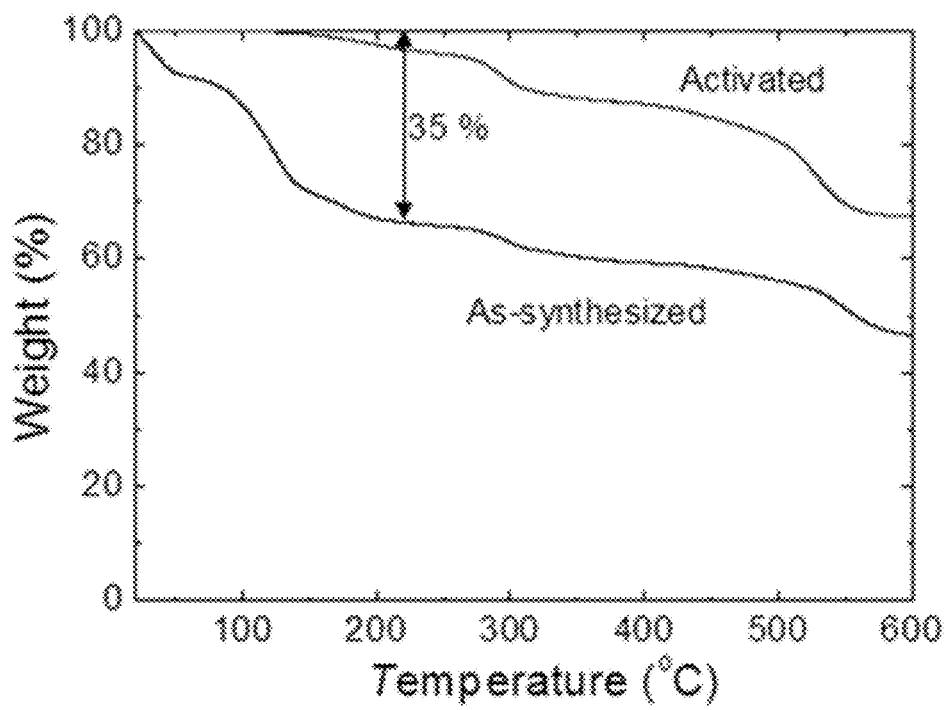
FIG. 84 presents a TGA trace for as-prepared MOF-841 and activated MOF-841, heating rate: 5° C. $min^{-1}$ in air. TGA shows that the stability of MOF-841 is at least up to 300° C.
Figure 85:
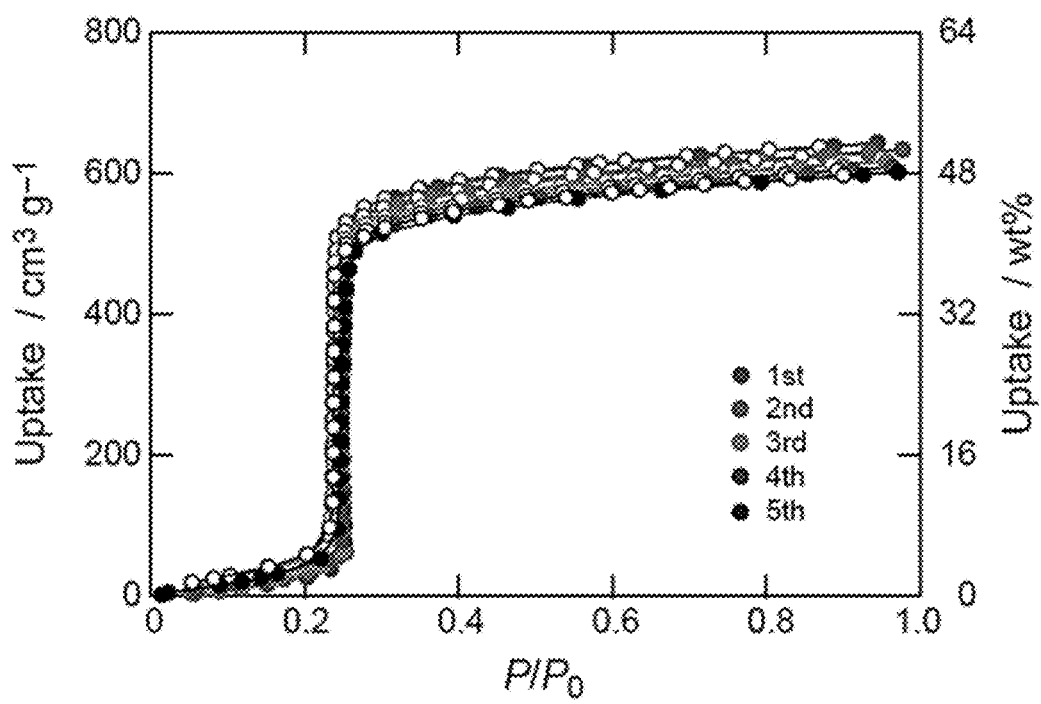
FIG. 85 provides for the cycle performance of water uptake in MOF-841 at 298 K. The sample was evacuated for 2 h at 298 K between the cycles.
Figure 86:
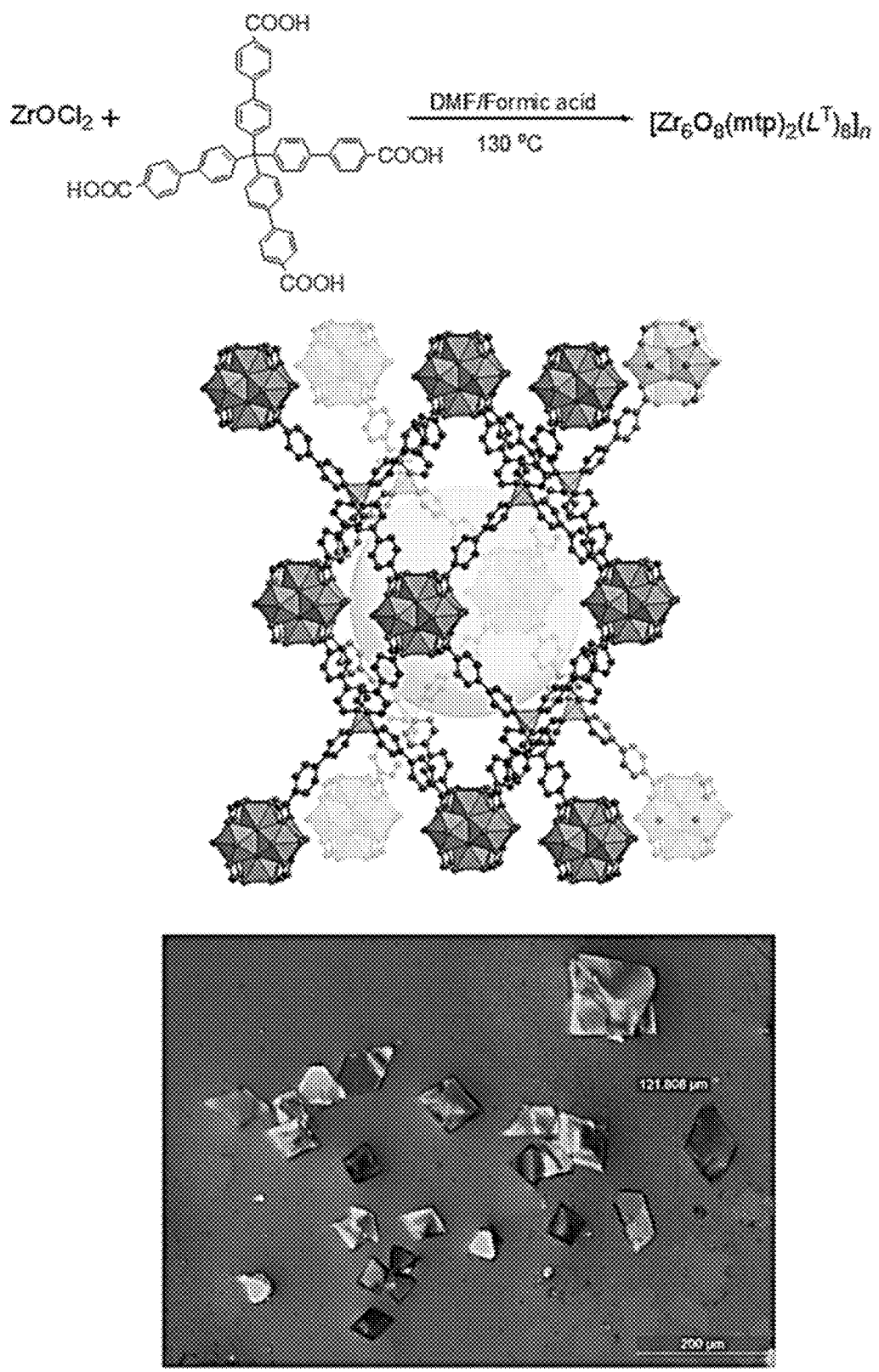
FIG. 86 presents a scheme to synthesize MOF-842, a Zr-carboxylate SBU based upon a tetrahedral linker. Also shown is an optical image of the crystals of MOF-842 and a depiction of the MOF-842 framework.
Figure 88:
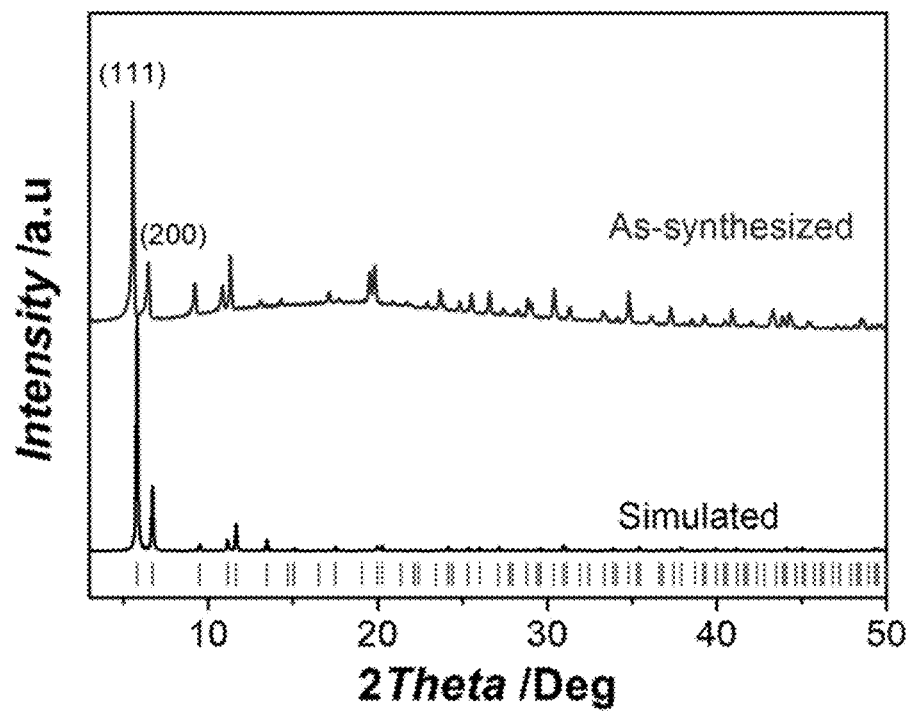
FIG. 88 provides a comparison of the experimental PXRD patterns for MOF-867: as-prepared (top) and simulated pattern (bottom) from single-crystal X-ray data.
Figure 89:
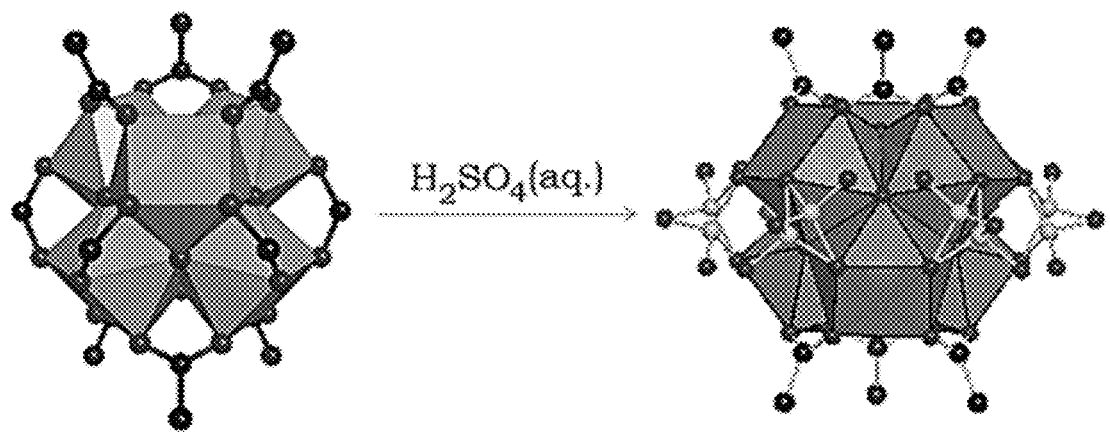
FIG. 89 provides that formate molecules in MOFs with Zr-SBUs can be replaced with sulfate molecules upon treatment with aqueous hydrogen sulfuric acid.
Figure 90:
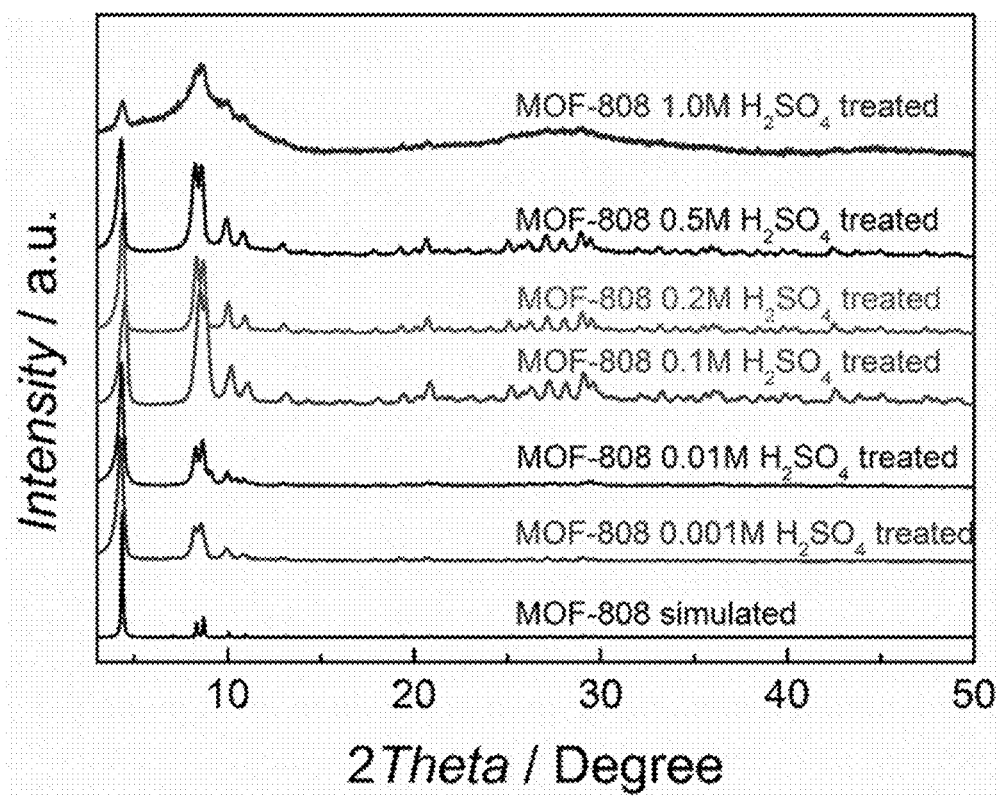
FIG. 90 provides PXRD patterns of MOF-808 treated with various molar concentrations of $H_2SO_4$ indicating that the MOF-808 framework is resistant and structurally stable up to 1.0M $H_2SO_4$.
Figure 91:
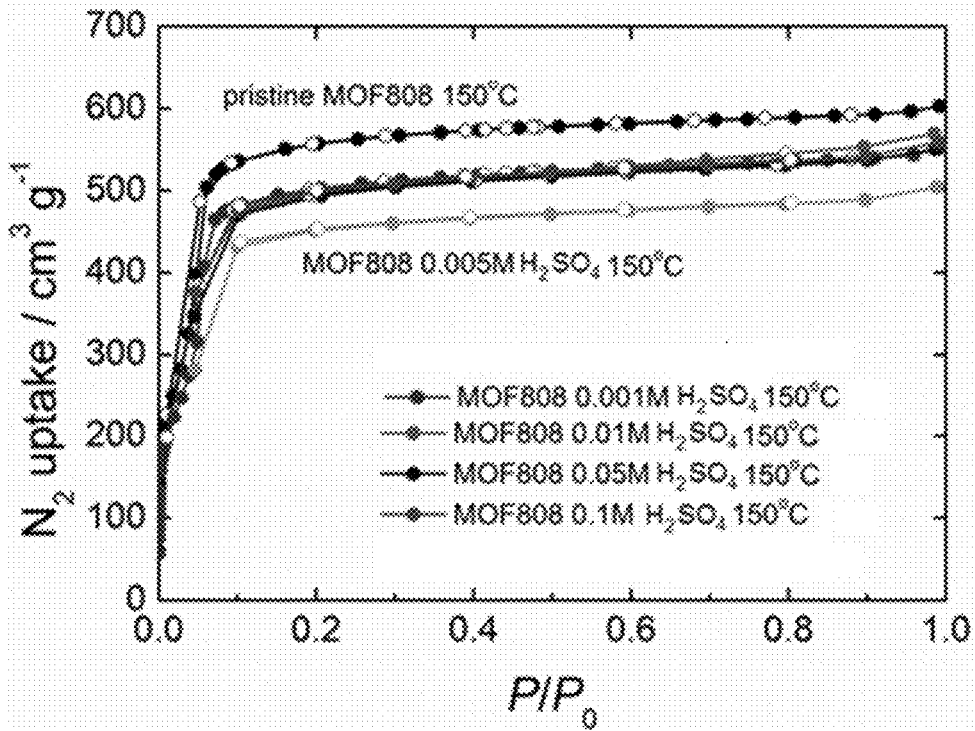
FIG. 91 presents $N_2$ isotherm data for MOF-808 with different molar concentrations of $H_2SO_4$ indicating that the porosity of the framework is maintained under acidic conditions.
Figure 92:
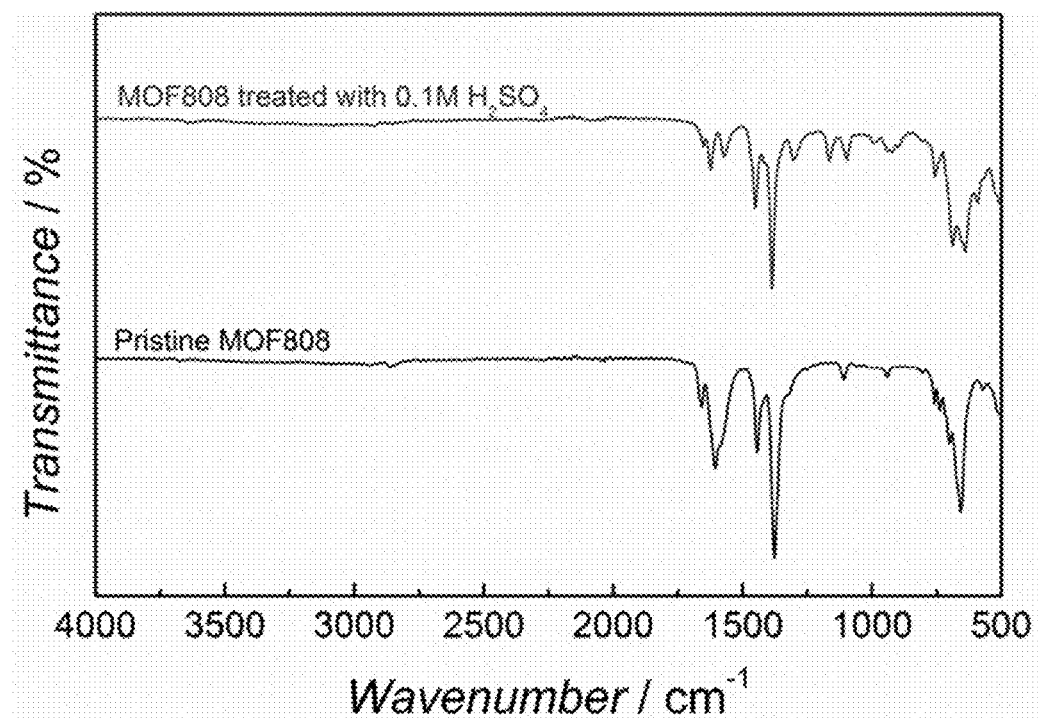
FIG. 92 provides IR tracings of MOF-808 and MOF-808 treated with 0.1M $H_2SO_4$. Extra peaks appearing at 996, 1165, 1301 $cm^{-1}$ corresponding to the $v_3$ vibrational modes of binding $SO_4$ groups.
Figure 93:
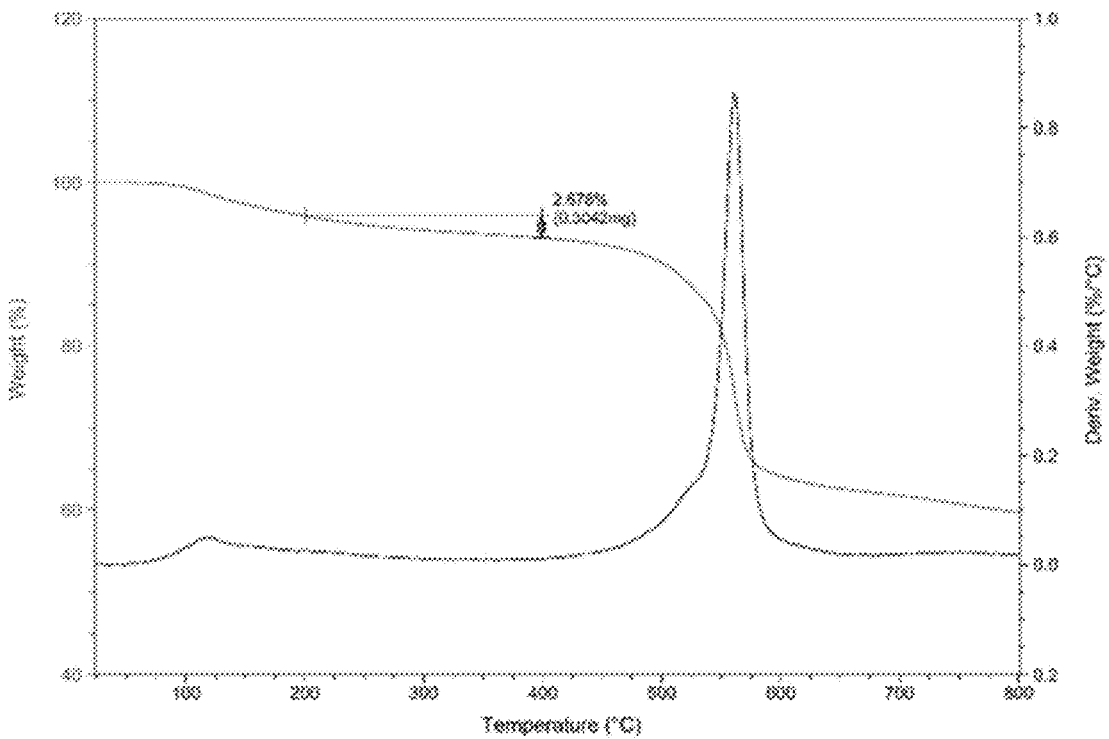
FIG. 93 presents TGA analysis of MOF-808 treated with 0.1M $H_2SO_4$ under a nitrogen atmosphere. A small step around 300° C. is attributed to the loss of the residue formate and adsorption of water. A big step at 500° C. correlates to the decomposition of the framework.
Figure 94:
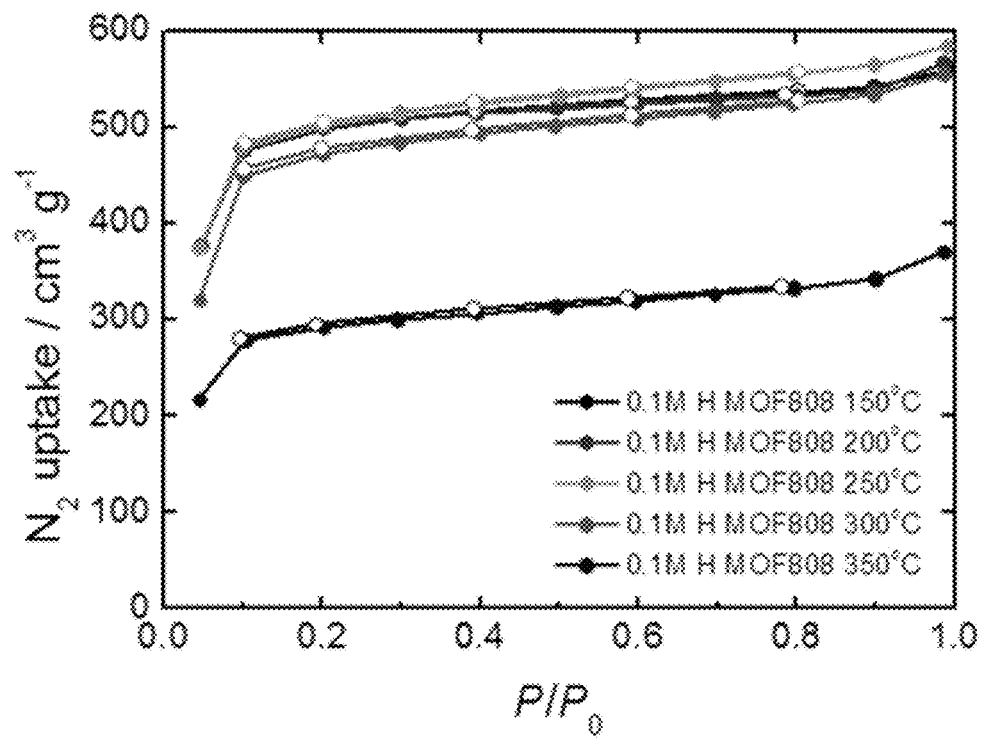
FIG. 94 provides $N_2$ isotherms for MOF-808 treated with 0.1M $H_2SO_4$ at various temperatures. When the sample was activated at a temperature higher than 300° C. a decrease in $N_2$ uptake was detected indicating the collapse of the framework with a corresponding color change of the framework from white to black.
Figure 95:
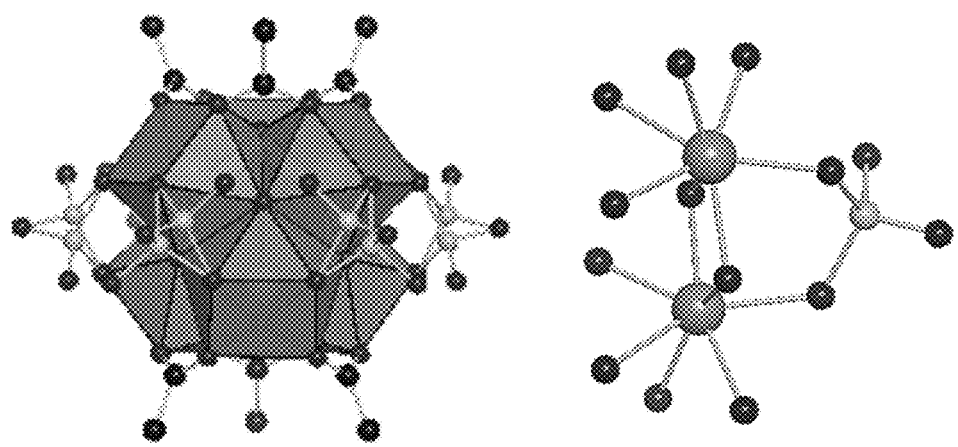
FIG. 95 provides an illustration of the zirconium-carboxylate SBU of MOF-808 that has been treated with 0.1M $H_2SO_4$. Sulfate molecules bound to the SBU is indicated (top). A close up of a bound sulfate molecule (bottom). Electron density indicates that coordinate sites which were previously occupied by formate anions are occupied by $SO_4$ groups having two orientations. Roughly there are 3 $SO_4$ per SBU based upon site occupancy.

Characterization of Hf-MOF-777:

Hf-MOF-777 was obtained using similar synthesis reaction conditions as MOF-777 (e.g., see FIG. 24), but replacing $HfCl_4$ for $ZrOCl_2$. The morphology of single crystals of Hf-MOF-777 was a hexagonal plane, the same as MOF-777. Further, the PXRD pattern of Hf-MOF-777 is comparable to MOF-777. Based upon these results, the structure of Hf-MOF-777 is comparable to MOF-777.

A number of embodiments have been described herein. Nevertheless, it will be understood that various modifications may be made without departing from the spirit and scope of this disclosure. Accordingly, other embodiments are within the scope of the following claims.

What is claimed is:

1. A thermal, acid, and/or solvent resistant metal organic framework (MOF) comprising a plurality of linked M-O-L secondary binding units (SBUs), wherein M is a zirconium metal containing complex comprising the formula $Zr_6O_4(OH)_4$, O are oxygen atoms of a carboxylate based linking cluster; and L is an organic linking ligand that forms bonds with the zirconium metal containing complex via the carboxylate based linking cluster, wherein the organic linking ligand is fumarate or has a structure selected from the group consisting of:

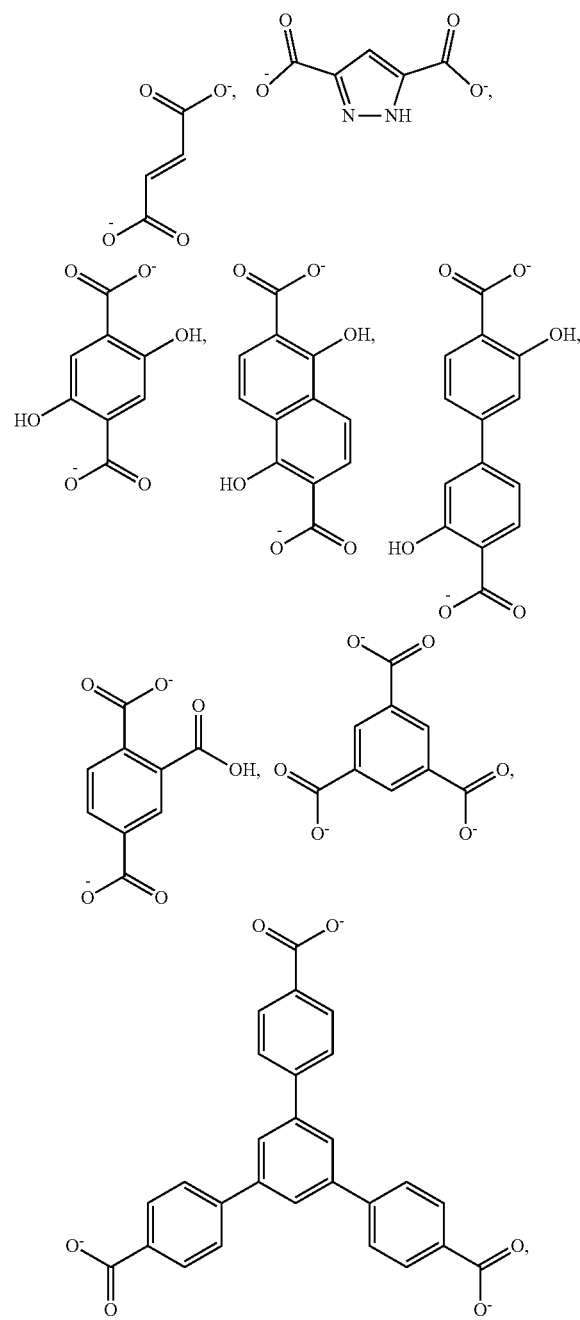

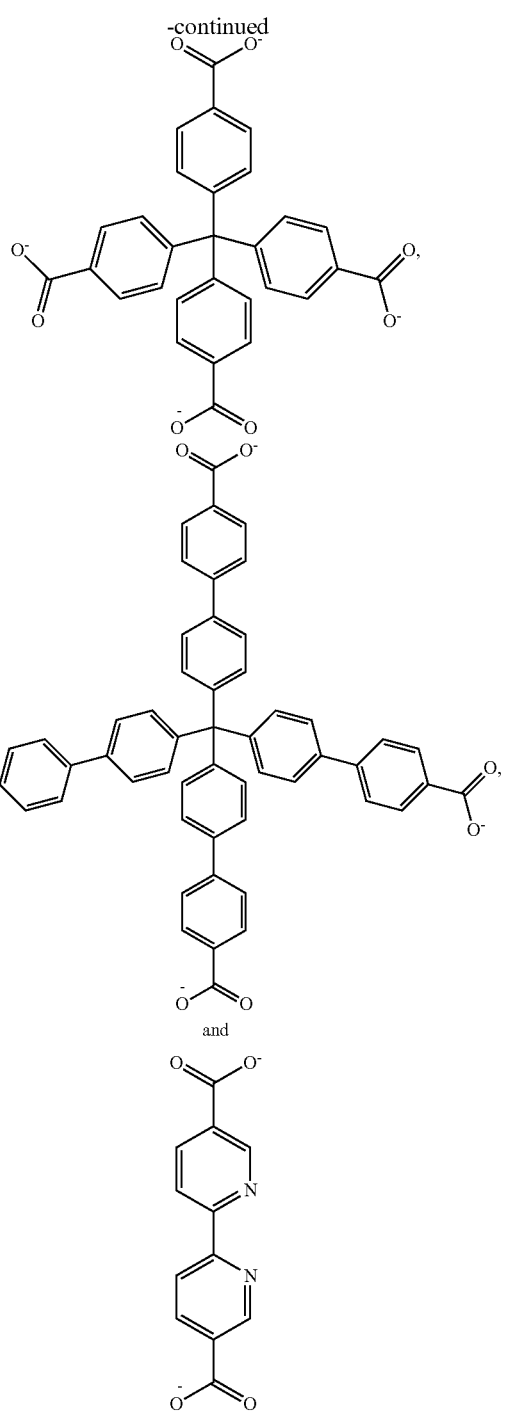

wherein the framework is thermally stable when exposed to a temperature between 50° C. to 525° C., and the framework is chemically stable in the presence of water and/or an acid.

2. The MOF of claim 1, wherein the plurality of linked M-O-L SBUs are zirconium carboxylate clusters that have 3-c, 4-c, 6-c, 8-c, 9-c, 10-c, or 12-c extensions.

3. The MOF of claim 1, wherein the MOF is:
MOF-801 $[Zr_6O_4(OH)_4(fa)_6]_n$, wherein fa is fumarate;
MOF-802 $[Zr_6O_4(OH)_4(PZDC)_5(HCOO)_2(H_2O)_2]_n$, wherein pzdc is 1H-pyrazole-3,5-dicarboxylate;
MOF-804 $[Zr_6O_4(OH)_4(BDC-(OH)_2)_6]n$, wherein BDC-$(OH)_2$ is 2,5-dihydroxy-terephthalate;

MOF-805 [Zr$_6$O$_4$(OH)$_4$(NDC-(OH)$_2$)$_6$]$_n$, wherein NDC-(OH)$_2$ is 1,5-dihydroxy-naphthalene-2,6-dicarboxylate, MOF-806 [Zr$_6$O$_4$(OH)$_4$(BPDC-(OH)$_2$)$_6$]$_n$, wherein BPDC-(OH)$_2$ is 3,3'-dihydroxy-biphenyl-4,4'-dicarboxylate;

MOF-807 [Zr$_6$O$_4$(OH)$_4$(tbc)$_6$]$_n$, wherein tbc is 1,2,4-Benzenetricarboxylate, MOF-808 [Zr$_6$O$_4$(OH)$_4$(BTC)$_2$(HCOO)$_6$]$_n$, wherein BTC is benzene-1,3,5-tricarboxylate, MOF-841 [Zr$_6$O$_4$(OH)$_4$(MTB)$_2$(HCOO)$_4$(H$_2$O)$_4$]$_n$, wherein MTB is methanetetrabenzoate;

MOF-867 [Zr$_6$O$_4$(OH)$_4$(bpydc)$_6$]$_n$, wherein bpydc is 2,2'-bipyridine-5,5'-dicarboxylate, or MOF-777 [Zr$_6$O$_4$(OH)$_4$](HCOO)$_4$(H$_2$O)$_2$(OH)$_2$ BTB$_2$]$_n$, wherein BTB is 1,3,5-Tris(4-carboxyphenyl)benzene.

4. The MOF of claim 1, wherein the plurality of linked M-O-L SBUs are hexagonal zirconium carboxylate clusters linked by benzene-tribenzoic acid (BTB)-based organic linking moieties.

5. The MOF of claim 4, wherein the MOF has tfz-d type 3D topology that is based upon the stacking of kgd-a type 2D layers.

6. The MOF of claim 5, wherein the layers are connected to each other via linking anions.

7. The MOF of claim 6, wherein the linking anions are selected from formate, acetate, phthalate, lactate, oxalate, citrate, fumurate, adipate, anthranilate, ascorbate, benzoate, butyrate, lactate, malate, malonate, tatrate, succinate, sorbate, cinnamate, glutamate, gluconate, propionate, pavalate, and valerate.

8. The MOF of claim 7, wherein the linking anion is formate.

9. The MOF of claim 6, wherein the linking anions comprise acid site precursors.

10. The MOF of claim 9, wherein the acid site precursors are selected from F$^-$, Cl$^-$, ClO$^-$, ClO$_2^-$, ClO$_3^-$, ClO$_4^+$, Br$^-$, BrO$^-$, I$^-$, IO$_3^-$, IO$_4^-$, NO$_3^-$, S$_2^-$, HS$^-$, HSO$_3^-$, SO$_3^{2-}$, SO$_4^{2-}$, HSO$_4^-$, H$_2$PO$_4^{231}$, PO$_4^{3-}$, CO$_3^{2-}$, HCO$_3^-$, H$_3$BO$_3$, SiO$_3^{2-}$, PF$_6^-$, CF$_3$CO$_2^-$ and CF$_3$SO$_3^-$.

11. The MOF of claim 10, wherein the acid site precursor is HS03.

12. The MOF of claim 9, wherein the MOF is a strong solid-acid (sa-MOF).

13. A method for producing a strong solid acid MOF (sa-MOF) comprising:

reacting an organic linking ligand of claim 1 with a zirconium metal ion at an elevated temperature for at least 2 hours, in the presence of an acid site precursor.

14. The method of claim 13, wherein the acid site precursor compound is selected from F$^-$, Cl$^-$, ClO$^-$, ClO$_2^-$, ClO$_3^-$, ClO$_4^+$, Br$^-$, BrO$^-$, I$^-$, IO$_3^-$, IO$_4^-$, NO$_3^-$, S$_2^-$, HS$^-$, HSO$_3^-$, SO$_3^{2-}$, SO$_4^{2-}$, HSO$_4^-$, H$_2$PO$_4^{231}$, PO$_4^{3-}$, CO$_3^{2-}$, HCO$_3^-$, H$_3$BO$_3$, SiO$_3^{2-}$, PF$_6^-$, CF$_3$CO$_2^-$ and CF$_3$SO$_3^-$.

15. The method of claim 13, wherein the organic linking ligand a) that forms bonds with the zirconium metal containing complex via the carboxylate based linking cluster, and which has a structure selected from:

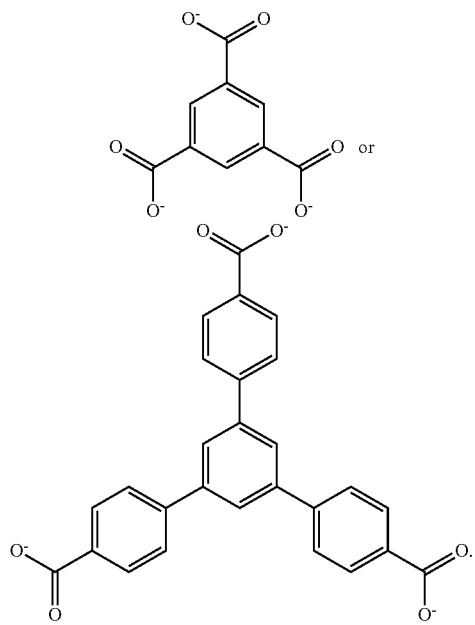

16. A gas storage and/or separation device comprising a MOF of claim 1.

17. A device comprising a thin film or membrane of a MOF of claim 4.

18. A catalytic device comprising a sa-MOF of claim 12.

* * * * *